US007335467B2

(12) United States Patent
Scanlan et al.

(10) Patent No.: US 7,335,467 B2
(45) Date of Patent: Feb. 26, 2008

(54) BREAST CANCER ANTIGENS

(75) Inventors: Matthew J. Scanlan, New York, NY (US); Ivan Gout, London (GB); Elisabeth Stockert, New York, NY (US); Lloyd J. Old, New York, NY (US); Ali Gure, New York, NY (US); Yao-Tseng Chen, New York, NY (US)

(73) Assignees: Ludwig Institute for Cancer Research, New York, NY (US); Cornell Research Foundation, Inc., Ithaca, NY (US); Memorial Sloan-Kettering Cancer Center, New York, NY (US)

( * ) Notice: Subject to any disclaimer, the term of this patent is extended or adjusted under 35 U.S.C. 154(b) by 718 days.

(21) Appl. No.: 10/146,473

(22) Filed: May 15, 2002

(65) Prior Publication Data

US 2003/0108888 A1 Jun. 12, 2003

Related U.S. Application Data

(60) Provisional application No. 60/291,150, filed on May 15, 2001.

(51) Int. Cl.

| | |
|---|---|
| ***C12Q 1/00*** | (2006.01) |
| ***C12Q 1/68*** | (2006.01) |
| ***G01N 33/567*** | (2006.01) |
| ***G01N 33/574*** | (2006.01) |
| ***G01N 1/00*** | (2006.01) |
| ***G01N 33/48*** | (2006.01) |
| ***C12P 19/34*** | (2006.01) |

(52) U.S. Cl. .............................. 435/4; 435/6; 435/7.1; 435/7.21; 435/7.23; 435/91.1; 435/91.2; 436/174; 436/63; 436/64; 436/86; 530/300; 530/350; 530/380; 530/386; 530/387.1; 530/387.7; 530/387.9

(58) Field of Classification Search .................... 435/4, 435/9.1, 7.21, 7.23, 6, 91.1, 91.2, 23.1, 23.5; 530/300, 350, 380, 385, 387.1, 387.7; 436/387.9, 436/174, 63, 64; 536/86, 18.7, 22.1

See application file for complete search history.

(56) References Cited

U.S. PATENT DOCUMENTS

2004/0072175 A1* 4/2004 Beruad et al. ................ 435/6

FOREIGN PATENT DOCUMENTS

WO WO 01/42467 * 6/2001

OTHER PUBLICATIONS

Scanlan et al. Humoral immunity to human breast cancer: antigen definition and quantitative analysis of mRNA expression. Cancer Immunity, vol. 1, p. 4, Mar. 30, 2001.*

Gencore sequence alignment between Applicants' SEQ ID NO: 33 and US20040072175; WO 0142467 A and Cancer Immun 1: 4, 2001.*

Chen, Y. et al., A testicular antigen aberrantly expressed in human cancers detected by autologous antibody screening. *Proceedings of the National Academy of Science USA* 94:1914-1918, 1997.

Disis, M.L. et al., Existent T-cell and antibody immunity to HER-2/neu protein in patients with breast cancer. *Cancer Research* 54:16-20, 1994.

Labrecque, S. et al., Analysis of the anti-p53 antibody response in cancer patients. *Cancer Research* 53:3468-3471, 1993.

Sahin et al., U. Human neoplasms elicit multiple specific immune responses in the autologous host. *Proceedings of the National Academy of Science USA* 92:11810-11813, 1995.

Scanlan, M.J. et al., Characterization of human colon cancer antigens recognized by autologous antibodies. *International Journal of Cancer* 76:652-658,1998.

Scanlan, M.J. et al., Antigens recognized by autologous antibody in patients with renal-cell carcinoma. *International Journal of Cancer* 83:456-464, 1999.

Stockert, E. et al., A survey of the humoral immune response of cancer patients to a panel of human tumor antigens. *Journal of Experimental Medicine* 187:1349-1354, 1998.

* cited by examiner

*Primary Examiner*—Alana M. Harris
(74) *Attorney, Agent, or Firm*—Wolf, Greenfield & Sacks, P.C.

(57) ABSTRACT

The invention provides methods for diagnosing cancer including breast cancer, based on the identification of certain breast cancer-associated polypeptides as antigens that elicit immune responses in breast cancer. The identified antigens can be utilized as markers for diagnosing breast cancer, and for following the course of treatment of breast cancer.

28 Claims, 1 Drawing Sheet

SEQUENCE LISTING

<160> NUMBER OF SEQ ID NOS: 82

<210> SEQ ID NO 1
<211> LENGTH: 9588
<212> TYPE: DNA
<213> ORGANISM: Homo sapiens

<400> SEQUENCE: 1

```
ccgaccaaca ccaacaccca gctccgacgc agctcctctg cgcccttgcc gccctccgag     60
ccacagcttt cctcccgctc ctgcccccgg cccgtcgccg tctccgcgct cgcagcggcc    120
tcgggagggc ccaggtagcg agcagcgacc tcgcgagcct tccgcactcc cgcccggttc    180
cccggccgtc cgcctatcct tggccccctc cgctttctcc gcgccggccc gcctcgctta    240
tgcctcggcg ctgagccgct ctcccgattg cccgccgaca tgagctgcaa cggaggctcc    300
cacccgcgga tcaacactct gggccgcatg atccgcgccg agtctggccc ggacctgcgc    360
tacgaggtga ccagcggcgg cgggggcacc agcaggatgt actattctcg gcgcggcgtg    420
atcaccgacc agaactcgga cggctactgt caaaccggca cgatgtccag gcaccagaac    480
cagaacacca tccaggagct gctgcagaac tgctccgact gcttgatgcg agcagagctc    540
atcgtgcagc ctgaattgaa gtatggagat ggaatacaac tgactcggag tcgagaattg    600
gatgagtgtt ttgcccaggc caatgaccaa atggaaatcc tcgacagctt gatcagagag    660
atgcggcaga tgggccagcc ctgtgatgct taccagaaaa ggcttcttca gctccaagag    720
caaatgcgag ccctttataa agccatcagt gtccctcgag tccgcagggc cagctccaag    780
ggtggtggag gctacacttg tcagagtggc tctggctggg atgagttcac caaacatgtc    840
accagtgaat gtttggggtg gatgaggcag caaagggcgg agatggacat ggtggcctgg    900
ggtgtggacc tggcctcagt ggagcagcac attaacagcc accggggcat ccacaactcc    960
atcggcgact atcgctggca gctggacaaa atcaaagccg acctgcgcga gaaatctgcg   1020
atctaccagt tggaggagga gtatgaaaac ctgctgaaag cgtcctttga gaggatggat   1080
cacctgcgac agctgcagaa catcattcag gccacgtcca gggagatcat gtggatcaat   1140
gactgcgagg aggaggagct gctgtacgac tggagcgaca agaacaccaa catcgctcag   1200
aaacaggagg ccttctccat acgcatgagt caactggaag ttaaagaaaa agagctcaat   1260
aagctgaaac aagaaagtga ccaacttgtc ctcaatcagc atccagcttc agacaaaatt   1320
gaggcctata tggacactct gcagacgcag tggagttgga ttcttcagat caccaagtgc   1380
attgatgttc atctgaaaga aaatgctgcc tactttcagt tttttgaaga ggcgcagtct   1440
actgaagcat acctgaaggg gctccaggac tccatcagga agaagtaccc ctgcgacaag   1500
aacatgcccc tgcagcacct gctggaacag atcaaggagc tggagaaaga acgagagaaa   1560
atccttgaat acaagcgtca ggtgcagaac ttggtaaaca agtctaagaa gattgtacag   1620
ctgaagcctc gtaacccaga ctacagaagc aataaaccca ttattctcag agctctctgt   1680
gactacaaac aagatcagaa aatcgtgcat aagggggatg agtgtatcct gaaggacaac   1740
aacgagcgca gcaagtggta cgtgacgggc ccgggaggcg ttgacatgct tgttccctct   1800
gtggggctga tcatccctcc tccgaaccca ctggccgtgg acctctcttg caagattgag   1860
cagtactacg aagccatctt ggctctgtgg aaccagctct acatcaacat gaagagcctg   1920
gtgtcctggc actactgcat gattgacata gagaagatca gggccatgac aatcgccaag   1980
ctgaaaacaa tgcggcagga agattacatg aagacgatag ccgaccttga gttacattac   2040
```

-continued

```
caagagttca tcagaaatag ccaaggctca gagatgtttg gagatgatga caagcggaaa   2100

atacagtctc agttcaccga tgcccagaag cattaccaga ccctggtcat tcagctccct   2160

ggctatcccc agcaccagac agtgaccaca actgaaatca ctcatcatgg aacctgccaa   2220

gatgtcaacc ataataaagt aattgaaacc aacagagaaa atgacaagca agaaacatgg   2280

atgctgatgg agctgcagaa gattcgcagg cagatagagc actgcgaggg caggatgact   2340

ctcaaaaacc tccctctagc agaccagggg tcttctcacc acatcacagt gaaaattaac   2400

gagcttaaga gtgtgcagaa tgattcacaa gcaattgctg aggttctcaa ccagcttaaa   2460

gatatgcttg ccaacttcag aggttctgaa aagtactgct atttacagaa tgaagtattt   2520

ggactatttc agaaactgga aaatatcaat ggtgttacag atggctactt aaatagctta   2580

tgcacagtaa gggcactgct ccaggctatt ctccaaacag aagacatgtt aaaggtttat   2640

gaagccaggc tcactgagga ggaaactgtc tgcctggacc tggataaagt ggaagcttac   2700

cgctgtggac tgaagaaaat aaaaaatgac ttgaacttga agaagtcgtt gttggccact   2760

atgaagacag aactacagaa agcccagcag atccactctc agacttcaca gcagtatcca   2820

ctttatgatc tggacttggg caagttcggt gaaaaagtca cacagctgac agaccgctgg   2880

caaaggatag ataaacagat cgactttaga ttatgggacc tggagaaaca aatcaagcaa   2940

ttgaggaatt atcgtgataa ctatcaggct ttctgcaagt ggctctatga tcgtaaacgc   3000

cgccaggatt ccttagaatc catgaaattt ggagattcca acacagtcat gcggtttttg   3060

aatgagcaga agaacttgca cagtgaaata tctggcaaac gagacaaatc agaggaagta   3120

caaaaaattg ctgaactttg cgccaattca attaaggatt atgagctcca gctggcctca   3180

tacacctcag gactggaaac tctgctgaac atacctatca agaggaccat gattcagtcc   3240

ccttctgggg tgattctgca agaggctgca gatgttcatg ctcggtacat tgaactactt   3300

acaagatctg gagactatta caggttctta agtgagatgc tgaagagttt ggaagatctg   3360

aagctgaaaa ataccaagat cgaagttttg gaagaggagc tcagactggc ccgagatgcc   3420

aactcggaaa actgtaataa gaacaaattc ctggatcaga acctgcagaa ataccaggca   3480

gagtgttccc agttcaaagc gaagcttgcg agcctggagg agctgaagag acaggctgag   3540

ctggatggga agtcggctaa gcaaaatcta gacaagtgct acggccaaat aaaagaactc   3600

aatgagaaga tcacccgact gacttatgag attgaagatg aaaagagaag aagaaaatct   3660

gtggaagaca gatttgacca acagaagaat gactatgacc aactgcagaa agcaaggcaa   3720

tgtgaaaagg agaaccttgg ttggcagaaa ttagagtctg agaaagccat caaggagaag   3780

gagtacgaga ttgaaaggtt gagggttcta ctgcaggaag aaggcacccg gaagagagaa   3840

tatgaaaatg agctggcaaa ggtaagaaac cactataatg aggagatgag taatttaagg   3900

aacaagtatg aaacagagat taacattacg aagaccacca tcaaggagat atccatgcaa   3960

aaagaggatg attccaaaaa tcttagaaac cagcttgata gactttcaag ggaaaatcga   4020

gatctgaagg atgaaattgt caggctcaat gacagcatct tgcaggccac tgagcagcga   4080

aggcgagctg aagaaaacgc ccttcagcaa aaggcctgtg gctctgagat aatgcagaag   4140

aagcagcatc tggagataga actgaagcag gtcatgcagc agcgctctga ggacaatgcc   4200

cggcacaagc agtccctgga ggaggctgcc aagaccattc aggacaaaaa taaggagatc   4260

gagagactca aagctgagtt tcaggaggag gccaagcgcc gctgggaata tgaaaatgaa   4320

ctgagtaagg taagaaacaa ttatgatgag gagatcatta gcttaaaaaa tcagtttgag   4380
```

-continued

```
accgagatca acatcaccaa gaccaccatc caccagctca ccatgcagaa ggaagaggat   4440
accagtggct accgggctca gatagacaat ctcacccgag aaaacaggag cttatctgaa   4500
gaaataaaga ggctgaagaa cactctaacc cagaccacag agaatctcag gagggtggaa   4560
gaagacatcc aacagcaaaa ggccactggc tctgaggtgt ctcagaggaa acagcagctg   4620
gaggttgagc tgagacaagt cactcagatg cgaacagagg agagcgtaag atataagcaa   4680
tctcttgatg atgctgccaa aaccatccag gataaaaaca aggagataga aaggttaaaa   4740
caactgatcg acaaagaaac aaatgaccgg aaatgcctgg aagatgaaaa cgcgagatta   4800
caaagggtcc agtatgacct gcagaaagca aacagtagtg cgacggagac aataaacaaa   4860
ctgaaggttc aggagcaaga actgacacgc ctgaggatcg actatgaaag ggtttcccag   4920
gagaggactg tgaaggacca ggatatcacg cggttccaga actctctgaa agagctgcag   4980
ctgcagaagc agaaggtgga agaggagctg aatcggctga agaggaccgc gtcagaagac   5040
tcctgcaaga ggaagaagct ggaggaagag ctggaaggca tgaggaggtc gctgaaggag   5100
caagccatca aaatcaccaa cctgacccag cagctggagc aggcatccat tgttaagaag   5160
aggagtgagg atgacctccg gcagcagagg gacgtgctgg atggccacct gagggaaaag   5220
cagaggaccc aggaagagct gaggaggctc tcttctgagg tcgaggccct gaggcggcag   5280
ttactccagg aacaggaaag tgtcaaacaa gctcacttga ggaatgagca tttccagaag   5340
gcgatagaag ataaaagcag aagcttaaat gaaagcaaaa tagaaattga gaggctgcag   5400
tctctcacag agaacctgac caaggagcac ttgatgttag aagaagaact gcggaacctg   5460
aggctggagt acgatgacct gaggagagga cgaagcgaag cggacagtga taaaaatgca   5520
accatcttgg aactaaggag ccagctgcag atcagcaaca accggaccct ggaactgcag   5580
gggctgatta atgatttaca gagagagagg gaaaatttga gacaggaaat tgagaaattc   5640
caaaagcagg ctttagaggc atctaatagg attcaggaat caaagaatca gtgtactcag   5700
gtggtacagg aaagagagag ccttctggtg aaaatcaaag tcctggagca agacaaggca   5760
aggctgcaga ggctggagga tgagctgaat cgtgcaaaat caactctaga ggcagaaacc   5820
agggtgaaac agcgcctgga gtgtgagaaa cagcaaattc agaatgacct gaatcagtgg   5880
aagactcaat attcccgcaa ggaggaggct attaggaaga tagaatcgga aagagaaaag   5940
agtgagagag agaagaacag tcttaggagt gagatcgaaa gactccaagc agagatcaag   6000
agaattgaag agaggtgcag gcgtaagctg gaggattcta ccagggagac acagtcacag   6060
ttagaaacag aacgctcccg atatcagagg gagattgata aactcagaca gcgcccatat   6120
gggtcccatc gagagaccca gactgagtgt gagtggaccg ttgacacctc caagctggtg   6180
tttgatgggc tgaggaagaa ggtgacagca atgcagctct atgagtgtca gctgatcgac   6240
aaaacaacct tggacaaact attgaagggg aagaagtcag tggaagaagt tgcttctgaa   6300
atccagccat tccttcgggg tgcaggatct atcgctggag catctgcttc tcctaaggaa   6360
aaatactctt tggtagaggc caagagaaag aaattaatca gcccagaatc cacagtcatg   6420
cttctggagg cccaggcagc tacaggtggt ataattgatc cccatcggaa tgagaagctg   6480
actgtcgaca gtgccatagc tcgggacctc attgacttcg atgaccgtca gcagatatat   6540
gcagcagaaa aagctatcac tggttttgat gatccatttt caggcaagac agtatctgtt   6600
tcagaagcca tcaagaaaaa tttgattgat agagaaaccg gaatgcgcct gctggaagcc   6660
cagattgctt caggggggtgt agtagaccct gtgaacagtg tctttttgcc aaaagatgtc   6720
gccttggccc gggggctgat tgatagagat ttgtatcgat ccctgaatga tccccgagat   6780
```

-continued

```
agtcagaaaa actttgtgga tccagtcacc aaaaagaagg tcagttacgt gcagctgaag   6840
gaacggtgca gaatcgaacc acatactggt ctgctcttgc tttcagtaca gaagagaagc   6900
atgtccttcc aaggaatcag acaacctgtg accgtcactg agctagtaga ttctggtata   6960
ttgagaccgt ccactgtcaa tgaactggaa tctggtcaga tttcttatga cgaggttggt   7020
gagagaatta aggacttcct ccagggttca agctgcatag caggcatata caatgagacc   7080
acaaaacaga agcttggcat ttatgaggcc atgaaaattg gcttagtccg acctggtact   7140
gctctggagt tgctggaagc ccaagcagct actggcttta tagtggatcc tgttagcaac   7200
ttgaggttac cagtggagga agcctacaag agaggtctgg tgggcattga gttcaaagag   7260
aagctcctgt ctgcagaacg agctgtcact gggtataatg atcctgaaac aggaaacatc   7320
atctctttgt tccaagccat gaataaggaa ctcatcgaaa agggccacgg tattcgctta   7380
ttagaagcac agatcgcaac cggggggatc attgacccaa aggagagcca tcgtttacca   7440
gttgacatag catataagag gggctatttc aatgaggaac tcagtgagat tctctcagat   7500
ccaagtgatg ataccaaagg atttttgac cccaacactg aagaaaatct tacctatctg   7560
caactaaaag aaagatgcat taaggatgag gaaacagggc tctgtcttct gcctctgaaa   7620
gaaaagaaga aacaggtgca gacatcacaa aagaataccc tcaggaagcg tagagtggtc   7680
atagttgacc cagaaaccaa taaagaaatg tctgttcagg aggcctacaa gaagggccta   7740
attgattatg aaaccttcaa agaactgtgt gagcaggaat gtgaatggga agaaataacc   7800
atcacgggat cagatggctc caccagggtg gtcctggtag atagaaagac aggcagtcag   7860
tatgatattc aagatgctat tgacaagggc cttgttgaca ggaagttctt tgatcagtac   7920
cgatccggca gcctcagcct cactcaattt gctgacatga tctccttgaa aaatggtgtc   7980
ggcaccagca gcagcatggg cagtggtgtc agcgatgatg tttttagcag ctcccgacat   8040
gaatcagtaa gtaagatttc caccatatcc agcgtcagga atttaaccat aaggagcagc   8100
tctttttcag acaccctgga agaatcgagc cccattgcag ccatctttga cacagaaaac   8160
ctggagaaaa tctccattac agaaggtata gagcggggca tcgttgacag catcacgggt   8220
cagaggcttc tggaggctca ggcctgcaca ggtggcatca tccacccaac cacgggccag   8280
aagctgtcac ttcaggacgc agtctcccag ggtgtgattg accaagacat ggccaccagc   8340
gtgaagcctg ctcagaaagc cttcataggc ttcgagggtg tgaagggaaa gaagaagatg   8400
tcagcagcag aggcagtgaa agaaaaatgg ctcccgtatg aggctggcca gcgcttcctg   8460
gagttccagt acctcacggg aggtcttgtt gacccggaag tgcatgggag gataagcacc   8520
gaagaagcca tccggaaggg gttcatagat ggccgcgccg cacagaggct gcaagacacc   8580
agcagctatg ccaaaatcct gacctgcccc aaaaccaaat taaaaatatc ctataaggat   8640
gccataaatc gctccatggt agaagatatc actgggctgc gccttctgga agccgcctcc   8700
gtgtcgtcca agggcttacc cagcccttac aacatgtctt cggctccggg gtcccgctcc   8760
ggctcccgct cgggatctcg ctccggatct cgctccgggt cccgcagtgg gtcccggaga   8820
ggaagctttg acgccacagg gaattcttcc tactcttatt cctactcatt tagcagtagt   8880
tctattgggc actagtagtc agttgggagt ggttgctata ccttgacttc atttatatga   8940
atttccactt tattaaataa tagaaaagaa aatcccggtg cttgcagtag agtgatagga   9000
cattctatgc ttacagaaaa tatagccatg attgaaatca aatagtaaag gctgttctgg   9060
ctttttatct tcttagctca tcttaaataa gcagtacact tggatgcagt gcgtctgaag   9120
```

-continued

```
tgctaatcag ttgtaacaat agcacaaatc gaacttagga tttgtttctt ctcttctgtg   9180

tttcgatttt tgatcaattc tttaattttg gaagcctata atacagtttt ctattcttgg   9240

agataaaaat taaatggatc actgatattt tagtcattct gcttctcatc taaatatttc   9300

catattctgt attaggagaa aattaccctc ccagcaccag ccccccctctc aaaccccccaa   9360

cccaaaacca agcattttgg aatgagtctc ctttagtttc agagtgtgga ttgtataacc   9420

catatactct tcgatgtact tgtttggttt ggtattaatt tgactgtgca tgacagcggc   9480

aatcttttct ttggtcaaag ttttctgttt attttgcttg tcatattcga tgtactttaa   9540

ggtgtcttta tgaagtttgc tattctggca ataaactttt agactttt               9588
```

<210> SEQ ID NO 2
<211> LENGTH: 4693
<212> TYPE: DNA
<213> ORGANISM: Homo sapiens

<400> SEQUENCE: 2

```
ggactgcggg ataggaagct ggggatatgg acaagcagca gcgttatagc gctctgggtt     60

tcgggacata ggcctgggcc atgcggcccc cttggcccct tggcgcgacc cccaggaacg    120

ttcggaaagc tggtcctcgt ggctgggggga aaggcggggg gtgggggga agcgggcacg    180

tgaccccggt cagccaatct gggtgctgct gacgtggccg cgcggccccg atgctctccc    240

caccccccca gcccgttccg gaagggaggg gctgggggct acgcccccctc ccccagcacg    300

gcttcgtttt ctgggggggg gttgacaccc cggattacat accccgtacc aagccgaggg    360

caactttgga ggccccctgg aaggctttag gatccagatt cttcgctgct gctgccttac    420

cgccgagaac caccacccgc caggcgtctt gcggccacac ccctggcggg ttcaggcagg    480

ctacgcccac gcgacccctc ccgtttccct gctttggcca atggaggagc tacgaatggc    540

acgacctgct cgagcttggc agtctccagt tgggctgtgc atggaagctt gggaagactt    600

tgttggaagg ggaggcgggg agagagtgct ggaggctctg gggcgatggc ttccgcacct    660

cttccaacca ccctctttcc ctggagtcgg cggaccacag ctcagccaat tggcttggag    720

atgtggcggg ttgccacttc cctgtgggtc tctgcggcac tcttctgcct ggtgactgac    780

accttggaaa tgaagtttat gacgtcatcg ctgcggctgg ccaatagaaa aagctcccgc    840

ggagaggtgt tccttcccct tcgactcagc ttcttcaccc gcgtgagcga gcgcgcgcgc    900

gcggaggggg tggggaaaat ctcaagcagg gtggcgcgca tgagcggcga agctcctcct    960

ccccgcctat atataaaggg ctggcgcggg gctcggcggc gccatttcgt gctggagtgg   1020

agcagcctct agaacgagct ggaggattct gcctaccgat acagagcctt cgagtcgtcc   1080

ggggccgcca ttacaatcca cctccatccg cttggaaatg gccttcgtcc cggcctatga   1140

ctggtcccag cgggcagtac agaccccccta gaagccccctg gagctcccct ttttcgggcc   1200

ccgcccaatc ctcggagtct gtccaccccc tctactccgc cctcaagagg atttcaaaga   1260

tggaggcggc ggctccctaa accacttttc gtgttcatcc gcctccatcc gagatcgaaa   1320

cgggacctcg tcggccccgt aggggcccga caagaagagg gaatccctgc agaccaacag   1380

cgggctatat tgacgacggt gtctgagatc ggggaccgtc ttttgaagag tcagtccctc   1440

cttagttgcc cgcctcagct gaggccgccg ccattttctt gctgtccgcc gtctgcagag   1500

cgcgccaagc tgcccggagc tctccgagag gccccaaaga gactgctttc gtgccggcca   1560

ggcagggggt ttgtcgcctg gaggcccaag aggaacggcc tccccccaac ttagcgggtt   1620

atgctggacc gggcggtgag ggaaaccgag gccacccgga ctttccgcgg ctgagggcag   1680
```

```
cgccggttcc ttgcggtcaa gatgctgcaa aacgtgactc cccacaataa gctccctggg   1740

gaagggaatg cagggttgct ggggctgggc ccagaagcag cagcaccagg gaaaaggatt   1800

cgaaaaccct ctctcttgta tgagggcttt gagagcccca caatggcttc ggtgcctgct   1860

ttgcaactta cccctgccaa cccaccaccc ccggaggtgt ccaatcccaa aaagccagga   1920

cgagttacca accagctgca atacctacac aaggtagtga tgaaggctct gtggaaacat   1980

cagttcgcat ggccattccg gcagcctgtg gatgctgtca aactgggtct accggattat   2040

cacaaaatta taaaacagcc tatggacatg ggtactatta agaggagact tgaaaacaat   2100

tattattggg ctgcttcaga gtgtatgcaa gattttaata ccatgttcac caactgttac   2160

atttacaaca agcccactga tgatattgtc ctaatggcac aaacgctgga aaagatattc   2220

ctacagaagg ttgcatcaat gccacaagaa gaacaagagc tggtagtgac catccctaag   2280

aacagccaca agaagggggc caagttggca gcgctccagg gcagtgttac cagtgcccat   2340

caggtgcctg ccgtctcttc tgtgtcacac acagccctgt atactcctcc acctgagata   2400

cctaccactg tcctcaacat tccccaccca tcagtcattt cctctccact tctcaagtcc   2460

ttgcactctg ctggaccccc gctccttgct gttactgcag ctcctccagc ccagcccctt   2520

gccaagaaaa aaggcgtaaa gcggaaagca gatactacca cccctacacc tacagccatc   2580

ttggctcctg gttctccagc tagccctcct gggagtcttg agcctaaggc agcacggctt   2640

ccccctatgc gtagagagag tggtcgcccc atcaagcccc cacgcaaaga cttgcctgac   2700

tctcagcaac aacaccagag ctctaagaaa ggaaagcttt cagaacagtt aaaacattgc   2760

aatggcattt tgaaggagtt actctctaag aagcatgctg cctatgcttg gcctttctat   2820

aaaccagtgg atgcttctgc acttggcctg catgactacc atgacatcat taagcacccc   2880

atggacctca gcactgtcaa gcggaagatg gagaaccgtg attaccggga tgcacaggag   2940

tttgctgctg atgtacggct tatgttctcc aactgctata agtacaatcc cccagatcac   3000

gatgttgtgg caatggcacg aaagctacag gatgtatttg agttccgtta tgccaagatg   3060

ccagatgaac cactagaacc agggccttta ccagtctcta ctgccatgcc ccctggcttg   3120

gccaaatcgt cttcagagtc ctccagtgag gaaagtagca gtgagagctc ctctgaggaa   3180

gaggaggagg aagatgagga ggacgaggag gaagaagaga gtgaaagctc agactcagag   3240

gaagaaaggg ctcatcgctt agcagaacta caggaacagc ttcgggcagt acatgaacaa   3300

ctggctgctc tgtcccaggg tccaatatcc aagcccaaga ggaaaagaga gaaaaaagag   3360

aaaaagaaga aacggaaggc agagaagcat cgaggccgag ctggggccga tgaagatgac   3420

aaggggccta gggcaccccg cccacctcaa cctaagaagt ccaagaaagc aagtggcagt   3480

gggggtggca gtgctgcttt aggcccttct ggctttggac cttctggagg aagtggcacc   3540

aagctcccca aaaaggccac aaagacagcc ccacctgccc tgcctacagg ttatgattca   3600

gaggaggagg aagagagcag gcccatgagt tacgatgaga agcggcagct gagcctggac   3660

atcaacaaat tacctgggga gaagctgggc cgagttgtgc atataatcca agccagggag   3720

ccctctttac gtgattcaaa cccagaagag attgagattg attttgaaac actcaagcca   3780

tccacactta gagagcttga gcgctatgtc ctttcctgcc tacgtaagaa accccggaag   3840

ccctacacca ttaagaagcc tgtgggaaag acaaaggagg aactggcttt ggagaaaaag   3900

cgggaattag aaaagcggtt acaagatgtc agcggacagc tcaattctac taaaaagccc   3960

cccaagaaag cgaatgagaa aacagagtca tcctctgcac agcaagtagc agtgtcacgc   4020
```

```
cttagcgctt ccagctccag ctcagattcc agctcctcct cttcctcgtc gtcgtcttca   4080

gacaccagtg attcagactc aggctaaggg gtcaggccag atggggcagg aaggctccgc   4140

aggaccggac ccctagacca ccctgcccca cctgcccctt ccccctttgc tgtgacactt   4200

cttcatctca ccccccccccg cccccctcta ggagagctgg ctctgcagtg ggggagggat   4260

gcagggacat ttactgaagg agggacatgg acaaaacaac attgaattcc cagccccatt   4320

ggggagtgat ctcttggaca cagagccccc attcaaaatg gggcagggca agggtgggag   4380

tgtgcaaagc cctgatctgg agttacctga ggccatagct gccctattca cttctaaggg   4440

ccctgttttg agattgtttg ttctaattta ttttaagcta ggtaaggctg gggggagggt   4500

ggggccgtgg tcccctcagc ctccatgggg agggaagaag gggagctct tttttacgt   4560

tgattttttt ttttctactc tgttttccct ttttccttcc gctccatttg ggccctggg   4620

ggtttcagtc atctccccat ttggtcccct ggactgtctt tgttgattct aacttgtaaa   4680

taaagaaaat att                                                      4693
```

<210> SEQ ID NO 3
<211> LENGTH: 3064
<212> TYPE: DNA
<213> ORGANISM: Homo sapiens

<400> SEQUENCE: 3

```
agacgggttc agttcgtcat ggggctgttt ggaaagaccc aggagaagcc gcccaaagaa     60

ctggtcaatg agtggtcatt gaagataaga aaggaaatga gagttgttga caggcaaata    120

agggatatcc aaagagaaga agaaaaagtg aaacgatctg tgaaagatgc tgccaagaag    180

ggccagaagg atgtctgcat agttctggcc aaggagatga tcaggtcaag gaaggctgtg    240

agcaagctgt atgcatccaa agcacacatg aactcagtgc tcatggggat gaagaaccag    300

ctcgcggtct tgcgagtggc tggttccctg cagaagagca cagaagtgat gaaggccatg    360

caaagtcttg tgaagattcc agagattcag gccaccatga gggagttgtc caaagaaatg    420

atgaaggctg ggatcataga ggagatgtta gaggacactt ttgaaagcat ggacgatcag    480

gaagaaatgg aggaagaagc agaaatggaa attgacagaa ttctctttga aattacagca    540

ggggccttgg gcaaagcacc cagtaaagtg actgatgccc ttccagagcc agaacctcca    600

ggagcgatgg ctgcctcaga ggatgaggag gaggaggaag aggctctgga ggccatgcag    660

tcccggctgg ccacactccg cagctagggg ctgcctaccc cgctgggtgt gcacacactc    720

ctctcaagag ctgccatttt atgtgtctct tgcactacac ctctgttgtg aggactacca    780

ttttggagaa ggttctgttt gtctcttttc attctctgcc caggttttgg gatcgcaaag    840

ggattgttct tataaaagtg gcataaataa atgcatcatt tttaggagta tagacagata    900

tatcttattg tggggagggg aaagaaatcc atctgctcat gaagcacttc tgaaaatata    960

ggtgattgcc tgaatgtcga agatctactt ttgtctataa aacactatat aaatgaattt   1020

taataaattt ttgctttagc acttggcccc attgtagatt gccctgtgca gtaaactttc   1080

aaggtgtcgg ctgccccaga ttgcttcatt tgctgggtgt ggaaagagtt gctatggcca   1140

ggcatatggg atttggaagc tcagcagaag tgacttctgc tctgtggttg ctgctccccg   1200

gctttcacag acatggtatg gcagccattc ttttatctat ttaaccaaga ggatgctggg   1260

gaattgtgct gcttgtcctg ttggctggtg gctgcattat gtcctggggt gtgcatgtgg   1320

gtctatttag agcttctgtc ccttccttcc cattgcaagt tgcacccaga tgagacagct   1380

gtagtactag gtctctttca cctctcattg cctgtccctg cttcgagctg gttgtcttgt   1440
```

-continued

```
gcgtgggaca tgggccttcc tatctgtgtt ttctcaaagt caggagctga ccaggagcac   1500

actaaggtgt ggtcatgcat cataaccaac attcactcat ctgggacatt cttaagatac   1560

atttataaat catttcagca gtagtacttt gtatgtgttg agagtttaca gagctctttg   1620

acatacgcga tcttagtctt tacaaataag gaaaacagct cagtttggga agtatcagag   1680

atgggattca aacccagatc ctctggtcca agttgtatgt gcactgaact aatcaggcag   1740

gaaaaaagcc cagccactgt ctcacagatt gttttttgta tattgtagca aaatcctgaa   1800

acaatggggt ccttccagtc tcatcataca aaatggcaat cttggctggg tgcggtggtt   1860

catgcctata atcccagtgc tttacaaggc tgaggcagga ggctctcttg agaataggag   1920

ttcaagacca gcctgggcaa catagcaaga tcctgtctct ccaaaaaaaa aaaaaaaaaa   1980

aaaaaaaaat ttcatttttg agtccagagg ccctcctatt actcttgatt tcatcttcag   2040

agtgtagtta aaaaattatt ttaaataatt attttttttaa atcagttgta ggttcacagc   2100

aaaagtggac aaaaagaaat ttctcatata tcccctgccc tcacacatgc atagcctccc   2160

accactatca gtatcccaca ccagagtggt acatttgtta caatcaataa acctccattg   2220

acacatcatt atcacccaaa gtccatagtt tacatgaaga ttcactctgg tgttgtacat   2280

tgtatgggct tagacaaatg tatgatgata tctacaatta tagaatcata cagaataggt   2340

tcactggcct aaaacctccc caaggcttaa cctggttcat ccctttcttc cctaatcccc   2400

tgggcaacca ctttaaaaaa aaaattaggt tcagggggta catgtgcagg taaactcgtg   2460

acaagggggt ttgttataca gattatttag tgacccaggt actaagccta gtacccaata   2520

gttacttttc tggtcctgtc ccttttccca ccctccaccc tcaggtaggc cccagtatgt   2580

tattcctttg tgtccatgtt atttcactcc cacttgtgag aacatggaat atttggtttc   2640

ctgttcctat gttagtttgt taaggataat ggcctccagc cccatccatg ttcctgcaaa   2700

ggacatgatc tttctttggc aaccactttt tactgtcgcc atagttcttc cttttctaga   2760

atgtcatatt ggaatcatat agtatgtagc cttttcagac tggcttcttt cacttaataa   2820

tatgcaatta aggttcctcc atgtcatttc atggcttaat agtgcattta tttttagcac   2880

tgaataatac tccattgtct agatgaatag tttatccatt cacctattga aagacttctt   2940

ggtggtttcc aagttttggc aattatgaat aaagctgttg taaacatctt tgtgcaggtt   3000

tttctatggg catgttttta attcatttga ataaatacca agagcttcag tgctggatca   3060

taaa                                                                3064
```

```
<210> SEQ ID NO 4
<211> LENGTH: 5404
<212> TYPE: DNA
<213> ORGANISM: Homo sapiens

<400> SEQUENCE: 4
```

```
gcggccgctc tttgccaggg agggtggcat ctatgctgtg ctggtctgca tgcaagaata     60

taagacttct gtcttggtgc agcaggctgg gctggcggca ctgaagatgc tggccgtcgc    120

cagctcctcg gagatcccca cttttgttac tggccgagat tctatccact ctttgtttga    180

tgctcagatg accagagaga tcttcgccag catcgactca gccacacgcc cgggctctga    240

gagcctgctc ctcactgtcc ctgcagccgt gatcctgatg ctgaatactg aggggtgctc    300

ttctgcagcg agaaatggct tactcctgct caacctactt ttgtgcaacc accacactct    360

gggagaccag attataaccc aagagctgag agacacgttg tttaggcact cagggatagc    420
```

-continued

```
accaagaaca gaacctatgc ctaccacacg caccatcctc atgatgcttc tcaatcgcta    480
ctcagagccg ccgggcagcc ctgagcgtgc agcactagag acccccatca tccagggtca    540
ggatgggtcc cctgagctac tgattcgatc cctggttggg ggcccatctg cagaactact    600
cctggacttg gagcgtgtgc tgtgccgtga gggcagcccc ggaggtgccg tgaggcccct    660
cctcaagcgc ctccagcagg agacccagcc tttcctcctg ttgctgcgga ctctggatgc    720
tccggggccc aacaagactc tgctgctgtc tgtgctgagg gtcataaccc gactgctgga    780
tttccctgag gcaatggtcc tcccctggca cgaggtcttg gagccctgcc tcaactgcct    840
gagtggccct agcagtgact ccgagattgt tcaggagctg acctgcttcc tacatcgcct    900
ggcctcgatg cataaggact atgctgtggt gctctgctgc ctgggagcaa aagagatcct    960
ctccaaagtc ctggacaagc actcagctca gctgctgctg ggctgtgagc ttcgggacct   1020
ggtgacagag tgtgagaagt acgcacagct ctatagcaac ctcacctcca gcatcctggc   1080
cggctgcatt cagatggtgc tgggccagat cgaagaccac agacgaaccc accaacccat   1140
caatatcccc ttctttgatg tgttcctcag gcatctctgc cagggctcca gtgtggaagt   1200
gaaggaggac aagtgctggg agaaggtgga ggtgtcctcc aacccgcacc gagccagcaa   1260
gctgacggac cacaacccca agacctactg ggagtccaac ggcagcaccg gctcccacta   1320
catcaccctg cacatgcacc gtggtgttct tgttaggcag ctcactttgc tggtggccag   1380
tgaggactca agctacatgc cagccagggt ggtggtgttt gggggtgaca gcaccagctg   1440
catcggcact gagctcaaca cggtgaatgt gatgccctct gccagccggg tgatcctctt   1500
ggagaacctg aaccgcttct ggcccatcat ccagatccgc ataaagcgct gccagcaggg   1560
cggcattgac acccgggttc ggggtgtgga ggtcctgggc cctaagccca cattctggcc   1620
actgttccgg gagcagctgt gtcgccgaac atgtctcttc tacacaattc gggcacaagc   1680
ctggagccgg gacatagcag aggaccaccg gcgcctcctc cagctctgtc ccagactgaa   1740
cagggttttg cgccacgagc agaattttgc tgaccgcttc ctccctgatg atgaggccgc   1800
ccaggcactg ggcaagacct gctgggaggc cctggtcagc cccctggtgc agaacatcac   1860
ctctcccgat gcggaaggcg tgagtgccct gggatggctg ctggatcagt acttagaaca   1920
gagagagacc tctcggaacc ccttgagtcg agcagcgtcc tttgcttctc gagttcgtcg   1980
cctttgccac ttgctggtgc atgtggaacc tcctcctggg ccttctcctg agccatccac   2040
tcggcccttc agcaagaaca gcaagggtcg ggaccggagc ccggcgcctt cgccagtgct   2100
tccaagcagc agcctgagga acataaccca gtgctggctg agcgtggtgc aggagcaggt   2160
cagcagattc ctggctgcag cttggagggc cccagacttt gtgcctcgtt actgtaaact   2220
ctatgagcac ttgcagagag caggctccga gctgtttggg cctcgggcag ccttcatgct   2280
ggctctgcgc agtggcttct ctggcgcctt gctgcagcag tccttcctca ctgctgctca   2340
catgagtgag cagtttgcca ggtacattga ccaacagatc cagggtggcc tgattggtgg   2400
agcccctgga gtggaaatgc tggggcagct tcagcggcac ctggaaccca ttatggtcct   2460
ttctggtctg gaactggcca caacttttga gcacttctat cagcattata tggcggaccg   2520
tctcctgagc tttggttcga gctggctgga gggggctgtg ctagagcaga ttggcctctg   2580
ttttcccaac cgcctcccac agctgatgct gcagagcctg agcacctctg aggagctgca   2640
gcgccagttc cacctcttcc agctccagcg gctcgacaag ttgttcttgg agcaggaaga   2700
tgaggaggaa aagagactag aggaagagga ggaggaagag gaggaagagg aagctgagaa   2760
agaattattt atcgaagatc caagtccagc catttctata ctggtcctgt caccacgctg   2820
```

-continued

```
ctggcccgtc tccccactct gctacctgta ccatcccaga aagtgccttc ccacagaatt   2880
ctgtgatgcc cttgaccgtt tctccagttt ctacagccag agtcagaacc atccagtcct   2940
ggacatggga ccacatcggc gactgcagtg gacgtggctg ggccgggctg agctgcagtt   3000
tgggaagcag atactgcatg tgtccaccgt gcagatgtgg ctgctgctga aattcaatca   3060
gacagaggag gtgtcagtag agaccttgct gaaggattct gacctctccc cagagctgct   3120
gctccaggca ctcgtgcccc tcacctcagg gaatggccct ttgaccctgc atgagggcca   3180
ggactttcca cacgggggtg tgctgcggct tcatgagcct gggccccagc gcagtgggga   3240
ggccctgtgg ctgatacctc cccaggcata cctgaacgta gagaaggatg aaggccgaac   3300
cctggaacag aagaggaatc tcttgagctg tcttcttgtt cgtattctca aagcccatgg   3360
ggaaaagggc ctccacattg atcagctggt ttgtctggtg ctggaggcct ggcagaaggg   3420
tccaaatcct cctggaaccc tgggccacac tgttgctggg ggtgtggcct gtaccagtac   3480
agatgtcctc tcttgcatcc tgcacctctt aggccagggc tacgtgaaac ggcgtgatga   3540
ccggccccag atcctgatgt atgccgctcc agagcccatg ggccctgcc ggggtcaggc    3600
agatgtccct ttctgtggca gccagagcga aacctccaag cccagcccag aagctgtggc   3660
taccctggca tctctacagc tgcctgcagg ccgcaccatg agcccccagg aagtagaagg   3720
gttgatgaag cagacggtgc gtcaggtgca ggagacgctg aacttagagc cagatgtcgc   3780
tcagcacctt ttggctcatt cccactgggg cgctgaacag ctgctgcaga gctacagtga   3840
ggaccctgag ccactgctgc tggcagctgg gctgtgcgta caccaggctc aggctgtacc   3900
cgtacggcct gaccactgcc ccgtctgtgt gagcccccctg ggtgtgacg acgacctgcc   3960
ctctctctgc tgcatgcact attgctgtaa gtcttgctgg aatgagtacc tgacaactcg   4020
gatcgagcag aaccttgttt tgaattgcac ctgccccatt gccgactgcc ccgcccagcc   4080
caccggagcc ttcattcgtg ccatcgtctc ctcgccagag gtcatctcca agtatgagaa   4140
ggcgctcctg cgtggctatg tggagagctg ctccaacctg acctggtgca ccaaccccca   4200
gggctgcgac cgcatcctgt gccgccaggg cctgggctgt gggaccacct gctccaagtg   4260
tggctgggcc tcttgcttca actgtagctt ccctgaggca cactaccctg ctagctgtgg   4320
ccatatgtct cagtgggtcg atgacggtgg ctactatgac ggcatgagcg tggaggcgca   4380
gagcaagcac ctggccaagc tcatctccaa gcgctgtccc agctgtcagg ctcccatcga   4440
gaagaacgag gggtgcctgc acatgacctg tgccaaatgt aaccatggat tctgctggcg   4500
ctgcctcaag tcctggaagc caaatcacaa agactattac aactgctctg ccatggtaag   4560
caaggcagct cgccaggaga agcggtttca ggactataat gagaggtgca ctttccatca   4620
ccaggcgcgg gagtttgctg tgaacttgcg gaaccgggtg tctgccatcc atgaagtgcc   4680
cccgcccaga tccttcacct tcctcaatga tgcctgccag ggactggagc aggctcggaa   4740
ggtgctggcc tacgcctgcg tgtacagctt ctacagccag gacgcagagt acatggatgt   4800
ggtggagcag cagacagaga acctggagct gcacaccaat gccctgcaga tcctcctgga   4860
ggaaaccctg ctgcggtgca gagacctggc ctcctccctg cgcctcctgc gggccgactg   4920
cctcagcacg ggcatggagc tgctccggcg gatccaggag aggctgcttg ccatcctgca   4980
gcattctgcc caggatttcc gggttggtct tcagagtcca tcagtagagg cctgggaggc   5040
aaaaggaccc aacatgcctg gcagtcagcc ccaggcctcc tcagggccag aggcagaaga   5100
ggaggaggaa gacgatgagg atgatgtgcc cgagtggcag caggatgagt ttgatgagga   5160
```

-continued

```
gctggacaat gacagcttct cctacgatga gtctgagaac ctggaccaag agactttctt   5220

ctttggtgat gaggaagagg atgaagatga ggcctatgac tgaggggggca gatgcaggaa   5280

acacctagag cagccccaga gtcacggggc tgaggggggcg ggagctgccc ctgtcatagg   5340

gagggggatt cccagcgtct gtagtgcttc ctgtttgctg aataaaggtc tctttctcac   5400

acac                                                                 5404
```

<210> SEQ ID NO 5
<211> LENGTH: 2107
<212> TYPE: DNA
<213> ORGANISM: Homo sapiens

<400> SEQUENCE: 5

```
cggtccggac agccgcgcgc tgagggtctc ggggcgggcg ccgcgggacc tctccgggcc     60

atggcagccc ctgtcaaagg gaacaggaag cagtccacgg agggtgacgc cctagaccca    120

cctgcatccc ccaaacctgc tggcaagcag aacggaatcc agaaccccat ctcgctggag    180

gactcccccg aggcaggcgg ggagcgggag gaggagcagg agcgggagga ggagcaggcc    240

ttcctggtca gcctctacaa gttcatgaag gagcgacaca cgcccatcga gagggtgccc    300

catctcggct tcaagcagat taacctgtgg aagatctaca aagcagtgga gaagctgggg    360

gcctatgagc tggtgaccgg gcgccgcctc tggaagaacg tgtacgacga gctgggggggc    420

agcccaggca gcaccagcgc ggccacgtgc acgcgccgcc actacgagag gctggtcctg    480

ccatacgtgc ggcacctgaa gggggaggat gacaagccgc tgcccacctc caagcccagg    540

aaacagtaca agatggctaa ggagaacagg ggggatgatg ggccaccgga gaggccgaag    600

aaggccaagg aggagcggcg catggaccag atgatgccag gaaagaccaa agcagatgct    660

gctgacccag caccacttcc cagccaggag ccccccagga acagcacaga acagcagggc    720

ctggcctctg ggtcttctgt gtcctttgtg ggtgccagcg gctgtcctga ggcctacaag    780

cggctcctat ccagcttcta ctgcaagggg acacacggca tcatgtcacc actggccaaa    840

aagaagctcc tggcccaggt gagcaaggtg gaggccttgc agtgccagga ggagggctgc    900

cgccatgggg cagagcccca ggcgtcccca gctgttcacc tcccagagag tccccagagc    960

cccaaagggc tgactgagaa ctccaggcac cggctgaccc ctcaggaggg attgcaggcc   1020

ccaggtggca gcctcagaga ggaggcgcag gcaggcccct gcccggcagc cccccatcttc   1080

aagggctgct tctacaccca ccccaccgag gtgctgaagc ctgtcagcca gcaccccagg   1140

gacttcttct ctagacttaa agatggggtg ctattggggc ctcctggcaa agaggggctg   1200

tcagtgaaag agccccagct ggtgtggggc ggagacgcta accgcccttc tgcgttccat   1260

aaaggtggct ccagaaaggg catcctctac cccaagccca aagcctgctg ggtgtccccc   1320

atggccaagg tcccagccga gagccccacg ctcccgccca ccttccccag tagcccaggc   1380

ctgggcagca agcgcagcct ggaggaagag ggtgctgccc acagtgggaa gagactgcgg   1440

gccgtgtctc cctttcttaa ggaggcggat gccaagaagt gtggggccaa acctgcaggg   1500

tccggcctgg tctcctgcct tctgggccca gccctggggc ctgtgccccc agaggcctac   1560

aggggcacca tgctgcactg cccgctgaac ttcactggca ccccgggccc cttgaagggc   1620

caggctgcac tccccttcag ccccctggtc atcccggcct tcccggccca cttcctggcc   1680

accgcaggcc cctcgcccat ggccgctggc ctgatgcact tccccccaac gtccttcgac   1740

agtgccctcc gccacagact ttgcccggcc tcatctgcct ggcacgcacc accagtcaca   1800

acctatgcag cgccccactt cttccacctc aacaccaagc tgtaggccag cccatggtgt   1860
```

-continued

```
tgtgtacact gtggagtcga caggggccta caacaggcag gtactgctgc caggggggctc   1920

tgaactagtg cctgctaccc aggacacccg ggccatgccc ctggctgggc agcctggcac   1980

aagtgaagaa gaaggcagtg ggaaaactgg gtttatctca aggcagcagc ctgagcccag   2040

gagcagagga cccagttgtt ataaggcgct gggagaggat gggcagctcc cactgcccca   2100

gagcgga                                                             2107
```

<210> SEQ ID NO 6
<211> LENGTH: 2587
<212> TYPE: DNA
<213> ORGANISM: Homo sapiens

<400> SEQUENCE: 6

```
ggcacacacg aggaggaggg ttgagctgct gccgccgccg cctctgtcgt cgtcgcgagt     60

gtggagtcgg gactggagct gctgccgcgg cgacgccggg gatctttgtc gctagctccc    120

ggcccttctg ccccgccgcc ttccctcagt cagcgttgcc cactcctctc cggccgggcg    180

cccctgcctc catttctcgc tctctgtcca ccacacacac ggcccccccg atcatggatc    240

cgggcagtgg cggcggcggc ggcggcggcg gcggcggcgg gagcagcagc ggcagcagca    300

gcagcgactc ggcgcctgac tgctgggacc aggcggacat ggaagccccc gggccgggcc    360

cttgcggcgg cggcggcttc cctggcggcg gcggccgagg cccagcggga gaacctcagc    420

gcggccttca gccggcaact caacgtcaac gccaagccct tcgtgcccaa cgtccacgcc    480

gccgagttcg tgccgtcctt cctgcggggc ccggcagcgc cgccaccccc agctggcggc    540

gccgccaata accacggagc cggcagcggc gcgggaggcc gtgcggcacc tgtggaatcc    600

tctcaagagg aacagtcatt gtgtgaaggt tcaaattcag ctgttagcat ggaactttca    660

gaacctattg tagaaaatgg agagacagaa atgtctccag aagaatcatg ggagcacaaa    720

gaagaaataa gtgaagcaga gccagggggt ggttccttgg gagatggaag gccgccagag    780

gaaagtgccc atgaaatgat ggaggaggaa gaggaaatcc caaaacctaa gtctgtggtt    840

gcaccgccag gtgctcctaa gaaagagcat gtaaatgtag tattcattgg gcacgtagat    900

gctggcaagt caaccattgg aggacaaata atgtatttga ctggaatggt tgacaaaagg    960

acgcttgaaa agtatgaaag agaagctaaa gagaaaaaca gagaaacttg gtacttgtct   1020

tgggccttag acacaaatca ggaagaacga gacaagggta aaacagtaga agtgggtcgt   1080

gcctattttg aaaccgaaaa gaagcatttc acaattctag atgcccctgg ccacaagagt   1140

tttgtcccaa atatgattgg tggtgcctct caagctgatt tggctgtgct ggtaatctca   1200

gccaggaaag gagagtttga aactggattt gaaaaaggag gacagacaag agaacatgca   1260

atgttggcaa agacagcagg tgtaaaacac ctaattgtgc taattaataa gatggatgat   1320

ccaacagtaa attggagcaa tgagagatat gaagaatgta aggagaaact agtgccattt   1380

ttgaaaaaag ttggcttcaa tcccaaaaag gacattcact ttatgccctg ctcaggactt   1440

actggagcaa atctcaaaga gcagtcggat ttctgtcctt ggtacattgg attaccgttt   1500

attccatatc tggataattt gccgaacttc aatagatcag ttgatggacc aatcaggctg   1560

ccaattgtgg ataagtacaa ggatatgggc actgtggtcc tgggaaagct ggaatcagga   1620

tctatttgta aaggccagca gcttgtgatg atgccaaaca agcacaacgt ggaagttctt   1680

ggaatacttt ccgatgatgt agagactgat accgtagccc caggtgaaaa cctcaaaatc   1740

agactgaaag gaattgaaga agaggagatt cttccagggt ttatactttg tgatcctaat   1800
```

-continued

```
aatctttgtc attctggacg cacatttgat gcccagatag tgattataga gcacaaatcc   1860

atcatctgcc caggctataa tgcggtgctg catattcata cctgtattga ggaggtggaa   1920

ataacagcct taatctgctt ggtagacaaa aaatcaggag aaaaaagtaa gacccgaccc   1980

cgttttgtga aacaagatca agtatgcatt gctcgcttaa ggacagcagg aaccatctgc   2040

cttgagacct ttaaagactt ccctcagatg ggtcgtttca ccttaagaga tgagggtaag   2100

accattgcaa ttggaaaagt tctgaaactg gttccagaga aagactaagc attttcttga   2160

tgaccctgca caatactgtg aggaaaattg actgcagaag cctacttcac accgccttct   2220

cttattttct gcccattgat aaacctctcc ccatattttg caaagaggaa attcacagca   2280

aaagtccaca ttatgtcagc tttctcatat tgagagctct gctatgccac tgttgaattt   2340

ttcccaagat tcctgtccct agccctcact tcaaactctg cttccttgga cagatttggc   2400

aatagctttg taagtgatgt ggacataatt gcctacaata atgaaaacct acaggaattt   2460

ttttattttt cattttcccc ttaggcatat ttagtatttt tcccccaggc cagatcattc   2520

gtgagtgtgc gagtgtgtgt gcacatgtta caaaggcaac taccatgtta ataaaatatt   2580

caatttg                                                             2587
```

<210> SEQ ID NO 7
<211> LENGTH: 3290
<212> TYPE: DNA
<213> ORGANISM: Homo sapiens

<400> SEQUENCE: 7

```
cggaggaggc ccagagaccg gagcgcggag acctcagcca gcggcctacg cccaggcctt     60

tctccaccgg aggaccaggg aaccgcagtc ttcatcacag aggtaccgtg ctccgcgctc    120

cccgcctgac ccggcccagc ccgctgcggc ggtgcctcct tccttcctcc ttccctcgcg    180

ctctctcttt cgcccgcccg cgccttccct gcccgcctgc gtcaccgcgg ccgccatggc    240

tgagaatggc gagagcagcg gcccccccgcg cccctcccgc ggccctgctg cggcccaagg    300

ctcggctgct gccccggctg agcctaaaat catcaaagtc acggtgaaga ctcccaaaga    360

gaaagaggag ttcgcggtgc ccgagaacag ctcggttcag cagtttaagg aagcgatttc    420

gaaacgcttc aaatcccaaa ccgatcagct agtgctgatt tttgccggaa aaatcttaaa    480

agatcaagat accttgatcc agcatggcat ccatgatggg ctgactgttc accttgtcat    540

caaaagccag aaccgacctc agggccagtc cacgcagcct agcaatgccg cgggaactaa    600

cactacctcg gcgtcgactc ccaggagtaa ctccacacct atttccacaa atagcaaccc    660

gtttgggttg gggagcctgg gaggacttgc aggccttagc agcctgggct tgagctcgac    720

caacttctct gagctccaga gccagatgca gcagcagctt atggccagcc ctgagatgat    780

gatccaaata atggaaaatc cctttgttca gagcatgctt tcgaatcccg atctgatgag    840

gcagctgatt atggctaatc cacagatgca gcaattgatt cagagaaacc cagaaatcag    900

tcacctgctc aacaacccag acataatgag gcagacactc gaaattgcca ggaatccagc    960

catgatgcaa gagatgatga gaaatcaaga cctggctctt agcaatctag aaagcatccc   1020

aggtggctat aatgctttac ggcgcatgta cactgacatt caagagccga tgctgaatgc   1080

cgcacaagag cagtttgggg gtaatccatt tgcctccgtg gggagtagtt cctcctctgg   1140

ggaaggtacg cagccttccc gcacagaaaa tcgcgatcca ctacccaatc catgggcacc   1200

accgccagct acccagagtt ctgcaactac cagcacgacc acaagcactg gtagtgggtc   1260

tggcaatagt tccagcaatg ctactgggaa caccgttgct gccgctaatt atgtcgccag   1320
```

```
catctttagt accccaggca tgcagagcct gctgcaacag ataactgaaa acccccagct   1380

gattcagaat atgctgtcgg cgccctacat gagaagcatg atgcagtcgc tgagccagaa   1440

tccagatttg gctgcacaga tgatgctgaa tagcccgctg tttactgcaa atcctcagct   1500

gcaggagcag atgcggccac agctcccagc cttcctgcag cagatgcaga atccagacac   1560

actatcagcc atgtcaaacc caagagcaat gcaggcttta atgcagatcc agcaggggct   1620

acagacatta gccactgaag cacctggcct gattccgagc ttcactccag gtgtgggggt   1680

gggggtgctg ggaaccgcta taggccctgt aggcccagtc acccccatag gccccatagg   1740

ccctatagtc ccttttaccc ccataggccc cattgggccc ataggaccca ctggccctgc   1800

agcccccct ggctccaccg gctctggtgg ccccacgggg cctactgtgt ccagcgctgc    1860

acctagagaa accacgagtc ctacatcaga atctggaccc aaccagcagt tcattcagca   1920

aatggtgcag gccctggctg gagcaaatgc tccacagctg ccgaatccag aagtcagatt   1980

tcagcaacaa ctggaacagc tcaacgcaat ggggttctta aaccgtgaag caaacttgca   2040

ggccctaata gcaacaggag gcgacatcaa tgcagccatt gaaaggctgc tgggctccca   2100

gccatcgtaa tcacatttct gtacctggaa aaaaaatgta tcttattttt gataatggct   2160

cttaaatctt taaacacaca cacaaaatcg ttctttactt tcattttgat tcttttaaat   2220

ctgtctagtt gtaagtctaa tatgatgcat tttaagatgg agtccctccc tcctacttcc   2280

ctcactccct ttctcctttg cttatttttc ctaccttccc ttcctcttgt ctccccactc   2340

cctccctctt tgtttccttc cttccttatt tcctttagtt tccttcctta gccgttttta   2400

gtggtgggaa tcaaatgctg tttcactcaa aagtgttgca tgcaaacact tctctttatt   2460

ctgcatttat tgtgattttt ggaaacaggt atcaaccttc acaggttggg tgcaacaagt   2520

gttgtcctac agatgtccaa tttatttgca tttttaaaca ttagcctatg atagtaattt   2580

aatgtagaat gaagatatta aaaccagaag caaattattt gaagccctct aatttgtggt   2640

acgatattgc cttattgtga ctttggcakg tatttttgct agcaaaatgc tgtaagattt   2700

ataccattga tctttttgc tatatttgta tacagtacag taagcacaat tggccctgta    2760

catctaaaaa tattacagta gaatctgagt gtaatatgtg taaccaaaat gagaaagaat   2820

acaagaaatg tttctggagc tagttatgtc tcacaatttt gtagaatctt acagcatctt   2880

tgataaactt ctcagtgaaa atgttggcta ggcaagttca gttaaaacat agtacaaatg   2940

tttatcctgg catctctaag tacacattta attgcacaga aaatttacag tgtaacattg   3000

cgtcaacatt tgcagattga ctgcatatga ccttaatctt tgtgcagcct gaaggatcag   3060

tgtagtaatg ccaggaaagt gctttttacc taagacttcc ttctcagctt ctcccataaa   3120

cagaccctaa tatgcatttt gatttgtaat tggaaatgta actttccctg aaagtgtcat   3180

gtgatgtttg cattactttt aactgctatg tataaaggaa agtgtgtctt ttgacttcat   3240

cagttatttc tcttgcgccc acagaaaaat gcattaaaaa tgactaaaaa              3290
```

```
<210> SEQ ID NO 8
<211> LENGTH: 2410
<212> TYPE: DNA
<213> ORGANISM: Homo sapiens

<400> SEQUENCE: 8

gccccaccga cctgctttcc agctctcttg gtaccagtgg tgtggattgc aaccgcaaac     60

ggaaaggcag ctccactgac taccattcac aggtcgaatt tggggagcac aatggctgga    120
```

-continued

```
ggtcagatgc ccactaggag atgctatgat taatatagaa agcatggaca cagacaaaga    180

tgaccctcat ggaaggttag aatatacaga acaccaagga aggataaaaa atgcaaggga    240

agctcacagt cagattgaaa agcggcgtcg ggataaaatg aacagtttta tagatgaatt    300

ggcttctttg gtaccaacat gcaacgcaat gtccaggaaa ttagataaac ttactgtgct    360

aaggatggct gttcagcaca tgaaaacatt aagaggtgcc accaatccat acacagaagc    420

aaactacaaa ccaacttttc tatcagacga tgaattgaaa cacctcattc tcagggcagc    480

agatggattt ttgtttgtcg taggatgtga ccgagggaag atactctttg tctcagagtc    540

tgtcttcaag atcctcaact acagccagaa tgatctgatt ggtcagagtt tgtttgacta    600

cctgcatcct aaagatattg ccaaagtcaa ggagcagctc tcctcctctg acaccgcacc    660

ccgggagcgg ctcatagatg caaaaactgg acttccagtt aaaacagata taacccctgg    720

gccatctcga ttatgttctg gagcacgacg ttctttcttc tgtaggatga agtgtaacag    780

gccttcagta aaggttgaag acaaggactt cccctctacc tgctcaaaga aaaaagcaga    840

tcgaaaaagc ttctgcacaa tccacagcac aggctatttg aaaagctggc cacccacaaa    900

gatggggctg gatgaagaca acgaaccaga caatgagggg tgtaacctca gctgcctcgt    960

cgcaattgga cgactgcatt ctcatgtagt tccacaacca gtgaacgggg aaatcagggt   1020

gaaatctatg gaatatgttt ctcggcacgc gatagatggc aagtttgttt ttgtagacca   1080

gagggcaaca gctattttgg catatttacc acaagaactt ctaggcacat cgtgttatga   1140

atattttcac caagatgaca taggacatct tgcagaatgt cataggcaag ttttacagac   1200

gagagaaaaa attacaacta attgctataa atttaaaatc aaagatggtt cttttatcac   1260

actacggagt cgatggttca gtttcatgaa cccttggacc aaggaagtag aatatattgt   1320

ctcaactaac actgttgttt tagccaacgt cctggaaggc ggggacccaa ccttcccaca   1380

gctcacagca tccccccaca gcatggacag catgctgccc tctggagaag gtggcccaaa   1440

gaggacccac cccactgttc cagggattcc agggggaacc cgggctgggg caggaaaaat   1500

aggccgaatg attgctgagg aaatcatgga aatccacagg ataagagggt catcgccttc   1560

tagctgtggc tccagcccat tgaacatcac gagtacgcct ccccctgatg cctcttctcc   1620

aggaggcaag aagattttaa atggagggac tccagacatt ccttccagtg gcctactatc   1680

aggccaggct caggagaacc caggttatcc atattctgat agttcttcta ttcttggtga   1740

gaacccccac ataggtatag acatgattga caacgaccaa ggatcaagta gtcccagtaa   1800

tgatgaggca gcaatggctg tcatcatgag cctcttggaa gcagatgctg gactgggtgg   1860

ccctgttgac tttagtgact tgccatggcc gctgtaaaca ctacatgttg ctttggcaac   1920

agctatagta tcaaagtgca ttactggtgg agttttacag tctgtgaagc ttactggata   1980

aggagagaat agcttttatg tactgacttc ataaaagcca tctcagagcc attgatacaa   2040

gtcaatctta ctatatgtaa cttcagacaa agtggaacta agcctgctcc agtgtttcct   2100

catcattgat tattgggcca gctgtggata gcttgcatta attgtatatt ttggattctg   2160

tttgtgttga attttttaat cattgtgcac agaagcatca ttggtagctt ttatatgcaa   2220

atggtcattt cagatgtatg gtgtttttac actacaaaga agtcccccat gtggatattt   2280

cttatactaa ttgtatcata aagccgttta ttcttccttg taagaatcct ttactataaa   2340

tatgggttaa agtataatgt actagacagt taaatatttt taataaatgt ttcccttgtt   2400

ctattaaaaa                                                          2410
```

-continued

<210> SEQ ID NO 9
<211> LENGTH: 15150
<212> TYPE: DNA
<213> ORGANISM: Homo sapiens

<400> SEQUENCE: 9
gaattccgcc tctgcggagc cgggctcggg tcgccggagc cgcgccccac cccgccagct 60
ccagagccac gactaatggc tgaaggataa atcaacatgg caactatgat tccaccagtg 120
aagctgaaat ggcttgaaca cttgaacagc tcctggatta cagaggacag tgaatctatt 180
gctacaagag agggagttgc tgttctgtat tctaaactgg ttagcaataa ggaagtagta 240
cctttgcccc aacaagtttt atgcctcaaa ggaccacagt tgccagactt tgaacgtgag 300
tctctttcaa gtgatgagca ggaccactat ttggatgccc ttcttagcag ccagctagca 360
ttggcaaaga tggtatgttc agattcccca tttgccgggg cacttagaaa acgactgctt 420
gtactccagc gtgtctttta tgcactttct aataaatacc atgacaaagg caaggtgaag 480
cagcagcagc attctccgga gagcagttct ggttcagcag atgtccattc tgttagtgaa 540
cgcccccggt caagcactga tgcacttata gaaatgggtg ttcgaactgg tctaagttta 600
ttatttgcgc ttctaagaca aagttggatg atgcctgtgt caggacctgg tctcagtctt 660
tgcaacgatg tcattcatac tgcaattgaa gttgtgagct ctttgccacc attatcatta 720
gcaaatgaaa gcaagattcc tcctatgggc ttggactgct tatcgcaagt aacaacattt 780
cttaaaggag tcactattcc taattctggg gcagacactt taggtcgtag attagcttct 840
gagttgctgc ttggtttggc agctcaacga ggctcattgc gatatcttct tgaatggata 900
gaaatggctt tgggggcttc ggcagttgta cacaccatgg agaaaggcaa actactctca 960
agccaggaag gaatgatcag ctttgactgc tttatgacca tattaatgca gatgaggcgt 1020
tctttgggtt catctgctga tcggagtcag tggagagaac caaccagaac atcggatggc 1080
ttgtgctccc tttacgaggc agcattatgt ctctttgaag aggtttgcag aatggcttct 1140
gattattcga gaacatgtgc tagcccagat agcattcaga ctggtgatgc tcccattgtc 1200
tccgaaacct gtgaggttta tgtttggggg agcaatagca gccatcagtt ggtagaaggt 1260
acacaggaga aaatactgca acccaaactg gctcctagtt tctctgatgc acagaccatt 1320
gaagctggac agtactgcac ttttgtcatt tctacggatg gctcagttag agcttgcggg 1380
aaaggcagct atgggagact gggccttgga gactccaata atcagtcaac tttaaaaaag 1440
ttaacattcg agcctcacag atccattaaa aaggtttcat cttctaaagg atctgatggt 1500
cacactttag cctttacgac agaaggagaa gtcttcagtt ggggagatgg tgattatggg 1560
aaactggggc atggaaatag ttcaacacag aaatatccca agcttattca gggacctcta 1620
caaggaaagg tagttgtttg tgtgtcagct ggatacagac atagtgctgc tgtcacagag 1680
gatggggaat tatacacatg ggtgaagga gactttggaa gattaggtca tggtgacagc 1740
aatagtcgta acattccaac attagtaaaa gacatcagca atgtaggaga ggtttcttgt 1800
ggcagttcac atactattgc tctgtctaaa gatgggagaa ctgtatggtc ttttggagga 1860
ggagacaatg gtaaacttgg tcatggtgat accaacagag tgtataaacc taaagttatt 1920
gaagctttac aaggaatgtt cattcgcaaa gtttgtgctg ggagccagtc ttcacttgct 1980
ttgacatcaa cagggcaggt ctatgcttgg ggctgtggag cttgtctagg ttgtggttct 2040
tcagaagcta ctgctttgag acccaagctt attgaagaac tggctgccac aagaatagtt 2100
gatgtttcta ttggagacag tcattgtttg gctctttctc atgataatga agtttatgcc 2160

-continued

```
tggggcaata actcaatggg gcaatgtggt cagggaaatt ccacaggtcc tattactaaa   2220
ccaaagaaag tgagtggctt agatggcata gctattcagc agatttcggc tggaacatca   2280
catagtctgg catggactgc tcttcctagg gacagacaag ttgttgcatg gcaccgacct   2340
tattgtgtag atcttgaaga gagtaccttc tcacacctgc gttcttttct tgagagatac   2400
tgtgataaaa taaacagtga gattccccca ctccctttcc cttcatcaag agaacaccac   2460
agttttctca agctgtgcct gaagctactt tcaaatcacc ttgctcttgc acttgcggga   2520
ggggtagcta ccagcattct cgggaggcag gcaggtccac ttcgaaattt gctcttcaga   2580
ctgatggact caactgtccc agatgaaatc caagaggtgg taattgaaac tttatcagtg   2640
ggagcaacca tgctgttacc tccattacga gaacggatgg aattacttca ttctctttta   2700
cctcaaggac ctgatagatg ggaaagctta tctaaaggac agagaatgca actggatatc   2760
atcctgacaa gtttgcaaga tcatacccac gtagcctccc tacttggcta tagttcaccc   2820
tctgatgctg ctgacctatc ttctgtgtgt actggctacg gaaatctgtc agatcaacct   2880
tacggcactc agagctgcca tccagatacc cacctggctg aaattttgat gaagaccctc   2940
ttaagaaatt taggatttta tacagatcaa gcatttggag agctagaaaa gaatagtgat   3000
aaatttctac ttggaacatc atcatcagaa aacagtcagc ctgctcatct tcatgaactg   3060
ctatgttcac tacagaaaca gctgctggca ttttgccata tcaataacat tagtgagaac   3120
tcaagcagtg tggcattgct tcataaacat cttcagcttt tgttgcctca tgccacagat   3180
atttattcac gttctgcaaa tttgctcaaa gaaagtcctt ggaatggcag tgttggagaa   3240
aaattaagag atgtgatata cgtctcagct gctggcagta tgctctgcca gattgttaac   3300
tccctgctgt tactccctgt gtcagtggct cggcctttat tgagttacct cctcgacttg   3360
ttgccacctc ttgattgcct taatagactc ctgccagctg ctgatctttt agaagaccag   3420
gagttacagt ggcctcttca tggagggcca gaactaattg atcctgctgg tctgccatta   3480
cctcagccag ctcagtcctg ggtatggctt gtggatctag aaagaacaat tgctctcctt   3540
attgggcggt gtcttggtgg catgcttcag ggctcccctg tgtctccaga ggaacaggac   3600
actgcatatt ggatgaaaac gccactgttc agtgacggtg tagaaatgga cactcctcaa   3660
ttggataaat gtatgagttg cctgttagaa gtagcacttt ctggaaatga agaacagaag   3720
ccttttgatt ataaattgcg gcctgaaatt gctgtctatg tagacttggc attgggttgt   3780
tctaaagagc ctgcccgaag cctttggatc agcatgcagg actatgctgt tagtaaagat   3840
tgggacagtg caactttaag taatgagtca ctcttggaca ctgtgtctag atttgttctt   3900
gcagctcttc tgaaacacac aaatttactt agtcaagcat gtggagaaag ccgatatcaa   3960
cctggtaaac acttatcaga agtgtaccgt tgtgtataca aagttcgaag tcgtttactt   4020
gcttgcaaga accttgaact tattcaaaca aggtcatcat cacgggacag atggatatca   4080
gaaaaccagg actctgcaga tgttgatcct caggagcatt catttactcg aactattgat   4140
gaagaagctg aaatggaaga acaggctgag agagaccggg aagaggggca tccggagcca   4200
gaggatgaag aggaggaacg ggaacatgaa gtgatgacag ctggcaaaat ctttcagtgt   4260
ttcctctcag cccgtgaagt agctcgtagc cgagaccgag atagaatgaa cagtggggca   4320
gggtctgggg ctcgagctga tgatccacct cctcagtctc agcaagagcg aagggtcagc   4380
acagaccttc ctgagggtca ggatgtgtac actgctgcat gcaactccgt gatccatcgg   4440
tgtgccctgt taatattagg agtaagtcct gtgatagatg agcttcagaa gcgaagagaa   4500
gaaggacagt tgcagcaacc ttcaacaagt gcctctgaag gggtggact tatgaccagg    4560
```

-continued

```
agtgaaagtc ttactgcaga gagccggcta gtccacacaa gcccaaatta tagactgatc   4620
aaatcgagga gtgaatctga tttgtctcag cctgaatcag atgaagaggg ttacgcactg   4680
agtggcagac aaaatgttga tttggatttg gcagcatctc acagaaagag aggtcctatg   4740
cacagtcaat tggaatccct gagtgactct tgggctcgcc tgaaacatag cagagactgg   4800
ttatgcaact cctcctattc ctttgagtca gattttgatc ttaccaagtc tttgggagtt   4860
cacactttga ttgaaaatgt tgtaagcttt gtgagtggag atgtggggaa tgccccaggt   4920
tttaaagagc cagaggaaag tatgtctaca agtccccagg cctccatcat tgcaatggaa   4980
cagcagcagt taagggcaga acttcgttta gaggcacttc atcagatcct cgttctattg   5040
tctgggatgg aagaaaaagg tagcatctca ctggcaggaa gcagattgag ttcaggcttc   5100
cagtcctcca cactactcac gtctgtgagg ctgcagttcc tagcagggtg ttttggttta   5160
ggcactgttg gacacacagg agccaaggga gagagtggcc gattgcatca ctatcaggat   5220
gggatcagag cagctaagag aaatattcag attgaaatcc aggtagctgt gcataaaatt   5280
tatcaacagt tgtctgctac cctggaaaga gccctgcaag caaacaagca tcacattgaa   5340
gcccagcaac gtctgcttct ggttacagtt tttgccctaa gtgttcatta tcaaccagta   5400
gatgtttctt tggcaatttc cactggtctg ctaaacgtat tgtcacagtt gtgtggtaca   5460
gacaccatgc taggacagcc cctgcagttg ttgccaaaga cgggtgtttc ccagcttagc   5520
acagctttga aagtggccag tacaaggttg ctccagattc tagccatcac tactgggacc   5580
tatgctgata aactgagtcc caaagtagtt caatccttgt tggatctact ctgtagtcag   5640
ttgaagaatt tattgtccca aactggtgta ctacatatgg cctctttcgg agaaggggag   5700
caagaagacg gtgaagaaga agaaaaaaaa gttgactcca gtggagaaac tgagaagaaa   5760
gatttcagag ctgctcttag gaaacaacat gcagccgaac tccatctagg ggattttttta  5820
gtttttcttc gcagagttgt atcttcaaaa gcaattcaat caaaaaatggc ttccccaaag  5880
tggaccgaag tgcttctaaa tatagcatct cagaaatgtt cttcaggtat ccctctggtt   5940
ggtaacttaa gaacaaggct ccttgcactt catgtccttg aagctgtgct gccagcttgt   6000
gaatctggtg tagaagatga tcaaatggcc cagattgttg agcgcttatt ttcccttctc   6060
tctgattgta tgtgggagac acccattgct caggccaaac atgctattca gataaaggaa   6120
aaagaacaag aaataaaact acagaagcag ggcgagttgg aagaagaaga tgagaatctt   6180
cctatccaag aagtatcctt tgacccggag aaagctcagt gttgcctagt ggagaatgga   6240
cagattttaa ctcacggcag tggagggaaa ggatatggat tggcatctac aggagtaact   6300
tctgggtgct atcagtggaa gttttatatt gtgaaggaaa acagaggtaa tgaaggcacg   6360
tgtgttggag tttctcgctg gccagtacat gactttaatc accgcactac ctcggatatg   6420
tggctctata gggcctacag tggtaacctc tatcacaatg gagaacagac tctcacattg   6480
tccagcttta ctcaaggaga tttcattacc tgtgtgttag acatggaagc caggaccatt   6540
tcttttggga aaaatggaga ggaacccaaa ttagcttttg aagatgtgga tgcagcagag   6600
ttgtacccat gtgtgatgtt ctatagtagc aatccagggg aaaaggtgaa aatttgtgat   6660
atgcagatgc gtggcacacc ccgagactta cttccaggag accctatttg tagtccagta   6720
gcagcagtgc tggctgaggc cactattcag ctcgtccgta tccttcaccg aacagaccgt   6780
tggacttact gcattaacaa aaaaatgatg gaaaggcttc acaaaattaa gatatgtatt   6840
aaagagtcag gtcagaagct aaagaaaagc cgctcggttc agagccgaga ggaaaatgaa   6900
```

-continued

```
atgagagagg agaaggagag caaagaggaa gagaaaggta aacatactag gcatggcctc   6960
gctgacctct cagagctgca gctgaggact ctttgcatag aggtgtggcc cgtgctggct   7020
gtgataggag gagttgatgc tggtcttaga gttggaggtc ggtgtgttca caagcaaact   7080
gggcgccatg ccacgctgct gggagtggtc aaagagggca gcacgtctgc caaggtccaa   7140
tgggatgaag cagaaattac tatcagcttc ccaacttttt ggtcgcctag tgatactcca   7200
ttgtataatc tggaaccctg tgaaccattg ccgtttgatg tggcgcgatt ccgaggcctg   7260
acggcttctg tgctgctgga cctaacatat ctcactggcg ttcatgaaga catgggcaaa   7320
cagagcacca aacgacatga aaagaaacac cgacatgaat ccgaggagaa aggggatgtt   7380
gagcagaaac ctgagagtga atccgcttta gatatgcgaa caggcctaac atctgatgac   7440
gtcaaaagtc agagtaccac aagctccaaa tcagaaaatg aaatcgcttc attttcttta   7500
gatccaacac tgccaagtgt ggaatcccaa catcaaataa cagaagggaa aagaaaaaat   7560
catgaacaca tgtccaaaaa ccatgatgta gcccagtcag aaatcagagc agtccagctg   7620
tcctatcttt acctcggtgc tatgaagtca cttagtgccc ttcttggctg tagtaaatat   7680
gctgagctgt tgctgatacc aaaagttctg gctgaaaatg gccacaactc agactgtgca   7740
agttctccag ttgttcatga agacgtggag atgcgagcag ccctgcagtt cttgatgcga   7800
cacatggtga agcgagcagt catgcggtca cccataaaga gagcattggg attagctgat   7860
ctggaacgag cgcaagccat gatctataaa ttagtggttc atgggctttt ggaagaccag   7920
tttgggggca aaattaagca agagattgat caacaagctg aagaaagtga ccctgcccag   7980
caggcacaga caccagttac tactagccca tcagcctcaa gcacgacctc ctttatgagc   8040
agctctctgg aggacaccac aactgccacc actccagtca ctgacacaga aacagtgcct   8100
gcatccgagt ccccgggagt gatgcctctt agtcttctca ggcaaatgtt ctctagttac   8160
ccaactacca ctgtacttcc cacacgtcgg gcacagactc ctccaatatc ttcgttacca   8220
acctctcctt ctgatgaagt aggaaggagg caaagtttaa cttctcctga ttcccagtca   8280
gcaaggccag ctaaccgcac agccttgtca gacccaagca gtagactttc aacttctcct   8340
cctcctccag caattgcagt tcccttgctg gaaatggggt tctctcttcg gcagattgcc   8400
aaagccatgg aagctacagg tgctagggga gaggctgatg cccagaatat cactgtcctt   8460
gccatgtgga tgatagagca ccctgggcat gaggatgaag aggagcccca gtcgggcagc   8520
acagcagact ctaggcctgg agcagccgtt ctaggcagtg gcgggaagtc aaatgatccc   8580
tgttatttgc agtcacctgg agacatacca tcagctgatg ctgctgaaat ggaggaaggt   8640
tttagtgaaa gccctgataa tttggatcat acagagaatg cagcttctgg aagtggacca   8700
tcagctagag gtcgctcagc ggtaacaaga agacacaagt ttgacttagc tgctcgcaca   8760
ctgctagcaa gagcagcggg attataccgc tctgtgcagg cccacaggaa tcaaagtcgg   8820
agagaaggaa tatctttgca gcaagaccca ggggcgttgt atgactttaa tttagatgag   8880
gaattggaaa ttgatcttga tgatgaggcg atggaagcta tgtttggaca agacctgacc   8940
agtgacaatg atattctggg aatgtggatc ccagaggtac tggattggcc tacctggcat   9000
gtttgtgagt ctgaagacag ggaagaagtg gtggtgtgtg aactgtgtga atgcagcgtc   9060
gtcagcttca atcagcacat gaagagaaac catccaggct gtgggcgcag tgcaaaccgc   9120
cagggctatc gcagcaatgg ttcctatgtg gatggctggt ttggcggtga atgtgggagt   9180
ggaaatccat actacctgtt atgtggcacc tgcagggaga agtacttagc catgaagacc   9240
aaatctaagt caacaagttc tgaaaggtac aagggacaag ctccagatct aattggcaag   9300
```

-continued

```
caagacagtg tgtatgaaga agactgggac atgttggatg ttgatgaaga tgaaaagcta   9360
actggtgaag aagaatttga attacttgct ggaccgcttg gtttaaatga ccggcgcatt   9420
gtaccagaac cagttcagtt ccctgacagc gatccactgg gagcatcagt agcaatggtc   9480
acagccacca acagtatgga agagactctg atgcaaatag gttgccatgg ctccgtagaa   9540
aagagctcct ctgggagaat aacgttagga gagcaggcag ctgccctagc aaaccctcat   9600
gaccgtgtgg tggctttaag gagagtgact gctgctgctc aggttcttct ggccagaacc   9660
atggtcatga gagcgctgtc tcttctctca gtcagtggtt ccagttgtag cctggctgct   9720
ggtcttgagt ctctggggct aacagatatc cgaacgctag ttcgattaat gtgcttggca   9780
gcagcaggga gagctggcct ctccaccagc ccttctgcca tggctagcac ctcagaacga   9840
tcacgaggtg ggcatagcaa ggctaacaag cctatctctt gcctggccta tttgagcaca   9900
gcagtgggat gtctggcatc aaatgctcct agtgctgcca aactgcttgt acagttgtgt   9960
acacagaact tgatttctgc tgcaacaggt gtaaatctaa cccacagttga tgactcaatt  10020
cagcgaaagt ttctacccag ctttctccga ggaattgctg aagagaacaa gcttgtgacc  10080
tccccaaact ttgttgtaac acaggccctt gtggcattgc tagcagacaa aggggccaaa  10140
ctaagaccta actatgataa gtcagaagtt gaaaagaaag gccctctgga gttggctaat  10200
gccctggcag cctgctgcct ctcctccagg ctgtcctcac agcatcggca atgggcagct  10260
cagcaactcg tgcgcactct tgctgcacac gaccgtgaca accaaactac tctgcagaca  10320
cttgctgata tgggaggaga tcttagaaaa tgctccttta tcaaattgga ggctcatcag  10380
aacagagtaa tgacatgtgt ttggtgtaat aaaaaaggtc ttttggctac aagtggcaat  10440
gatggcacca tccgcgtatg gaatgttacc aagaagcaat attcactgca acagacctgt  10500
gtgttcaaca gattggaagg ggatgctgag gaaagcctgg gatcacccag tgatccaagt  10560
ttctcaccag tttcctggag tatcagtggc aaatatctag caggcgcttt ggaaaagatg  10620
gtgaatatct ggcaagttaa tggaggaaaa ggattagtag atattcagcc tcattgggta  10680
tctgccctgg cttggccaga agagggtccg gctacagcct ggtcaggaga gtctccagaa  10740
ttgttgttgg tgggacggat ggatggatct ctgggactga ttgaagttgt tgatgtgtcc  10800
accatgcacc gtcgagaatt ggagcattgc tatcgaaagg atgtgtctgt tacttgcatt  10860
gcatggttca gtgaagacag accatttgca gtgggatatt ttgatggaaa actgttactg  10920
ggaacaaagg aaccacttga gaaaggaggc attgttctaa ttgatgcaca taaggatact  10980
cttattagca tgaagtggga ccctacaggt catattctta tgacatgtgc caaagaagac  11040
agtgtgaaac tctggggctc tatttcggga tgctggtgct gtctacattc actctgccat  11100
ccatctattg taaatggcat tgcttggtgc cgccttccag ggaaaggatc caagttgcag  11160
ttactgatgg ctactggctg tcagagtggc ttagtatgtg tttggcgcat tcctcaagat  11220
actacacaga ccaatgtgac tagtgcagaa ggatggtggg accaggaatc aaattgccag  11280
gatggatata ggaaatcatc aggagccaag tgtgtttatc agctgcgggg acacatcact  11340
cctgttcgga ctgttgcctt tagttctgat gggttggccc tggtgtctgg tggactaggt  11400
gggctcatga acatttggtc tttaagggat ggctctgtct tgcaaactgt tgtgataggc  11460
tctggagcta ttcagaccac agtatggatt ccagaagttg gagtagctgc ttgctcaaat  11520
agatcaaagg atgttttggt cgtgaattgt acagcagaat gggcagctgc caatcatgtt  11580
ttggcaacct gtaggacagc attgaaacag cagggtgttc tgggattgaa catggctccc  11640
```

-continued

```
tgcatgagag cattttttgga gcggctcccc atgatgcttc aggagcagta tgcctatgaa  11700
aagcctcatg tggtttgtgg tgaccaactt gttcatagcc cctatatgca atgcttggct  11760
tcccttgctg tgggacttca tctggatcag ctgttgtgta accctccagt gccaccacac  11820
caccagaact gtctgcctga ccctgcatcc tggaatccaa atgaatgggc ctggttagaa  11880
tgtttctcaa ccactataaa agctgccgaa gccctgacca atggagccca gtttccagaa  11940
tcttttaccg ttccagatct agaacctgtt ccagaggatg aacttgtatt tctaatggat  12000
aacagtaaat ggattaacgg catggatgaa caaattatgt cttgggcaac ttccagacct  12060
gaggactggc acctgggagg taaatgtgat gtctacttat ggggtgctgg taggcatgga  12120
cagctggcag aagctggaag aaatgtaatg gtacctgcag cagctccctc attctcacag  12180
gcccaacagg tcatttgtgg tcagaattgt acctttgtca tccaggccaa tggcacagtg  12240
ttggcttgtg gggaaggaag ttatggcaga ttaggacaag gaaattcaga tgaccttcat  12300
gtgctgacag ttatttcagc cttacaaggc tttgtggtga cccagctggt gacttcctgt  12360
ggttctgatg ggcactctat ggccctaact gaaagtggtg aggtctttag ctggggagat  12420
ggtgactatg gtaaacttgg ccatgggaac agcgacaggc agcggcggcc caggcagatc  12480
gaggccttac aaggagaaga agtggtgcag atgtcttgtg gcttcaagca ctcagcagtg  12540
gtcacttcag atggcaaact gttcaccttt gggaatggtg actatggtcg tctgggtctt  12600
ggaaatacct ctaacaaaaa acttccagag agagtgactg cactggaggg atatcagatt  12660
ggacaggtgg cctgtggatt aaaccacact ttggcagtgt cagcagatgg ttccatggtg  12720
tgggcttttg gagatggaga ctatggaaaa ctaggcttag gaaattccac tgcaaaatct  12780
tcacctcaga aaattgacgt cctttgtgga attggaataa aaaaggttgc ttgtggaact  12840
cagttttctg ttgctttgac caaagatggt catgtgtata cctttggtca agatcgcctg  12900
ataggcttgc cagaggggcg tgctcgcaat cacaatcgac cgcaacaaat ccctgtcctg  12960
gctggagtaa tcattgaaga tgtggcagtt ggagctgaac acacacttgc tttggcatca  13020
aatggagatg tgtatgcctg gggggagcaat tcagaagggc agctcggctt aggccatacc  13080
aaccatgttc gagaaccaac cctggtaaca ggtctgcaag ggaaaaatgt tcggcagatc  13140
tcggctggcc gctgccacag tgctgcatgg acagcaccac ctgtcccacc aagagcacca  13200
ggtgtgtcag tacctctgca gctgggcctg cctgacacag tgccccccca gtatggggcg  13260
ctgagagaag tcagcattca cacggtgcgg gccaggctcc ggctgctcta ccacttctct  13320
gacctcatgt actcatcctg gagactgctg aaccttagcc ccaacaacca gaacagcaca  13380
tcccattata atgctggaac ttggggcatt gtacagggac aacttcggcc tttgttagcc  13440
ccaagagtct acactctgcc aatggtgcgc tccataggaa aaaccatggt tcaaggcaaa  13500
aactatggac ctcagataac tgtaaagagg atatcaacca gaggacggaa gtgtaagcct  13560
atttttgtcc aaatagcgag acaagtagtt aagctgaatg cttcagacct ccgcctgcct  13620
tcccgagcgt ggaaggttaa gctggttgga gaaggggctg atgatgctgg aggagtgttt  13680
gatgacacca tcacagagat gtgccaggaa cttgaaactg gtattgttga ccttcttata  13740
ccctctccca atgccaccgc agaagtgggt tacaataggg acaggttcct tttaaccct  13800
tctgcctgcc tcgatgaaca cttaatgcag tttaagtttt taggaatttt aatgggggtt  13860
gccattcgca caaagaagcc tctggacctc cacttggccc ctctggtgtg gaagcagctg  13920
tgctgtgtcc cactcaccct agaggacctg gaggaggtgg atctgctcta cgtgcagact  13980
ctcaacagca ttcttcacat tgaagacagt gggattaccg aggagagttt ccatgagatg  14040
```

```
attcctcttg attcttttgt tggccagagt gctgatggca aaatggttcc tataatccct  14100

ggtggaaata gtatcccact cacattttcc aacaggaagg aatatgtgga gagggccatt  14160

gaatatcgac ttcatgagat ggacagacag gtggctgcag tccgagaagg gatgtcctgg  14220

attgttcctg tgccgctgct gtccctcctc acagcaaaac aactggagca gatggtgtgt  14280

gggatgcccg agatctctgt ggaagtcttg aagaaagtgg tgcggtaccg tgaggtggat  14340

gagcagcatc agctggtgca gtggttctgg cacacgctgg aagagttctc caatgaggag  14400

cgggtgcttt tcatgaggtt tgtgtcagga agatctcgac taccagccaa cactgctgac  14460

atttctcaga gatttcaaat catgaaggtt gataggcctt acgacagtct gcctacctca  14520

cagacctgct tcttccagct gaggctgccc ccgtactcca gccagctggt catggccgag  14580

cgcctgcgct atgccatcaa caactgccgc tcaatcgaca tggacaacta catgctctcg  14640

agaaacgtgg acaacgccga gggctccgac actgactact gaccgtgcgg gtgctctcac  14700

cctcccttct ctccctcaat aatgctcact tctgatttga tgttgatata cttttatggt  14760

aactacatag atgttataag aacataaacc aacattataa acaatggcca catttagtta  14820

ctctaaatgt aacaaagaaa ttagatgttt ttattttttct gtgattgtac aaaaacaaca  14880

aaaacgaagt gctctcagtc aggtttttcc ctccatattt ttggtcactt ttgataagtt  14940

tgcatgaaac cattttggtg catttttagt tgggaatggt acatttttgt aaatccaccc  15000

agtgaacatg aaattgtaca ttgtgtataa ttgttcatta gaaaggacag ttttacatga  15060

atattcatat atttattttg ttttaatttg aattgcctgt tcagggttcc ttatgcagag  15120

aaataaagca gattcaggaa ttggaaaaaa                                   15150
```

<210> SEQ ID NO 10
<211> LENGTH: 9126
<212> TYPE: DNA
<213> ORGANISM: Homo sapiens

<400> SEQUENCE: 10

```
ccagagcccc ctcgccccaa aggtcactgg gactatttgt gcgaagagat gcagtggctc    60

tctgctgact ttgctcagga gcgccgttgg aaacggggtg tggcccggaa ggtggtgcgc   120

atggtgatcc ggcaccacga ggagcagcgg cagaaagagg aacgggcccg gagggaggag   180

caggccaagc tgcgtcgaat tgcttccacc atggccaagg atgtcaggca gttctggagc   240

aatgtggaga aggtggtgca attcaagcaa cagtcccggc ttgaggaaaa gcgcaaaaaa   300

gccctggacc tgcatttgga cttcattgtg gggcaaactg aaaagtactc ggaccttctg   360

tctcagagcc tcaaccagcc attaacctcc agcaaagcag gctcttcccc ttgcctcggc   420

tcttcctcag ctgcctccag tcctccaccc cctgcttctc gcctggatga tgaagatggg   480

gactttcaac cccaagagga tgaggaagag gatgatgagg aaacgattga agttgaagaa   540

caacaggaag gcaatgatgc agaggcccag aggcgtgaga ttgagctgct tcgccgtgag   600

ggagaattgc cactggaaga gctgctccgt tcccttcccc ctcagctgtt ggaagggcct   660

tccagcccct ctcaaacccc ctcatctcat gatagtgaca cccgagatgg gcctgaagaa   720

ggtgctgaag aagagccccc tcaggtgttg gagataaagc ccccaccctc tgctgtcaca   780

cagcgcaaca aacagccttg gcatccagat gaagatgatg aagagtttac tgccaacgaa   840

gaggaagcgg aggatgaaga ggatactata gcagctgagg aacagttgga aggggaggtg   900

gatcatgcca tggagctgag cgagttggct cgagaaggtg agctttccat ggaggagcta   960
```

-continued

```
ttgcagcagt atgcaggagc ctatgcccca ggctctggga gcagtgaaga tgaggatgaa   1020

gatgaggttg atgctaatag ctctgactgt gaaccagagg ggcccgtgga agcggaagag   1080

cctcctcagg aggatagtag cagtcagtca gactctgtgg aggaccggag tgaggatgag   1140

gaagatgaac attcagagga ggaagaaaca agtggaagtt cagcatcaga ggaatctgag   1200

tctgaagagt ctgaggatgc ccaatcacag agccaagcag atgaagagga ggaagatgat   1260

gattttgggg tggagtactt gcttgccagg gatgaagagc agagtgaggc agatgcaggc   1320

agtgggcctc ctactccagg gcccactact ctaggtccaa agaaagaaat tactgacatt   1380

gctgcagcag ctgaaagtct ccagcccaag ggttacacgc tggccacgac ccaggtaaag   1440

acgcccattc ccctgcttct gcggggccag ctccgggagt accagcacat tgggctagac   1500

tggctggtta ccatgtatga gaagaagctt aatggcattc ttgctgatga gatggggctt   1560

gggaagacca tccagaccat ctctctgctt gcccacttgg cttgtgagaa aggtaactgg   1620

ggtccccatt taatcattgt tcccaccagc gtgatgttga actgggagat ggagttgaaa   1680

cgttggtgcc ccagctttaa aatcctcact tactatggag cccagaaaga gaggaagctc   1740

aagcggcagg gctggaccaa gcccaatgcc tttcatgtgt gtatcacatc ttacaagctg   1800

gtgctgcagg accaccaggc cttccgtcgc aagaactggc gctatctcat tctggatgag   1860

gcgcagaaca tcaagaactt caagtcacag cgctggcagt cactcctcaa cttcaacagc   1920

cagagacgcc tgctcctgac aggaactccc ttgcagaaca gcctcatgga gctgtggtcc   1980

ttgatgcact tttgatgcc ccatgtcttc cagtctcatc gcgagttcaa ggagtggttc   2040

tctaatcccc taactggcat gattgagggc agccaagagt ataatgaagg tctagtcaaa   2100

cgcctccaca aggttttgag gcctttttta ctgcgccgag ttaaggtgga tgttgagaag   2160

cagatgccca aaaagtacga gcatgttatc cgctgcaggc tctccaagcg tcaacgctgt   2220

ctctatgatg acttcatggc acagaccaca actaaggaga cactagccac aggccatttc   2280

atgagcgtca tcaacatttt gatgcagctg agaaaagttt gcaatcatcc aaatctgttc   2340

gaccctcgac cggttacctc ccctttcatc accccaggca tctgcttcag caccgcctct   2400

ctggtgctaa gggccacgga tgtccatccc ctccagcgga tagacatggg tcgatttgac   2460

cttattggcc tggaaggtcg tgtctctcga tatgaggcag acacatttct gccccggcac   2520

cgcctctctc gccgggtact gttagaagtg gctactgctc ctgacccccc accccggccc   2580

aagccagtca agatgaaggt caacaggatg ctgcagccag tacctaagca agaaggccgg   2640

acagtggtgg tggtgaacaa cccacgggcg cccctgggcc ctgtcccagt tcgacctcct   2700

ccaggtcctg agctctcagc ccagcccacc cctggcccag tcccccaagt gctgccagca   2760

tcactgatgg tttcagcctc acctgccggg cccccgctta ttcctgcatc tcggcctcct   2820

ggccctgtcc tcttgcctcc actgcagccc aacagtggtt ctctccccca ggtgttgcca   2880

tccccccctgg gggtcctgag tgggacctca cggcctccca cgccaacctt gtccctaaag   2940

ccaacaccac ctgccccagt tcgcctgagc ccagccccac ctccaggctc ctctagcctg   3000

ttgaagcccc tgacagtgcc accaggctac accttccctc ctgctgctgc caccaccact   3060

tctaccacca cggcaactgc taccaccaca gcagtgccag ctccgactcc tgcaccacag   3120

cgcctcattc tatctcccga tatgcaggct cgcctgccct caggcgaagt ggtcagcatc   3180

gggcagttag cctcactggc acaacgtcca gtggctaatg caggggggaag caaacctctc   3240

accttccaaa tccagggcaa caagctgact ttgactggtg cccaggtgcg ccagcttgct   3300

gtggggcagc cccgcccgct gcaaatgcca ccaaccatgg tgaataatac aggcgtggtg   3360
```

-continued

```
aagattgtag tgagacaagc ccctcgggat ggactgactc ctgttcctcc attggcccca   3420
gcaccccggc ctccgagctc tgggcttcca gctgtgttga atccacgccc cacgttaacc   3480
cctggccggc tacccacacc tactctgggt actgctcgag cccccatgcc cacacccact   3540
ctggtgaggc ctcttctcaa gctggtccac agtccttcac ctgaagtcag tgcttcagcc   3600
cccggagctg ccccttgac catctcttct cctctccacg tgccatcctc actccctggg   3660
ccagcctctt ctccaatgcc aattcccaac tcctctcccc ttgctagtcc tgtgtcctct   3720
acagtctcag ttccattgtc atcttcactc cccatctctg tccccaccac acttcctgcc   3780
ccagcctcgg ctccactcac catccccatc tcagccccct tgactgtttc tgcttcgggc   3840
ccagctctgt tgaccagtgt gactccacca ttggcacctg ttgtcccagc ggctcctgga   3900
cctccctcct tgcagccatc tggtgcttcc ccgtcagcat cagccttgac tctaggtttg   3960
gccacagctc catccctgtc ttcatctcag acacctggtc accctctgtt gttggctccc   4020
acctcttcac atgttccagg gttgaactca accgtggccc cagcatgctc acctgtcctg   4080
gtgccagctt cggctctggc cagtcctttt ccgtcagcac caaatccagc tccagctcag   4140
gcttcccttc tggctccagc atcttctgca tctcaggctc tagccacccc tctggctcct   4200
atggcggctc cacagacagc aattctggct ccttctccag ctcctcctct ggctcctctt   4260
ccggtcctgg caccatcgcc aggtgctgct cctgtcctgg cttcatcaca gactccggtt   4320
ccagttatgg ctccatcgtc tactccagga acctctttag cctcagcttc accggtacca   4380
gctccaaccc ctgtgttggc tccatcatca actcaaacta tgctaccagc cccggttccg   4440
tcacctctcc cgagcccggc ttctacgcag acactggccc tagccccagc tttagcaccc   4500
actcttggag gctcatctcc atctcagaca ctctctttgg gaacggggaa cccccaggga   4560
ccctttccaa ctcagacatt gtcattaact ccagcatcat ccctggtacc aactccagcc   4620
cagacactgt ctttggcacc aggaccacca ctgggtccaa ctcagacgct gtctctggct   4680
ccagcacccc ctctggctcc agcttctcca gtgggcccag ccccagctca cacgctgact   4740
ttggctccag catcgtcatc tgcttcactc ctggccccag cttcagtgca gacactgacc   4800
ttgagccctg ccccagttcc taccctgggc ccggccgcag ctcagacctt ggcgctggcc   4860
ccagcctcca cacagtcccc agcttcccag gcatcttccc ttgtggtttc ggcatctggt   4920
gccgctccct tgcctgtcac catggtatcc cggctgcctg tttccaagga tgagcctgac   4980
acactgacat tgcgctctgg tccccccagc cctccctcca ctgctacctc gtttggtggc   5040
ccccggcctc gacgccagcc ccccccacca cctcgttccc ctttttatct ggactccctg   5100
gaggaaaagc ggaagcggca gcggtctgaa cgcctggaac ggattttcca acttagtgag   5160
gctcatgggg ccctggcacc tgtgtatggg actgaagtcc tggatttctg taccctgccc   5220
caacctgttg ccagccccat cggccctcgt tctcctggcc ccagccaccc caccttttgg   5280
acttataccg aggctgccca ccgggctgta ctgtttcccc agcagcgact agaccagctg   5340
tcagaaatca ttgagaggtt catctttgtc atgcctcctg tggaggcacc tcccccttcc   5400
ctgcatgcct gccacccacc tccttggctg gccccacgtc aggcagcctt ccaggagcaa   5460
ttggcctctg agctctggcc ccgggctcgt cctttgcacc gtattgtgtg taacatgcgc   5520
acccagttcc ctgacttaag actcatccag tatgattgcg gaaagttgca gacgttggca   5580
gtgctgttgc ggcagctcaa ggcagagggc caccgagtgc tcatcttcac ccagatgacc   5640
cgaatgctgg atgtattgga gcagtttctc acctaccatg gccatctcta cctgcgcctg   5700
```

-continued

```
gatggatcta ctagagttga acagagacag gccttgatgg aacggttcaa tgcagacaaa   5760
cgcatattct gcttcatcct ttcaactcgg agtgggggtg tgggcgtgaa cctgacagga   5820
gcagacactg ttgtttttta tgacagcgac tggaatccca ccatggatgc tcaggcccag   5880
gaccgctgtc accgaattgg ccagacccgg gatgtccaca tatataggct tatcagtgaa   5940
cggacagtgg aggagaacat cctaaaaaag gcaaatcaga agagaatgtt gggggacatg   6000
gccattgagg gaggcaactt caccacagcc tatttcaaac agcagaccat ccgagagctg   6060
tttgatatgc cctggagga accttctagc tcatccgtgc cctctgcccc tgaagaggag   6120
gaagagactg tggccagcaa gcagactcat attctggagc aggcattgtg tcgggcagaa   6180
gatgaagagg atatccgtgc agccacccag gccaaggctg aacaggtggc tgagcttgca   6240
gaatttaatg agaacgatgg gtttcctgct ggtgagggag aggaagctgg ccggcctggg   6300
gctgaggatg aggagatgtc ccgggctgag caggaaattg ctgccctcgt agaacagctg   6360
acccccattg agcgctatgc catgaaattc ctggaggcct cactggagga ggtgagccga   6420
gaggagctca aacaggcaga agagcaagtg gaagctgccc gcaaagacct ggaccaagcc   6480
aaggaggagg tgttccgcct accccaagag gaggaggagg ggccgggggc tggggatgag   6540
agttcctgtg ggactggtgg aggcacccac cggcgcagta aaaaggccaa agcccctgag   6600
aggccgggga ctcgtgtcag tgagcgtctt cgtggagccc gggctgagac tcaaggggca   6660
aaccacactc ctgtcatatc cgcccatcaa actcgcagca ccaccacacc accccgctgc   6720
agtcctgcca gggagcgagt tcccaggcca gcacctaggc ctcgacccac tccagcttca   6780
gctccggctg caattcctgc ccttgttcct gtcccagttt ctgccccagt acccatttca   6840
gccccaaatc caataaccat tctccctgtc catatcttgc cttctcctcc ccctccttca   6900
cagattcctc cttgttcttc tcctgcctgc acccctcctc ctgcctgtac ccctccacca   6960
gctcatacac cgcctccagc ccaaacctgt cttgtaactc cttcctctcc tctcttgctt   7020
ggtccacctt ctgtgcccat ctctgcctca gtcactaatc tccccttggg cttgaggcct   7080
gaggcagagc tgtgtgccca ggcattggca tctccagagt ccctggagct ggcttctgtg   7140
gccagttcag aaacctcctc actttctctt gtgcccccta aagatctgtt gccagttgct   7200
gtggagatcc tgcctgtgtc agagaagaac ctttctctca ccccttctgc acccagcctg   7260
accttggagg ctggcagcat ccccaatggt caagagcagg aggcaccaga ttctgctgag   7320
gggaccaccc ttacagtgct gcctgaaggt gaggagttgc cctgtgtgt gagtgagagc   7380
aatggcctgg agctcccacc ctcagcagca tctgatgagc cacttcagga gccactggag   7440
gctgacagga cctcggaaga gctgacagag gccaagaccc caacctccag cccagagaag   7500
ccacaggaac tcgttacagc tgaggttgca gctccatcca cctcatcttc agccacttcc   7560
tcgcctgagg gtccttcacc tgcccgacct cctcggcgtc gcaccagtgc tgatgtggaa   7620
attaggggtc aagggactgg tcggccagga caaccaccag gccccaaagt gcttcgaaag   7680
ctgccaggac ggctggtaac tgtggtagag gaaaaggaac tggtgcagcg gcggcggcag   7740
cagcggggag ctgccagcac cctagtgcct ggggtctctg agactagtgc cagcccggga   7800
agcccgtctg tccgcagcat gtcagggcca gaatcctccc ctcccattgg tgggccctgt   7860
gaagctgctc cttcatcctc actgcccact ccaccccagc agcccttcat tgctcgccgt   7920
cacattgagc tgggggtgac tggtggtggc agccccgaga atggagacgg agcactgctc   7980
gccatcaccc cacctgctgt gaaacgtcgg agggggaggc cccccaagaa gaacaggtct   8040
ccagcagatg ctgggagagg tgtggatgag gcaccctcat ccaccttgaa gggaaaaacc   8100
```

-continued aatggggctg acccagtccc tgggcctgag accctaattg ttgcagatcc tgtcctggaa 8160
ccacagctta ttcctgggcc ccagcctctt ggaccccagc cagttcacag acccaatccc 8220
ctcctgtcac ctgtggagaa aagaaggcga ggacgacccc ctaaagcacg agatttgccc 8280
atccctggga ccatttcctc tgcaggggat ggcaactccg aaagtcggac acagccaccc 8340
ccacacccat cacccctaac cccactccca ccactgctag tttgtcccac tgctactgtt 8400
gccaacactg tcaccactgt caccatttca acgtccccac ccaaacggaa gaggggccga 8460
cctcccaaga atcctccatc acctcggccc agccagctcc ccgtcttgga ccgtgacagc 8520
acttctgttc tcgagagctg tggattgggg aggcgacggc aaccccaggg ccaaggggag 8580
agtgagggta gttcctctga tgaggatgga agccgccccc tcacccgcct ggcccgcctt 8640
cggcttgaag cagaaggaat gcgaggacgg aagagtggag ggtccatggt ggtggctgta 8700
attcaggatg acctggactt agcagatagc gggccaggcg ggttggaatt gacaccacct 8760
gtggtctcac taaccccaaa actgcgctcg acccggctgc gtccagggtc tctagtcccc 8820
ccactagaga ctgagaagtt gcctcgcaaa cgagcagggg ccccagttgg tgggagtcct 8880
gggctggcaa agcggggccg cctacagccc ccaagtcccc tggggcctga gggttcagta 8940
gaggagtctg aggctgaagc ctcaggtgag gaggaggaag gggatgggac ccccacgccga 9000 cgtcctggcc cccgccggct tgttgggacc accaaccaag ggaccagcg catcctgcgc 9060 agcagcgccc ctccctccct ggctggccct gctgttagtc acagaggccg caaggccaag 9120
acgtga 9126

<210> SEQ ID NO 11
<211> LENGTH: 971
<212> TYPE: DNA
<213> ORGANISM: Homo sapiens

<400> SEQUENCE: 11
cggctgcagc tcgggcggcg gccgcggggg acaaagggcg ggcggatcgg cggggagggg 60
gcggggcgcg gccaggccaa gcccgggggc tccgcaatgc tgcagctgcc cccgggcgcc 120
cccgccgccg ccctcgccgc ggagccgcgc ggagcggacg ccggcgagct aacccgagcc 180
agccggcggg cgtccccgga ggcggtggcg cagggagggg cccgacgctc gcacgtggcc 240
ccggcggccg ccatggcgga cagcggcacc gcggggggcg cggcgttggc ggccccggcc 300
cccgggccgg gcagtggcgg cccaggacca cgcgtctact ttcagagccc ccccggggcc 360
gcaggagagg gcccgggcgg ggcggacgat gagggcccag tgaggcgcca agggaaggtc 420
accgtcaagt atgaccgcaa ggagctacgg aagcgcctca acctagagga gtggatcctg 480
gagcagctca cgcgcctcta cgactgccag gaagaggaga tcccagaact ggagattgac 540
gtggatgagc tcctggacat ggagagtgac gatgcccggg ctgccagggt caaggagctg 600
ctggttgact gttacaaacc cacagaggcc ttcatttctg gcctgctgga caagatccgg 660
ggcatgcaga agctgagcac accccagaag aagtgaggga tccccgaccc aggagaacgg 720
tggctcccac aggacaatcg ctgcccccca acctcgtagc aacagcaata ccgggggacc 780
ctgcggccag gcctggtgcc atgagcaggg ctcctcgtgc ccctggccca ggggtctctt 840
cccctgcccc ctcagttttc cacttttggg gttttttatt gttattaaac tgatgggact 900
ttttgtgttt ttatattgac tctgcggcgc gggcccttta ataaagctag gatacgcctt 960
tggtgcagct a 971

-continued

<210> SEQ ID NO 12
<211> LENGTH: 1629
<212> TYPE: DNA
<213> ORGANISM: Homo sapiens

<400> SEQUENCE: 12
gggccgcccc aagggctcct cccgacctcc cggcctgccg ctccggccac tgcgggatcc 60
agaaacatgt cgaccacact tctgtccgcc ttctacgatg tcgacttctt gtgcaagaca 120
gagaaatccc tggccaacct caacctgaac aacatgctgg acaagaaggc ggtggggacg 180
cctgtggccg ccgcccccag ctcgggcttc gcgccgggat tcctccgacg gcactcggcc 240
agcaacctgc atgcactcgc ccaccccgcg cccagccccg gcagctgctc gcccaagttc 300
ccgggcgccg ctaacggcag cagctgcggc agcgcggcgg ccggcggtcc gacctcctac 360
ggcaccctta aggagccgtc gggggcgggc ggcacagccc tgctcaacaa ggagaacaaa 420
ttccgggacc gctcgtttag cgagaacggc gatcgcagcc agcacctcct gcacctgcag 480
cagcagcaga aggggggcgg cggctcccag atcaactcca cgcgctacaa gaccgagctg 540
tgccggccct tcgaggagag cggcacgtgc aagtacggcg aaaagtgcca gttcgcgcat 600
ggcttccacg agctgcgcag cctgactcgc catccgaagt acaagaccga gctgtgccgc 660
acctttcata ccatcggctt ctgcccctat gggccgcgct gccacttcat ccacaacgcg 720
gacgagcggc ggcccgcgcc gtcgggggc gcctccgggg acctgcgtgc ctttggcacg 780
cgcgatgcgt tgcacctggg cttcccgcgg gagccgcggc ccaagttgca ccacagcctc 840
agcttctcgg gcttcccgtc gggccaccat cagcccccgg gcggcctcga gtcgccgctg 900
ctgctcgaca gccccacgtc gcgcacgccg ccgccgccct cctgctcttc ggcctcgtcc 960
tgctcctcct ccgcctcctc ctgttcctcg gcctccgcgg cctccacgcc ctcggggacc 1020
ccgacatgct gcgcctccgc ggcggccgcg ctgcgtctgc tgtacggcac cgggggcgcc 1080
gaggacctgc tggcgccggg ggccccgtgc gcggcctgct cgtcggcctc gtgcgccaac 1140
aacgccttcg ccttcggtcc ggagctcagc agcctcatca cgccgctcgc catccagacc 1200
cacaactttg ccgccgtggc cgccgccgcc tactaccgca gtcagcagca gcagcagcag 1260
cagggcctgg cgccccccgc gcagccgccg gcgccgccca gcgcgaccct ccccgccggg 1320
gccgccgcac ctccctcgcc gcccttcagc ttccagctgc cgcgccgcct gtccgactcg 1380
cccgtgttcg acgcgccccc cagccccccg gactcgctgt cggaccgcga cagctaccta 1440
agcggctccc tgagctccgg cagcctcagc ggctctgagt ctcccagcct cgaccctggc 1500
cgccgcctgc caatcttcag ccgcctctcc atctccgacg actgaggcaa gagggcgcca 1560
gtgaggagga agggaaggcg gttcagagat gttggaggac acccctcgcc atctcgccct 1620
tgctggggg 1629

<210> SEQ ID NO 13
<211> LENGTH: 945
<212> TYPE: DNA
<213> ORGANISM: Homo sapiens

<400> SEQUENCE: 13
atgcctcttg agcagaggag tcagcactgc aagcctgaag aaggccttga ggcccgagga 60
gaggccctgg gcctggtggg tgcgcaggct cctgctactg aggagcagga ggctgcctcc 120
tcctcttcta ctctagttga agtcaccctg ggggaggtgc ctgctgccga gtcaccagat 180
cctccccaga gtcctcaggg agcctccagc ctccccacta ccatgaacta ccctctctgg 240

```
agccaatcct atgaggactc cagcaaccaa gaagaggagg ggccaagcac cttccctgac    300

ctggagtccg agttccaagc agcactcagt aggaaggtgg ccgagttggt tcattttctg    360

ctcctcaagt atcgagccag ggagccggtc acaaaggcag aaatgctggg gagtgtcgtc    420

ggaaattggc agtatttctt tcctgtgatc ttcagcaaag cttccagttc cttgcagctg    480

gtctttggca tcgagctgat ggaagtggac cccatcggcc acttgtacat ctttgccacc    540

tgcctgggcc tctcctacga tggcctgctg ggtgacaatc agatcatgcc caaggcaggc    600

ctcctgataa tcgtcctggc cataatcgca agagagggcg actgtgcccc tgaggagaaa    660

atctgggagg agctgagtgt gttagaggtg tttgaggggga gggaagacag tatcttgggg    720

gatcccaaga agctgctcac ccaacatttc gtgcaggaaa actacctgga gtaccggcag    780

gtccccggca gtgatcctgc atgttatgaa ttcctgtggg gtccaagggc cctcgttgaa    840

accagctatg tgaaagtcct gcaccatatg gtaaagatca gtggaggacc tcacatttcc    900

tacccacccc tgcatgagtg ggttttgaga gagggggaag agtga                    945
```

<210> SEQ ID NO 14
<211> LENGTH: 2930
<212> TYPE: DNA
<213> ORGANISM: Homo sapiens

<400> SEQUENCE: 14

```
tttgttagtt tgtctgtttg cacttaaagt tctaagcact ttggaaagtt tctaagcaac     60

ttctcacttc caagcaacaa cttaaccaac actaacaact tactattatt aattagtatt    120

ttcttggctc acccccgcac agcaccgtgc ccgagcacca cccacacccc atctcgccct    180

atgagcacct gcttcggggc gtgagtggcg tggacctgta tcgcagccac atccccctgg    240

ccttcgaccc cacctccata ccccgcggca tccctctgga cgcagccgct gcctactacc    300

tgccccgaca cctggccccc aaccccacct acccgcacct gtacccaccc tacctcatcc    360

gcggctaccc cgacacggcg gcgctggaga accggcagac catcatcaat gactacatca    420

cctcgcagca gatgcaccac aacgcggcca ccgccatggc ccagcgagct gatatgctga    480

ggggcctctc gccccgcgag tcctcgctgg cactcaacta cgctgcgggt ccccgaggca    540

tcatcgacct gtcccaagtg ccacacctgc ctgtgctcgt gcccccgaca ccaggcaccc    600

cagccaccgc catggaccgc cttgcctacc tccccaccgc gccccagccc ttcagcagcc    660

gccacagcag ctccccactc tccccaggag gtccaacaca cttgacaaaa ccaaccacca    720

cgtcctcgtc cgagcgggag cgagaccggg atcgagagcg ggaccgggat cgggagcggg    780

aaaagtccat cctcacgtcc accacgacgg tggagcacgc acccatctgg agacctggta    840

cagagcagag cagcggcagc agcggcagca gcggcggggg tgggggcagc agcagccgcc    900

ccgcctccca ctcccatgcc caccagcact cgcccatctc ccctcggacc caggatgccc    960

tccagcagag acccagtgtg cttcacaaca caggcatgaa gggtatcatc accgctgtgg   1020

agcccagcac gcccacggtc ctgaggtcca cctccacctc ctcacccgtt cgcccagctg   1080

ccacattccc acctgccacc cactgcccac tgggcggcac cctcgatggg gtctacccta   1140

ccctcatgga gcccgtcttg ctgcccaagg aggccccccg ggtcgcccgg ccagagcggc   1200

cccgagcaga caccggccat gccttcctcg ccaagccccc agcccgctcc gggctggagc   1260

ccgcctcctc ccccagcaag ggctcggagc ccccggcccct agtgcctcct gtctctggcc   1320

acgccaccat cgcccgcacc cctgcgaaga acctcgcacc tcaccacgcc agcccggacc   1380
```

```
cgccggcgcc acctgcctcg gcctcggacc cgcaccggga aaagactcaa agtaaaccct   1440

tttccatcca ggaactggaa ctccgttctc tgggttacca cggcagcagc tacagccccg   1500

aaggggtgga gcccgtcagc cctgtgagct cacccagtct gacccacgac aaggggctcc   1560

ccaagcacct ggaagagctc gacaagagcc acctggaggg ggagctgcgg cccaagcagc   1620

caggccccgt gaagcttggc ggggaggccg cccacctccc acacctgcgg ccgctgcctg   1680

agagccagcc ctcgtccagc ccgctgctcc agaccgcccc aggggtcaaa ggtcaccagc   1740

gggtggtcac cctggcccag cacatcagtg aggtcatcac acaggactac acccggcacc   1800

acccacagca gctcagcgca cccctgcccg ccccccctcta ctccttccct ggggccagct   1860

gccccgtcct ggacctccgc cgcccaccca gtgacctcta cctcccgccc ccggaccatg   1920

gtgccccggc ccgtggctcc ccccacagcg aagggggcaa gaggtctcca gagccaaaca   1980

agacgtcggt cttgggtggt ggtgaggacg gtattgaacc tgtgtcccca ccggagggca   2040

tgacggagcc agggcactcc cggagtgctg tgtacccgct gctgtaccgg gatgggggaac   2100

agacggagcc cagcaggatg ggctccaagt ctccaggcaa caccagccag ccgccagcct   2160

tcttcagcaa gctgaccgag agcaactccg ccatggtcaa gtccaagaag caagagatca   2220

acaagaagct gaacacccac aaccggaatg agcctgaata caatatcagc cagcctggga   2280

cggagatctt caatatgccc gccatcaccg gaacaggcct tatgacctat agaagccagg   2340

cggtgcagga acatgccagc accaacatgg ggctggaggc cataattaga aaggcactca   2400

tgggtggcgg cgggaaggcc aaggtctctg gcagacccag cagccgaaaa gccaagtccc   2460

cggccccggg cctggcatct ggggaccggc caccctctgt ctcctcagtg cactcggagg   2520

gagactgcaa ccgccggacg ccgctcacca accgcgtgtg ggaggacagg ccctcgtccg   2580

caggttccac gccattcccc tacaaccccc tgatcatgcg gctgcaggcg ggtgtcatgg   2640

cttccccacc cccaccgggc ctccccgcgg gcagcgggcc cctcgctggc gcccaccacg   2700

cctgggacga ggagcccaag ccactgctct gctcgcagta cgagacactc tccgacagcg   2760

agtgactcag aacagggcgg ggggggcggg gggcggtgtc aggtcccagc gagccacagg   2820

aacggccctg caggagcagg gcggctgccg actcccccaa ccaaggaagg agcccctgag   2880

tccgcctgcg cctccatcca tctgtccgtc cagagccggc atccttgcct              2930
```

<210> SEQ ID NO 15
<211> LENGTH: 4169
<212> TYPE: DNA
<213> ORGANISM: Homo sapiens

<400> SEQUENCE: 15

```
ggcggcttcc aggtgggcgc gcaaggccgt ggtcctgctt tgtgcctctg acctgctgct     60

gctgctgcta ctgctaccac cgcctgggtc ctgcgcggcc gaaggctcgc ccgggacgcc    120

cgacgagtct accccacctc cccggaagaa gaagaaggat attcgcgatt acaatgatgc    180

agacatggcg cgtcttctgg agcaatggga gaaagatgat gacattgaag aaggagatct    240

tccagagcac aagagacctt cagcacctgt cgacttctca aagatagacc caagcaagcc    300

tgaaagcata ttgaaaatga cgaaaaaagg gaagactctc atgatgtttg tcactgtatc    360

aggaagccct actgagaagg agacagagga aattacgagc ctctggcagg gcagcctttt    420

caatgccaac tatgacgtcc agaggttcat tgtgggatca gaccgtgcta tcttcatgct    480

tcgcgatggg agctacgcct gggagatcaa ggactttttg gtcggtcaag acaggtgtgc    540

tgatgtaact ctggagggcc aggtgtaccc cggcaaagga ggaggaagca aagagaaaaa    600
```

-continued

```
taaaacaaag caagacaagg gcaaaaaaaa gaaggaagga gatctgaaat ctcggtcttc    660
caaggaagaa aatcgagctg ggaataaaag agaagacctg tgatggggca gcagtgacgc    720
gctgtggggg gacaggtgga cgtggagagc tctttgccca gctcctgggg tgggagtggt    780
ctcaggcaac tgcacaccgg atgacattct agtgtcttct agaaagggtc tgccacatga    840
ccagtttgtg gtcaaagaat tactgcttaa taggcttcaa gtaagaagac agatgttttc    900
taattaatac tggacactga caaattcatg tttactataa aatctcctta catggaaatg    960
tgactgtgtt gctttttccc atttacactt ggtgagtcat caactctact gagattccac   1020
tcccctccaa gcacctgctg tgattgggtg gcctgctctg atcagatagc aaattctgat   1080
cagagaagac tttaaaactc ttgacttaat tgagtaaact cttcatgcca tatacatcat   1140
tttcattatg ttaaaggtaa aatatgcttt gtgaactcag atgtctgtag ccaggaagcc   1200
agggtgtgta aatccaaaat ctatgcagga aatgcggaga atagaaaata tgtcacttga   1260
aatcctaagt agttttgaat ttctttgact tgaatcttac tcatcagtaa gagaactctt   1320
ggtgtctgtc aggttttatg tggtctgtaa agttaggggt tctgttttgt ttccttattt   1380
aggaaagagt actgctggtg tcgaggggtt atatgttcca tttaatgtga cagttttaaa   1440
ggatttaagt agggaatcag agtcctttgc agagtgtgac agacgactca ataacctcat   1500
ttgtttctaa acatttttct ttgataaagt gcctaaatct gtgctttcgt atagagtaac   1560
atgatgtgct actgttgatg tctgattttg ccgttcatgt tagagcctac tgtgaataag   1620
agttagaaca tttatataca gatgtcattt ctaagaacta aaattctttg ggaaaaaccc   1680
tcaattgtga ttttaataaa ttaaaagtag cacattacat ggttagaaaa tgtcagtgtt   1740
aaagaatggt acaaagtgaa aagtgtatcc ctctcttgcc gccggtggta gcttgtccca   1800
gtggaagctg ctgttaacaa tttgtgcccc cacatccccc tccctgccca tccaccaaaa   1860
aaaagtacat ttacttatgt aaatgtactt atggtgatgt atgtttgttt tggcctcaca   1920
gcatctgttt ccccttaatt tggtagctgc tcacatttcc ctcgaaagaa ccacaccctc   1980
tgcattctca gttctttgct ttggatggga catttgccct gcagtccccc caccctccag   2040
gccatgccct ctccagggtg aggcctgtgt gatctaccgt actagggtac taggccctga   2100
aagaggcttt tcttgttcct cctgcatctt gaacctggag cgggagctgt tgtaggcccc   2160
gcccttggag aagagaactg tctgacagtg gggagagagc gccacaccct ggtggcataa   2220
acgagtccct gaatcatgcc gtggctgaac caagccctgt ctgtgggctt tttctgttgt   2280
actcagggca gtttgatggg gttactgtcc tgcatagcca taatggccca gtataaagca   2340
gctgttttga tgagataatt gctttaatta agcaaaaggt agcaaagctt tcactccgcc   2400
ctgtaccttc tgtttccact taggagcctt cccatgtcag aatgtgcaga tctgtctcat   2460
tgtttcctgt gcagtgtgcc cccacttcac ccagtagttt ctgtgtgtct gttatgtact   2520
aggtactaca aggtgccagg acggtgtaga tacagcctct gctatcgtaa aactcaatga   2580
ttcggtgggg gaagacaaat gtcagtaatg tacaaagtaa aatggcagct gttagaagta   2640
tgaaagggc agggtagggg gaggtagaat cttccctgac caggttaaga aaaccagagg   2700
ccttctctga gggcaagagg aggagaggag aaatagagta aggcaggcag aggaaacagt   2760
ctgagctaag accctgtggc tagaagtggc agagggagag gcagcaggaa ggccagcggg   2820
gaggctgggg cccagtgcag gcccaggttg gaggagcgta gcacatggag tttggtagga   2880
gtttgggacg ccctggtgga tcttaattgt gatggggtgg gtgtgaaagg cagtccaggt   2940
```

```
tgcactggtt gcacaggaga agtgatcaga agaggacccc agcaggtgtg agccgtgagc   3000

tgggaggtgc ttcagtagtg caggccatag ctgaaggtgt cctacatcag cagggtgatg   3060

gtgaggtttg aaccactgtt tcactgcata gtccctgctg atggacactt gagtgttcag   3120

attttttgct ggtatattca gtgctgcagt ggacattttc atacaaaata tttcggtaca   3180

cttttgttta tatctgaaag gtaaattcct agcagtagaa ttattagagc aaacggaatt   3240

taacattttg gtgtgtattg ccaaattgcc ctcccaagtg gtttagtcag cttacccttg   3300

ccaacaatag atctatcctt gccagccttg ggcatcacat ttaccagttt aatagattgt   3360

aaaaccatat cttaattggc taccctgaag ccaccatact ggagaggctg cgtacagtgt   3420

ttcacgtaga gagagggata cccaggaggc ccacctgctc caaccccagc tgcatgagtc   3480

ttcccagccc aggcacagac atgtggataa gatttaaaca tttccagccc cagccttcaa   3540

gcaatcctag ttgacactga ggggagccaa cataagctga gctgagaaac agtctgccca   3600

gtctgcagat tcatgagcaa aagaaatgtt gggctgggta cagtggctca cgcctgtaat   3660

cccagtactt tgggaggccg aggtgggtgg atcagttgag gtcaggagtt tgagaccagc   3720

ctggccaaca tggtgaagcc ctgtctctac taaaaattag ccgagtgtgg tggtgcgggc   3780

ctgtaatccc agctactcag gtggctgagg caggagaatg gcttgaaccc gggaggcgga   3840

ggttgcagtg agccaagatc aggccactgc actccagcct ggatgacggg atgagactct   3900

gtctcaaaaa aacgaaacaa aaattttta agagaaatgt catttgtttt tgtttttgag   3960

acagggtctc actctgttgc cctcactaga gtgcagtagg gatcacggct cactgaagtc   4020

tctacctacc ggctcaattg atcttcccac cacagcctcc caaatagctg ggagaaatgt   4080

cctgttttta atgaatttgt cttccttttt gtcttgtttg ttttaatatc tagtgatcta   4140

ataaatttgg atgatatctt ttgactatc                                      4169
```

<210> SEQ ID NO 16
<211> LENGTH: 714
<212> TYPE: DNA
<213> ORGANISM: Homo sapiens

<400> SEQUENCE: 16

```
gtcgccatgg gccgccgccc cgcccgttgt taccggtatt gtaagaacaa gccgtaccca     60

aagtctcgct tctgccgagg tgtccctgat gccaagattc gcatttttga cctggggcgg    120

aaaaaggcaa aagtggatga gtttccgctt tgtggccaca tggtgtcaga tgaatatgag    180

cagctgtcct ctgaagccct ggaggctgcc cgaatttgtg ccaataagta catggtaaaa    240

agttgtggca aagatggctt ccatatccgg gtgcggctcc acccccttcca cgtcatccgc    300

atcaacaaga tgttgtcctg tgctggggct gacaggctcc aaacaggcat gcgaggtgcc    360

tttggaaagc cccagggcac tgtggccagg gttcacattg gccaagttat catgtccatc    420

cgcaccaagc tgcagaacaa ggagcatgtg attgaggccc tgcgcagggc caagttcaag    480

tttcctggcc gccagaagat ccacatctca aagaagtggg gcttcaccaa gttcaatgct    540

gatgaatttg aagacatggt ggctgaaaag cggctcatcc cagatggctg tggggtcaag    600

tacatcccca gtcgtggccc tctggacaag tggcgggccc tgcactcatg agggcttcca    660

atgtgctgcc cccctcttaa tactcaccaa taaattctac ttcctgtcca ccta          714
```

<210> SEQ ID NO 17
<211> LENGTH: 1652
<212> TYPE: DNA
<213> ORGANISM: Homo sapiens

<400> SEQUENCE: 17

```
ccgtgtgggg tcagggcgct tgagttccac gacaccgtca ccggttcggg aaagtagtcc     60

ttgaccaggc agcccagggc cgcttgtgcc cccagaggtg ctcttggagg agggtgccag    120

gggaaagacc gatgggccct tggtggaggc tgaggagacg gtgacctcgt gccgaattcg    180

gcacgagccc cgatccagaa tggcttcatg aaaggagaaa actttgaagt agggtccaag    240

gttcagtttt tctgtaatga gggttatgag cttgttggtg acagttcttg gacatgtcag    300

aaatctggca aatggaataa gaagtcaaat ccaaagtgca tgcctgccaa gtgcccagag    360

ccgcccctct tggaaaacca gctagtatta aaggagttga ccaccgaggt aggagttgtg    420

acattttcct gtaaagaagg gcatgtcctg caaggcccct ctgtcctgaa atgcttgcca    480

tcccagcaat ggaatgactc tttccctgtt tgtaagattg ttctttgtac cccacctccc    540

ctaatttcct ttggtgtccc cattccttct tctgctcttc attttggaag tactgtcaag    600

tattcttgtg taggtgggtt tttcctaaga ggaaattcta ccaccctctg ccaacctgat    660

ggcacctgga gctctccact gccagaatgt gttccagtag aatgtcccca acctgaggaa    720

atccccaatg gaatcattga tgtgcaaggc cttgcctatc tcagcacagc tctctatacc    780

tgcaagccag gctttgaatt ggtgggaaat actaccaccc tttgtggaga aaatggtcac    840

tggcttggag gaaaaccaac atgtaaagcc attgagtgcc tgaaacccaa ggagattttg    900

aatggcaaat tctcttacac ggacctacac tatggacaga ccgttaccta ctcttgcaac    960

cgaggctttc ggctcgaagg tcccagtgcc ttgacctgtt tagagacagg tgattgggat   1020

gtagatgccc catcttgcaa tgccatccac tgtgattccc cacaacccat tgaaaatggt   1080

tttgtagaag gtgcagatta cagctatggt gccataatca tctacagttg cttccctggg   1140

tttcaggtgg ctggtcatgc catgcagacc tgtgaagagt caggatggtc aagttccatc   1200

ccaacatgta tgccaataga ctgtggcctc cctcctcata tagattttgg agcttgtact   1260

aaactcaaag atgccaggga tattttgagc aagaagcgac atgatggaag ttccatatgt   1320

gactcctcac cctccttatc atttggagca gtggctaaaa cctgggaaaa tacaaaggag   1380

tctcctgcta cacattcatc aaactttctg tatggtacca tggtttcata cacctgtaat   1440

ccaggatatg aacttctggg gaaccctgtg ctgatctgcc aggaagatgg aacttggaat   1500

ggcagtgcac catcctgcat ttcaattgaa tgtgacttgc ctactgctcc tgaaaatggc   1560

tttttgcgtt ttacagagac tagcatggga agtgctgtgc agtatagctg taaacctgga   1620

cacattctag caggctctga cttaaggctt tg                                 1652
```

<210> SEQ ID NO 18
<211> LENGTH: 443
<212> TYPE: DNA
<213> ORGANISM: Homo sapiens

<400> SEQUENCE: 18

```
ccacgcccgg ccccggagca ggcttttacg catgccccgc gcgcccccctt gtgtccggaa     60

tttattcctt ccggtgggtt cgcggtctag ctgaccaaga acggaactgg ggactttcgc    120

agtgagagtt acagctctta aagatggcac cgacccaggc cgggcgcggt ggctcaggcc    180

tgcaatccca gcactttggg aggcggaggc aggtgaatca cgaggtcagg aaatcgagac    240

catcctggct aacatggtga aaccccgtct ccactaaaaa tacaaaaaat tagccaggca    300

tggtggctgg cacctgtagt cccagctact tgggaggctg agccaggaaa gtggcatgaa    360
```

-continued

```
cccgcgaggc agagcttgca ataagccgag atcgtgccaa tgcactccag cctgggcaac    420

agaaggagac actgtctcaa aaa                                            443


<210> SEQ ID NO 19
<211> LENGTH: 2356
<212> TYPE: DNA
<213> ORGANISM: Homo sapiens

<400> SEQUENCE: 19

ggcacgaggc gaggctcaag cgggcctctg cccccacctt cgataacgac tacagcctct     60

ccgagcttct ctcacagctg gactctggag tttcccaggc tgtcgagggc cccgaggagc    120

tcagccgcag ctcctctgag tccaagctgc catcgtccgg cagtgggaag aggctctcgg    180

gggtgtcctc ggtggactcc gccttctctt ccagaggatc actgtcgctg tcctttgagc    240

gggaaccttc aaccagcgat ctgggtacca cagacgtcca gaagaagaag cttgtggatg    300

ccatcgtgtc cggggacacc agcaaactga tgaagatcct gcagccgcag gacgtggacc    360

tggcactgga cagcggtgcc agcctgctgc acctggcggt ggaggccggg caagaggagt    420

gcgccaagtg gctgctgctc aacaatgcca accccaacct gagcaaccgt aggggctcca    480

ccccgttgca catggccgtg gagaggaggg tgcggggtgt cgtggagctc ctgctggcac    540

ggaagatcag tgtcaacgcc aaggatgagg accagtggac agccctccac tttgcagccc    600

agaacgggga tgagtctagc acacggctgc tgttggagaa gaacgcctcg gtcaacgagg    660

tggactttga gggccggacg cccatgcacg tggcctgcca gcacgggcag gagaatatcg    720

tgcgcatcct gctgcgccga ggcgtggacg tgagcctgca gggcaaggat gcctggctgc    780

actgcactac gctgctggca gggccacctg cccatcgtca agctgctggc caagcagccg    840

ggggtgagtg tgaacgccca gacgctggat gggaggacgc cattgcacct ggccgcacag    900

cgcgggcact accgcgtggc ccgcatcctc atcgacctgt gctccgacgt caacgtctgc    960

agcctgctgg cacagacacc cctgcacgtg gcccgcggag acggggcaca cgagcactgc   1020

caggctgctc ctgcatcggg gcgctggcaa ggaggccgtg acttcagacg gctacaccgc   1080

tctgcacctg gctgccgcaa cggacacctg gccactgtca agctgcttgt cgaggagaag   1140

gccgaagctg gctcaggtgc acatgcccgc tccatcatcg atctaggcac ctgctgtctg   1200

aagggaccgt gggtcagaat catttcgttg tgctcctaat gggtcgctga ggctggtctc   1260

tcaatgatga agccccagcg tggaagcatc cactctctcc tgaggcgagc caccttgggt   1320

tgctggagct caccagtctt gagggaggtg caggggaaac tgtgtttttt atcttcatac   1380

atgacggtgg gcagagaggc ctgtcttaaa gtttccatgg aattgtttta taaaatatct   1440

taagagatga ataccttatc agctgttgct tgaaacctgt taaaaatgtt cataacattg   1500

gatagtctag tctctaaatg atggctaagt agtggggttg gctttgaaaa caatgtttta   1560

tgcaacaagg aacgaatggt agcagccagc tttgcggggc gtatgtgtgg ccagctctta   1620

accattccag tctattactt gggtgagtcc ttgtggacaa ccacacacac gtgcccacat   1680

ggtactagct gccgttcgtt tctcgttgcc taagatgttt tggcaactct agactcgagc   1740

aagcttatgc atgcatgcgg ccgcaattcg agctcggccg acttggccaa ttcgccctat   1800

agtgagtcgt ataagccgaa ttccagcaca ctggcggccg ttactagtgg atccgagctc   1860

ggtaccaagc ttggcgtaat catggtcata gctgtttcct gtgtgaaatt gttatccgct   1920

cacaattcca cacaacatac gagccggaag cataaagtgt aaagcctggg gtgcctaatg   1980

agtgagctaa ctcacattaa ttgcgttgcg ctcactgccc gctttccagt cgggaaacct   2040
```

gtcgtgccag ctgcattaat gaatcggcca acgcgcgggg agaggcggtt tgcgtattgg 2100
gcgctcttcc gcttcctcgc tcactgactc gctgcgctcg gtcgttcggc tgcggcgagc 2160
ggtatcagct cactcaaagg cggtaatacg gttatccaca gaatcagggg ataacgcagg 2220
aaagaacatg tgagcaaaag gccagcaaaa ggccaggaac cgtaaaaagg ccgcgttgct 2280
ggcgtttttt cataggctcc gcccccctgac gagcatcaca aaaatcgacg ctcaagtcag 2340
aggtggcgaa acccg 2356

<210> SEQ ID NO 20
<211> LENGTH: 567
<212> TYPE: DNA
<213> ORGANISM: Homo sapiens

<400> SEQUENCE: 20
ataatttgtt tcattttcaa ggcacaaaga gtttatgtca atcattttaa tgtctaagaa 60
tacaaagtta gcactagtaa catctggtag tctaatcatt tatcatgctt aaatgtaaca 120
ttacaaacta cattttaaaa tctgcccccct aaccagatgt gaaacaacgt ggacaagggt 180
gacatgtgct agacccaatc tccaaaaacg tatggttgac aaagacagct gactgctggg 240
gtaaaactgc agcagtcata atcgaagagc gaaagaggcc actctattaa agactttgtt 300
tcttttgcta gacatttttc acctaatccc aggatagttt ctgttaatgc atcttactct 360
ctttcaaacg aatcgtccct agagcaggtg tacacattaa aaatgagctt tatagcatca 420
aacacatacc acaaccaact ctacaaggag ggtttctgt aagatgtgta cgactgtccg 480
aagaacacat tctggctgat aagtctcaag ctcctgtgag gtcctgatga gtatctaaac 540
aacctcacat tttctcttcc acgccta 567

<210> SEQ ID NO 21
<211> LENGTH: 723
<212> TYPE: DNA
<213> ORGANISM: Homo sapiens

<400> SEQUENCE: 21
cctatgaagt gctgtcttgt atcccagccc ccagccttcc ttataaccaa ccaggaatat 60
gttacactct tgttcgtttg cctgatgatg accctacagc agttgcaggc tcctttagct 120
gcaccatgaa gtttacagtc cgggactgtg accctaacac tggagttcca gatgaggatg 180
ggtatgatga tgagtatgtg ctggaagatc tcgaagtgac tgtgtctgac catattcaga 240
aagtactgaa gcctaacttt gctgctgctt gggaagaggt gggagatacc tttgagaaag 300
aggaaacctt tgccctcagt tctaccaaaa cccttgaaga ggctgtcaac aatatcatca 360
catttctggg catgcagcca tgtgagaggt ccgataaagt acctgagaac aagaattccc 420
attcgctcta tctggcaggt atattcagag gtggctatga tttattggtg aggtccaggc 480
tggccttagc cgatggagtg accatgcagg tgactgtcag aagtaaagag agaacacctg 540
tagatgttat cttagcttct gttggataaa tgcttactgg acaagaggaa actgatgcac 600
actacatggt cagtgggctt ttaggctagt ggcatcagtt tcccagaatc agactttga 660 agatgaatga ctttggagaa gcaaaattaa acatttggcc ctgagccaca gatcaagcca 720
aaa 723

<210> SEQ ID NO 22
<211> LENGTH: 1049
<212> TYPE: DNA

<213> ORGANISM: Homo sapiens

<400> SEQUENCE: 22

```
caaggaccaa gttaacttat caccaaagct gattcagcca ggaacgttta ctaaaacaaa     60
agaagacatt ttagaatcta aatctgaaca aactaaaagt aagcaaagag atacacaaga    120
aagaaaaaga gaagagaaaa gaaaagctaa caggagaaaa tcaaaacgta tgtcaaaata    180
taaagagaat aaaagcgaaa ataaaaaaac tgttccccaa aaaaaaatgc acaaatctgt    240
cagttccaat gatgcttaca attttaattt ggaagagggt gttcatctta ctcctttccg    300
acaaaaagtg agcaatgact ctaatagaga agaaaacaac gagtctgaag tgagcctctg    360
tgaatcaagt ggttcaggag atgattccga tgacctctat ttgcccactt gcaagtacat    420
tcagaatccc acgagcaatt cagatagacc agtcaccagg cctctagcta aaagagcact    480
gaaatacaca gatgaaaaag agacggaggg ttctaagcca acaaaaactc ctaccactac    540
accacctgaa actcagcagt cacctcatct tagcctgaag gatatcacca atgtctcctt    600
gtatcctgtt gtgaaaatca gaagactttc tctttctcca aaaaagaata aagcaagccc    660
agcagtggct ctgcctaaac gtaggtgcac agccagcgtg aactataagg agcccaccct    720
cgcttcgaaa ctgagaagag gggacccttt tacagatttg tgtttttga attctcctat    780
tttcaagcag aaaaaggatt tgagacgttc taaaaaaagt atgaaacaaa tacaatgaag    840
gttttgttgg atattgttta aattcaatct acacctcttt ctgttgcttc aggagaggat    900
ctgtaagagt acacaaacag agtgagccat tgccatagaa tattctcttg acaggaccct    960
agctcataaa catttcttca gaactatact tcaaatggga tgctttgtat taaaacttta   1020
ataaatttaa tttattttt cttttgaaa                                      1049
```

<210> SEQ ID NO 23
<211> LENGTH: 1636
<212> TYPE: DNA
<213> ORGANISM: Homo sapiens

<400> SEQUENCE: 23

```
ggctggcgtc ccctttccgg ccggtcccca tggaggcgct ggggaagctg aagcagttcg     60
atgcctaccc caagactttg gaggacttcc gggtcaagac ctgcgggggc gccaccgtga    120
ccattgtcag tggccttctc atgctgctac tgttcctgtc cgagctgcag tattacctca    180
ccacggaggt gcatcctgag ctctacgtgg acaagtcgcg gggagataaa ctgaagatca    240
acatcgatgt actttttccg cacatgcctt gtgcctatct gagtattgat gccatggatg    300
tggccggaga acagcagctg gatgtggaac acaacctgtt caagcaacga ctagataaag    360
atggcatccc cgtgagctca gaggctgagc ggcatgagct tgggaaagtc gaggtgacgg    420
tgtttgaccc tgactccctg gaccctgatc gctgtgagag ctgctatggt gctgaggcag    480
aagatatcaa gtgctgtaac acctgtgaag atgtgcggga ggcatatcgc cgtagaggct    540
gggccttcaa gaacccagat actattgagc agtgccggcg agagggcttc agccagaaga    600
tgcaggagca gaagaatgaa ggctgccagg tgtatggctt cttggaagtc aataaggtgg    660
ccggaaactt ccactttgcc cctgggaaga gcttccagca gtcccatgtg cacggtgagt    720
gatctgcact agctggggag atttagatgc tggccacctt cttggtgagc ttgagtggtc    780
ctcttctgcc tgctgctcat ttgtcttggg caaccatttg gccagagcag gccttcatct    840
cagggcagca gtttggcaca gtggctaaga gcacaggccg aggagccaga ctgcctgcat    900
tcagatacca gtttcagacc ttactggctg tgtgactttg agaaggtttc ttaatctttt    960
```

```
tgactcctgt tttctacttt ataaaatgtt gatgagggca cttatctcac agggtgtgtg   1020

tgcaggttaa agatgatagc acggagcctg gcttgtggta ggtacttgtt gaaatggtag   1080

ccccccgtgt ccgatgatga cctgtgcatg aggctttggg agaagcagag ctaggttgga   1140

gcacaggttc tgccacacct gggctatgtc atatttgggc cctatttagt tgcttcttct   1200

gtaaaatggg gatgatgata atagtaccca ctcacagggc tgttggggtg aacaaatgag   1260

atttattctc attcatttgt tcattcatgc attcacaaaa tatttagtaa tcacctacta   1320

gtctagttgc taagggtaca gtagtgaaca atctgtgccc tcagaacatt ctagtaaaga   1380

aatagacaat aagtatataa aatataaata gtccccaatt aacaatggtt cagcttgcaa   1440

tttttaactt catgatgggt attacatgca tttttcactt aacgatattt tctttttctt   1500

ttttgagaca gagtctcact ctgtcgccca ggctggagtg cagtggcatg atcttgactc   1560

actgcaacct ccacctcctg gattcaagtg attctcctac ctcagcctct tgagtagctg   1620

ggtgtacagg tgccgt                                                   1636
```

<210> SEQ ID NO 24
<211> LENGTH: 1844
<212> TYPE: DNA
<213> ORGANISM: Homo sapiens

<400> SEQUENCE: 24

```
ccggggattc agtcaagacc atcgccaagc tatgggatag taagatgttt gctgagatta     60

tgatgaagat tgaggagtat atcaagcaag caagccaaag cttcagaagt gatgggacca    120

gtggaggccg cgcctgaata ccgcgtcatc gtggatgcca acaacctgac cgtggagatc    180

gaaaacgagc tgaacatcat ccataagttc atccgggata agtactcaaa gagattccct    240

gaactggagt ccttggtccc caatgcactg attacatccg cacggtcaag gagctgggca    300

acagcctgga caagtgcaag aacaatgaga acctgcagca gatcctcacc aatgccacca    360

tcatggtcgt cagcgtcacc gcctccacca cccaggggca gcagctgtcg gaggaggagc    420

tggagcggct ggaggaggcc tgcgacatgg cgctggagct gaacgcctcc aagcaccgca    480

tctacgagta tgtggagtcc cggatgtcct tcatcgcacc caacctgtcc atcattatcg    540

gggcatccac ggccgccaag atcatgggtg tggcggcgg cctgaccaac ctctccaaga    600

tgcccgcctg caacatcatg ctgctcgggg cccagcgcaa gacgctgtcg ggcttctcgt    660

ctacctcagt gctgccccac accggctaca tctaccacag tgacatcgtg cagtccctgc    720

caccggatct gcggcggaaa gcggcccggc tggtggccgc caagtgcaca ctggcagccc    780

gtgtggacag tttccacgag agcacagaag ggaaggtggg ctacgaactg aaggatgaga    840

tcgagcgcaa attcgacaag tggcaggagc cgccgcctgt gaagcaggtg aagccgctgc    900

ctgcgcccct ggatggacag cggaagaagc gaggcggccg caggtgaggg gccctggggg    960

tccggtaggc atgggggtca tggaggggag aagccggcgt cctcctccca gccgactccc   1020

tggcgccgcc cacccacccg tccccaggta ccgcaagatg aaggagcggc tggggctgac   1080

ggagatccgg aagcaggcca accgtatgag cttcggagag atcgaggagg acgcctacca   1140

ggaggacctg ggattcagcc tgggccacct gggcaagtcg ggcagtgggc gtgtgcggca   1200

gacacaggta aacgaggcca ccaaggccag gatctccaag acgctgcagg tatgggccag   1260

acccaggtgg ggctggggac cgagggacac aaggtggggg gagcccagat cgcagcctcc   1320

ctgtcctccc cacagcggac cctgcagaag cagagcgtcg tatatggcgg gaagtccacc   1380
```

-continued

```
atccgcgacc gctcctcggg cacggcctcc agcgtggcct tcaccccact ccagggcctg   1440

gagattgtga acccacaggc ggcagagaag aaggtggctg aggccaacca gaagtatttc   1500

tccagcatgg ctgagttcct caaggtcaag ggcgagaaga gtggccttat gtccacctga   1560

atgactgcgt gtgtccaagg tggcttccca ctgaagggac acagaggtcc agtccttctg   1620

aagggctagg atcgggttct ggcagggaga acctgccctg ccactggccc cattgctggg   1680

actgcccagg gaggaggcct tggaagagtc cggcctggcc tcccccagga ccgagatcac   1740

cgcccagtat gggctagagc aggtcttcat catgccttgt cttttttaac tgagaaagga   1800

gattttttga aaagagtaca attaaaagga cattgtcaaa aaaa                    1844
```

```
<210> SEQ ID NO 25
<211> LENGTH: 3570
<212> TYPE: DNA
<213> ORGANISM: Homo sapiens
<220> FEATURE:
<221> NAME/KEY: Unsure
<222> LOCATION: (178)..(178)
<223> OTHER INFORMATION: n = a, c, g, or t
<220> FEATURE:
<221> NAME/KEY: Unsure
<222> LOCATION: (1943)..(1943)
<223> OTHER INFORMATION: n = a, c, g, or t
<220> FEATURE:
<221> NAME/KEY: Unsure
<222> LOCATION: (1973)..(1973)
<223> OTHER INFORMATION: n = a, c, g, or t
<220> FEATURE:
<221> NAME/KEY: Unsure
<222> LOCATION: (1981)..(1981)
<223> OTHER INFORMATION: n = a, c, g, or t
<220> FEATURE:
<221> NAME/KEY: Unsure
<222> LOCATION: (1997)..(1997)
<223> OTHER INFORMATION: n = a, c, g, or t
<220> FEATURE:
<221> NAME/KEY: Unsure
<222> LOCATION: (2027)..(2027)
<223> OTHER INFORMATION: n = a, c, g, or t
<220> FEATURE:
<221> NAME/KEY: Unsure
<222> LOCATION: (2029)..(2029)
<223> OTHER INFORMATION: n = a, c, g, or t
<220> FEATURE:
<221> NAME/KEY: Unsure
<222> LOCATION: (2032)..(2032)
<223> OTHER INFORMATION: n = a, c, g, or t
<220> FEATURE:
<221> NAME/KEY: Unsure
<222> LOCATION: (2058)..(2058)
<223> OTHER INFORMATION: n = a, c, g, or t
<220> FEATURE:
<221> NAME/KEY: Unsure
<222> LOCATION: (2069)..(2069)
<223> OTHER INFORMATION: n = a, c, g, or t
<220> FEATURE:
<221> NAME/KEY: Unsure
<222> LOCATION: (2072)..(2072)
<223> OTHER INFORMATION: n = a, c, g, or t
<220> FEATURE:
<221> NAME/KEY: Unsure
<222> LOCATION: (2081)..(2082)
<223> OTHER INFORMATION: n = a, c, g, or t
<220> FEATURE:
<221> NAME/KEY: Unsure
<222> LOCATION: (2087)..(2087)
<223> OTHER INFORMATION: n = a, c, g, or t
<220> FEATURE:
<221> NAME/KEY: Unsure
<222> LOCATION: (2090)..(2090)
<223> OTHER INFORMATION: n = a, c, g, or t
<220> FEATURE:
<221> NAME/KEY: Unsure
```

```
<222> LOCATION: (2116)..(2116)
<223> OTHER INFORMATION: n = a, c, g, or t
<220> FEATURE:
<221> NAME/KEY: Unsure
<222> LOCATION: (2128)..(2129)
<223> OTHER INFORMATION: n = a, c, g, or t
<220> FEATURE:
<221> NAME/KEY: Unsure
<222> LOCATION: (2134)..(2134)
<223> OTHER INFORMATION: n = a, c, g, or t
<220> FEATURE:
<221> NAME/KEY: Unsure
<222> LOCATION: (2159)..(2159)
<223> OTHER INFORMATION: n = a, c, g, or t
<220> FEATURE:
<221> NAME/KEY: Unsure
<222> LOCATION: (2173)..(2173)
<223> OTHER INFORMATION: n = a, c, g, or t
<220> FEATURE:
<221> NAME/KEY: Unsure
<222> LOCATION: (2181)..(2181)
<223> OTHER INFORMATION: n = a, c, g, or t
<220> FEATURE:
<221> NAME/KEY: Unsure
<222> LOCATION: (2185)..(2185)
<223> OTHER INFORMATION: n = a, c, g, or t
<220> FEATURE:
<221> NAME/KEY: Unsure
<222> LOCATION: (2194)..(2195)
<223> OTHER INFORMATION: n = a, c, g, or t
<220> FEATURE:
<221> NAME/KEY: Unsure
<222> LOCATION: (2203)..(2203)
<223> OTHER INFORMATION: n = a, c, g, or t
<220> FEATURE:
<221> NAME/KEY: Unsure
<222> LOCATION: (2210)..(2210)
<223> OTHER INFORMATION: n = a, c, g, or t
<220> FEATURE:
<221> NAME/KEY: Unsure
<222> LOCATION: (2218)..(2218)
<223> OTHER INFORMATION: n = a, c, g, or t
<220> FEATURE:
<221> NAME/KEY: Unsure
<222> LOCATION: (2220)..(2220)
<223> OTHER INFORMATION: n = a, c, g, or t
<220> FEATURE:
<221> NAME/KEY: Unsure
<222> LOCATION: (2238)..(2238)
<223> OTHER INFORMATION: n = a, c, g, or t
<220> FEATURE:
<221> NAME/KEY: Unsure
<222> LOCATION: (2306)..(2306)
<223> OTHER INFORMATION: n = a, c, g, or t
<220> FEATURE:
<221> NAME/KEY: Unsure
<222> LOCATION: (2310)..(2310)
<223> OTHER INFORMATION: n = a, c, g, or t
<220> FEATURE:
<221> NAME/KEY: Unsure
<222> LOCATION: (2330)..(2330)
<223> OTHER INFORMATION: n = a, c, g, or t
<220> FEATURE:
<221> NAME/KEY: Unsure
<222> LOCATION: (2526)..(2526)
<223> OTHER INFORMATION: n = a, c, g, or t

<400> SEQUENCE: 25

ccattgcaca cagacaggca gcatggctag caaacgaaaa tctacaactc catgcatggt      60

tcggacatca caagtagtag aacaagatgt gcccgaggca agtagacagg gccaaagaga     120

aaggaatcgg cacaccacag cctgacgtgg ccaaggacag ttgggcanca gaacttgaaa     180

actcttccaa agaaaacgaa gtgatagagg tgaaatctat gggggaaagc cagtccaaaa     240

aactccaagg tggttatgag tgcaaatact gcccctactc cacgcaaaac ctgaacgagt     300
```

-continued

```
tcacggagca tgtcgacatg cagcatccca acgtgattct caaccccctc tacgtgtgtg    360
cagaatgtaa cttcacaacc aaaaagtacg actccctatc cgaccacaac tccaagttcc    420
atcccgggga ggccaacttc aagctgaagt taattaaacg caataatcaa actgtcttgg    480
aacagtccat cgaaaccacc aaccatgtcg tgtccatcac caccagtggc cctggaactg    540
gtgacagtga ttctgggatc tcggtgagta aaaccccccat catgaagcct ggaaaaccaa    600
aagcggatgc caagaaggtg cccaagaagc ccgaggagat cacccccgag aaccacgtgg    660
aagggaccgc ccgcctggtg acagacacag ctgagatcct ctcgagactc ggcggggtgg    720
agctcctcca agacacatta ggacacgtca tgccttctgt acagctgcca ccaaatatca    780
accttgtgcc caaggtccct gtcccactaa atactaccaa atacaactct gccctggata    840
caaatgccac gatgatcaac tctttcaaca agtttcctta cccgacccag gctgagttgt    900
cctggctgac agctgcctcc aaacacccag aggagcacat cagaatctgg tttgccaccc    960
agcgcttaaa gcatggcatc agctggtccc cagaagaggt ggaggaggcc cggaagaaga   1020
tgttcaacgg caccatccag tcagtacccc cgaccatcac tgtgctgccc gcccagttgg   1080
cccccacaaa gatgacgcag cccatcctcc agacggctct accgtgccag atcctcggcc   1140
agactagcct ggtgctgact caggtgacca gcgggtcaac aaccgtctct tgctccccca   1200
tcacacttgc cgtggcagga gtcaccaacc atggccagaa gagacccttg gtgactcccc   1260
aagctgcccc cgaacccaag cgtccacaca tcgctcaggt gccagagccc ccacccaagg   1320
tggccaaccc cccgctcaca ccagccagtg accgcaagaa gacaaaggag cagatagcac   1380
atctcaaggc cagctttctc cagagccagt tccctgacga tgccgaggtt taccggctca   1440
tcgaggtgac tggccttgcc aggagcgaga tcaagaagtg gttcagtgac caccgatatc   1500
ggtgtcaaag gggcatcgtc cacatcacca gcgaatccct tgccaaagac cagttggcca   1560
tcgcggcctc ccgacacggt cgcacgtatc atgcgtaccc agactttgcc ccccagaagt   1620
tcaaagagaa aacacagggt caggttaaaa tcttggaaga cagctttttg aaaagttctt   1680
ttcctaccca agcagaactg gatcggctaa gggtggagac caagctgagc aggagagaga   1740
tcgactcctg gttctcggag aggcggaagc ttcgagacag catggaacaa gctgtcttgg   1800
attccatggg gtctgggcaa aaaaggccaa gatgtgggaa gcccccaatg gtgctctgtc   1860
tcgactcgaa cagctctccg gtgcccagtt aacaagttct ctgcccagcc cttcgccagc   1920
aatttgcaaa aagtcaagaa cangttcatc tcctgaagga gcacgtttgc aanaaaccca   1980
nttgggctac tccccangag taacgaccag tttaaccggg ccaagancng gnctgggtcc   2040
cgaactgaaa attgtgcntt tgggttcang gngaacaaga nngcttnccn gaaaacgggg   2100
aaccgttaaa attggnttgg agcaaatnnc aagnaaccaa gcccaatggg caaaattgnt   2160
caacgggtta ccnaatgccg nttcnaaggg aaannacaaca aanacccaan ggccgganan  2220
gcccaaagaa acgggggntt aatgttggtt cccacaatta ttacaaggga cccccaaaaa   2280
agctcttgcg aaggaggact ttgganaaan tttgttgacc agggtaaaan tagggcaggg   2340
acccagcaaa aagactgttt tcccagcaaa gcccttcaga ggccaccttc agaccgttca   2400
gagggcagca gccgggacgg ccagggtagc gacgagaacg aggagtcgag cgttgtggat   2460
tacgtggagg tgacggtcgg ggaggaggat gccatcttca gatagatcag atagctggag   2520
tcaggntgcg gcagaaggtg tgtcggaact ggctgaatca gactccgact gcgtccctgc   2580
agaggctggc caggcctaga cagggaagtc tgttagaact gctgtgctga tcaacgggac   2640
gctccgtctt tgaagaaaga agagatggtc tctccccagc catgggccac ccttgccagt   2700
```

```
gactccaagt ggaactactt agctcgcgtg tgcctggagg gtgcgggaag tccagcgact   2760

ctcagacgca cctcccagag gaccggtggg aattgttcat agtgccaaag tcctactact   2820

gcgttttcaa tgggtccttg tacatagttt gctcctctgc cctagccctc acctcttgct   2880

atactggaac cgatttgtac aatgtgggaa ttttgttacc tttttaatca agggcaactt   2940

ccttttccag cactaccatt gtaaggtttt tttcaggagg gagggctaac caccttgctt   3000

ttctcttttc tctttttctt ttttttattt ttgttttatt aatttgggga aaggggtgtt   3060

agcattagtg ccatgatatc tactggattt taagtaggga gactttattt ttaaaggtag   3120

gttgaaattt gggagatttc tcggcaggaa gggctgaaat ccaggcccct gtctcaactt   3180

ggagagaggt gacagacggc agatcttcca aatcaaattc ctttccagtt cttcccctgg   3240

ctgccttttt gggggtccct gccttagccc cacacaaggc tttctgaact gccaagaggg   3300

gatctggctt ctcaactgct cggcctcttg ggccaggctg tgcccagcca gccctgggag   3360

aactgggtag caggtggctg acttctttaa gcacctttct aaataccagc agaagaggct   3420

cccgcctctg ttagcatgat cagtactatt gtgacattaa aacaacaaca ataagatctt   3480

cctatctgga gggtacagag gtgaatggct ttggttttca tttctctttc ttcactgctt   3540

ttctcggtgt ggtatttgac aagattttag                                    3570
```

<210> SEQ ID NO 26
<211> LENGTH: 2306
<212> TYPE: DNA
<213> ORGANISM: Homo sapiens

<400> SEQUENCE: 26

```
cgggccgccg ggacgggcac gggcgcgcgg gctccggcgg gcgccggctg ccttcctccg     60

tcgctcgctg tctctcccgg ccgcattctc ctccgctgcg gggccgagct ctccccagcg    120

ctcgcaggaa ggaagaaggg agccgaggac gccgagaagt tcccgcggca gccgcggatc    180

ccggccaagg cggaggctgc ggctccgacg gggcaggagc gcgatccacg gcgaggggcg    240

tacggccaaa gggtccgcgg cgtggagcgc tcggaccttc cgctctcccc cgggcgtggg    300

ccgggacccc atgagacgcg cccacgaggg gcgcgagatt cctagcttgg gcggcgctag    360

gcggagggag gtgttgcagg ccggccggag ccagagagct gccggcagga ggcggcggcg    420

gcaagaactt gaacttggcg tcgggagcgg gcgccccgga ggccccccgc cggggccggg    480

gcgccgaggg acctgcgccg cagcgctgcc ccccgaatgg ccgcggcggc ggaccgggct    540

cccgcgccgc ggccctaggc cgcctctcgc catggccaag tggctaaaca agtacttcag    600

cttgggcaac agcaagacca agagcccccc gcagccgccg cggccagact accgcgagca    660

gcggcgccga ggcgagcggc cttcgcagcc cccccaggcc gtgccgcagg cctcctccgc    720

cgcctcggcg tcctgcggtc cggccaccgc ctcctgcttc tcagcctctt cgggctcgct    780

gcccgacgac agcggcagca ccagcgacct catccgcgcc taccgcgcgc agaaggagcg    840

acacttccag gaccccctaca acgggcctgg ctcgtcgctg cgcaaactgc gcgccatgtg    900

ccgcctggac tactgcggcg gcagcgggga gccaggcggg gtccagcgcg ccttctcggc    960

ctcgtccgcg tcgggcgccg cgggctgttg ctgcgcctcc tcgggcgcgg gcgccgccgc   1020

gtcctcgtcc tcgtcctccg gctctccgca tctctaccgc agcagcagcg agcggcggcc   1080

cgccacgccg gccgaggtgc gctacatctc ccccaagcac cgcctcatca aagtggagag   1140

cgccgcgggc ggtggggccg gggacccccct gggggcgcc tgcgcgggcg gccgcacctg   1200
```

-continued

```
gagcccgacg gcctgcggag gcaagaaact gctcaacaag tgcgccgcct cagccgcgga   1260

ggagagcggg gccggcaaga aggacaaggt gaccatagcc gatgactact cagatccctt   1320

tgatgccaag aatgatctca agagcaaagc aggaaagggg gagagtgctg gctacatgga   1380

gccctatgag gcacagagga tcatgacaga atttcagagg caggaaagtg tccggtccca   1440

gcataaaggt atccagttat atgacacccc ttacgaacct gaaggccaaa gtgttgactc   1500

ggactcggag agcacagtca gcccccgact gcgggagagc aagctgcccc aggatgacga   1560

caggcccgcc gatgagtacg accagccttg ggagtggaac cgggtcacca gcccagccct   1620

ggcagcacag tttaatggca acgagaagcg gcagtcatcc ccctcacctt cgcgggaccg   1680

gcggcgccag cttcgtgccc ctggaggggg ctttaagcct atcaaacatg ggagccctga   1740

gttctgcggg atcctaggag aaagggtgga tcctgccgtc cccctggaga agcaaatatg   1800

gtatcacgga gccatcagca gaggagacgc cgagaacctg ctgcgactct gcaaggagtg   1860

tagctacctt gtccggaaca gccagaccag caagcatgac taccccctct ccctgaggag   1920

caaccagggt tttatgcaca tgaaactggc caaaaccaaa gagaaatacg ttctgggtca   1980

gaacagccct ccgttcgaca gtgtcccgga agtcatccac tactacacca ccagaaagct   2040

acccatcaaa ggggctgagc acttgtccct cctctatccc gtggctgtga ggaccctgtg   2100

agcggaccag acctgccctg ctctgtgaca gagcctggag acttggaggt gccagaggcc   2160

ccccaccaac cagcccccag ccactgttgc tggctgtgtc gtttgtgttg tgtgtatggt   2220

actagcacac cactgcatgt ctctagaatg ctgttgccac ttacgggggc tggaggcctg   2280

gataaagaca gaagggcggc aacacc                                        2306
```

```
<210> SEQ ID NO 27
<211> LENGTH: 1532
<212> TYPE: DNA
<213> ORGANISM: Homo sapiens

<400> SEQUENCE: 27

aagccatggg tagctgttgt agctgtccag ataaagacac tgtcccagat aaccatcgga     60

acaagtttaa ggtcattaat gtggatgatg atgggaatga gttaggttct ggcataatgg    120

aacttacaga cacagaactg attttataca cccgcaaacg tgactcagta aaatggcact    180

acctctgcct gcgacgctat ggctatgact cgaatctctt ttcttttgaa agtggtcgaa    240

ggtgtcaaac tggacaagga atctttgcct ttaagtgtgc ccgtgcagaa gaattattta    300

acatgttgca agagattatg caaaataata gtataaatgt ggtggaagag ccagttgtag    360

aaagaaataa tcatcagaca gaattggaag tccctagaac acctcgaaca cctacaactc    420

caggatttgc tgctcagaac ttacctaatg gatatccccg atatccctca tttggagatg    480

cttcatccca tccgtcaagc agacatcctt ctgtgggaag tgctcgcctg ccttcagtag    540

gggaagaatc tacacatcct ttgcttgtgg ctgaggaaca agtacatacc tatgtcaaca    600

ctacaggtgt gcaagaagag cggaaaaacc gcacaagtgt gcatgttcca ttggaggcaa    660

gggtttctaa cgctgaaagc agcacaccaa aagaagaacc aagtagtatt gaggacaggg    720

atcctcagat tcttcttgaa cctgaaggag tcaaatttgt tttagggcca acccctgttc    780

aaaagcagtt aatggaaaaa gagaaactgg agcaacttgg aagagatcaa gttagtggaa    840

gtggagcaaa taacacagaa tgggacactg gctatgacag tgatgaacga agagatgcac    900

cctctgttaa caaactggtg tatgaaaata taaatgggct atctatccct agtgcctcag    960

gggtcaggag aggtcgtctg acatccacca gtacctcaga tacccagaat atcaacaact   1020
```

```
cagctcagag aagaactgca ttattaaact atgaaaatct accatctttg cctcctgttt   1080

gggaagcccg caagctaagt agggatgaag atgacaattt aggaccaaag accccatctc   1140

taaatggcta ccataataat ctagatccaa tgcataacta tgtaaataca gagaatgtaa   1200

cagtgccagc aagtgctcac aaaatagaat attcaaggcg tcgggactgt acaccaacag   1260

tctttaactt tgatatcaga cgcccaagtt tagaacacag gcagcttaat tacatacagg   1320

ttgacttgga aggtggcagt gactctgaca accctcagac tccaaaaacg cctacaactc   1380

cccttccaca aacccctacc aggcgcacag agctgtatgc cgtgatagac atcgagagaa   1440

ctgctgctat gtcaaatttg cagaaagcac tgccacgaga tgatggtaca tctaggaaaa   1500

ctagacacaa tagtactgat ctgcccatgt ga                                 1532
```

<210> SEQ ID NO 28
<211> LENGTH: 2308
<212> TYPE: DNA
<213> ORGANISM: Homo sapiens

<400> SEQUENCE: 28

```
gaattcgggc gagcgggact ggctgggtcg gctgggctgc tggtgcgagg agccgcgggg     60

ctgtgctcgg cggccaaggg gacagcgcgt gggtggccga ggatgctgcg gggcggtagc    120

tccggcgccc ctagctggtg actgctgcgc cgtgcctcac acagccgagg cgggctcggc    180

gcacagtcgc tgctccgcgc gcgcgcccgg cggcgctcca ggtgctgaca gcgcgagaga    240

gcgcggccct caggagcaag gcgaatgtat gacaccatgt ccacaatggt gtacataaag    300

gaagacaagt tggagaagct tacacaggat gaaattattt ctaagacaaa gcaagtaatt    360

caggggctgg aagctttgaa gaatgagcac aattccattt tacaaagttt gctggagaca    420

ctgaagtgtt tgaagaaaga tgatgaaagt aatttggtgg aggagaaatc aaacatgatc    480

cggaagtcac tggagatgtt ggagctcggc ctgagtgagg cacaggttat gatggctttg    540

tcaaatcacc tgaatgctgt ggagtccgag aagcagaaac tgcgtgcgca ggttcgtcgt    600

ctgtgccagg agaatcagtg gctacgggat gaactggcca acacgcagca gaaactgcag    660

aagagtgagc agtctgtggc tcaactggag gaggagaaga agcatctgga gtttatgaat    720

cagctaaaaa aatatgatga cgacatttcc ccatccgagg acaaagacac tgattctacc    780

aaagagcctc tggatgacct tttccccaat gatgaagacg acccagggca aggaatccag    840

cagcagcaca gcagtgcagc cgcggctgcc cagcagggcg gctacgagat ccccgcgcgg    900

ctgcggacgc tccacaacct ggtgatccag tacgcctcgc aggggcgcta cgaggtagct    960

gtgcccctct gcaagcaggc cctggaggac ctggagaaga cttcaggaca cgaccacccg   1020

gacgtggcca ccatgctcaa catcctggcc ttggtgtaca gggatcagaa taaatacaaa   1080

gatgcagcta acctactgaa tgatgccttg gctattcgtg agaaaacttt gggcaaagat   1140

catcctgcgg tggcggcgac tttgaataac cttgcagtcc tttatggtaa aagagggaag   1200

tacaaagaag cagagccgtt gtgtaaaaga gctctggaaa tccgagaaaa ggttttgggg   1260

aaggatcacc ccgatgttgc caagcagtta aataacttgg ccttactgtg ccagaaccag   1320

ggcaagtatg aagaagtaga atattattat caaagagccc tcgagatcta ccagacaaaa   1380

ctgggacctg atgaccccaa cgtggctaag acgaaaaata acctggcatc ctgctatttg   1440

aaacaaggaa agttcaagca agcagaaaca ctgtacaaag agattctcac tcgtgcacat   1500

gaaagggagt ttggttctgt agatgatgaa aataaaccca tctggatgca tgctgaagaa   1560
```

-continued

```
agagaagaat gcaaaggaaa gcaaaaggat gggacatctt ttggagagta tggcggctgg   1620

tacaaagcct gcaaagttga tagtccaact gttacaacca ctctaaaaaa ccttggggca   1680

ctttacagac gtcaaggcaa atttgaagct gcagaaacgt tagaagaagc tgctatgagg   1740

tctcgtaaac agggtcttga caatgttcac aaacagaggg tggcagaagt gctcaatgac   1800

cctgagaaca tggagaagcg caggagccgt gagagcctca acgtggacgt ggtcaagtac   1860

gagagtggcc ctgacggagg ggaggaagtg agtatgagcg tagagtggaa cgggggcgtc   1920

tctggccgag cctctttttg tggaaaacga cagcagcagc agtggcctgg aagacgccac   1980

cgctaactga ccccgacctg gccccgctcc aggatgggac tgccgagtgt ggcccggagc   2040

tggcccggga cagccagggc ggcagggagg cccctggccg ggagcgcagc gctcactcat   2100

ttctcctgcg tctgtgtgca taggacatga tactaataac cacacggctg gcgtgacctt   2160

ggggctgggg ctgggcctaa gctggtgccc tggtgcggcg tggtctctcc caggagacct   2220

ggggcatgag ctgggcccac ggctcccttc ccatgtgtaa cttcctcacg ttgtgtgcga   2280

taacgtattt tattgtacac ccgaattc                                      2308
```

<210> SEQ ID NO 29
<211> LENGTH: 750
<212> TYPE: DNA
<213> ORGANISM: Homo sapiens

<400> SEQUENCE: 29

```
atcctcgtgg gccctgacct tctctctgag agccgggcag aggctccgga gccatgcagg     60

ccgaaggcca gggcacaggg ggttcgacgg gcgatgctga tggcccagga ggccctggca    120

ttcctgatgg cccagggggc aatgctggcg gcccaggaga ggcgggtgcc acgggcggca    180

gaggtccccg gggcgcaggg gcagcaaggg cctcggggcc gagaggaggc gccccgcggg    240

gtccgcatgg cggtgccgct tctgcgcagg atggaaggtg cccctgcggg gccaggaggc    300

cggacagccg cctgcttcag ttgcacatca cgatgccttt ctcgtcgccc atggaagcgg    360

agctggtccg caggatcctg tcccgggatg ccgcacctct cccccgacca ggggcggttc    420

tgaaggactt caccgtgtcc ggcaacctac tgtttatccg actgactgct gcagaccacc    480

gccaactgca gctctccatc agctcctgtc tccagcagct ttccctgttg atgtggatca    540

cgcagtgctt tctgcccgtg tttttggctc aggctccctc agggcagagg cgctaagccc    600

agcctggcgc cccttcctag gtcatgcctc ctcccctagg gaatggtccc agcacgagtg    660

gccagttcat tgtgggggcc tgattgtttg tcgctggagg aggacggctt acatgtttgt    720

ttctgtagaa aataaagctg agctacgaaa                                     750
```

<210> SEQ ID NO 30
<211> LENGTH: 1560
<212> TYPE: DNA
<213> ORGANISM: Homo sapiens

<400> SEQUENCE: 30

```
ccctgagtca ctgcctgcgc acgtccggcc gcctggctcc ccatactagt cgccgatatt     60

tggagttctt acaacatggc agacattgac aacaaagaac agtctgaact tgatcaagat    120

ttggatgatg ttgaagaagt agaagaagag gaaactggtg aagaaacaaa actcaaagca    180

cgtcagctaa ctgttcagat gatgcaaaat cctcagattc ttgcagccct tcaagaaaga    240

cttgatggtc tggtagaaac accaacagga tacattgaaa gcctgcctag ggtagttaaa    300

agacgagtga atgctctcaa aaacctgcaa gttaaatgtg cacagataga agccaaattc    360
```

```
tatgaggaag ttcatgatct tgaaaggaag tatgctgttc tctatcagcc tctatttgat    420

aagcgatttg aaattattaa tgcaatttat gaacctacgg aagaagaatg tgaatggaaa    480

ccagatgaag aagatgagat ttcggaggaa ttgaaagaaa aggccaagat tgaagatgag    540

aaaaaggatg aagaaaaaga agaccccaaa ggaattcctg aattttggtt aactgttttt    600

aagaatgttg acttgctcag tgatatggtt caggaacacg atgaacctat tctgaagcac    660

ttgaaagata ttaaagtgaa gttctcagat gctggccagc ctatgagttt tgtcttagaa    720

tttcactttg aacccaatga atattttaca aatgaagtgc tgacaaagac atacaggatg    780

aggtcagaac cagatgattc tgatcccttt tcttttgatg gaccagaaat tatgggttgt    840

acagggtgcc agatagattg gaaaaaagga aagaatgtca ctttgaaaac tattaagaag    900

aagcagaaac acaagggacg tgggacagtt cgtactgtga ctaaaacagt ttccaatgac    960

tctttcttta actttttgc ccctcctgaa gttcctgaga gtggagatct ggatgatgat    1020

gctgaagcta tccttgctgc agacttcgaa attggtcact tttacgtgga gcgtataatc    1080

ccaagatcag tgttatattt tactggagaa gctattgaag atgatgatga tgattatgat    1140

gaagaaggtg aagaagcgga tgaggaaggg gaagaagaag gagatgagga aaatgatcca    1200

gactatgacc caaagaagga tcaaaaccca gcagagtgca agcagcagtg aagcaggatg    1260

tatgtggcct tgaggataac ctgcactggt ctaccttctg cttccctgga aaggatgaat    1320

ttacatcatt tgacaagcct attttcaagt tatttgttgt ttgtttgctt gtttttgttt    1380

ttgcagctaa aataaaaatt tcaaatacaa ttttagttct tacaagataa tgtcttaatt    1440

ttgtaccaat tcaggtagaa gtagaggcct accttgaatt aagggttata ctcagttttt    1500

aacacattgt tgaagaaaag gtaccagctt tggaacgaga tgctatacta ataagcaagt    1560
```

<210> SEQ ID NO 31
<211> LENGTH: 1139
<212> TYPE: DNA
<213> ORGANISM: Homo sapiens

<400> SEQUENCE: 31

```
ccggcggcgc ctcaggtcgc ggggcgccta ggcctgggtt gtccttcgca tctgcacgtg     60

ttcgcagtcg tttccgcgat gctgcctctg ctgcgctgcg tgccccgtgt gctgggctcc    120

tccgtcgccg gcctccgcgc tgccgcgccc gcctcgcctt tccggcagct cctgcagccg    180

gcaccccggc tgtgcacccg gcccttcggg ctgctcagcg tgcgcgcagg ttccgagcgg    240

cggccgggcc tcctgcggcc tcgcggaccc tgcgcctgtg gctgtggctg cggctcgctg    300

cacaccgacg gagacaaagc ttttgttgat ttcctgagtg atgaaattaa ggaggaaaga    360

aaaattcaga agcataaaac cctccctaag atgtctggag gttgggagct ggaactgaat    420

gggacagaag cgaaattagt gcggaaagtt gccggggaaa aatcacggt cactttcaac    480

attaacaaca gcatcccacc aacatttgat ggtgaggagg aaccctcgca agggcagaag    540

gttgaagaac aggagcctga actgacatca actcccaatt tcgtggttga agttataaag    600

aatgatgatg gcaagaaggc ccttgtgttg gactgtcatt atccagagga tgaggttgga    660

caagaagacg aggctgagag tgacatcttc tctatcaggg aagttagctt tcagtccact    720

ggcgagtctg aatggaagga tactaattat acactcaaca cagattcctt ggactgggcc    780

ttatatgacc acctaatgga tttccttgcc gaccgagggg tggacaacac ttttgcagat    840

gagctggtgg agctcagcac agccctggag caccaggagt acattacttt tcttgaagac    900
```

ctcaagagtt ttgtcaagag ccagtagagc agacagatgc tgaaagccat agtttcatgg 960
caggctttgg ccagtgaaca aatcctactc tgaagctaga catgtgcttt gaaatgatta 1020
tcatcctaat atcatggggg aaaaaatacc aaatttaaat tatatgtttt gtgttctcat 1080
ttattatcat ttttttctgt acaaatctat tatttctaga tttttgtata acatgataag 1139

<210> SEQ ID NO 32
<211> LENGTH: 4473
<212> TYPE: DNA
<213> ORGANISM: Homo sapiens

<400> SEQUENCE: 32
aaggggaggt aaccctggcc cctttggtcg gggccccggg cagccgcgcg ccccttccca 60
cggggccctt tactgcgccg cgcgcccggc ccccacccct cgcagcaccc cgcgccccgc 120
gccctcccag ccgggtccag ccggagccat ggggccggag ccgcagtgag caccatggag 180
ctggcggcct tgtgccgctg ggggctcctc ctcgccctct tgccccccgg agccgcgagc 240
acccaagtgt gcaccggcac agacatgaag ctgcggctcc ctgccagtcc cgagacccac 300
ctggacatgc tccgccacct ctaccagggc tgccaggtgg tgcagggaaa cctggaactc 360
acctacctgc ccaccaatgc cagcctgtcc ttcctgcagg atatccagga ggtgcagggc 420
tacgtgctca tcgctcacaa ccaagtgagg caggtcccac tgcagaggct gcggattgtg 480
cgaggcaccc agctctttga ggacaactat gccctggccg tgctagacaa tggagacccg 540
ctgaacaata ccacccctgt cacaggggcc tccccaggag gcctgcggga gctgcagctt 600
cgaagcctca cagagatctt gaaaggaggg gtcttgatcc agcggaaccc ccagctctgc 660
taccaggaca cgattttgtg gaaggacatc ttccacaaga acaaccagct ggctctcaca 720
ctgatagaca ccaaccgctc tcgggcctgc cacccctgtt ctccgatgtg taagggctcc 780
cgctgctggg gagagagttc tgaggattgt cagagcctga cgcgcactgt ctgtgccggt 840
ggctgtgccc gctgcaaggg gccactgccc actgactgct gccatgagca gtgtgctgcc 900
ggctgcacgg gccccaagca ctctgactgc ctggcctgcc tccacttcaa ccacagtggc 960
atctgtgagc tgcactgccc agccctggtc acctacaaca cagacacgtt tgagtccatg 1020
cccaatcccg agggccggta tacattcggc gccagctgtg tgactgcctg tccctacaac 1080
tacctttcta cggacgtggg atcctgcacc ctcgtctgcc ccctgcacaa ccaagaggtg 1140
acagcagagg atggaacaca gcggtgtgag aagtgcagca agccctgtgc ccgagtgtgc 1200
tatggtctgg gcatggagca cttgcgagag gtgagggcag ttaccagtgc caatatccag 1260
gagtttgctg gctgcaagaa gatctttggg agcctggcat ttctgccgga gagctttgat 1320
ggggacccag cctccaacac tgccccgctc cagccagagc agctccaagt gtttgagact 1380
ctggaagaga tcacaggtta cctatacatc tcagcatggc cggacagcct gcctgacctc 1440
agcgtcttcc agaacctgca agtaatccgg ggacgaattc tgcacaatgg cgcctactcg 1500
ctgaccctgc aagggctggg catcagctgg ctggggctgc gctcactgag ggaactgggc 1560
agtggactgg ccctcatcca ccataacacc cacctctgct tcgtgcacac ggtgccctgg 1620
gaccagctct ttcggaaccc gcaccaagct ctgctccaca ctgccaaccg gccagaggac 1680
gagtgtgtgg gcgagggcct ggcctgccac cagctgtgcg cccgagggca ctgctggggt 1740
ccagggccca cccagtgtgt caactgcagc cagttccttc ggggccagga gtgcgtggag 1800
gaatgccgag tactgcaggg gctccccagg gagtatgtga atgccaggca ctgtttgccg 1860
tgccaccctg agtgtcagcc ccagaatggc tcagtgacct gttttggacc ggaggctgac 1920

-continued

```
cagtgtgtgg cctgtgccca ctataaggac cctcccttct gcgtggcccg ctgccccagc   1980
ggtgtgaaac ctgacctctc ctacatgccc atctggaagt ttccagatga ggagggcgca   2040
tgccagcctt gccccatcaa ctgcacccac tcctgtgtgg acctggatga caagggctgc   2100
cccgccgagc agagagccag ccctctgacg tccatcatct ctgcggtggt tggcattctg   2160
ctggtcgtgg tcttgggggt ggtctttggg atcctcatca agcgacggca gcagaagatc   2220
cggaagtaca cgatgcggag actgctgcag gaaacggagc tggtggagcc gctgacacct   2280
agcggagcga tgcccaacca ggcgcagatg cggatcctga aagagacgga gctgaggaag   2340
gtgaaggtgc ttggatctgg cgcttttggc acagtctaca agggcatctg gatccctgat   2400
ggggagaatg tgaaaattcc agtggccatc aaagtgttga gggaaaacac atcccccaaa   2460
gccaacaaag aaatcttaga cgaagcatac gtgatggctg gtgtgggctc cccatatgtc   2520
tcccgccttc tgggcatctg cctgacatcc acggtgcagc tggtgacaca gcttatgccc   2580
tatggctgcc tcttagacca tgtccgggaa aaccgcggac gcctgggctc ccaggacctg   2640
ctgaactggt gtatgcagat tgccaagggg atgagctacc tggaggatgt gcggctcgta   2700
cacagggact tggccgctcg gaacgtgctg gtcaagagtc ccaaccatgt caaaattaca   2760
gacttcgggc tggctcggct gctggacatt gacgagacag agtaccatgc agatgggggc   2820
aaggtgccca tcaagtggat ggcgctggag tccattctcc gccggcggtt cacccaccag   2880
agtgatgtgt ggagttatgg tgtgactgtg tgggagctga tgacttttgg ggccaaacct   2940
tacgatggga tcccagcccg ggagatccct gacctgctgg aaaaggggga gcggctgccc   3000
cagcccccca tctgcaccat tgatgtctac atgatcatgg tcaaatgttg gatgattgac   3060
tctgaatgtc ggccaagatt ccgggagttg gtgtctgaat tctcccgcat ggccagggac   3120
ccccagcgct ttgtggtcat ccagaatgag gacttgggcc cagccagtcc cttggacagc   3180
accttctacc gctcactgct ggaggacgat gacatggggg acctggtgga tgctgaggag   3240
tatctggtac cccagcaggg cttcttctgt ccagaccctg ccccgggcgc tgggggcatg   3300
gtccaccaca ggcaccgcag ctcatctacc aggagtggcg gtggggacct gacactaggg   3360
ctggagccct ctgaagagga ggcccccagg tctccactgg caccctccga aggggctggc   3420
tccgatgtat ttgatggtga cctgggaatg gggggcagcca aggggctgca aagcctcccc   3480
acacatgacc ccagccctct acagcggtac agtgaggacc ccacagtacc cctgccctct   3540
gagactgatg gctacgttgc ccccctgacc tgcagccccc agcctgaata tgtgaaccag   3600
ccagatgttc ggccccagcc cccttcgccc cgagagggcc ctctgcctgc tgcccgacct   3660
gctggtgcca ctctggaaag gcccaagact ctctccccag ggaagaatgg ggtcgtcaaa   3720
gacgtttttg cctttggggg tgccgtggag aaccccgagt acttgacacc ccagggagga   3780
gctgcccctc agccccaccc tcctcctgcc ttcagcccag ccttcgacaa cctctattac   3840
tgggaccagg acccaccaga gcgggggct ccacccagca ccttcaaagg gacacctacg   3900
gcagagaacc cagagtacct gggtctggac gtgccagtgt gaaccagaag gccaagtccg   3960
cagaagccct gatgtgtcct cagggagcag ggaaggcctg acttctgctg gcatcaagag   4020
gtgggagggc cctccgacca cttccagggg aacctgccat gccaggaacc tgtcctaagg   4080
aaccttcctt cctgcttgag ttcccagatg gctggaaggg gtccagcctc gttggaagag   4140
gaacagcact ggggagtctt tgtggattct gaggccctgc ccaatgagac tctagggtcc   4200
agtggatgcc acagcccagc ttggcccttt ccttccagat cctgggtact gaaagcctta   4260
```

-continued

```
gggaagctgg cctgagaggg gaagcggccc taagggagtg tctaagaaca aaagcgaccc   4320

attcagagac tgtccctgaa acctagtact gccccccatg aggaaggaac agcaatggtg   4380

tcagtatcca ggctttgtac agagtgcttt tctgtttagt ttttactttt tttgttttgt   4440

ttttttaaag atgaaataaa gacccagggg gag                                4473
```

<210> SEQ ID NO 33
<211> LENGTH: 1608
<212> TYPE: DNA
<213> ORGANISM: Homo sapiens

<400> SEQUENCE: 33

```
gcttcaagag actcaaacta aaaatgactt tttgaaaagt gaggtacatg acctgcgagt     60

agtccttcat tctgctgaca aggagctttc ttcagtgaaa ttggaatata gttcattcaa    120

aacgaatcag gagaaagaat tcaacaaact ttccgaaaga cacatgcatg tacagcttca    180

attagataat ctcaggttag aaaacgaaaa gctgcttgag agcaaagcct gcctacagga    240

ttcctatgac aacttacaag aaataatgaa atttgagatt gaccaacttt caagaaacct    300

ccaaaacttc aaaaaagaaa atgaaactct gaaatctgat ctgaataatt tgatggagct    360

tcttgaggca gaaaaagaac gcaataacaa attatcatta cagtttgaag aagataaaga    420

aaacagttct aaagaaatct taaaagttct tgaggctgta cgtcaggaga aacagaaaga    480

gacggccaag tgtgagcagc agatggcaaa agtacagaaa ctagaagaga gcttgcttgc    540

tactgaaaaa gtgatcagtt ccctggaaaa gtctagagat tctgataaga aagttgtagc    600

tgacctcatg aaccagatcc aggagctaag aacatcggtc tgtgagaaaa cagaaactat    660

agacaccctg aaacaagaac tgaaggacat aaattgcaaa tacaactctg ctttggttga    720

cagagaagag agcagagtgt tgatcaagaa gcaggaagtg gatattctgg atctgaaaga    780

aacccttagg ctgagaatac tttctgagga cataaagagg gatatgctct gtgaggacct    840

gctcatgcca ctgacagctg acatgctcac agaggcctca aaaaaacact cgggctgctg    900

cagtctgccc aggaaagaac tgccaagaaa gaagccctga ttcaggaact tcagcacaag    960

ctaaaccaaa agaaagagga agtagaacag aagaagaatg aatataactt caaaatgagg   1020

caactagaac atgtgatgga ttctgctgct gaggatcccc agagtcctaa gacaccacct   1080

cactttcaaa cacatttggc aaaactcctg gaaacacaag aacaagagat agaagatgga   1140

agagcctcta agacttcttt ggaacacctt gtaacaaagc taaatgaaga cagagaagtc   1200

aaaaatgctg aaatcctcag aatgaaggag cagttgcgtg aaatggaaaa cctacgcatg   1260

gaaagtcagc agttaataga gaaaaactgg ctcctgcaag gtcagctgga tgatattaaa   1320

agacaaaagg aaaacagtga tcagaatcat ccagataatc aacagctgaa gaatgaacaa   1380

gaagaaagta tcaaagaaag acttgcaaaa agtaaaatag ttgaagaaat gctgaaaatg   1440

aaagcagacc tagaagaagt ccaaagtgcc ctttcaacaa agagatggaa tgccttagaa   1500

tgactgatga agtcgaacga acccaaactt tggagtctaa agcattccag gaaaaagaac   1560

aactgagatc aaagctggaa gaaatgtttg aagaaagaga gagaacat                1608
```

<210> SEQ ID NO 34
<211> LENGTH: 3247
<212> TYPE: DNA
<213> ORGANISM: Homo sapiens

<400> SEQUENCE: 34

```
gaggagctct gcgcggcgcg gcgggcgatc cgagccggga cgggctgcag gcgggggtgc     60
```

-continued

```
tgcagaggac acgaggcggc gggctggaga catggaccgc ggcgagcaag gtctgctgag    120
aacagaccca gtccctgagg aaggagaaga tgttgctgcc acgatcagtg ccacagagac    180
cctctcggaa gaggagcagg aagagctaag aagagaactt gcaaaggtag aagaagaaat    240
ccagactctg tctcaagtgt tagcagcaaa agagaagcat ctagcagaga tcaagcggaa    300
acttggaatc aattctctac aggaactaaa acagaacatt gccaaagggt ggcaagacgt    360
gacagcaaca tctgcttaca agaagacatc tgaaacctta tcccaggctg gacagaaggc    420
ctcagctgct ttttcgtctg ttggctcagt catcaccaaa aagctggaag atgtaaaaaa    480
ctccccaact tttaaatcat ttgaagaaaa ggtcgaaaac ttaaagtcta aagtaggggg    540
aaccaagcct gctggtggtg attttggaga agtcttgaat tcggctgcaa atgctagtgc    600
caccaccacg gagcctcttc cagaaaagac acaggagagc ctgtgagatt cctacctttg    660
ttctgctacc cactgccaga tgctgcaagc gaggtccaag cacatcttgt caacatgcat    720
tgccatgaat ttctaccaga tgtgctttta tttagcttta catattcctt tgaccaaata    780
gtttgtgggt taaacaaaat gaaaatatct tcacctctat tcttgggaaa caccctttag    840
tgtacattta tgttccttta tttaggaaac accattataa aaacacttat agtaaatggg    900
gacattcact ataatgatct aagaagctac agattgtcat agttgttttc ctgctttaca    960
aaattgctcc agatctggaa tgccagtttg acctttgtct tctataatat ttcctttttt   1020
tcccctcttt gaatctctgt atatttgatt cttaactaaa attgttctct taaatattct   1080
gaatcctggt aattaaaagt ttgggtgtat tttctttacc tccaaggaaa gaactactag   1140
ctacaaaaaa tattttggaa taagcattgt tttggtataa ggtacatatt ttggttgaag   1200
acaccagact gaagtaaaca gctgtgcatc caatttatta tagttttgta agtaacaata   1260
tgtaatcaaa cttctaggtg acttgagagt ggaacctcct atatcattat ttagcaccgt   1320
ttgtgacagt aaccatttca gtgtattgtt tattatacca cttatatcaa cttatttttc   1380
accaggttaa aattttaatt tctacaaaat aacattctga atcaagcaca ctgtatgttc   1440
agtaggttga actatgaaca ctgtcatcaa tgttcagttc aaaagcctga aagtttagat   1500
ctagaagctg gtaaaaatga caatatcaat cacattaggg gaaccattgt tgtcttcact   1560
taatccattt agcactattt aaaataagca caccaagtta tatgactaat ataacttgaa   1620
aatttttat actgaggggt tggtgataac tcttgaggat gtaatgcatt aataaaaatc   1680
aactcatcat tttctacttg ttttcaatgt gttggaaact gtaaaatgat actgtagaac   1740
ctgtctccta ctttgaaaac tgaatgtcag ggctgagtga atcaaagtgt ctagacatat   1800
ttgcatagag gccaaggtat tctattctaa taactgctta ctcaacacta ccaccttttc   1860
cttatactgt atatgattat ggcctacaat gttgtatttg ttatttatta aattgtgatt   1920
gttttattat tgtttatgcc aaatgttaac tgccaagctt ggagtgacct aaagcatttt   1980
ttaaaagcat ggctagattt acttcagtat aaattatctt atgaaaacca aattttaaaa   2040
gccacaggtg ttgattgtta taaaataaca tgctgccatt cttgattgct agagtttttg   2100
ttagtacttt ggatgcaatt aaaactatgt gctatcacat gtgaaaagct taataaattc   2160
catctatcag tagtataggt ctcaatattt attatgagac cagtggtctg gaaacagctt   2220
gttgtaccga atcaactgga gtctatgctt aaaaaaaaaa attttttttt aaccatcctt   2280
aaattattgc ttaatggtat catattaaca tattctaaat aagggcttta aggcacaggc   2340
tgttgaagca ttttctcaga ggagtggatc tgtagaagtc tgtctttcta tagaaatatt   2400
```

-continued

```
gtgcttactc aagtgttaaa ttattttttc tatgaactag tctacttctt aaaattcaaa   2460

catattcttt tgatcacatt gtttcttgag catcctgccc tgctactaac ttttcaacaa   2520

ggcaaaatgg agtaaagtgg caatttcttt agatgagtga aataccctca agtctctttt   2580

ctgcccaaaa agggaaaagt gatagaaatg ggggtggcaa gtggggtgag tggatgaagg   2640

tgggtattgg gggtggctgt gaaagaaaat aatggagaat cacttttcta gacatctacc   2700

tatacttaat ctaagaaaca aagtaatcta ctgtaaagta ctctgcccct tgaaagaagt   2760

attaaaaaga gtgaggatgg atttagaaaa aaacatgaat ttagaaatat tcaaaatggt   2820

ttttgtggca gattcaatat tatgaattca cagatattta aagaatgaga aacatagtaa   2880

ttagtagaaa tgccagaaac agttcctggt tcctcttgtg tttgacacta agaaaatagc   2940

aagagtgtga aatctcagat acttatgaaa tctcacagat gtaaggactc aagtgtagaa   3000

gaaaatatcc ccttcttaca aaaagaaatg tcaatttatg gagtttgtgg gaaatagggc   3060

aagaattctt atgcttatga gagccaagta gtcagtggaa gagagtagag ctcaaaactg   3120

gattatcacc ttagcaactt agaatagttt gaaatagaaa aaaagtattt aatttggatc   3180

tggatctgtt aagatatgca cagtctattt tttgtatagt attggaaaat aaaaatgcta   3240

taatttg                                                             3247
```

<210> SEQ ID NO 35
<211> LENGTH: 1564
<212> TYPE: DNA
<213> ORGANISM: Homo sapiens

<400> SEQUENCE: 35

```
gccagtgggt ctccattgcc cagctcctgc ccacactccc gcctgttgcc ctgaccagag     60

tcatcatgcc tcttgagcag aggagtcagc actgcaagcc tgaagaaggc cttgaggccc    120

gaggagaggc cctgggcctg gtgggtgcgc aggctcctgc tactgaggag caggaggctg    180

cctcctcctc ttctactcta gttgaagtca ccctgggga ggtgcctgct gccgagtcac    240

cagatcctcc ccagagtcct cagggagcct ccagcctccc cactaccatg aactaccctc    300

tctggagcca atcctatgag gactccagca accaagaaga ggaggggcca agcaccttcc    360

ctgacctgga gtctgagttc caagcagcac tcagtaggaa ggtggccaag ttggttcatt    420

ttctgctcct caagtatcga gccagggagc cggtcacaaa ggcagaaatg ctggggagtg    480

tcgtcggaaa ttggcagtac ttctttcctg tgatcttcag caaagcttcc gattccttgc    540

agctggtctt tggcatcgag ctgatggaag tggaccccat cggccacgtg tacatctttg    600

ccacctgcct gggcctctcc tacgatggcc tgctgggtga caatcagatc atgcccaaga    660

caggcttcct gataatcatc ctggccataa tcgcaaaaga gggcgactgt gcccctgagg    720

agaaaatctg ggaggagctg agtgtgttag aggtgtttga ggggagggaa gacagtatct    780

tcggggatcc caagaagctg ctcacccaat atttcgtgca ggaaaactac ctggagtacc    840

ggcaggtccc cggcagtgat cctgcatgct atgagttcct gtggggtcca agggccctca    900

ttgaaaccag ctatgtgaaa gtcctgcacc atatggtaaa gatcagtgga ggacctcgca    960

tttcctaccc actcctgcat gagtgggctt tgagagaggg ggaagagtga gtctgagcac   1020

gagttgcagc cagggccagt gggagggggt ttgggccagt gcaccttccg ggccccatc   1080

ccttagtttc cactgcctcc tgtgacgtga ggcccattct tcactctttg aagcgagcag   1140

tcagcattct tagtagtggg tttctgttct gttggatgac tttgagatta ttctttgttt   1200

cctgttggag ttgttcaaat gttcctttta acggatggtt gaatgagcgt cagcatccag   1260
```

```
gtttatgaat gacagtagtc acacatagtg ctgtttatat agtttaggag taagagtctt   1320

gttttttatt cagattggga aatccattcc attttgtgaa ttgtgacata ataatagcag   1380

tggaaaaagt atttgcttaa aattgtgagc gaattagcaa taacatacat gagataactc   1440

aagaaatcaa aagatagttg attcttgcct tgtacctcaa tctattctgt aaaattaaac   1500

aaatatgcaa accaggattt ccttgacttc tttgagaatg caagcgaaat taaatctgaa   1560

taaa                                                                1564
```

<210> SEQ ID NO 36
<211> LENGTH: 2459
<212> TYPE: DNA
<213> ORGANISM: Homo sapiens

<400> SEQUENCE: 36

```
gaggaaatac cgatggacct aacggtagtg aagcaggaaa ttatagactg gccaggtaca     60

gaaggcaggt tggctggcca gtgggtagaa caggaggtgg aggataggcc tgaggtgaag    120

gatgagaacg caggcgtatt ggaggtgaag caggagacgg atagtagttt agtggtaaaa    180

gaagcgaagg tgggtgaacc agaggtaaag gaagagaagg taaaggaaga ggtaatggac    240

tggtcagaag tgaaggaaga gaaggataac ttggagataa aacaggagga gaagtttgtt    300

ggtcaatgca taaaagagga attgatgcat ggagagtgtg taaaagaaga gaaggatttc    360

ctgaagaaag aaatcgtgga tgatacaaag gtgaaagaag agcctccgat aaatcacccg    420

gtgggctgca agcggaaact ggccatgtca aggtgtgaga cttgtggtac agaagaagca    480

aagtacagat gtccacgttg tatgcgatat tcctgcagtt tgccctgtgt aaagaaacac    540

aaagcagaac tgacatgtaa tggagttcga gataaaactg catacatttc aatacaacag    600

tttactgaaa tgaatctcct aagtgattat cgatttttgg aagatgtggc aagaacagcg    660

gaccatattt ctagagatgc ttttttgaag agaccaataa gcaataaata tatgtacttt    720

atgaaaaatc gtgcccggag gcaaggtatt aacttaaaac ttctacccaa tggattcacc    780

aagaggaagg agaattcaac ctttttgat aagaaaaaac aacagttttg ttggcatgtg    840

aagctccagt ttcctcaaag tcaagctgag tacatagaaa aaagagtcca gatgataaaa    900

ctattaatga aatcctaaaa ccttacattg atcctgaaaa gtctgatcct gtaattcgtc    960

aaaggttgaa agcctacatt cgctctcaga ctggggttca gattttaatg aagattgaat   1020

atatgcagca aaaatttagt aaggatatta tgactagatc cttataaaag tctcctagac   1080

aatttgagga caaaatgatc attgagtatc caacattaca tgtggtattg aaaggatcca   1140

ataatgacat gaaagttctt caccaagtga agagtgaatc taccaagaac gttggcaatg   1200

aaaattgagc atttttttctg gaagaagaaa gtgaaaactt ccagacaact gcagcagact   1260

ctgcattgat gggctgttgg ctgattgggg tattgtcaat gggtgattgg aattttttct   1320

ttgtatgaaa aataagctta actcttttaa aaaatgtatt ttataacctc ttgaattaat   1380

tgacttgtaa gacccattta ttcatattaa gaactctcct ttgcacttga tcagcatagt   1440

acttattagg ccctggcttt ttaatatgct taattgctta attccataaa ctgaaaactt   1500

tttttttctt ttttctttct ttttttgaga tggggtcttg gagtgcaagt ggtatgagca   1560

tagcttcctc aaattcctgg gctcgaatgg tcctctcact gcagcctccc aacaggctgg   1620

taccaccaca ctcagctaag ttttttgttg ttgctttttt ttggtagaga cagggttgcg   1680

ctctttcgcc caggctggtc tcaaatttgt ggcctcaagc aatccttcca cctcagactc   1740
```

```
caaagcattg ggattacagg catcagccac cacacctggc cttgaacatt ttttatttgg   1800

taatttcatg cgtgacgaaa cccaaggatc acccatgtca acccacaaag ttggcatttc   1860

ctttagtaga acctcactaa acggaaaggc tgtacaacgc accgtctagc cacaggagaa   1920

ctaatcttct atcagttgcc ctttcttctt tggagttttt atgtaactta cccttgtgag   1980

acaagttttc tacttgagaa actcctagta caatgtctta tactagaagc ctggataaat   2040

actattaact actgtttctt atattcactt cagaaaatca gtggctccac attgtttgag   2100

ccattagtga taacaaattt ggatctactt actcaagtct tatgaattct gtgcctttca   2160

tcacattcct agcccactct catcattact gcagaagggt gttgtgatga ccagttttat   2220

actgtgtttt gatatgtcta gcaataactt aaagaaaaaa aaacctggga aatcttcaac   2280

atgttattgg aacatatatg tatgtattaa tgtatataca tggcttaact tatacgttat   2340

ggcagctctg tatacagttt gaactcatgt ctgaaaaaaa attcttaatt ttattggagt   2400

ttataccact ggaaactgca atatgactga agagagtaaa aagattgttc atctttaaa    2459
```

<210> SEQ ID NO 37
<211> LENGTH: 3282
<212> TYPE: DNA
<213> ORGANISM: Homo sapiens

<400> SEQUENCE: 37

```
atgagttggt tcaacgcctc ccagctctcc agcttcgcta agcaggccct gtcccaggcc     60

cagaagtcta ttgacagggt tctggacatc caggaagagg agccgagcat ctgggccgag    120

accattccgt atggagagcc gggaataagt tcccctgtca gtggaggatg ggatacttca    180

acctgggggt tgaaatcaaa cactgaacct cagagtccac caatagcctc tcctaaagca    240

atcacaaagc cagttcggag gactgtggtc gatgaatctg aaaatttctt cagtgccttt    300

ctctcgccaa ccgatgtcca gaccattcag aagagtccag tggtatcaaa acctccagca    360

aaatcacaac gaccagaaga agaagtgaaa agcagcttac atgaatcctt gcacattggc    420

cagtcaagaa ctcctgaaac aactgaatca caagtaaaag actcttcttt gtgtgtttca    480

ggggaaactc tggcagcagg tacttcatca cctaaaactg aaggcaagca cgaagaaact    540

gttaataaag aatcggatat gaaggtgcca actgtaagtt tgaaagtatc tgaaagtgta    600

attgatgtga aaacaactat ggaaagtata tctaatacgt ctacgcagtc tctcacagca    660

gaaacaaagg acatagcttt ggaacctaag gaacaaaaac atgaagacag gcagagcaat    720

acaccttctc ctcctgttag taccttttca tcaggtactt ctaccaccag tgatattgaa    780

gttttagatc atgaaagtgt aataagtgag agctcagcga gctcgagaca agagactaca    840

gattcaaaat caagtcttca cttgatgcag acatcttttc agcttctctc tgcatctgct    900

tgtcctgaat ataatcgttt agatgatttc caaaaactca ctgagagttg ctgttcatct    960

gatgcttttg aaagaataga ctcatttagt gtacagtcat tagatagccg gagtgtaagt   1020

gaaatcaatt cagatgatga attgtcaggc aagggatatg ctttagtgcc tattatagtt   1080

aattcttcaa ctccaaagtc taaaacagtt gaatctgctg aaggaaaatc tgaagaagta   1140

aatgaaacat tagttatacc cactgaggaa gcagaaatgg aagaaagtgg acgaagtgca   1200

actcctgtta actgtgaaca gcctgatatc ttggtttctt ctacaccaat aaatgaagga   1260

cagactgtgt tagacaaggt ggctgagcag tgtgaacctg ctgaaagtca gccagaagca   1320

ctttctgaga aggaagatgt ttgcaagaca gttgaatttc tgaatgaaaa gctggaaaaa   1380

agggaggctc agttattatc tcttagtaag gaaaaagcac ttctagaaga agcttttgat   1440
```

```
aacctgaaag atgaaatgtt cagagtgaaa gaagaaagca gtagcatttc ttccttgaaa   1500

gatgagttta ctcaaagaat tgcagaagca gaaaagaaag ttcaactagc ctgcaaagag   1560

agagatgctg ctaaaaagga aatcaaaaac ataaaagaag aacttgccac tagattaaat   1620

agtagtgaaa ctgcagacct tttgaaagag aaagatgagc agatccgagg gttaatggaa   1680

gaaggagaaa aactttcaaa acagcagctg cacaattcta acatcatcaa gaaattaaga   1740

gctaaagaca aggagaatga aaatatggtt gcaaagctga acaaaaaagt taaagagcta   1800

gaagaggagt tgcagcattt gaaacaggtc cttgatggca aagaagaggt tgagaaacaa   1860

catagagaaa atattaaaaa actaaattcc atggtagaac gccaagagaa agatcttggc   1920

cgtcttcagg tagacatgga tgaacttgaa gaaaagaacc gaagtattca ggctgccctg   1980

gatagtgcat acaaagaact tactgatctt cacaaagcca atgctgcaaa ggatagtgag   2040

gcacaggaag ctgctctgag ccgtgaaatg aaagctaaag aagaactttc tgcagcatta   2100

gagaaggccc aagaagaagc ccgtcagcag caagaaacat tagccattca agtgggggac   2160

cttaggcttg cattgcagcg tacagaacaa gcggctgcca gaaaggagga ttatttacgc   2220

catgagatcg gtgaacttca gcagagactc caggaagcag agaatcgaaa ccaggaactg   2280

agtcaaagtg tttcatcaac aacaagacca ttgcttcgac aaatagaaaa tttgcaagca   2340

accctgggat cccagacatc gtcgtgggag aaattagaga agaatctttc tgataggctt   2400

ggtgaatccc agaccttgct ggcagcagca gttgagagag aacgtgcagc tacagaagaa   2460

ctccttgcta acaaaattca gatgtcttcc atggagtcac agaattctct tttaagacag   2520

gaaaacagta gatttcaagc ccagctagaa tcagagaaaa ataggctgtg taaactggag   2580

gatgagaaca ataggtacca ggttgaattg gaaaacctaa aagatgaata tgtaagaaca   2640

cttgaagaga cgaggaaaga aaagacattg ttgaatagtc agttagaaat ggaaagaatg   2700

aaagttgaac aagaaaggaa gaaagccatt tttactcaag aaacaataaa agaaaaggaa   2760

cgcaagccat tttctgtttc tagcactccc accatgtcac gctcaagttc aataagtggt   2820

gttgatatgg caggactaca gacatctttt ctgtctcagg atgagtctca tgatcactca   2880

tttggaccaa tgcctatatc agccaaatgg aagcatcttt atgctgcctg taaggatggg   2940

agcaggatca agcatattga aaacctacag tctcagctaa agctaaggga aggggaaatc   3000

actcatttac agctagaaat tggcaatcta gaaaaaactc gatcaataat ggctgaagaa   3060

ctagttaaat taacaaatca aaatgatgaa cttgaagaga aggtgaagga gatacccaaa   3120

cttagaactc agctaagaga tttggatcaa aggtacaaca ctattctgca gatgtatgga   3180

gaaaaagcag aagaggcaga agaacttcga ttagatctcg aagatgtaaa aaatatgtac   3240

aaaactcaaa tagatgaact tttaagacaa agtctcagtt aa                      3282
```

<210> SEQ ID NO 38
<211> LENGTH: 1182
<212> TYPE: DNA
<213> ORGANISM: Homo sapiens

<400> SEQUENCE: 38

```
atggaggagc cgcagtcaga tcctagcgtc gagccccctc tgagtcagga aacattttca     60

gacctatgga aactacttcc tgaaaacaac gttctgtccc ccttgccgtc ccaagcaatg    120

gatgatttga tgctgtcccc ggacgatatt gaacaatggt tcactgaaga cccaggtcca    180

gatgaagctc ccagaatgcc agaggctgct ccccgcgtgg cccctggacc agcagctcct    240
```

-continued

```
acaccggcgg cccctgcacc agccccctcc tggcccctgt catcttctgt cccttcccag    300

aaaacctacc agggcagcta cggtttccgt ctgggcttct tgcattctgg gacagccaag    360

tctgtgactt gcacgtactc ccctgccctc aacaagatgt tttgccaact ggccaagacc    420

tgccctgtgc agctgtgggt tgattccaca cccccgcccg gcacccgcgt ccgcgccatg    480

gccatctaca agcagtcaca gcacatgacg gaggttgtga ggcgctgccc ccaccatgag    540

cgctgctcag atagcgatgg tctggcccct cctcagcatc ttatccgagt ggaaggaaat    600

ttgcgtgtgg agtatttgga tgacagaaac acttttcgac atagtgtggt ggtgccctat    660

gagccgcctg aggttggctc tgactgtacc accatccact acaactacat gtgtaacagt    720

tcctgcatgg gcggcatgaa ccggaggccc atcctcacca tcatcacact ggaagactcc    780

agtggtaatc tactgggacg gaacagcttt gaggtgcgtg tttgtgcctg tcctgggaga    840

gaccggcgca cagaggaaga gaatctccgc aagaaagggg agcctcacca cgagctgccc    900

ccagggagca ctaagcgagc actgcccaac aacaccagct cctctcccca gccaaagaag    960

aaaccactgg atggagaata tttcaccctt cagatccgtg ggcgtgagcg cttcgagatg   1020

ttccgagagc tgaatgaggc cttggaactc aaggatgccc aggctgggaa ggagccaggg   1080

gggagcaggg ctcactccag ccacctgaag tccaaaaagg gtcagtctac ctcccgccat   1140

aaaaaactca tgttcaagac agaagggcct gactcagact ga                      1182
```

<210> SEQ ID NO 39
<211> LENGTH: 2172
<212> TYPE: DNA
<213> ORGANISM: Homo sapiens

<400> SEQUENCE: 39

```
gcggcgcggc agtaaaactg aggaggcgga gccaagacgg tcggggctgc ttgctaactc     60

caggaacagg tttaagtttt tgaaactgaa gtaggtctac acagtaggaa ctcatgtcat    120

ttcttgtaag taaaccagag cgaatcaggc ggtgggtctc ggaaaagttc attgttgagg    180

gcttaagaga tttggaacta tttggagagc agcctccggg tgacactcgg agaaaaacca    240

atgatgcgag ctcagagtca atagcatcct tctctaaaca ggaggtcatg agtagctttc    300

tgccagaggg agggtgttac gagctgctca ctgtgatagg caaaggattt gaggacctga    360

tgactgtgaa tctagcaagg tacaaaccaa caggagagta cgtgactgta cggaggatta    420

acctagaagc ttgttccaat gagatggtaa cattcttgca gggcgagctg catgtctcca    480

aactcttcaa ccatcccaat atcgtgccat atcgagccac ttttattgca gacaatgagc    540

tgtgggttgt cacatcattc atggcatacg gttctgcaaa agatctcatc tgtacacact    600

tcatggatgg catgaatgag ctggcgattg cttacatcct gcagggggtg ctgaaggccc    660

tcgactacat ccaccacatg ggatatgtac acaggagtgt caaagccagc cacatcctga    720

tctctgtgga tgggaaggtc tacctgtctg gtttgcgcag caacctcagc atgataagcc    780

atgggcagcg gcagcgagtg gtccacgatt ttcccaagta cagtgtcaag gttctgccgt    840

ggctcagccc cgaggtcctc cagcagaatc tccagggtta tgatgccaag tctgacatct    900

acagtgtggg aatcacagcc tgtgaactgg ccaacggcca tgtccccttt aaggatatgc    960

ctgccaccca gatgctgcta gagaaactga acggcacagt gccctgcctg ttggatacca   1020

gcaccatccc cgctgaggag ctgaccatga gcccttcgcg ctcagtggcc aactctggcc   1080

tgagtgacag cctgaccacc agcacccccc ggccctccaa cggtgactgg ccctcccacc   1140

cctaccaccg aacctttccc ccccacttcc accactttgt ggagcagtgc cttcagcgca   1200
```

```
acccggatgc caggcccagt gccagcaccc ttctgaacca ctctttcttc aagcagatca   1260

agcgacgtgc ctcaaaggct ttgcccgaat tgcttcgtcc tgtcaccccc atcaccaatt   1320

ttgagggcag ccagtctcag gaccacagtg gaatctttgg cctggtaaca aacctggaag   1380

agctggaggt ggacgattgg gagttctgag cctctgcaaa ctgtgcgcat tctccagcca   1440

gggatgcaga ggccacccag aggcccttcc tgagggccgg ccacattccc gccctcctgg   1500

gcagattggg tagaaaggac attcttccag gaaagttgac tgctgactga ttgggaaaga   1560

aaatcctgga gagatacttc actgctccaa ggcttttgag acacaaggga atctcaacaa   1620

ccagggatca ggagggtcca aagccgacat tcccagtcct gtgagctcag gtgacctcct   1680

ccgcagaaga gagatgctgc tctggccctg ggagctgaat tccaagccca gggtttggct   1740

ccttaaaccc gaggaccgcc acctcttccc agtgcttgcg accagcctca ttctatttaa   1800

ctttgctctc agatgcctca gatgctatag gtcagtgaaa gggcaagtag taagctgcct   1860

gcctcccttc cctcagacct ctccctcata attccagaga agggcatttc tgtcttttta   1920

agcacagact aaggctggaa cagtccatcc ttatccctct tctggcttgg gccctgacac   1980

ctaagtcttt cccacggttt atgtgtgtgc ctcattcctt tcccaccaag aatccatctt   2040

agcgcctcct gccagctgcc ctggtgcttt ctccaagggc catcagtgtc ttgcctagct   2100

tgagggctta agtccttatg ctgtgttagt ttcgttgtca gaacaaatta aaattttcag   2160

agacgctgaa aa                                                        2172
```

```
<210> SEQ ID NO 40
<211> LENGTH: 1904
<212> TYPE: DNA
<213> ORGANISM: Homo sapiens

<400> SEQUENCE: 40

tagagaaggc agacgcatcc cgaactcgct ggaggacaag gctcagctct tgccaggcca     60

aattgagaca tgtctgacac aagcgagagt ggtgcaggtc taactcgctt ccaggctgaa    120

gcttcagaaa aggacagtag ctcgatgatg cagactctgt tgacagtgac ccagaatgtg    180

gaggtcccag agacaccgaa ggcctcaaag gcactggagg tctcagagga tgtgaaggtc    240

tcaaaagcct ctggggtctc aaaggccaca gaggtctcaa agaccccaga ggctcgggag    300

gcacctgcca cccaggcctc gtctactact cagctgactg atacccaggt tctggcagct    360

gaaaacaaga gtctagcagc tgacaccaag aaacagaatg ctgacccgca ggctgtgaca    420

atgcctgcca ctgagaccaa aaaggtcagc catgtggctg atacgaaggt caatacaaag    480

gctcaggaga ctgaggctgc accctctcag gccccagcag atgaacctga gcctgagagt    540

gcagctgccc agtctcagga gaatcaggat actcggccca aggtcaaagc caagaaagcc    600

cgaaaggtga agcatctgga tggggaagag gatggcagca gtgatcagag tcaggcttct    660

ggaaccacag gtggccgaag ggtctcaaag gctctaatgg cctcaatggc ccgcagggct    720

tcaaggggtc ccatagcctt ttgggcccgc agggcatcaa ggactcggtt ggctgcttgg    780

gcccggagag ccttgctctc cctgagatca cctaaagccc gtaggggcaa ggctcgccgt    840

agagctgcca agctccagtc atcccaagag cctgaagcac caccacctcg ggatgtggcc    900

cttttgcaag ggagggcaaa tgatttggtg aagtaccttt tggctaaaga ccagacgaag    960

attcccatca agcgctcgga catgctgaag gacatcatca aagaatacac tgatgtgtac   1020

cccgaaatca ttgaacgagc aggctattct ttggagaagg tatttgggat tcaattgaag   1080
```

```
gaaattgata agaatgacca cttgtacatt cttctcagca ccttagagcc cactgatgca   1140

ggcatactgg gaacgactaa ggactcaccc aagctgggtc tgctcatggt gcttcttagc   1200

atcatcttca tgaatggaaa tcggtccagt gaggctgtca tctgggaggt gctgcgcaag   1260

ttggggctgc gccctgggat acatcattca ctctttgggg acgtgaagaa gctcatcact   1320

gatgagtttg tgaagcagaa gtacctggac tatgccagag tccccaatag caatcccccct   1380

gaatatgagt tcttctgggg cctgcgctct tactatgaga ccagcaagat gaaagtcctc   1440

aagtttgcct gcaaggtaca aaagaaggat cccaaggaat gggcagctca gtaccgagag   1500

gcgatggaag cggatttgaa ggctgcagct gaggctgcag ctgaagccaa ggctagggcc   1560

gagattagag ctcgaatggg cattgggctc ggctcggaga atgctgccgg gccctgcaac   1620

tgggacgaag ctgatatcgg accctgggcc aaagcccgga tccaggcggg agcagaagct   1680

aaagccaaag cccaagagag tggcagtgcc agcactggtg ccagtaccag taccaataac   1740

agtgccagtg ccagtgccag caccagtggt ggcttcagtg ctggtgccag cctgaccgcc   1800

actctcacat ttgggctctt cgctggcctt ggtggagctg gtgccagcac cagtggcagc   1860

tctggtgcct gtggtttctc ctacaagtga gattttagat attg                    1904
```

<210> SEQ ID NO 41
<211> LENGTH: 2871
<212> TYPE: PRT
<213> ORGANISM: Homo sapiens

<400> SEQUENCE: 41

```
Met Ser Cys Asn Gly Gly Ser His Pro Arg Ile Asn Thr Leu Gly Arg
1               5                   10                  15

Met Ile Arg Ala Glu Ser Gly Pro Asp Leu Arg Tyr Glu Val Thr Ser
            20                  25                  30

Gly Gly Gly Gly Thr Ser Arg Met Tyr Tyr Ser Arg Arg Gly Val Ile
        35                  40                  45

Thr Asp Gln Asn Ser Asp Gly Tyr Cys Gln Thr Gly Thr Met Ser Arg
    50                  55                  60

His Gln Asn Gln Asn Thr Ile Gln Glu Leu Leu Gln Asn Cys Ser Asp
65                  70                  75                  80

Cys Leu Met Arg Ala Glu Leu Ile Val Gln Pro Glu Leu Lys Tyr Gly
                85                  90                  95

Asp Gly Ile Gln Leu Thr Arg Ser Arg Glu Leu Asp Glu Cys Phe Ala
            100                 105                 110

Gln Ala Asn Asp Gln Met Glu Ile Leu Asp Ser Leu Ile Arg Glu Met
        115                 120                 125

Arg Gln Met Gly Gln Pro Cys Asp Ala Tyr Gln Lys Arg Leu Leu Gln
    130                 135                 140

Leu Gln Glu Gln Met Arg Ala Leu Tyr Lys Ala Ile Ser Val Pro Arg
145                 150                 155                 160

Val Arg Arg Ala Ser Ser Lys Gly Gly Gly Gly Tyr Thr Cys Gln Ser
                165                 170                 175

Gly Ser Gly Trp Asp Glu Phe Thr Lys His Val Thr Ser Glu Cys Leu
            180                 185                 190

Gly Trp Met Arg Gln Gln Arg Ala Glu Met Asp Met Val Ala Trp Gly
        195                 200                 205

Val Asp Leu Ala Ser Val Glu Gln His Ile Asn Ser His Arg Gly Ile
    210                 215                 220

His Asn Ser Ile Gly Asp Tyr Arg Trp Gln Leu Asp Lys Ile Lys Ala
```

-continued

```
225                 230                 235                 240

Asp Leu Arg Glu Lys Ser Ala Ile Tyr Gln Leu Glu Glu Glu Tyr Glu
                245                 250                 255

Asn Leu Leu Lys Ala Ser Phe Glu Arg Met Asp His Leu Arg Gln Leu
            260                 265                 270

Gln Asn Ile Ile Gln Ala Thr Ser Arg Glu Ile Met Trp Ile Asn Asp
        275                 280                 285

Cys Glu Glu Glu Glu Leu Leu Tyr Asp Trp Ser Asp Lys Asn Thr Asn
    290                 295                 300

Ile Ala Gln Lys Gln Glu Ala Phe Ser Ile Arg Met Ser Gln Leu Glu
305                 310                 315                 320

Val Lys Glu Lys Glu Leu Asn Lys Leu Lys Gln Glu Ser Asp Gln Leu
                325                 330                 335

Val Leu Asn Gln His Pro Ala Ser Asp Lys Ile Glu Ala Tyr Met Asp
            340                 345                 350

Thr Leu Gln Thr Gln Trp Ser Trp Ile Leu Gln Ile Thr Lys Cys Ile
        355                 360                 365

Asp Val His Leu Lys Glu Asn Ala Ala Tyr Phe Gln Phe Phe Glu Glu
    370                 375                 380

Ala Gln Ser Thr Glu Ala Tyr Leu Lys Gly Leu Gln Asp Ser Ile Arg
385                 390                 395                 400

Lys Lys Tyr Pro Cys Asp Lys Asn Met Pro Leu Gln His Leu Leu Glu
                405                 410                 415

Gln Ile Lys Glu Leu Glu Lys Glu Arg Glu Lys Ile Leu Glu Tyr Lys
            420                 425                 430

Arg Gln Val Gln Asn Leu Val Asn Lys Ser Lys Lys Ile Val Gln Leu
        435                 440                 445

Lys Pro Arg Asn Pro Asp Tyr Arg Ser Asn Lys Pro Ile Ile Leu Arg
    450                 455                 460

Ala Leu Cys Asp Tyr Lys Gln Asp Gln Lys Ile Val His Lys Gly Asp
465                 470                 475                 480

Glu Cys Ile Leu Lys Asp Asn Asn Glu Arg Ser Lys Trp Tyr Val Thr
                485                 490                 495

Gly Pro Gly Gly Val Asp Met Leu Val Pro Ser Val Gly Leu Ile Ile
            500                 505                 510

Pro Pro Pro Asn Pro Leu Ala Val Asp Leu Ser Cys Lys Ile Glu Gln
        515                 520                 525

Tyr Tyr Glu Ala Ile Leu Ala Leu Trp Asn Gln Leu Tyr Ile Asn Met
    530                 535                 540

Lys Ser Leu Val Ser Trp His Tyr Cys Met Ile Asp Ile Glu Lys Ile
545                 550                 555                 560

Arg Ala Met Thr Ile Ala Lys Leu Lys Thr Met Arg Gln Glu Asp Tyr
                565                 570                 575

Met Lys Thr Ile Ala Asp Leu Glu Leu His Tyr Gln Glu Phe Ile Arg
            580                 585                 590

Asn Ser Gln Gly Ser Glu Met Phe Gly Asp Asp Asp Lys Arg Lys Ile
        595                 600                 605

Gln Ser Gln Phe Thr Asp Ala Gln Lys His Tyr Gln Thr Leu Val Ile
    610                 615                 620

Gln Leu Pro Gly Tyr Pro Gln His Gln Thr Val Thr Thr Thr Glu Ile
625                 630                 635                 640

Thr His His Gly Thr Cys Gln Asp Val Asn His Asn Lys Val Ile Glu
                645                 650                 655
```

-continued

```
Thr Asn Arg Glu Asn Asp Lys Gln Glu Thr Trp Met Leu Met Glu Leu
            660                 665                 670

Gln Lys Ile Arg Arg Gln Ile Glu His Cys Glu Gly Arg Met Thr Leu
        675                 680                 685

Lys Asn Leu Pro Leu Ala Asp Gln Gly Ser Ser His His Ile Thr Val
    690                 695                 700

Lys Ile Asn Glu Leu Lys Ser Val Gln Asn Asp Ser Gln Ala Ile Ala
705                 710                 715                 720

Glu Val Leu Asn Gln Leu Lys Asp Met Leu Ala Asn Phe Arg Gly Ser
                725                 730                 735

Glu Lys Tyr Cys Tyr Leu Gln Asn Glu Val Phe Gly Leu Phe Gln Lys
            740                 745                 750

Leu Glu Asn Ile Asn Gly Val Thr Asp Gly Tyr Leu Asn Ser Leu Cys
        755                 760                 765

Thr Val Arg Ala Leu Leu Gln Ala Ile Leu Gln Thr Glu Asp Met Leu
    770                 775                 780

Lys Val Tyr Glu Ala Arg Leu Thr Glu Glu Glu Thr Val Cys Leu Asp
785                 790                 795                 800

Leu Asp Lys Val Glu Ala Tyr Arg Cys Gly Leu Lys Lys Ile Lys Asn
                805                 810                 815

Asp Leu Asn Leu Lys Lys Ser Leu Leu Ala Thr Met Lys Thr Glu Leu
            820                 825                 830

Gln Lys Ala Gln Gln Ile His Ser Gln Thr Ser Gln Gln Tyr Pro Leu
        835                 840                 845

Tyr Asp Leu Asp Leu Gly Lys Phe Gly Glu Lys Val Thr Gln Leu Thr
    850                 855                 860

Asp Arg Trp Gln Arg Ile Asp Lys Gln Ile Asp Phe Arg Leu Trp Asp
865                 870                 875                 880

Leu Glu Lys Gln Ile Lys Gln Leu Arg Asn Tyr Arg Asp Asn Tyr Gln
                885                 890                 895

Ala Phe Cys Lys Trp Leu Tyr Asp Arg Lys Arg Arg Gln Asp Ser Leu
            900                 905                 910

Glu Ser Met Lys Phe Gly Asp Ser Asn Thr Val Met Arg Phe Leu Asn
        915                 920                 925

Glu Gln Lys Asn Leu His Ser Glu Ile Ser Gly Lys Arg Asp Lys Ser
    930                 935                 940

Glu Glu Val Gln Lys Ile Ala Glu Leu Cys Ala Asn Ser Ile Lys Asp
945                 950                 955                 960

Tyr Glu Leu Gln Leu Ala Ser Tyr Thr Ser Gly Leu Glu Thr Leu Leu
                965                 970                 975

Asn Ile Pro Ile Lys Arg Thr Met Ile Gln Ser Pro Ser Gly Val Ile
            980                 985                 990

Leu Gln Glu Ala Ala Asp Val His  Ala Arg Tyr Ile Glu  Leu Leu Thr
        995                 1000                1005

Arg Ser  Gly Asp Tyr Tyr Arg  Phe Leu Ser Glu Met  Leu Lys Ser
    1010                1015                1020

Leu Glu  Asp Leu Lys Leu Lys  Asn Thr Lys Ile Glu  Val Leu Glu
    1025                1030                1035

Glu Glu  Leu Arg Leu Ala Arg  Asp Ala Asn Ser Glu  Asn Cys Asn
    1040                1045                1050

Lys Asn  Lys Phe Leu Asp Gln  Asn Leu Gln Lys Tyr  Gln Ala Glu
    1055                1060                1065
```

-continued

```
Cys Ser Gln Phe Lys Ala Lys Leu Ala Ser Leu Glu Glu Leu Lys
    1070                1075                1080

Arg Gln Ala Glu Leu Asp Gly Lys Ser Ala Lys Gln Asn Leu Asp
    1085                1090                1095

Lys Cys Tyr Gly Gln Ile Lys Glu Leu Asn Glu Lys Ile Thr Arg
    1100                1105                1110

Leu Thr Tyr Glu Ile Glu Asp Glu Lys Arg Arg Arg Lys Ser Val
    1115                1120                1125

Glu Asp Arg Phe Asp Gln Gln Lys Asn Asp Tyr Asp Gln Leu Gln
    1130                1135                1140

Lys Ala Arg Gln Cys Glu Lys Glu Asn Leu Gly Trp Gln Lys Leu
    1145                1150                1155

Glu Ser Glu Lys Ala Ile Lys Glu Lys Glu Tyr Glu Ile Glu Arg
    1160                1165                1170

Leu Arg Val Leu Leu Gln Glu Glu Gly Thr Arg Lys Arg Glu Tyr
    1175                1180                1185

Glu Asn Glu Leu Ala Lys Val Arg Asn His Tyr Asn Glu Glu Met
    1190                1195                1200

Ser Asn Leu Arg Asn Lys Tyr Glu Thr Glu Ile Asn Ile Thr Lys
    1205                1210                1215

Thr Thr Ile Lys Glu Ile Ser Met Gln Lys Glu Asp Asp Ser Lys
    1220                1225                1230

Asn Leu Arg Asn Gln Leu Asp Arg Leu Ser Arg Glu Asn Arg Asp
    1235                1240                1245

Leu Lys Asp Glu Ile Val Arg Leu Asn Asp Ser Ile Leu Gln Ala
    1250                1255                1260

Thr Glu Gln Arg Arg Arg Ala Glu Glu Asn Ala Leu Gln Gln Lys
    1265                1270                1275

Ala Cys Gly Ser Glu Ile Met Gln Lys Lys Gln His Leu Glu Ile
    1280                1285                1290

Glu Leu Lys Gln Val Met Gln Gln Arg Ser Glu Asp Asn Ala Arg
    1295                1300                1305

His Lys Gln Ser Leu Glu Glu Ala Ala Lys Thr Ile Gln Asp Lys
    1310                1315                1320

Asn Lys Glu Ile Glu Arg Leu Lys Ala Glu Phe Gln Glu Glu Ala
    1325                1330                1335

Lys Arg Arg Trp Glu Tyr Glu Asn Glu Leu Ser Lys Val Arg Asn
    1340                1345                1350

Asn Tyr Asp Glu Glu Ile Ile Ser Leu Lys Asn Gln Phe Glu Thr
    1355                1360                1365

Glu Ile Asn Ile Thr Lys Thr Thr Ile His Gln Leu Thr Met Gln
    1370                1375                1380

Lys Glu Glu Asp Thr Ser Gly Tyr Arg Ala Gln Ile Asp Asn Leu
    1385                1390                1395

Thr Arg Glu Asn Arg Ser Leu Ser Glu Glu Ile Lys Arg Leu Lys
    1400                1405                1410

Asn Thr Leu Thr Gln Thr Thr Glu Asn Leu Arg Arg Val Glu Glu
    1415                1420                1425

Asp Ile Gln Gln Gln Lys Ala Thr Gly Ser Glu Val Ser Gln Arg
    1430                1435                1440

Lys Gln Gln Leu Glu Val Glu Leu Arg Gln Val Thr Gln Met Arg
    1445                1450                1455

Thr Glu Glu Ser Val Arg Tyr Lys Gln Ser Leu Asp Asp Ala Ala
```

-continued

```
    1460                1465                1470

Lys Thr  Ile Gln Asp Lys Asn  Lys Glu Ile Glu Arg  Leu Lys Gln
    1475                1480                1485

Leu Ile  Asp Lys Glu Thr Asn  Asp Arg Lys Cys Leu  Glu Asp Glu
    1490                1495                1500

Asn Ala  Arg Leu Gln Arg Val  Gln Tyr Asp Leu Gln  Lys Ala Asn
    1505                1510                1515

Ser Ser  Ala Thr Glu Thr Ile  Asn Lys Leu Lys Val  Gln Glu Gln
    1520                1525                1530

Glu Leu  Thr Arg Leu Arg Ile  Asp Tyr Glu Arg Val  Ser Gln Glu
    1535                1540                1545

Arg Thr  Val Lys Asp Gln Asp  Ile Thr Arg Phe Gln  Asn Ser Leu
    1550                1555                1560

Lys Glu  Leu Gln Leu Gln Lys  Gln Lys Val Glu Glu  Glu Leu Asn
    1565                1570                1575

Arg Leu  Lys Arg Thr Ala Ser  Glu Asp Ser Cys Lys  Arg Lys Lys
    1580                1585                1590

Leu Glu  Glu Glu Leu Glu Gly  Met Arg Arg Ser Leu  Lys Glu Gln
    1595                1600                1605

Ala Ile  Lys Ile Thr Asn Leu  Thr Gln Gln Leu Glu  Gln Ala Ser
    1610                1615                1620

Ile Val  Lys Lys Arg Ser Glu  Asp Asp Leu Arg Gln  Gln Arg Asp
    1625                1630                1635

Val Leu  Asp Gly His Leu Arg  Glu Lys Gln Arg Thr  Gln Glu Glu
    1640                1645                1650

Leu Arg  Arg Leu Ser Ser Glu  Val Glu Ala Leu Arg  Arg Gln Leu
    1655                1660                1665

Leu Gln  Glu Gln Glu Ser Val  Lys Gln Ala His Leu  Arg Asn Glu
    1670                1675                1680

His Phe  Gln Lys Ala Ile Glu  Asp Lys Ser Arg Ser  Leu Asn Glu
    1685                1690                1695

Ser Lys  Ile Glu Ile Glu Arg  Leu Gln Ser Leu Thr  Glu Asn Leu
    1700                1705                1710

Thr Lys  Glu His Leu Met Leu  Glu Glu Glu Leu Arg  Asn Leu Arg
    1715                1720                1725

Leu Glu  Tyr Asp Asp Leu Arg  Arg Gly Arg Ser Glu  Ala Asp Ser
    1730                1735                1740

Asp Lys  Asn Ala Thr Ile Leu  Glu Leu Arg Ser Gln  Leu Gln Ile
    1745                1750                1755

Ser Asn  Asn Arg Thr Leu Glu  Leu Gln Gly Leu Ile  Asn Asp Leu
    1760                1765                1770

Gln Arg  Glu Arg Glu Asn Leu  Arg Gln Glu Ile Glu  Lys Phe Gln
    1775                1780                1785

Lys Gln  Ala Leu Glu Ala Ser  Asn Arg Ile Gln Glu  Ser Lys Asn
    1790                1795                1800

Gln Cys  Thr Gln Val Val Gln  Glu Arg Glu Ser Leu  Leu Val Lys
    1805                1810                1815

Ile Lys  Val Leu Glu Gln Asp  Lys Ala Arg Leu Gln  Arg Leu Glu
    1820                1825                1830

Asp Glu  Leu Asn Arg Ala Lys  Ser Thr Leu Glu Ala  Glu Thr Arg
    1835                1840                1845

Val Lys  Gln Arg Leu Glu Cys  Glu Lys Gln Gln Ile  Gln Asn Asp
    1850                1855                1860
```

-continued

```
Leu Asn  Gln Trp Lys Thr Gln  Tyr Ser Arg Lys Glu  Glu Ala Ile
    1865                 1870                 1875

Arg Lys  Ile Glu Ser Glu Arg  Glu Lys Ser Glu Arg  Glu Lys Asn
    1880                 1885                 1890

Ser Leu  Arg Ser Glu Ile Glu  Arg Leu Gln Ala Glu  Ile Lys Arg
    1895                 1900                 1905

Ile Glu  Glu Arg Cys Arg Arg  Lys Leu Glu Asp Ser  Thr Arg Glu
    1910                 1915                 1920

Thr Gln  Ser Gln Leu Glu Thr  Glu Arg Ser Arg Tyr  Gln Arg Glu
    1925                 1930                 1935

Ile Asp  Lys Leu Arg Gln Arg  Pro Tyr Gly Ser His  Arg Glu Thr
    1940                 1945                 1950

Gln Thr  Glu Cys Glu Trp Thr  Val Asp Thr Ser Lys  Leu Val Phe
    1955                 1960                 1965

Asp Gly  Leu Arg Lys Lys Val  Thr Ala Met Gln Leu  Tyr Glu Cys
    1970                 1975                 1980

Gln Leu  Ile Asp Lys Thr Thr  Leu Asp Lys Leu Leu  Lys Gly Lys
    1985                 1990                 1995

Lys Ser  Val Glu Glu Val Ala  Ser Glu Ile Gln Pro  Phe Leu Arg
    2000                 2005                 2010

Gly Ala  Gly Ser Ile Ala Gly  Ala Ser Ala Ser Pro  Lys Glu Lys
    2015                 2020                 2025

Tyr Ser  Leu Val Glu Ala Lys  Arg Lys Lys Leu Ile  Ser Pro Glu
    2030                 2035                 2040

Ser Thr  Val Met Leu Leu Glu  Ala Gln Ala Ala Thr  Gly Gly Ile
    2045                 2050                 2055

Ile Asp  Pro His Arg Asn Glu  Lys Leu Thr Val Asp  Ser Ala Ile
    2060                 2065                 2070

Ala Arg  Asp Leu Ile Asp Phe  Asp Asp Arg Gln Gln  Ile Tyr Ala
    2075                 2080                 2085

Ala Glu  Lys Ala Ile Thr Gly  Phe Asp Asp Pro Phe  Ser Gly Lys
    2090                 2095                 2100

Thr Val  Ser Val Ser Glu Ala  Ile Lys Lys Asn Leu  Ile Asp Arg
    2105                 2110                 2115

Glu Thr  Gly Met Arg Leu Leu  Glu Ala Gln Ile Ala  Ser Gly Gly
    2120                 2125                 2130

Val Val  Asp Pro Val Asn Ser  Val Phe Leu Pro Lys  Asp Val Ala
    2135                 2140                 2145

Leu Ala  Arg Gly Leu Ile Asp  Arg Asp Leu Tyr Arg  Ser Leu Asn
    2150                 2155                 2160

Asp Pro  Arg Asp Ser Gln Lys  Asn Phe Val Asp Pro  Val Thr Lys
    2165                 2170                 2175

Lys Lys  Val Ser Tyr Val Gln  Leu Lys Glu Arg Cys  Arg Ile Glu
    2180                 2185                 2190

Pro His  Thr Gly Leu Leu Leu  Leu Ser Val Gln Lys  Arg Ser Met
    2195                 2200                 2205

Ser Phe  Gln Gly Ile Arg Gln  Pro Val Thr Val Thr  Glu Leu Val
    2210                 2215                 2220

Asp Ser  Gly Ile Leu Arg Pro  Ser Thr Val Asn Glu  Leu Glu Ser
    2225                 2230                 2235

Gly Gln  Ile Ser Tyr Asp Glu  Val Gly Glu Arg Ile  Lys Asp Phe
    2240                 2245                 2250
```

-continued

```
Leu Gln  Gly Ser Ser Cys Ile  Ala Gly Ile Tyr Asn  Glu Thr Thr
    2255                 2260                 2265

Lys Gln  Lys Leu Gly Ile Tyr  Glu Ala Met Lys Ile  Gly Leu Val
    2270                 2275                 2280

Arg Pro  Gly Thr Ala Leu Glu  Leu Leu Glu Ala Gln  Ala Ala Thr
    2285                 2290                 2295

Gly Phe  Ile Val Asp Pro Val  Ser Asn Leu Arg Leu  Pro Val Glu
    2300                 2305                 2310

Glu Ala  Tyr Lys Arg Gly Leu  Val Gly Ile Glu Phe  Lys Glu Lys
    2315                 2320                 2325

Leu Leu  Ser Ala Glu Arg Ala  Val Thr Gly Tyr Asn  Asp Pro Glu
    2330                 2335                 2340

Thr Gly  Asn Ile Ile Ser Leu  Phe Gln Ala Met Asn  Lys Glu Leu
    2345                 2350                 2355

Ile Glu  Lys Gly His Gly Ile  Arg Leu Leu Glu Ala  Gln Ile Ala
    2360                 2365                 2370

Thr Gly  Gly Ile Ile Asp Pro  Lys Glu Ser His Arg  Leu Pro Val
    2375                 2380                 2385

Asp Ile  Ala Tyr Lys Arg Gly  Tyr Phe Asn Glu Glu  Leu Ser Glu
    2390                 2395                 2400

Ile Leu  Ser Asp Pro Ser Asp  Asp Thr Lys Gly Phe  Phe Asp Pro
    2405                 2410                 2415

Asn Thr  Glu Glu Asn Leu Thr  Tyr Leu Gln Leu Lys  Glu Arg Cys
    2420                 2425                 2430

Ile Lys  Asp Glu Glu Thr Gly  Leu Cys Leu Leu Pro  Leu Lys Glu
    2435                 2440                 2445

Lys Lys  Lys Gln Val Gln Thr  Ser Gln Lys Asn Thr  Leu Arg Lys
    2450                 2455                 2460

Arg Arg  Val Val Ile Val Asp  Pro Glu Thr Asn Lys  Glu Met Ser
    2465                 2470                 2475

Val Gln  Glu Ala Tyr Lys Lys  Gly Leu Ile Asp Tyr  Glu Thr Phe
    2480                 2485                 2490

Lys Glu  Leu Cys Glu Gln Glu  Cys Glu Trp Glu Glu  Ile Thr Ile
    2495                 2500                 2505

Thr Gly  Ser Asp Gly Ser Thr  Arg Val Val Leu Val  Asp Arg Lys
    2510                 2515                 2520

Thr Gly  Ser Gln Tyr Asp Ile  Gln Asp Ala Ile Asp  Lys Gly Leu
    2525                 2530                 2535

Val Asp  Arg Lys Phe Phe Asp  Gln Tyr Arg Ser Gly  Ser Leu Ser
    2540                 2545                 2550

Leu Thr  Gln Phe Ala Asp Met  Ile Ser Leu Lys Asn  Gly Val Gly
    2555                 2560                 2565

Thr Ser  Ser Ser Met Gly Ser  Gly Val Ser Asp Asp  Val Phe Ser
    2570                 2575                 2580

Ser Ser  Arg His Glu Ser Val  Ser Lys Ile Ser Thr  Ile Ser Ser
    2585                 2590                 2595

Val Arg  Asn Leu Thr Ile Arg  Ser Ser Ser Phe Ser  Asp Thr Leu
    2600                 2605                 2610

Glu Glu  Ser Ser Pro Ile Ala  Ala Ile Phe Asp Thr  Glu Asn Leu
    2615                 2620                 2625

Glu Lys  Ile Ser Ile Thr Glu  Gly Ile Glu Arg Gly  Ile Val Asp
    2630                 2635                 2640

Ser Ile  Thr Gly Gln Arg Leu  Leu Glu Ala Gln Ala  Cys Thr Gly
```

-continued

```
    2645                2650                2655

Gly Ile  Ile His Pro Thr Thr  Gly Gln Lys Leu Ser  Leu Gln Asp
    2660                2665                2670

Ala Val  Ser Gln Gly Val Ile  Asp Gln Asp Met Ala  Thr Ser Val
    2675                2680                2685

Lys Pro  Ala Gln Lys Ala Phe  Ile Gly Phe Glu Gly  Val Lys Gly
    2690                2695                2700

Lys Lys  Lys Met Ser Ala Ala  Glu Ala Val Lys Glu  Lys Trp Leu
    2705                2710                2715

Pro Tyr  Glu Ala Gly Gln Arg  Phe Leu Glu Phe Gln  Tyr Leu Thr
    2720                2725                2730

Gly Gly  Leu Val Asp Pro Glu  Val His Gly Arg Ile  Ser Thr Glu
    2735                2740                2745

Glu Ala  Ile Arg Lys Gly Phe  Ile Asp Gly Arg Ala  Ala Gln Arg
    2750                2755                2760

Leu Gln  Asp Thr Ser Ser Tyr  Ala Lys Ile Leu Thr  Cys Pro Lys
    2765                2770                2775

Thr Lys  Leu Lys Ile Ser Tyr  Lys Asp Ala Ile Asn  Arg Ser Met
    2780                2785                2790

Val Glu  Asp Ile Thr Gly Leu  Arg Leu Leu Glu Ala  Ala Ser Val
    2795                2800                2805

Ser Ser  Lys Gly Leu Pro Ser  Pro Tyr Asn Met Ser  Ser Ala Pro
    2810                2815                2820

Gly Ser  Arg Ser Gly Ser Arg  Ser Gly Ser Arg Ser  Gly Ser Arg
    2825                2830                2835

Ser Gly  Ser Arg Ser Gly Ser  Arg Arg Gly Ser Phe  Asp Ala Thr
    2840                2845                2850

Gly Asn  Ser Ser Tyr Ser Tyr  Ser Tyr Ser Phe Ser  Ser Ser Ser
    2855                2860                2865

Ile Gly  His
    2870


<210> SEQ ID NO 42
<211> LENGTH: 801
<212> TYPE: PRT
<213> ORGANISM: Homo sapiens

<400> SEQUENCE: 42

Met Leu Gln Asn Val Thr Pro His Asn Lys Leu Pro Gly Glu Gly Asn
1               5                   10                  15

Ala Gly Leu Leu Gly Leu Gly Pro Glu Ala Ala Ala Pro Gly Lys Arg
            20                  25                  30

Ile Arg Lys Pro Ser Leu Leu Tyr Glu Gly Phe Glu Ser Pro Thr Met
        35                  40                  45

Ala Ser Val Pro Ala Leu Gln Leu Thr Pro Ala Asn Pro Pro Pro Pro
    50                  55                  60

Glu Val Ser Asn Pro Lys Lys Pro Gly Arg Val Thr Asn Gln Leu Gln
65                  70                  75                  80

Tyr Leu His Lys Val Val Met Lys Ala Leu Trp Lys His Gln Phe Ala
                85                  90                  95

Trp Pro Phe Arg Gln Pro Val Asp Ala Val Lys Leu Gly Leu Pro Asp
            100                 105                 110

Tyr His Lys Ile Ile Lys Gln Pro Met Asp Met Gly Thr Ile Lys Arg
        115                 120                 125
```

-continued

```
Arg Leu Glu Asn Asn Tyr Tyr Trp Ala Ala Ser Glu Cys Met Gln Asp
    130                 135                 140

Phe Asn Thr Met Phe Thr Asn Cys Tyr Ile Tyr Asn Lys Pro Thr Asp
145                 150                 155                 160

Asp Ile Val Leu Met Ala Gln Thr Leu Glu Lys Ile Phe Leu Gln Lys
                165                 170                 175

Val Ala Ser Met Pro Gln Glu Glu Gln Glu Leu Val Val Thr Ile Pro
            180                 185                 190

Lys Asn Ser His Lys Lys Gly Ala Lys Leu Ala Ala Leu Gln Gly Ser
        195                 200                 205

Val Thr Ser Ala His Gln Val Pro Ala Val Ser Ser Val Ser His Thr
    210                 215                 220

Ala Leu Tyr Thr Pro Pro Pro Glu Ile Pro Thr Thr Val Leu Asn Ile
225                 230                 235                 240

Pro His Pro Ser Val Ile Ser Ser Pro Leu Leu Lys Ser Leu His Ser
                245                 250                 255

Ala Gly Pro Pro Leu Leu Ala Val Thr Ala Ala Pro Pro Ala Gln Pro
            260                 265                 270

Leu Ala Lys Lys Lys Gly Val Lys Arg Lys Ala Asp Thr Thr Thr Pro
        275                 280                 285

Thr Pro Thr Ala Ile Leu Ala Pro Gly Ser Pro Ala Ser Pro Pro Gly
    290                 295                 300

Ser Leu Glu Pro Lys Ala Ala Arg Leu Pro Pro Met Arg Arg Glu Ser
305                 310                 315                 320

Gly Arg Pro Ile Lys Pro Pro Arg Lys Asp Leu Pro Asp Ser Gln Gln
                325                 330                 335

Gln His Gln Ser Ser Lys Lys Gly Lys Leu Ser Glu Gln Leu Lys His
            340                 345                 350

Cys Asn Gly Ile Leu Lys Glu Leu Leu Ser Lys Lys His Ala Ala Tyr
        355                 360                 365

Ala Trp Pro Phe Tyr Lys Pro Val Asp Ala Ser Ala Leu Gly Leu His
    370                 375                 380

Asp Tyr His Asp Ile Ile Lys His Pro Met Asp Leu Ser Thr Val Lys
385                 390                 395                 400

Arg Lys Met Glu Asn Arg Asp Tyr Arg Asp Ala Gln Glu Phe Ala Ala
                405                 410                 415

Asp Val Arg Leu Met Phe Ser Asn Cys Tyr Lys Tyr Asn Pro Pro Asp
            420                 425                 430

His Asp Val Val Ala Met Ala Arg Lys Leu Gln Asp Val Phe Glu Phe
        435                 440                 445

Arg Tyr Ala Lys Met Pro Asp Glu Pro Leu Glu Pro Gly Pro Leu Pro
    450                 455                 460

Val Ser Thr Ala Met Pro Pro Gly Leu Ala Lys Ser Ser Ser Glu Ser
465                 470                 475                 480

Ser Ser Glu Glu Ser Ser Ser Glu Ser Ser Ser Glu Glu Glu Glu Glu
                485                 490                 495

Glu Asp Glu Glu Asp Glu Glu Glu Glu Glu Ser Glu Ser Ser Asp Ser
            500                 505                 510

Glu Glu Glu Arg Ala His Arg Leu Ala Glu Leu Gln Glu Gln Leu Arg
        515                 520                 525

Ala Val His Glu Gln Leu Ala Ala Leu Ser Gln Gly Pro Ile Ser Lys
    530                 535                 540

Pro Lys Arg Lys Arg Glu Lys Lys Glu Lys Lys Lys Lys Arg Lys Ala
```

-continued

```
545                 550                 555                 560

Glu Lys His Arg Gly Arg Ala Gly Ala Asp Glu Asp Asp Lys Gly Pro
                565                 570                 575

Arg Ala Pro Arg Pro Pro Gln Pro Lys Lys Ser Lys Lys Ala Ser Gly
            580                 585                 590

Ser Gly Gly Gly Ser Ala Ala Leu Gly Pro Ser Gly Phe Gly Pro Ser
        595                 600                 605

Gly Gly Ser Gly Thr Lys Leu Pro Lys Lys Ala Thr Lys Thr Ala Pro
    610                 615                 620

Pro Ala Leu Pro Thr Gly Tyr Asp Ser Glu Glu Glu Glu Glu Ser Arg
625                 630                 635                 640

Pro Met Ser Tyr Asp Glu Lys Arg Gln Leu Ser Leu Asp Ile Asn Lys
                645                 650                 655

Leu Pro Gly Glu Lys Leu Gly Arg Val Val His Ile Ile Gln Ala Arg
            660                 665                 670

Glu Pro Ser Leu Arg Asp Ser Asn Pro Glu Glu Ile Glu Ile Asp Phe
        675                 680                 685

Glu Thr Leu Lys Pro Ser Thr Leu Arg Glu Leu Glu Arg Tyr Val Leu
    690                 695                 700

Ser Cys Leu Arg Lys Lys Pro Arg Lys Pro Tyr Thr Ile Lys Lys Pro
705                 710                 715                 720

Val Gly Lys Thr Lys Glu Glu Leu Ala Leu Glu Lys Lys Arg Glu Leu
                725                 730                 735

Glu Lys Arg Leu Gln Asp Val Ser Gly Gln Leu Asn Ser Thr Lys Lys
            740                 745                 750

Pro Pro Lys Lys Ala Asn Glu Lys Thr Glu Ser Ser Ser Ala Gln Gln
        755                 760                 765

Val Ala Val Ser Arg Leu Ser Ala Ser Ser Ser Ser Ser Asp Ser Ser
    770                 775                 780

Ser Ser Ser Ser Ser Ser Ser Ser Ser Asp Thr Ser Asp Ser Asp Ser
785                 790                 795                 800

Gly


<210> SEQ ID NO 43
<211> LENGTH: 222
<212> TYPE: PRT
<213> ORGANISM: Homo sapiens

<400> SEQUENCE: 43

Met Gly Leu Phe Gly Lys Thr Gln Glu Lys Pro Pro Lys Glu Leu Val
1               5                   10                  15

Asn Glu Trp Ser Leu Lys Ile Arg Lys Glu Met Arg Val Val Asp Arg
            20                  25                  30

Gln Ile Arg Asp Ile Gln Arg Glu Glu Glu Lys Val Lys Arg Ser Val
        35                  40                  45

Lys Asp Ala Ala Lys Lys Gly Gln Lys Asp Val Cys Ile Val Leu Ala
    50                  55                  60

Lys Glu Met Ile Arg Ser Arg Lys Ala Val Ser Lys Leu Tyr Ala Ser
65                  70                  75                  80

Lys Ala His Met Asn Ser Val Leu Met Gly Met Lys Asn Gln Leu Ala
                85                  90                  95

Val Leu Arg Val Ala Gly Ser Leu Gln Lys Ser Thr Glu Val Met Lys
            100                 105                 110

Ala Met Gln Ser Leu Val Lys Ile Pro Glu Ile Gln Ala Thr Met Arg
```

```
        115                 120                 125

Glu Leu Ser Lys Glu Met Met Lys Ala Gly Ile Ile Glu Glu Met Leu
    130                 135                 140

Glu Asp Thr Phe Glu Ser Met Asp Asp Gln Glu Glu Met Glu Glu Glu
145                 150                 155                 160

Ala Glu Met Glu Ile Asp Arg Ile Leu Phe Glu Ile Thr Ala Gly Ala
                165                 170                 175

Leu Gly Lys Ala Pro Ser Lys Val Thr Asp Ala Leu Pro Glu Pro Glu
            180                 185                 190

Pro Pro Gly Ala Met Ala Ala Ser Glu Asp Glu Glu Glu Glu Glu Glu
        195                 200                 205

Ala Leu Glu Ala Met Gln Ser Arg Leu Ala Thr Leu Arg Ser
    210                 215                 220


<210> SEQ ID NO 44
<211> LENGTH: 1753
<212> TYPE: PRT
<213> ORGANISM: Homo sapiens

<400> SEQUENCE: 44

Arg Pro Leu Phe Ala Arg Glu Gly Gly Ile Tyr Ala Val Leu Val Cys
1               5                   10                  15

Met Gln Glu Tyr Lys Thr Ser Val Leu Val Gln Gln Ala Gly Leu Ala
            20                  25                  30

Ala Leu Lys Met Leu Ala Val Ala Ser Ser Ser Glu Ile Pro Thr Phe
        35                  40                  45

Val Thr Gly Arg Asp Ser Ile His Ser Leu Phe Asp Ala Gln Met Thr
    50                  55                  60

Arg Glu Ile Phe Ala Ser Ile Asp Ser Ala Thr Arg Pro Gly Ser Glu
65                  70                  75                  80

Ser Leu Leu Leu Thr Val Pro Ala Ala Val Ile Leu Met Leu Asn Thr
                85                  90                  95

Glu Gly Cys Ser Ser Ala Ala Arg Asn Gly Leu Leu Leu Leu Asn Leu
            100                 105                 110

Leu Leu Cys Asn His His Thr Leu Gly Asp Gln Ile Ile Thr Gln Glu
        115                 120                 125

Leu Arg Asp Thr Leu Phe Arg His Ser Gly Ile Ala Pro Arg Thr Glu
    130                 135                 140

Pro Met Pro Thr Thr Arg Thr Ile Leu Met Met Leu Leu Asn Arg Tyr
145                 150                 155                 160

Ser Glu Pro Pro Gly Ser Pro Glu Arg Ala Ala Leu Glu Thr Pro Ile
                165                 170                 175

Ile Gln Gly Gln Asp Gly Ser Pro Glu Leu Leu Ile Arg Ser Leu Val
            180                 185                 190

Gly Gly Pro Ser Ala Glu Leu Leu Leu Asp Leu Glu Arg Val Leu Cys
        195                 200                 205

Arg Glu Gly Ser Pro Gly Gly Ala Val Arg Pro Leu Leu Lys Arg Leu
    210                 215                 220

Gln Gln Glu Thr Gln Pro Phe Leu Leu Leu Leu Arg Thr Leu Asp Ala
225                 230                 235                 240

Pro Gly Pro Asn Lys Thr Leu Leu Leu Ser Val Leu Arg Val Ile Thr
                245                 250                 255

Arg Leu Leu Asp Phe Pro Glu Ala Met Val Leu Pro Trp His Glu Val
            260                 265                 270
```

-continued

```
Leu Glu Pro Cys Leu Asn Cys Leu Ser Gly Pro Ser Ser Asp Ser Glu
        275                 280                 285

Ile Val Gln Glu Leu Thr Cys Phe Leu His Arg Leu Ala Ser Met His
    290                 295                 300

Lys Asp Tyr Ala Val Val Leu Cys Cys Leu Gly Ala Lys Glu Ile Leu
305                 310                 315                 320

Ser Lys Val Leu Asp Lys His Ser Ala Gln Leu Leu Leu Gly Cys Glu
                325                 330                 335

Leu Arg Asp Leu Val Thr Glu Cys Glu Lys Tyr Ala Gln Leu Tyr Ser
            340                 345                 350

Asn Leu Thr Ser Ser Ile Leu Ala Gly Cys Ile Gln Met Val Leu Gly
        355                 360                 365

Gln Ile Glu Asp His Arg Arg Thr His Gln Pro Ile Asn Ile Pro Phe
    370                 375                 380

Phe Asp Val Phe Leu Arg His Leu Cys Gln Gly Ser Ser Val Glu Val
385                 390                 395                 400

Lys Glu Asp Lys Cys Trp Glu Lys Val Glu Val Ser Ser Asn Pro His
                405                 410                 415

Arg Ala Ser Lys Leu Thr Asp His Asn Pro Lys Thr Tyr Trp Glu Ser
            420                 425                 430

Asn Gly Ser Thr Gly Ser His Tyr Ile Thr Leu His Met His Arg Gly
        435                 440                 445

Val Leu Val Arg Gln Leu Thr Leu Leu Val Ala Ser Glu Asp Ser Ser
    450                 455                 460

Tyr Met Pro Ala Arg Val Val Val Phe Gly Gly Asp Ser Thr Ser Cys
465                 470                 475                 480

Ile Gly Thr Glu Leu Asn Thr Val Asn Val Met Pro Ser Ala Ser Arg
                485                 490                 495

Val Ile Leu Leu Glu Asn Leu Asn Arg Phe Trp Pro Ile Ile Gln Ile
            500                 505                 510

Arg Ile Lys Arg Cys Gln Gln Gly Gly Ile Asp Thr Arg Val Arg Gly
        515                 520                 525

Val Glu Val Leu Gly Pro Lys Pro Thr Phe Trp Pro Leu Phe Arg Glu
    530                 535                 540

Gln Leu Cys Arg Arg Thr Cys Leu Phe Tyr Thr Ile Arg Ala Gln Ala
545                 550                 555                 560

Trp Ser Arg Asp Ile Ala Glu Asp His Arg Arg Leu Leu Gln Leu Cys
                565                 570                 575

Pro Arg Leu Asn Arg Val Leu Arg His Glu Gln Asn Phe Ala Asp Arg
            580                 585                 590

Phe Leu Pro Asp Asp Glu Ala Ala Gln Ala Leu Gly Lys Thr Cys Trp
        595                 600                 605

Glu Ala Leu Val Ser Pro Leu Val Gln Asn Ile Thr Ser Pro Asp Ala
    610                 615                 620

Glu Gly Val Ser Ala Leu Gly Trp Leu Leu Asp Gln Tyr Leu Glu Gln
625                 630                 635                 640

Arg Glu Thr Ser Arg Asn Pro Leu Ser Arg Ala Ala Ser Phe Ala Ser
                645                 650                 655

Arg Val Arg Arg Leu Cys His Leu Leu Val His Val Glu Pro Pro Pro
            660                 665                 670

Gly Pro Ser Pro Glu Pro Ser Thr Arg Pro Phe Ser Lys Asn Ser Lys
        675                 680                 685

Gly Arg Asp Arg Ser Pro Ala Pro Ser Pro Val Leu Pro Ser Ser Ser
```

-continued

```
    690                 695                 700

Leu Arg Asn Ile Thr Gln Cys Trp Leu Ser Val Val Gln Glu Gln Val
705                 710                 715                 720

Ser Arg Phe Leu Ala Ala Ala Trp Arg Ala Pro Asp Phe Val Pro Arg
            725                 730                 735

Tyr Cys Lys Leu Tyr Glu His Leu Gln Arg Ala Gly Ser Glu Leu Phe
            740                 745                 750

Gly Pro Arg Ala Ala Phe Met Leu Ala Leu Arg Ser Gly Phe Ser Gly
        755                 760                 765

Ala Leu Leu Gln Gln Ser Phe Leu Thr Ala Ala His Met Ser Glu Gln
    770                 775                 780

Phe Ala Arg Tyr Ile Asp Gln Gln Ile Gln Gly Gly Leu Ile Gly Gly
785                 790                 795                 800

Ala Pro Gly Val Glu Met Leu Gly Gln Leu Gln Arg His Leu Glu Pro
            805                 810                 815

Ile Met Val Leu Ser Gly Leu Glu Leu Ala Thr Thr Phe Glu His Phe
            820                 825                 830

Tyr Gln His Tyr Met Ala Asp Arg Leu Leu Ser Phe Gly Ser Ser Trp
        835                 840                 845

Leu Glu Gly Ala Val Leu Glu Gln Ile Gly Leu Cys Phe Pro Asn Arg
    850                 855                 860

Leu Pro Gln Leu Met Leu Gln Ser Leu Ser Thr Ser Glu Glu Leu Gln
865                 870                 875                 880

Arg Gln Phe His Leu Phe Gln Leu Gln Arg Leu Asp Lys Leu Phe Leu
            885                 890                 895

Glu Gln Glu Asp Glu Glu Glu Lys Arg Leu Glu Glu Glu Glu Glu Glu
            900                 905                 910

Glu Glu Glu Glu Glu Ala Glu Lys Glu Leu Phe Ile Glu Asp Pro Ser
        915                 920                 925

Pro Ala Ile Ser Ile Leu Val Leu Ser Pro Arg Cys Trp Pro Val Ser
    930                 935                 940

Pro Leu Cys Tyr Leu Tyr His Pro Arg Lys Cys Leu Pro Thr Glu Phe
945                 950                 955                 960

Cys Asp Ala Leu Asp Arg Phe Ser Ser Phe Tyr Ser Gln Ser Gln Asn
            965                 970                 975

His Pro Val Leu Asp Met Gly Pro His Arg Arg Leu Gln Trp Thr Trp
            980                 985                 990

Leu Gly Arg Ala Glu Leu Gln Phe  Gly Lys Gln Ile Leu  His Val Ser
        995                 1000                 1005

Thr Val  Gln Met Trp Leu Leu  Leu Lys Phe Asn Gln  Thr Glu Glu
    1010                 1015                 1020

Val Ser  Val Glu Thr Leu Leu  Lys Asp Ser Asp Leu  Ser Pro Glu
    1025                 1030                 1035

Leu Leu  Leu Gln Ala Leu Val  Pro Leu Thr Ser Gly  Asn Gly Pro
    1040                 1045                 1050

Leu Thr  Leu His Glu Gly Gln  Asp Phe Pro His Gly  Gly Val Leu
    1055                 1060                 1065

Arg Leu  His Glu Pro Gly Pro  Gln Arg Ser Gly Glu  Ala Leu Trp
    1070                 1075                 1080

Leu Ile  Pro Pro Gln Ala Tyr  Leu Asn Val Glu Lys  Asp Glu Gly
    1085                 1090                 1095

Arg Thr  Leu Glu Gln Lys Arg  Asn Leu Leu Ser Cys  Leu Leu Val
    1100                 1105                 1110
```

-continued

```
Arg Ile  Leu Lys Ala His Gly  Glu Lys Gly Leu His  Ile Asp Gln
    1115                 1120                 1125

Leu Val  Cys Leu Val Leu Glu  Ala Trp Gln Lys Gly  Pro Asn Pro
    1130                 1135                 1140

Pro Gly  Thr Leu Gly His Thr  Val Ala Gly Gly Val  Ala Cys Thr
    1145                 1150                 1155

Ser Thr  Asp Val Leu Ser Cys  Ile Leu His Leu Leu  Gly Gln Gly
    1160                 1165                 1170

Tyr Val  Lys Arg Arg Asp Asp  Arg Pro Gln Ile Leu  Met Tyr Ala
    1175                 1180                 1185

Ala Pro  Glu Pro Met Gly Pro  Cys Arg Gly Gln Ala  Asp Val Pro
    1190                 1195                 1200

Phe Cys  Gly Ser Gln Ser Glu  Thr Ser Lys Pro Ser  Pro Glu Ala
    1205                 1210                 1215

Val Ala  Thr Leu Ala Ser Leu  Gln Leu Pro Ala Gly  Arg Thr Met
    1220                 1225                 1230

Ser Pro  Gln Glu Val Glu Gly  Leu Met Lys Gln Thr  Val Arg Gln
    1235                 1240                 1245

Val Gln  Glu Thr Leu Asn Leu  Glu Pro Asp Val Ala  Gln His Leu
    1250                 1255                 1260

Leu Ala  His Ser His Trp Gly  Ala Glu Gln Leu Leu  Gln Ser Tyr
    1265                 1270                 1275

Ser Glu  Asp Pro Glu Pro Leu  Leu Leu Ala Ala Gly  Leu Cys Val
    1280                 1285                 1290

His Gln  Ala Gln Ala Val Pro  Val Arg Pro Asp His  Cys Pro Val
    1295                 1300                 1305

Cys Val  Ser Pro Leu Gly Cys  Asp Asp Asp Leu Pro  Ser Leu Cys
    1310                 1315                 1320

Cys Met  His Tyr Cys Cys Lys  Ser Cys Trp Asn Glu  Tyr Leu Thr
    1325                 1330                 1335

Thr Arg  Ile Glu Gln Asn Leu  Val Leu Asn Cys Thr  Cys Pro Ile
    1340                 1345                 1350

Ala Asp  Cys Pro Ala Gln Pro  Thr Gly Ala Phe Ile  Arg Ala Ile
    1355                 1360                 1365

Val Ser  Ser Pro Glu Val Ile  Ser Lys Tyr Glu Lys  Ala Leu Leu
    1370                 1375                 1380

Arg Gly  Tyr Val Glu Ser Cys  Ser Asn Leu Thr Trp  Cys Thr Asn
    1385                 1390                 1395

Pro Gln  Gly Cys Asp Arg Ile  Leu Cys Arg Gln Gly  Leu Gly Cys
    1400                 1405                 1410

Gly Thr  Thr Cys Ser Lys Cys  Gly Trp Ala Ser Cys  Phe Asn Cys
    1415                 1420                 1425

Ser Phe  Pro Glu Ala His Tyr  Pro Ala Ser Cys Gly  His Met Ser
    1430                 1435                 1440

Gln Trp  Val Asp Asp Gly Gly  Tyr Tyr Asp Gly Met  Ser Val Glu
    1445                 1450                 1455

Ala Gln  Ser Lys His Leu Ala  Lys Leu Ile Ser Lys  Arg Cys Pro
    1460                 1465                 1470

Ser Cys  Gln Ala Pro Ile Glu  Lys Asn Glu Gly Cys  Leu His Met
    1475                 1480                 1485

Thr Cys  Ala Lys Cys Asn His  Gly Phe Cys Trp Arg  Cys Leu Lys
    1490                 1495                 1500
```

-continued

```
Ser Trp  Lys Pro Asn His Lys  Asp Tyr Tyr Asn Cys  Ser Ala Met
    1505                 1510                 1515

Val Ser  Lys Ala Ala Arg Gln  Glu Lys Arg Phe Gln  Asp Tyr Asn
    1520                 1525                 1530

Glu Arg  Cys Thr Phe His His  Gln Ala Arg Glu Phe  Ala Val Asn
    1535                 1540                 1545

Leu Arg  Asn Arg Val Ser Ala  Ile His Glu Val Pro  Pro Pro Arg
    1550                 1555                 1560

Ser Phe  Thr Phe Leu Asn Asp  Ala Cys Gln Gly Leu  Glu Gln Ala
    1565                 1570                 1575

Arg Lys  Val Leu Ala Tyr Ala  Cys Val Tyr Ser Phe  Tyr Ser Gln
    1580                 1585                 1590

Asp Ala  Glu Tyr Met Asp Val  Val Glu Gln Gln Thr  Glu Asn Leu
    1595                 1600                 1605

Glu Leu  His Thr Asn Ala Leu  Gln Ile Leu Leu Glu  Glu Thr Leu
    1610                 1615                 1620

Leu Arg  Cys Arg Asp Leu Ala  Ser Ser Leu Arg Leu  Leu Arg Ala
    1625                 1630                 1635

Asp Cys  Leu Ser Thr Gly Met  Glu Leu Leu Arg Arg  Ile Gln Glu
    1640                 1645                 1650

Arg Leu  Leu Ala Ile Leu Gln  His Ser Ala Gln Asp  Phe Arg Val
    1655                 1660                 1665

Gly Leu  Gln Ser Pro Ser Val  Glu Ala Trp Glu Ala  Lys Gly Pro
    1670                 1675                 1680

Asn Met  Pro Gly Ser Gln Pro  Gln Ala Ser Ser Gly  Pro Glu Ala
    1685                 1690                 1695

Glu Glu  Glu Glu Glu Asp Asp  Glu Asp Asp Val Pro  Glu Trp Gln
    1700                 1705                 1710

Gln Asp  Glu Phe Asp Glu Glu  Leu Asp Asn Asp Ser  Phe Ser Tyr
    1715                 1720                 1725

Asp Glu  Ser Glu Asn Leu Asp  Gln Glu Thr Phe Phe  Phe Gly Asp
    1730                 1735                 1740

Glu Glu  Glu Asp Glu Asp Glu  Ala Tyr Asp
    1745                 1750


<210> SEQ ID NO 45
<211> LENGTH: 614
<212> TYPE: PRT
<213> ORGANISM: Homo sapiens

<400> SEQUENCE: 45

Arg Ser Gly Gln Pro Arg Ala Glu Gly Leu Gly Ala Gly Ala Ala Gly
1               5                   10                  15

Pro Leu Arg Ala Met Ala Ala Pro Val Lys Gly Asn Arg Lys Gln Ser
            20                  25                  30

Thr Glu Gly Asp Ala Leu Asp Pro Pro Ala Ser Pro Lys Pro Ala Gly
        35                  40                  45

Lys Gln Asn Gly Ile Gln Asn Pro Ile Ser Leu Glu Asp Ser Pro Glu
    50                  55                  60

Ala Gly Gly Glu Arg Glu Glu Glu Gln Glu Arg Glu Glu Glu Gln Ala
65                  70                  75                  80

Phe Leu Val Ser Leu Tyr Lys Phe Met Lys Glu Arg His Thr Pro Ile
                85                  90                  95

Glu Arg Val Pro His Leu Gly Phe Lys Gln Ile Asn Leu Trp Lys Ile
            100                 105                 110
```

-continued

```
Tyr Lys Ala Val Glu Lys Leu Gly Ala Tyr Glu Leu Val Thr Gly Arg
        115                 120                 125

Arg Leu Trp Lys Asn Val Tyr Asp Glu Leu Gly Gly Ser Pro Gly Ser
    130                 135                 140

Thr Ser Ala Ala Thr Cys Thr Arg Arg His Tyr Glu Arg Leu Val Leu
145                 150                 155                 160

Pro Tyr Val Arg His Leu Lys Gly Glu Asp Asp Lys Pro Leu Pro Thr
                165                 170                 175

Ser Lys Pro Arg Lys Gln Tyr Lys Met Ala Lys Glu Asn Arg Gly Asp
            180                 185                 190

Asp Gly Ala Thr Glu Arg Pro Lys Lys Ala Lys Glu Glu Arg Arg Met
        195                 200                 205

Asp Gln Met Met Pro Gly Lys Thr Lys Ala Asp Ala Ala Asp Pro Ala
    210                 215                 220

Pro Leu Pro Ser Gln Glu Pro Pro Arg Asn Ser Thr Glu Gln Gln Gly
225                 230                 235                 240

Leu Ala Ser Gly Ser Ser Val Ser Phe Val Gly Ala Ser Gly Cys Pro
                245                 250                 255

Glu Ala Tyr Lys Arg Leu Leu Ser Ser Phe Tyr Cys Lys Gly Thr His
            260                 265                 270

Gly Ile Met Ser Pro Leu Ala Lys Lys Lys Leu Leu Ala Gln Val Ser
        275                 280                 285

Lys Val Glu Ala Leu Gln Cys Gln Glu Glu Gly Cys Arg His Gly Ala
    290                 295                 300

Glu Pro Gln Ala Ser Pro Ala Val His Leu Pro Glu Ser Pro Gln Ser
305                 310                 315                 320

Pro Lys Gly Leu Thr Glu Asn Ser Arg His Arg Leu Thr Pro Gln Glu
                325                 330                 335

Gly Leu Gln Ala Pro Gly Gly Ser Leu Arg Glu Glu Ala Gln Ala Gly
            340                 345                 350

Pro Cys Pro Ala Ala Pro Ile Phe Lys Gly Cys Phe Tyr Thr His Pro
        355                 360                 365

Thr Glu Val Leu Lys Pro Val Ser Gln His Pro Arg Asp Phe Phe Ser
    370                 375                 380

Arg Leu Lys Asp Gly Val Leu Leu Gly Pro Pro Gly Lys Glu Gly Leu
385                 390                 395                 400

Ser Val Lys Glu Pro Gln Leu Val Trp Gly Gly Asp Ala Asn Arg Pro
                405                 410                 415

Ser Ala Phe His Lys Gly Gly Ser Arg Lys Gly Ile Leu Tyr Pro Lys
            420                 425                 430

Pro Lys Ala Cys Trp Val Ser Pro Met Ala Lys Val Pro Ala Glu Ser
        435                 440                 445

Pro Thr Leu Pro Pro Thr Phe Pro Ser Ser Pro Gly Leu Gly Ser Lys
    450                 455                 460

Arg Ser Leu Glu Glu Glu Gly Ala Ala His Ser Gly Lys Arg Leu Arg
465                 470                 475                 480

Ala Val Ser Pro Phe Leu Lys Glu Ala Asp Ala Lys Lys Cys Gly Ala
                485                 490                 495

Lys Pro Ala Gly Ser Gly Leu Val Ser Cys Leu Leu Gly Pro Ala Leu
            500                 505                 510

Gly Pro Val Pro Pro Glu Ala Tyr Arg Gly Thr Met Leu His Cys Pro
        515                 520                 525
```

-continued

```
Leu Asn Phe Thr Gly Thr Pro Gly Pro Leu Lys Gly Gln Ala Ala Leu
    530                 535                 540

Pro Phe Ser Pro Leu Val Ile Pro Ala Phe Pro Ala His Phe Leu Ala
545                 550                 555                 560

Thr Ala Gly Pro Ser Pro Met Ala Ala Gly Leu Met His Phe Pro Pro
                565                 570                 575

Thr Ser Phe Asp Ser Ala Leu Arg His Arg Leu Cys Pro Ala Ser Ser
            580                 585                 590

Ala Trp His Ala Pro Pro Val Thr Thr Tyr Ala Ala Pro His Phe Phe
        595                 600                 605

His Leu Asn Thr Lys Leu
    610


<210> SEQ ID NO 46
<211> LENGTH: 499
<212> TYPE: PRT
<213> ORGANISM: Homo sapiens

<400> SEQUENCE: 46

Met Glu Leu Ser Glu Pro Ile Val Glu Asn Gly Glu Thr Glu Met Ser
1               5                   10                  15

Pro Glu Glu Ser Trp Glu His Lys Glu Glu Ile Ser Glu Ala Glu Pro
            20                  25                  30

Gly Gly Gly Ser Leu Gly Asp Gly Arg Pro Pro Glu Glu Ser Ala His
        35                  40                  45

Glu Met Met Glu Glu Glu Glu Glu Ile Pro Lys Pro Lys Ser Val Val
    50                  55                  60

Ala Pro Pro Gly Ala Pro Lys Lys Glu His Val Asn Val Val Phe Ile
65                  70                  75                  80

Gly His Val Asp Ala Gly Lys Ser Thr Ile Gly Gly Gln Ile Met Tyr
                85                  90                  95

Leu Thr Gly Met Val Asp Lys Arg Thr Leu Glu Lys Tyr Glu Arg Glu
            100                 105                 110

Ala Lys Glu Lys Asn Arg Glu Thr Trp Tyr Leu Ser Trp Ala Leu Asp
        115                 120                 125

Thr Asn Gln Glu Glu Arg Asp Lys Gly Lys Thr Val Glu Val Gly Arg
    130                 135                 140

Ala Tyr Phe Glu Thr Glu Lys Lys His Phe Thr Ile Leu Asp Ala Pro
145                 150                 155                 160

Gly His Lys Ser Phe Val Pro Asn Met Ile Gly Gly Ala Ser Gln Ala
                165                 170                 175

Asp Leu Ala Val Leu Val Ile Ser Ala Arg Lys Gly Glu Phe Glu Thr
            180                 185                 190

Gly Phe Glu Lys Gly Gly Gln Thr Arg Glu His Ala Met Leu Ala Lys
        195                 200                 205

Thr Ala Gly Val Lys His Leu Ile Val Leu Ile Asn Lys Met Asp Asp
    210                 215                 220

Pro Thr Val Asn Trp Ser Asn Glu Arg Tyr Glu Glu Cys Lys Glu Lys
225                 230                 235                 240

Leu Val Pro Phe Leu Lys Lys Val Gly Phe Asn Pro Lys Lys Asp Ile
                245                 250                 255

His Phe Met Pro Cys Ser Gly Leu Thr Gly Ala Asn Leu Lys Glu Gln
            260                 265                 270

Ser Asp Phe Cys Pro Trp Tyr Ile Gly Leu Pro Phe Ile Pro Tyr Leu
        275                 280                 285
```

```
Asp Asn Leu Pro Asn Phe Asn Arg Ser Val Asp Gly Pro Ile Arg Leu
    290                 295                 300

Pro Ile Val Asp Lys Tyr Lys Asp Met Gly Thr Val Val Leu Gly Lys
305                 310                 315                 320

Leu Glu Ser Gly Ser Ile Cys Lys Gly Gln Gln Leu Val Met Met Pro
                325                 330                 335

Asn Lys His Asn Val Glu Val Leu Gly Ile Leu Ser Asp Asp Val Glu
            340                 345                 350

Thr Asp Thr Val Ala Pro Gly Glu Asn Leu Lys Ile Arg Leu Lys Gly
        355                 360                 365

Ile Glu Glu Glu Glu Ile Leu Pro Gly Phe Ile Leu Cys Asp Pro Asn
    370                 375                 380

Asn Leu Cys His Ser Gly Arg Thr Phe Asp Ala Gln Ile Val Ile Ile
385                 390                 395                 400

Glu His Lys Ser Ile Ile Cys Pro Gly Tyr Asn Ala Val Leu His Ile
                405                 410                 415

His Thr Cys Ile Glu Glu Val Glu Ile Thr Ala Leu Ile Cys Leu Val
            420                 425                 430

Asp Lys Lys Ser Gly Glu Lys Ser Lys Thr Arg Pro Arg Phe Val Lys
        435                 440                 445

Gln Asp Gln Val Cys Ile Ala Arg Leu Arg Thr Ala Gly Thr Ile Cys
    450                 455                 460

Leu Glu Thr Phe Lys Asp Phe Pro Gln Met Gly Arg Phe Thr Leu Arg
465                 470                 475                 480

Asp Glu Gly Lys Thr Ile Ala Ile Gly Lys Val Leu Lys Leu Val Pro
                485                 490                 495

Glu Lys Asp


<210> SEQ ID NO 47
<211> LENGTH: 624
<212> TYPE: PRT
<213> ORGANISM: Homo sapiens

<400> SEQUENCE: 47

Met Ala Glu Asn Gly Glu Ser Ser Gly Pro Pro Arg Pro Ser Arg Gly
1               5                   10                  15

Pro Ala Ala Ala Gln Gly Ser Ala Ala Ala Pro Ala Glu Pro Lys Ile
            20                  25                  30

Ile Lys Val Thr Val Lys Thr Pro Lys Glu Lys Glu Glu Phe Ala Val
        35                  40                  45

Pro Glu Asn Ser Ser Val Gln Gln Phe Lys Glu Ala Ile Ser Lys Arg
    50                  55                  60

Phe Lys Ser Gln Thr Asp Gln Leu Val Leu Ile Phe Ala Gly Lys Ile
65                  70                  75                  80

Leu Lys Asp Gln Asp Thr Leu Ile Gln His Gly Ile His Asp Gly Leu
                85                  90                  95

Thr Val His Leu Val Ile Lys Ser Gln Asn Arg Pro Gln Gly Gln Ser
            100                 105                 110

Thr Gln Pro Ser Asn Ala Ala Gly Thr Asn Thr Thr Ser Ala Ser Thr
        115                 120                 125

Pro Arg Ser Asn Ser Thr Pro Ile Ser Thr Asn Ser Asn Pro Phe Gly
    130                 135                 140

Leu Gly Ser Leu Gly Gly Leu Ala Gly Leu Ser Ser Leu Gly Leu Ser
145                 150                 155                 160
```

```
Ser Thr Asn Phe Ser Glu Leu Gln Ser Gln Met Gln Gln Gln Leu Met
                165                 170                 175

Ala Ser Pro Glu Met Met Ile Gln Ile Met Glu Asn Pro Phe Val Gln
            180                 185                 190

Ser Met Leu Ser Asn Pro Asp Leu Met Arg Gln Leu Ile Met Ala Asn
        195                 200                 205

Pro Gln Met Gln Gln Leu Ile Gln Arg Asn Pro Glu Ile Ser His Leu
    210                 215                 220

Leu Asn Asn Pro Asp Ile Met Arg Gln Thr Leu Glu Ile Ala Arg Asn
225                 230                 235                 240

Pro Ala Met Met Gln Glu Met Met Arg Asn Gln Asp Leu Ala Leu Ser
                245                 250                 255

Asn Leu Glu Ser Ile Pro Gly Gly Tyr Asn Ala Leu Arg Arg Met Tyr
            260                 265                 270

Thr Asp Ile Gln Glu Pro Met Leu Asn Ala Ala Gln Glu Gln Phe Gly
        275                 280                 285

Gly Asn Pro Phe Ala Ser Val Gly Ser Ser Ser Ser Ser Gly Glu Gly
    290                 295                 300

Thr Gln Pro Ser Arg Thr Glu Asn Arg Asp Pro Leu Pro Asn Pro Trp
305                 310                 315                 320

Ala Pro Pro Pro Ala Thr Gln Ser Ser Ala Thr Thr Ser Thr Thr Thr
                325                 330                 335

Ser Thr Gly Ser Gly Ser Gly Asn Ser Ser Ser Asn Ala Thr Gly Asn
            340                 345                 350

Thr Val Ala Ala Ala Asn Tyr Val Ala Ser Ile Phe Ser Thr Pro Gly
        355                 360                 365

Met Gln Ser Leu Leu Gln Gln Ile Thr Glu Asn Pro Gln Leu Ile Gln
    370                 375                 380

Asn Met Leu Ser Ala Pro Tyr Met Arg Ser Met Met Gln Ser Leu Ser
385                 390                 395                 400

Gln Asn Pro Asp Leu Ala Ala Gln Met Met Leu Asn Ser Pro Leu Phe
                405                 410                 415

Thr Ala Asn Pro Gln Leu Gln Glu Gln Met Arg Pro Gln Leu Pro Ala
            420                 425                 430

Phe Leu Gln Gln Met Gln Asn Pro Asp Thr Leu Ser Ala Met Ser Asn
        435                 440                 445

Pro Arg Ala Met Gln Ala Leu Met Gln Ile Gln Gln Gly Leu Gln Thr
    450                 455                 460

Leu Ala Thr Glu Ala Pro Gly Leu Ile Pro Ser Phe Thr Pro Gly Val
465                 470                 475                 480

Gly Val Gly Val Leu Gly Thr Ala Ile Gly Pro Val Gly Pro Val Thr
                485                 490                 495

Pro Ile Gly Pro Ile Gly Pro Ile Val Pro Phe Thr Pro Ile Gly Pro
            500                 505                 510

Ile Gly Pro Ile Gly Pro Thr Gly Pro Ala Ala Pro Pro Gly Ser Thr
        515                 520                 525

Gly Ser Gly Gly Pro Thr Gly Pro Thr Val Ser Ser Ala Ala Pro Arg
    530                 535                 540

Glu Thr Thr Ser Pro Thr Ser Glu Ser Gly Pro Asn Gln Gln Phe Ile
545                 550                 555                 560

Gln Gln Met Val Gln Ala Leu Ala Gly Ala Asn Ala Pro Gln Leu Pro
                565                 570                 575
```

-continued

```
Asn Pro Glu Val Arg Phe Gln Gln Gln Leu Glu Gln Leu Asn Ala Met
            580                 585                 590

Gly Phe Leu Asn Arg Glu Ala Asn Leu Gln Ala Leu Ile Ala Thr Gly
        595                 600                 605

Gly Asp Ile Asn Ala Ala Ile Glu Arg Leu Leu Gly Ser Gln Pro Ser
    610                 615                 620


<210> SEQ ID NO 48
<211> LENGTH: 583
<212> TYPE: PRT
<213> ORGANISM: Homo sapiens

<400> SEQUENCE: 48

Met Ile Asn Ile Glu Ser Met Asp Thr Asp Lys Asp Asp Pro His Gly
1               5                   10                  15

Arg Leu Glu Tyr Thr Glu His Gln Gly Arg Ile Lys Asn Ala Arg Glu
            20                  25                  30

Ala His Ser Gln Ile Glu Lys Arg Arg Arg Asp Lys Met Asn Ser Phe
        35                  40                  45

Ile Asp Glu Leu Ala Ser Leu Val Pro Thr Cys Asn Ala Met Ser Arg
    50                  55                  60

Lys Leu Asp Lys Leu Thr Val Leu Arg Met Ala Val Gln His Met Lys
65                  70                  75                  80

Thr Leu Arg Gly Ala Thr Asn Pro Tyr Thr Glu Ala Asn Tyr Lys Pro
                85                  90                  95

Thr Phe Leu Ser Asp Asp Glu Leu Lys His Leu Ile Leu Arg Ala Ala
            100                 105                 110

Asp Gly Phe Leu Phe Val Val Gly Cys Asp Arg Gly Lys Ile Leu Phe
        115                 120                 125

Val Ser Glu Ser Val Phe Lys Ile Leu Asn Tyr Ser Gln Asn Asp Leu
    130                 135                 140

Ile Gly Gln Ser Leu Phe Asp Tyr Leu His Pro Lys Asp Ile Ala Lys
145                 150                 155                 160

Val Lys Glu Gln Leu Ser Ser Ser Asp Thr Ala Pro Arg Glu Arg Leu
                165                 170                 175

Ile Asp Ala Lys Thr Gly Leu Pro Val Lys Thr Asp Ile Thr Pro Gly
            180                 185                 190

Pro Ser Arg Leu Cys Ser Gly Ala Arg Arg Ser Phe Phe Cys Arg Met
        195                 200                 205

Lys Cys Asn Arg Pro Ser Val Lys Val Glu Asp Lys Asp Phe Pro Ser
    210                 215                 220

Thr Cys Ser Lys Lys Lys Ala Asp Arg Lys Ser Phe Cys Thr Ile His
225                 230                 235                 240

Ser Thr Gly Tyr Leu Lys Ser Trp Pro Pro Thr Lys Met Gly Leu Asp
                245                 250                 255

Glu Asp Asn Glu Pro Asp Asn Glu Gly Cys Asn Leu Ser Cys Leu Val
            260                 265                 270

Ala Ile Gly Arg Leu His Ser His Val Val Pro Gln Pro Val Asn Gly
        275                 280                 285

Glu Ile Arg Val Lys Ser Met Glu Tyr Val Ser Arg His Ala Ile Asp
    290                 295                 300

Gly Lys Phe Val Phe Val Asp Gln Arg Ala Thr Ala Ile Leu Ala Tyr
305                 310                 315                 320

Leu Pro Gln Glu Leu Leu Gly Thr Ser Cys Tyr Glu Tyr Phe His Gln
                325                 330                 335
```

```
Asp Asp Ile Gly His Leu Ala Glu Cys His Arg Gln Val Leu Gln Thr
            340                 345                 350

Arg Glu Lys Ile Thr Thr Asn Cys Tyr Lys Phe Lys Ile Lys Asp Gly
        355                 360                 365

Ser Phe Ile Thr Leu Arg Ser Arg Trp Phe Ser Phe Met Asn Pro Trp
    370                 375                 380

Thr Lys Glu Val Glu Tyr Ile Val Ser Thr Asn Thr Val Val Leu Ala
385                 390                 395                 400

Asn Val Leu Glu Gly Gly Asp Pro Thr Phe Pro Gln Leu Thr Ala Ser
                405                 410                 415

Pro His Ser Met Asp Ser Met Leu Pro Ser Gly Glu Gly Gly Pro Lys
            420                 425                 430

Arg Thr His Pro Thr Val Pro Gly Ile Pro Gly Gly Thr Arg Ala Gly
        435                 440                 445

Ala Gly Lys Ile Gly Arg Met Ile Ala Glu Glu Ile Met Glu Ile His
    450                 455                 460

Arg Ile Arg Gly Ser Ser Pro Ser Ser Cys Gly Ser Ser Pro Leu Asn
465                 470                 475                 480

Ile Thr Ser Thr Pro Pro Pro Asp Ala Ser Ser Pro Gly Gly Lys Lys
                485                 490                 495

Ile Leu Asn Gly Gly Thr Pro Asp Ile Pro Ser Ser Gly Leu Leu Ser
            500                 505                 510

Gly Gln Ala Gln Glu Asn Pro Gly Tyr Pro Tyr Ser Asp Ser Ser Ser
        515                 520                 525

Ile Leu Gly Glu Asn Pro His Ile Gly Ile Asp Met Ile Asp Asn Asp
    530                 535                 540

Gln Gly Ser Ser Ser Pro Ser Asn Asp Glu Ala Ala Met Ala Val Ile
545                 550                 555                 560

Met Ser Leu Leu Glu Ala Asp Ala Gly Leu Gly Gly Pro Val Asp Phe
                565                 570                 575

Ser Asp Leu Pro Trp Pro Leu
            580


<210> SEQ ID NO 49
<211> LENGTH: 4861
<212> TYPE: PRT
<213> ORGANISM: Homo sapiens

<400> SEQUENCE: 49

Met Ala Thr Met Ile Pro Pro Val Lys Leu Lys Trp Leu Glu His Leu
1               5                   10                  15

Asn Ser Ser Trp Ile Thr Glu Asp Ser Glu Ser Ile Ala Thr Arg Glu
            20                  25                  30

Gly Val Ala Val Leu Tyr Ser Lys Leu Val Ser Asn Lys Glu Val Val
        35                  40                  45

Pro Leu Pro Gln Gln Val Leu Cys Leu Lys Gly Pro Gln Leu Pro Asp
    50                  55                  60

Phe Glu Arg Glu Ser Leu Ser Ser Asp Glu Gln Asp His Tyr Leu Asp
65                  70                  75                  80

Ala Leu Leu Ser Ser Gln Leu Ala Leu Ala Lys Met Val Cys Ser Asp
                85                  90                  95

Ser Pro Phe Ala Gly Ala Leu Arg Lys Arg Leu Leu Val Leu Gln Arg
            100                 105                 110

Val Phe Tyr Ala Leu Ser Asn Lys Tyr His Asp Lys Gly Lys Val Lys
```

-continued

```
        115                 120                 125

Gln Gln Gln His Ser Pro Glu Ser Ser Ser Gly Ser Ala Asp Val His
    130                 135                 140

Ser Val Ser Glu Arg Pro Arg Ser Ser Thr Asp Ala Leu Ile Glu Met
145                 150                 155                 160

Gly Val Arg Thr Gly Leu Ser Leu Leu Phe Ala Leu Leu Arg Gln Ser
                165                 170                 175

Trp Met Met Pro Val Ser Gly Pro Gly Leu Ser Leu Cys Asn Asp Val
            180                 185                 190

Ile His Thr Ala Ile Glu Val Val Ser Ser Leu Pro Pro Leu Ser Leu
        195                 200                 205

Ala Asn Glu Ser Lys Ile Pro Pro Met Gly Leu Asp Cys Leu Ser Gln
    210                 215                 220

Val Thr Thr Phe Leu Lys Gly Val Thr Ile Pro Asn Ser Gly Ala Asp
225                 230                 235                 240

Thr Leu Gly Arg Arg Leu Ala Ser Glu Leu Leu Leu Gly Leu Ala Ala
                245                 250                 255

Gln Arg Gly Ser Leu Arg Tyr Leu Leu Glu Trp Ile Glu Met Ala Leu
            260                 265                 270

Gly Ala Ser Ala Val Val His Thr Met Glu Lys Gly Lys Leu Leu Ser
        275                 280                 285

Ser Gln Glu Gly Met Ile Ser Phe Asp Cys Phe Met Thr Ile Leu Met
    290                 295                 300

Gln Met Arg Arg Ser Leu Gly Ser Ser Ala Asp Arg Ser Gln Trp Arg
305                 310                 315                 320

Glu Pro Thr Arg Thr Ser Asp Gly Leu Cys Ser Leu Tyr Glu Ala Ala
                325                 330                 335

Leu Cys Leu Phe Glu Glu Val Cys Arg Met Ala Ser Asp Tyr Ser Arg
            340                 345                 350

Thr Cys Ala Ser Pro Asp Ser Ile Gln Thr Gly Asp Ala Pro Ile Val
        355                 360                 365

Ser Glu Thr Cys Glu Val Tyr Val Trp Gly Ser Asn Ser Ser His Gln
    370                 375                 380

Leu Val Glu Gly Thr Gln Glu Lys Ile Leu Gln Pro Lys Leu Ala Pro
385                 390                 395                 400

Ser Phe Ser Asp Ala Gln Thr Ile Glu Ala Gly Gln Tyr Cys Thr Phe
                405                 410                 415

Val Ile Ser Thr Asp Gly Ser Val Arg Ala Cys Gly Lys Gly Ser Tyr
            420                 425                 430

Gly Arg Leu Gly Leu Gly Asp Ser Asn Asn Gln Ser Thr Leu Lys Lys
        435                 440                 445

Leu Thr Phe Glu Pro His Arg Ser Ile Lys Lys Val Ser Ser Ser Lys
    450                 455                 460

Gly Ser Asp Gly His Thr Leu Ala Phe Thr Thr Glu Gly Glu Val Phe
465                 470                 475                 480

Ser Trp Gly Asp Gly Asp Tyr Gly Lys Leu Gly His Gly Asn Ser Ser
                485                 490                 495

Thr Gln Lys Tyr Pro Lys Leu Ile Gln Gly Pro Leu Gln Gly Lys Val
            500                 505                 510

Val Val Cys Val Ser Ala Gly Tyr Arg His Ser Ala Ala Val Thr Glu
        515                 520                 525

Asp Gly Glu Leu Tyr Thr Trp Gly Glu Gly Asp Phe Gly Arg Leu Gly
    530                 535                 540
```

-continued

```
His Gly Asp Ser Asn Ser Arg Asn Ile Pro Thr Leu Val Lys Asp Ile
545                 550                 555                 560

Ser Asn Val Gly Glu Val Ser Cys Gly Ser Ser His Thr Ile Ala Leu
                565                 570                 575

Ser Lys Asp Gly Arg Thr Val Trp Ser Phe Gly Gly Gly Asp Asn Gly
            580                 585                 590

Lys Leu Gly His Gly Asp Thr Asn Arg Val Tyr Lys Pro Lys Val Ile
        595                 600                 605

Glu Ala Leu Gln Gly Met Phe Ile Arg Lys Val Cys Ala Gly Ser Gln
    610                 615                 620

Ser Ser Leu Ala Leu Thr Ser Thr Gly Gln Val Tyr Ala Trp Gly Cys
625                 630                 635                 640

Gly Ala Cys Leu Gly Cys Gly Ser Ser Glu Ala Thr Ala Leu Arg Pro
                645                 650                 655

Lys Leu Ile Glu Glu Leu Ala Ala Thr Arg Ile Val Asp Val Ser Ile
            660                 665                 670

Gly Asp Ser His Cys Leu Ala Leu Ser His Asp Asn Glu Val Tyr Ala
        675                 680                 685

Trp Gly Asn Asn Ser Met Gly Gln Cys Gly Gln Gly Asn Ser Thr Gly
    690                 695                 700

Pro Ile Thr Lys Pro Lys Lys Val Ser Gly Leu Asp Gly Ile Ala Ile
705                 710                 715                 720

Gln Gln Ile Ser Ala Gly Thr Ser His Ser Leu Ala Trp Thr Ala Leu
                725                 730                 735

Pro Arg Asp Arg Gln Val Val Ala Trp His Arg Pro Tyr Cys Val Asp
            740                 745                 750

Leu Glu Glu Ser Thr Phe Ser His Leu Arg Ser Phe Leu Glu Arg Tyr
        755                 760                 765

Cys Asp Lys Ile Asn Ser Glu Ile Pro Pro Leu Pro Phe Pro Ser Ser
    770                 775                 780

Arg Glu His His Ser Phe Leu Lys Leu Cys Leu Lys Leu Leu Ser Asn
785                 790                 795                 800

His Leu Ala Leu Ala Leu Ala Gly Gly Val Ala Thr Ser Ile Leu Gly
                805                 810                 815

Arg Gln Ala Gly Pro Leu Arg Asn Leu Leu Phe Arg Leu Met Asp Ser
            820                 825                 830

Thr Val Pro Asp Glu Ile Gln Glu Val Val Ile Glu Thr Leu Ser Val
        835                 840                 845

Gly Ala Thr Met Leu Leu Pro Pro Leu Arg Glu Arg Met Glu Leu Leu
    850                 855                 860

His Ser Leu Leu Pro Gln Gly Pro Asp Arg Trp Glu Ser Leu Ser Lys
865                 870                 875                 880

Gly Gln Arg Met Gln Leu Asp Ile Ile Leu Thr Ser Leu Gln Asp His
                885                 890                 895

Thr His Val Ala Ser Leu Leu Gly Tyr Ser Ser Pro Ser Asp Ala Ala
            900                 905                 910

Asp Leu Ser Ser Val Cys Thr Gly Tyr Gly Asn Leu Ser Asp Gln Pro
        915                 920                 925

Tyr Gly Thr Gln Ser Cys His Pro Asp Thr His Leu Ala Glu Ile Leu
    930                 935                 940

Met Lys Thr Leu Leu Arg Asn Leu Gly Phe Tyr Thr Asp Gln Ala Phe
945                 950                 955                 960
```

-continued

```
Gly Glu Leu Glu Lys Asn Ser Asp Lys Phe Leu Leu Gly Thr Ser Ser
              965                 970                 975

Ser Glu Asn Ser Gln Pro Ala His Leu His Glu Leu Leu Cys Ser Leu
            980                 985                 990

Gln Lys Gln Leu Leu Ala Phe Cys  His Ile Asn Asn Ile  Ser Glu Asn
        995                 1000                1005

Ser Ser  Ser Val Ala Leu Leu  His Lys His Leu Gln  Leu Leu Leu
    1010                 1015                 1020

Pro His  Ala Thr Asp Ile Tyr  Ser Arg Ser Ala Asn  Leu Leu Lys
    1025                 1030                 1035

Glu Ser  Pro Trp Asn Gly Ser  Val Gly Glu Lys Leu  Arg Asp Val
    1040                 1045                 1050

Ile Tyr  Val Ser Ala Ala Gly  Ser Met Leu Cys Gln  Ile Val Asn
    1055                 1060                 1065

Ser Leu  Leu Leu Leu Pro Val  Ser Val Ala Arg Pro  Leu Leu Ser
    1070                 1075                 1080

Tyr Leu  Leu Asp Leu Leu Pro  Pro Leu Asp Cys Leu  Asn Arg Leu
    1085                 1090                 1095

Leu Pro  Ala Ala Asp Leu Leu  Glu Asp Gln Glu Leu  Gln Trp Pro
    1100                 1105                 1110

Leu His  Gly Gly Pro Glu Leu  Ile Asp Pro Ala Gly  Leu Pro Leu
    1115                 1120                 1125

Pro Gln  Pro Ala Gln Ser Trp  Val Trp Leu Val Asp  Leu Glu Arg
    1130                 1135                 1140

Thr Ile  Ala Leu Leu Ile Gly  Arg Cys Leu Gly Gly  Met Leu Gln
    1145                 1150                 1155

Gly Ser  Pro Val Ser Pro Glu  Glu Gln Asp Thr Ala  Tyr Trp Met
    1160                 1165                 1170

Lys Thr  Pro Leu Phe Ser Asp  Gly Val Glu Met Asp  Thr Pro Gln
    1175                 1180                 1185

Leu Asp  Lys Cys Met Ser Cys  Leu Leu Glu Val Ala  Leu Ser Gly
    1190                 1195                 1200

Asn Glu  Glu Gln Lys Pro Phe  Asp Tyr Lys Leu Arg  Pro Glu Ile
    1205                 1210                 1215

Ala Val  Tyr Val Asp Leu Ala  Leu Gly Cys Ser Lys  Glu Pro Ala
    1220                 1225                 1230

Arg Ser  Leu Trp Ile Ser Met  Gln Asp Tyr Ala Val  Ser Lys Asp
    1235                 1240                 1245

Trp Asp  Ser Ala Thr Leu Ser  Asn Glu Ser Leu Leu  Asp Thr Val
    1250                 1255                 1260

Ser Arg  Phe Val Leu Ala Ala  Leu Leu Lys His Thr  Asn Leu Leu
    1265                 1270                 1275

Ser Gln  Ala Cys Gly Glu Ser  Arg Tyr Gln Pro Gly  Lys His Leu
    1280                 1285                 1290

Ser Glu  Val Tyr Arg Cys Val  Tyr Lys Val Arg Ser  Arg Leu Leu
    1295                 1300                 1305

Ala Cys  Lys Asn Leu Glu Leu  Ile Gln Thr Arg Ser  Ser Ser Arg
    1310                 1315                 1320

Asp Arg  Trp Ile Ser Glu Asn  Gln Asp Ser Ala Asp  Val Asp Pro
    1325                 1330                 1335

Gln Glu  His Ser Phe Thr Arg  Thr Ile Asp Glu Glu  Ala Glu Met
    1340                 1345                 1350

Glu Glu  Gln Ala Glu Arg Asp  Arg Glu Glu Gly His  Pro Glu Pro
```

```
    1355                1360                1365

Glu Asp  Glu Glu Glu Glu Arg  Glu His Glu Val Met  Thr Ala Gly
    1370                1375                1380

Lys Ile  Phe Gln Cys Phe Leu  Ser Ala Arg Glu Val  Ala Arg Ser
    1385                1390                1395

Arg Asp  Arg Asp Arg Met Asn  Ser Gly Ala Gly Ser  Gly Ala Arg
    1400                1405                1410

Ala Asp  Asp Pro Pro Pro Gln  Ser Gln Gln Glu Arg  Arg Val Ser
    1415                1420                1425

Thr Asp  Leu Pro Glu Gly Gln  Asp Val Tyr Thr Ala  Ala Cys Asn
    1430                1435                1440

Ser Val  Ile His Arg Cys Ala  Leu Leu Ile Leu Gly  Val Ser Pro
    1445                1450                1455

Val Ile  Asp Glu Leu Gln Lys  Arg Arg Glu Glu Gly  Gln Leu Gln
    1460                1465                1470

Gln Pro  Ser Thr Ser Ala Ser  Glu Gly Gly Gly Leu  Met Thr Arg
    1475                1480                1485

Ser Glu  Ser Leu Thr Ala Glu  Ser Arg Leu Val His  Thr Ser Pro
    1490                1495                1500

Asn Tyr  Arg Leu Ile Lys Ser  Arg Ser Glu Ser Asp  Leu Ser Gln
    1505                1510                1515

Pro Glu  Ser Asp Glu Glu Gly  Tyr Ala Leu Ser Gly  Arg Gln Asn
    1520                1525                1530

Val Asp  Leu Asp Leu Ala Ala  Ser His Arg Lys Arg  Gly Pro Met
    1535                1540                1545

His Ser  Gln Leu Glu Ser Leu  Ser Asp Ser Trp Ala  Arg Leu Lys
    1550                1555                1560

His Ser  Arg Asp Trp Leu Cys  Asn Ser Ser Tyr Ser  Phe Glu Ser
    1565                1570                1575

Asp Phe  Asp Leu Thr Lys Ser  Leu Gly Val His Thr  Leu Ile Glu
    1580                1585                1590

Asn Val  Val Ser Phe Val Ser  Gly Asp Val Gly Asn  Ala Pro Gly
    1595                1600                1605

Phe Lys  Glu Pro Glu Glu Ser  Met Ser Thr Ser Pro  Gln Ala Ser
    1610                1615                1620

Ile Ile  Ala Met Glu Gln Gln  Gln Leu Arg Ala Glu  Leu Arg Leu
    1625                1630                1635

Glu Ala  Leu His Gln Ile Leu  Val Leu Leu Ser Gly  Met Glu Glu
    1640                1645                1650

Lys Gly  Ser Ile Ser Leu Ala  Gly Ser Arg Leu Ser  Ser Gly Phe
    1655                1660                1665

Gln Ser  Ser Thr Leu Leu Thr  Ser Val Arg Leu Gln  Phe Leu Ala
    1670                1675                1680

Gly Cys  Phe Gly Leu Gly Thr  Val Gly His Thr Gly  Ala Lys Gly
    1685                1690                1695

Glu Ser  Gly Arg Leu His His  Tyr Gln Asp Gly Ile  Arg Ala Ala
    1700                1705                1710

Lys Arg  Asn Ile Gln Ile Glu  Ile Gln Val Ala Val  His Lys Ile
    1715                1720                1725

Tyr Gln  Gln Leu Ser Ala Thr  Leu Glu Arg Ala Leu  Gln Ala Asn
    1730                1735                1740

Lys His  His Ile Glu Ala Gln  Gln Arg Leu Leu Leu  Val Thr Val
    1745                1750                1755
```

-continued

```
Phe Ala Leu Ser Val His Tyr Gln Pro Val Asp Val Ser Leu Ala
    1760                1765                1770

Ile Ser Thr Gly Leu Leu Asn Val Leu Ser Gln Leu Cys Gly Thr
    1775                1780                1785

Asp Thr Met Leu Gly Gln Pro Leu Gln Leu Leu Pro Lys Thr Gly
    1790                1795                1800

Val Ser Gln Leu Ser Thr Ala Leu Lys Val Ala Ser Thr Arg Leu
    1805                1810                1815

Leu Gln Ile Leu Ala Ile Thr Thr Gly Thr Tyr Ala Asp Lys Leu
    1820                1825                1830

Ser Pro Lys Val Val Gln Ser Leu Leu Asp Leu Leu Cys Ser Gln
    1835                1840                1845

Leu Lys Asn Leu Leu Ser Gln Thr Gly Val Leu His Met Ala Ser
    1850                1855                1860

Phe Gly Glu Gly Glu Gln Glu Asp Gly Glu Glu Glu Glu Lys Lys
    1865                1870                1875

Val Asp Ser Ser Gly Glu Thr Glu Lys Lys Asp Phe Arg Ala Ala
    1880                1885                1890

Leu Arg Lys Gln His Ala Ala Glu Leu His Leu Gly Asp Phe Leu
    1895                1900                1905

Val Phe Leu Arg Arg Val Val Ser Ser Lys Ala Ile Gln Ser Lys
    1910                1915                1920

Met Ala Ser Pro Lys Trp Thr Glu Val Leu Leu Asn Ile Ala Ser
    1925                1930                1935

Gln Lys Cys Ser Ser Gly Ile Pro Leu Val Gly Asn Leu Arg Thr
    1940                1945                1950

Arg Leu Leu Ala Leu His Val Leu Glu Ala Val Leu Pro Ala Cys
    1955                1960                1965

Glu Ser Gly Val Glu Asp Asp Gln Met Ala Gln Ile Val Glu Arg
    1970                1975                1980

Leu Phe Ser Leu Leu Ser Asp Cys Met Trp Glu Thr Pro Ile Ala
    1985                1990                1995

Gln Ala Lys His Ala Ile Gln Ile Lys Glu Lys Glu Gln Glu Ile
    2000                2005                2010

Lys Leu Gln Lys Gln Gly Glu Leu Glu Glu Glu Asp Glu Asn Leu
    2015                2020                2025

Pro Ile Gln Glu Val Ser Phe Asp Pro Glu Lys Ala Gln Cys Cys
    2030                2035                2040

Leu Val Glu Asn Gly Gln Ile Leu Thr His Gly Ser Gly Gly Lys
    2045                2050                2055

Gly Tyr Gly Leu Ala Ser Thr Gly Val Thr Ser Gly Cys Tyr Gln
    2060                2065                2070

Trp Lys Phe Tyr Ile Val Lys Glu Asn Arg Gly Asn Glu Gly Thr
    2075                2080                2085

Cys Val Gly Val Ser Arg Trp Pro Val His Asp Phe Asn His Arg
    2090                2095                2100

Thr Thr Ser Asp Met Trp Leu Tyr Arg Ala Tyr Ser Gly Asn Leu
    2105                2110                2115

Tyr His Asn Gly Glu Gln Thr Leu Thr Leu Ser Ser Phe Thr Gln
    2120                2125                2130

Gly Asp Phe Ile Thr Cys Val Leu Asp Met Glu Ala Arg Thr Ile
    2135                2140                2145
```

-continued

```
Ser Phe  Gly Lys Asn Gly Glu  Glu Pro Lys Leu Ala  Phe Glu Asp
    2150                 2155                 2160

Val Asp  Ala Ala Glu Leu Tyr  Pro Cys Val Met Phe  Tyr Ser Ser
    2165                 2170                 2175

Asn Pro  Gly Glu Lys Val Lys  Ile Cys Asp Met Gln  Met Arg Gly
    2180                 2185                 2190

Thr Pro  Arg Asp Leu Leu Pro  Gly Asp Pro Ile Cys  Ser Pro Val
    2195                 2200                 2205

Ala Ala  Val Leu Ala Glu Ala  Thr Ile Gln Leu Val  Arg Ile Leu
    2210                 2215                 2220

His Arg  Thr Asp Arg Trp Thr  Tyr Cys Ile Asn Lys  Lys Met Met
    2225                 2230                 2235

Glu Arg  Leu His Lys Ile Lys  Ile Cys Ile Lys Glu  Ser Gly Gln
    2240                 2245                 2250

Lys Leu  Lys Lys Ser Arg Ser  Val Gln Ser Arg Glu  Glu Asn Glu
    2255                 2260                 2265

Met Arg  Glu Glu Lys Glu Ser  Lys Glu Glu Glu Lys  Gly Lys His
    2270                 2275                 2280

Thr Arg  His Gly Leu Ala Asp  Leu Ser Glu Leu Gln  Leu Arg Thr
    2285                 2290                 2295

Leu Cys  Ile Glu Val Trp Pro  Val Leu Ala Val Ile  Gly Gly Val
    2300                 2305                 2310

Asp Ala  Gly Leu Arg Val Gly  Gly Arg Cys Val His  Lys Gln Thr
    2315                 2320                 2325

Gly Arg  His Ala Thr Leu Leu  Gly Val Val Lys Glu  Gly Ser Thr
    2330                 2335                 2340

Ser Ala  Lys Val Gln Trp Asp  Glu Ala Glu Ile Thr  Ile Ser Phe
    2345                 2350                 2355

Pro Thr  Phe Trp Ser Pro Ser  Asp Thr Pro Leu Tyr  Asn Leu Glu
    2360                 2365                 2370

Pro Cys  Glu Pro Leu Pro Phe  Asp Val Ala Arg Phe  Arg Gly Leu
    2375                 2380                 2385

Thr Ala  Ser Val Leu Leu Asp  Leu Thr Tyr Leu Thr  Gly Val His
    2390                 2395                 2400

Glu Asp  Met Gly Lys Gln Ser  Thr Lys Arg His Glu  Lys Lys His
    2405                 2410                 2415

Arg His  Glu Ser Glu Glu Lys  Gly Asp Val Glu Gln  Lys Pro Glu
    2420                 2425                 2430

Ser Glu  Ser Ala Leu Asp Met  Arg Thr Gly Leu Thr  Ser Asp Asp
    2435                 2440                 2445

Val Lys  Ser Gln Ser Thr Thr  Ser Ser Lys Ser Glu  Asn Glu Ile
    2450                 2455                 2460

Ala Ser  Phe Ser Leu Asp Pro  Thr Leu Pro Ser Val  Glu Ser Gln
    2465                 2470                 2475

His Gln  Ile Thr Glu Gly Lys  Arg Lys Asn His Glu  His Met Ser
    2480                 2485                 2490

Lys Asn  His Asp Val Ala Gln  Ser Glu Ile Arg Ala  Val Gln Leu
    2495                 2500                 2505

Ser Tyr  Leu Tyr Leu Gly Ala  Met Lys Ser Leu Ser  Ala Leu Leu
    2510                 2515                 2520

Gly Cys  Ser Lys Tyr Ala Glu  Leu Leu Leu Ile Pro  Lys Val Leu
    2525                 2530                 2535

Ala Glu  Asn Gly His Asn Ser  Asp Cys Ala Ser Ser  Pro Val Val
```

```
    2540                2545                2550

His Glu  Asp Val Glu Met Arg  Ala Ala Leu Gln Phe  Leu Met Arg
    2555                2560                2565

His Met  Val Lys Arg Ala Val  Met Arg Ser Pro Ile  Lys Arg Ala
    2570                2575                2580

Leu Gly  Leu Ala Asp Leu Glu  Arg Ala Gln Ala Met  Ile Tyr Lys
    2585                2590                2595

Leu Val  Val His Gly Leu Leu  Glu Asp Gln Phe Gly  Gly Lys Ile
    2600                2605                2610

Lys Gln  Glu Ile Asp Gln Gln  Ala Glu Glu Ser Asp  Pro Ala Gln
    2615                2620                2625

Gln Ala  Gln Thr Pro Val Thr  Thr Ser Pro Ser Ala  Ser Ser Thr
    2630                2635                2640

Thr Ser  Phe Met Ser Ser Ser  Leu Glu Asp Thr Thr  Thr Ala Thr
    2645                2650                2655

Thr Pro  Val Thr Asp Thr Glu  Thr Val Pro Ala Ser  Glu Ser Pro
    2660                2665                2670

Gly Val  Met Pro Leu Ser Leu  Leu Arg Gln Met Phe  Ser Ser Tyr
    2675                2680                2685

Pro Thr  Thr Thr Val Leu Pro  Thr Arg Arg Ala Gln  Thr Pro Pro
    2690                2695                2700

Ile Ser  Ser Leu Pro Thr Ser  Pro Ser Asp Glu Val  Gly Arg Arg
    2705                2710                2715

Gln Ser  Leu Thr Ser Pro Asp  Ser Gln Ser Ala Arg  Pro Ala Asn
    2720                2725                2730

Arg Thr  Ala Leu Ser Asp Pro  Ser Ser Arg Leu Ser  Thr Ser Pro
    2735                2740                2745

Pro Pro  Pro Ala Ile Ala Val  Pro Leu Leu Glu Met  Gly Phe Ser
    2750                2755                2760

Leu Arg  Gln Ile Ala Lys Ala  Met Glu Ala Thr Gly  Ala Arg Gly
    2765                2770                2775

Glu Ala  Asp Ala Gln Asn Ile  Thr Val Leu Ala Met  Trp Met Ile
    2780                2785                2790

Glu His  Pro Gly His Glu Asp  Glu Glu Glu Pro Gln  Ser Gly Ser
    2795                2800                2805

Thr Ala  Asp Ser Arg Pro Gly  Ala Ala Val Leu Gly  Ser Gly Gly
    2810                2815                2820

Lys Ser  Asn Asp Pro Cys Tyr  Leu Gln Ser Pro Gly  Asp Ile Pro
    2825                2830                2835

Ser Ala  Asp Ala Ala Glu Met  Glu Glu Gly Phe Ser  Glu Ser Pro
    2840                2845                2850

Asp Asn  Leu Asp His Thr Glu  Asn Ala Ala Ser Gly  Ser Gly Pro
    2855                2860                2865

Ser Ala  Arg Gly Arg Ser Ala  Val Thr Arg Arg His  Lys Phe Asp
    2870                2875                2880

Leu Ala  Ala Arg Thr Leu Leu  Ala Arg Ala Ala Gly  Leu Tyr Arg
    2885                2890                2895

Ser Val  Gln Ala His Arg Asn  Gln Ser Arg Arg Glu  Gly Ile Ser
    2900                2905                2910

Leu Gln  Gln Asp Pro Gly Ala  Leu Tyr Asp Phe Asn  Leu Asp Glu
    2915                2920                2925

Glu Leu  Glu Ile Asp Leu Asp  Asp Glu Ala Met Glu  Ala Met Phe
    2930                2935                2940
```

-continued

```
Gly Gln  Asp Leu Thr Ser Asp  Asn Asp Ile Leu Gly  Met Trp Ile
    2945                 2950                 2955

Pro Glu  Val Leu Asp Trp Pro  Thr Trp His Val Cys  Glu Ser Glu
    2960                 2965                 2970

Asp Arg  Glu Glu Val Val Val  Cys Glu Leu Cys Glu  Cys Ser Val
    2975                 2980                 2985

Val Ser  Phe Asn Gln His Met  Lys Arg Asn His Pro  Gly Cys Gly
    2990                 2995                 3000

Arg Ser  Ala Asn Arg Gln Gly  Tyr Arg Ser Asn Gly  Ser Tyr Val
    3005                 3010                 3015

Asp Gly  Trp Phe Gly Gly Glu  Cys Gly Ser Gly Asn  Pro Tyr Tyr
    3020                 3025                 3030

Leu Leu  Cys Gly Thr Cys Arg  Glu Lys Tyr Leu Ala  Met Lys Thr
    3035                 3040                 3045

Lys Ser  Lys Ser Thr Ser Ser  Glu Arg Tyr Lys Gly  Gln Ala Pro
    3050                 3055                 3060

Asp Leu  Ile Gly Lys Gln Asp  Ser Val Tyr Glu Glu  Asp Trp Asp
    3065                 3070                 3075

Met Leu  Asp Val Asp Glu Asp  Glu Lys Leu Thr Gly  Glu Glu Glu
    3080                 3085                 3090

Phe Glu  Leu Leu Ala Gly Pro  Leu Gly Leu Asn Asp  Arg Arg Ile
    3095                 3100                 3105

Val Pro  Glu Pro Val Gln Phe  Pro Asp Ser Asp Pro  Leu Gly Ala
    3110                 3115                 3120

Ser Val  Ala Met Val Thr Ala  Thr Asn Ser Met Glu  Glu Thr Leu
    3125                 3130                 3135

Met Gln  Ile Gly Cys His Gly  Ser Val Glu Lys Ser  Ser Ser Gly
    3140                 3145                 3150

Arg Ile  Thr Leu Gly Glu Gln  Ala Ala Ala Leu Ala  Asn Pro His
    3155                 3160                 3165

Asp Arg  Val Val Ala Leu Arg  Arg Val Thr Ala Ala  Ala Gln Val
    3170                 3175                 3180

Leu Leu  Ala Arg Thr Met Val  Met Arg Ala Leu Ser  Leu Leu Ser
    3185                 3190                 3195

Val Ser  Gly Ser Ser Cys Ser  Leu Ala Ala Gly Leu  Glu Ser Leu
    3200                 3205                 3210

Gly Leu  Thr Asp Ile Arg Thr  Leu Val Arg Leu Met  Cys Leu Ala
    3215                 3220                 3225

Ala Ala  Gly Arg Ala Gly Leu  Ser Thr Ser Pro Ser  Ala Met Ala
    3230                 3235                 3240

Ser Thr  Ser Glu Arg Ser Arg  Gly Gly His Ser Lys  Ala Asn Lys
    3245                 3250                 3255

Pro Ile  Ser Cys Leu Ala Tyr  Leu Ser Thr Ala Val  Gly Cys Leu
    3260                 3265                 3270

Ala Ser  Asn Ala Pro Ser Ala  Ala Lys Leu Leu Val  Gln Leu Cys
    3275                 3280                 3285

Thr Gln  Asn Leu Ile Ser Ala  Ala Thr Gly Val Asn  Leu Thr Thr
    3290                 3295                 3300

Val Asp  Asp Ser Ile Gln Arg  Lys Phe Leu Pro Ser  Phe Leu Arg
    3305                 3310                 3315

Gly Ile  Ala Glu Glu Asn Lys  Leu Val Thr Ser Pro  Asn Phe Val
    3320                 3325                 3330
```

-continued

Val Thr Gln Ala Leu Val Ala Leu Leu Ala Asp Lys Gly Ala Lys
3335 3340 3345

Leu Arg Pro Asn Tyr Asp Lys Ser Glu Val Glu Lys Lys Gly Pro
3350 3355 3360

Leu Glu Leu Ala Asn Ala Leu Ala Ala Cys Cys Leu Ser Ser Arg
3365 3370 3375

Leu Ser Ser Gln His Arg Gln Trp Ala Ala Gln Gln Leu Val Arg
3380 3385 3390

Thr Leu Ala Ala His Asp Arg Asp Asn Gln Thr Thr Leu Gln Thr
3395 3400 3405

Leu Ala Asp Met Gly Gly Asp Leu Arg Lys Cys Ser Phe Ile Lys
3410 3415 3420

Leu Glu Ala His Gln Asn Arg Val Met Thr Cys Val Trp Cys Asn
3425 3430 3435

Lys Lys Gly Leu Leu Ala Thr Ser Gly Asn Asp Gly Thr Ile Arg
3440 3445 3450

Val Trp Asn Val Thr Lys Lys Gln Tyr Ser Leu Gln Gln Thr Cys
3455 3460 3465

Val Phe Asn Arg Leu Glu Gly Asp Ala Glu Glu Ser Leu Gly Ser
3470 3475 3480

Pro Ser Asp Pro Ser Phe Ser Pro Val Ser Trp Ser Ile Ser Gly
3485 3490 3495

Lys Tyr Leu Ala Gly Ala Leu Glu Lys Met Val Asn Ile Trp Gln
3500 3505 3510

Val Asn Gly Gly Lys Gly Leu Val Asp Ile Gln Pro His Trp Val
3515 3520 3525

Ser Ala Leu Ala Trp Pro Glu Glu Gly Pro Ala Thr Ala Trp Ser
3530 3535 3540

Gly Glu Ser Pro Glu Leu Leu Leu Val Gly Arg Met Asp Gly Ser
3545 3550 3555

Leu Gly Leu Ile Glu Val Val Asp Val Ser Thr Met His Arg Arg
3560 3565 3570

Glu Leu Glu His Cys Tyr Arg Lys Asp Val Ser Val Thr Cys Ile
3575 3580 3585

Ala Trp Phe Ser Glu Asp Arg Pro Phe Ala Val Gly Tyr Phe Asp
3590 3595 3600

Gly Lys Leu Leu Leu Gly Thr Lys Glu Pro Leu Glu Lys Gly Gly
3605 3610 3615

Ile Val Leu Ile Asp Ala His Lys Asp Thr Leu Ile Ser Met Lys
3620 3625 3630

Trp Asp Pro Thr Gly His Ile Leu Met Thr Cys Ala Lys Glu Asp
3635 3640 3645

Ser Val Lys Leu Trp Gly Ser Ile Ser Gly Cys Trp Cys Cys Leu
3650 3655 3660

His Ser Leu Cys His Pro Ser Ile Val Asn Gly Ile Ala Trp Cys
3665 3670 3675

Arg Leu Pro Gly Lys Gly Ser Lys Leu Gln Leu Leu Met Ala Thr
3680 3685 3690

Gly Cys Gln Ser Gly Leu Val Cys Val Trp Arg Ile Pro Gln Asp
3695 3700 3705

Thr Thr Gln Thr Asn Val Thr Ser Ala Glu Gly Trp Trp Asp Gln
3710 3715 3720

Glu Ser Asn Cys Gln Asp Gly Tyr Arg Lys Ser Ser Gly Ala Lys

-continued

```
    3725                3730                3735

Cys Val  Tyr Gln Leu Arg Gly  His Ile Thr Pro Val  Arg Thr Val
    3740                3745                3750

Ala Phe  Ser Ser Asp Gly Leu  Ala Leu Val Ser Gly  Gly Leu Gly
    3755                3760                3765

Gly Leu  Met Asn Ile Trp Ser  Leu Arg Asp Gly Ser  Val Leu Gln
    3770                3775                3780

Thr Val  Val Ile Gly Ser Gly  Ala Ile Gln Thr Thr  Val Trp Ile
    3785                3790                3795

Pro Glu  Val Gly Val Ala Ala  Cys Ser Asn Arg Ser  Lys Asp Val
    3800                3805                3810

Leu Val  Val Asn Cys Thr Ala  Glu Trp Ala Ala Ala  Asn His Val
    3815                3820                3825

Leu Ala  Thr Cys Arg Thr Ala  Leu Lys Gln Gln Gly  Val Leu Gly
    3830                3835                3840

Leu Asn  Met Ala Pro Cys Met  Arg Ala Phe Leu Glu  Arg Leu Pro
    3845                3850                3855

Met Met  Leu Gln Glu Gln Tyr  Ala Tyr Glu Lys Pro  His Val Val
    3860                3865                3870

Cys Gly  Asp Gln Leu Val His  Ser Pro Tyr Met Gln  Cys Leu Ala
    3875                3880                3885

Ser Leu  Ala Val Gly Leu His  Leu Asp Gln Leu Leu  Cys Asn Pro
    3890                3895                3900

Pro Val  Pro Pro His His Gln  Asn Cys Leu Pro Asp  Pro Ala Ser
    3905                3910                3915

Trp Asn  Pro Asn Glu Trp Ala  Trp Leu Glu Cys Phe  Ser Thr Thr
    3920                3925                3930

Ile Lys  Ala Ala Glu Ala Leu  Thr Asn Gly Ala Gln  Phe Pro Glu
    3935                3940                3945

Ser Phe  Thr Val Pro Asp Leu  Glu Pro Val Pro Glu  Asp Glu Leu
    3950                3955                3960

Val Phe  Leu Met Asp Asn Ser  Lys Trp Ile Asn Gly  Met Asp Glu
    3965                3970                3975

Gln Ile  Met Ser Trp Ala Thr  Ser Arg Pro Glu Asp  Trp His Leu
    3980                3985                3990

Gly Gly  Lys Cys Asp Val Tyr  Leu Trp Gly Ala Gly  Arg His Gly
    3995                4000                4005

Gln Leu  Ala Glu Ala Gly Arg  Asn Val Met Val Pro  Ala Ala Ala
    4010                4015                4020

Pro Ser  Phe Ser Gln Ala Gln  Gln Val Ile Cys Gly  Gln Asn Cys
    4025                4030                4035

Thr Phe  Val Ile Gln Ala Asn  Gly Thr Val Leu Ala  Cys Gly Glu
    4040                4045                4050

Gly Ser  Tyr Gly Arg Leu Gly  Gln Gly Asn Ser Asp  Asp Leu His
    4055                4060                4065

Val Leu  Thr Val Ile Ser Ala  Leu Gln Gly Phe Val  Val Thr Gln
    4070                4075                4080

Leu Val  Thr Ser Cys Gly Ser  Asp Gly His Ser Met  Ala Leu Thr
    4085                4090                4095

Glu Ser  Gly Glu Val Phe Ser  Trp Gly Asp Gly Asp  Tyr Gly Lys
    4100                4105                4110

Leu Gly  His Gly Asn Ser Asp  Arg Gln Arg Arg Pro  Arg Gln Ile
    4115                4120                4125
```

```
Glu Ala  Leu Gln Gly Glu Glu  Val Val Gln Met Ser  Cys Gly Phe
    4130                 4135                 4140

Lys His  Ser Ala Val Val Thr  Ser Asp Gly Lys Leu  Phe Thr Phe
    4145                 4150                 4155

Gly Asn  Gly Asp Tyr Gly Arg  Leu Gly Leu Gly Asn  Thr Ser Asn
    4160                 4165                 4170

Lys Lys  Leu Pro Glu Arg Val  Thr Ala Leu Glu Gly  Tyr Gln Ile
    4175                 4180                 4185

Gly Gln  Val Ala Cys Gly Leu  Asn His Thr Leu Ala  Val Ser Ala
    4190                 4195                 4200

Asp Gly  Ser Met Val Trp Ala  Phe Gly Asp Gly Asp  Tyr Gly Lys
    4205                 4210                 4215

Leu Gly  Leu Gly Asn Ser Thr  Ala Lys Ser Ser Pro  Gln Lys Ile
    4220                 4225                 4230

Asp Val  Leu Cys Gly Ile Gly  Ile Lys Lys Val Ala  Cys Gly Thr
    4235                 4240                 4245

Gln Phe  Ser Val Ala Leu Thr  Lys Asp Gly His Val  Tyr Thr Phe
    4250                 4255                 4260

Gly Gln  Asp Arg Leu Ile Gly  Leu Pro Glu Gly Arg  Ala Arg Asn
    4265                 4270                 4275

His Asn  Arg Pro Gln Gln Ile  Pro Val Leu Ala Gly  Val Ile Ile
    4280                 4285                 4290

Glu Asp  Val Ala Val Gly Ala  Glu His Thr Leu Ala  Leu Ala Ser
    4295                 4300                 4305

Asn Gly  Asp Val Tyr Ala Trp  Gly Ser Asn Ser Glu  Gly Gln Leu
    4310                 4315                 4320

Gly Leu  Gly His Thr Asn His  Val Arg Glu Pro Thr  Leu Val Thr
    4325                 4330                 4335

Gly Leu  Gln Gly Lys Asn Val  Arg Gln Ile Ser Ala  Gly Arg Cys
    4340                 4345                 4350

His Ser  Ala Ala Trp Thr Ala  Pro Pro Val Pro Pro  Arg Ala Pro
    4355                 4360                 4365

Gly Val  Ser Val Pro Leu Gln  Leu Gly Leu Pro Asp  Thr Val Pro
    4370                 4375                 4380

Pro Gln  Tyr Gly Ala Leu Arg  Glu Val Ser Ile His  Thr Val Arg
    4385                 4390                 4395

Ala Arg  Leu Arg Leu Leu Tyr  His Phe Ser Asp Leu  Met Tyr Ser
    4400                 4405                 4410

Ser Trp  Arg Leu Leu Asn Leu  Ser Pro Asn Asn Gln  Asn Ser Thr
    4415                 4420                 4425

Ser His  Tyr Asn Ala Gly Thr  Trp Gly Ile Val Gln  Gly Gln Leu
    4430                 4435                 4440

Arg Pro  Leu Leu Ala Pro Arg  Val Tyr Thr Leu Pro  Met Val Arg
    4445                 4450                 4455

Ser Ile  Gly Lys Thr Met Val  Gln Gly Lys Asn Tyr  Gly Pro Gln
    4460                 4465                 4470

Ile Thr  Val Lys Arg Ile Ser  Thr Arg Gly Arg Lys  Cys Lys Pro
    4475                 4480                 4485

Ile Phe  Val Gln Ile Ala Arg  Gln Val Val Lys Leu  Asn Ala Ser
    4490                 4495                 4500

Asp Leu  Arg Leu Pro Ser Arg  Ala Trp Lys Val Lys  Leu Val Gly
    4505                 4510                 4515
```

```
Glu Gly  Ala Asp Asp Ala Gly  Gly Val Phe Asp Asp  Thr Ile Thr
    4520                 4525                 4530

Glu Met  Cys Gln Glu Leu Glu  Thr Gly Ile Val Asp  Leu Leu Ile
    4535                 4540                 4545

Pro Ser  Pro Asn Ala Thr Ala  Glu Val Gly Tyr Asn  Arg Asp Arg
    4550                 4555                 4560

Phe Leu  Phe Asn Pro Ser Ala  Cys Leu Asp Glu His  Leu Met Gln
    4565                 4570                 4575

Phe Lys  Phe Leu Gly Ile Leu  Met Gly Val Ala Ile  Arg Thr Lys
    4580                 4585                 4590

Lys Pro  Leu Asp Leu His Leu  Ala Pro Leu Val Trp  Lys Gln Leu
    4595                 4600                 4605

Cys Cys  Val Pro Leu Thr Leu  Glu Asp Leu Glu Glu  Val Asp Leu
    4610                 4615                 4620

Leu Tyr  Val Gln Thr Leu Asn  Ser Ile Leu His Ile  Glu Asp Ser
    4625                 4630                 4635

Gly Ile  Thr Glu Glu Ser Phe  His Glu Met Ile Pro  Leu Asp Ser
    4640                 4645                 4650

Phe Val  Gly Gln Ser Ala Asp  Gly Lys Met Val Pro  Ile Ile Pro
    4655                 4660                 4665

Gly Gly  Asn Ser Ile Pro Leu  Thr Phe Ser Asn Arg  Lys Glu Tyr
    4670                 4675                 4680

Val Glu  Arg Ala Ile Glu Tyr  Arg Leu His Glu Met  Asp Arg Gln
    4685                 4690                 4695

Val Ala  Ala Val Arg Glu Gly  Met Ser Trp Ile Val  Pro Val Pro
    4700                 4705                 4710

Leu Leu  Ser Leu Leu Thr Ala  Lys Gln Leu Glu Gln  Met Val Cys
    4715                 4720                 4725

Gly Met  Pro Glu Ile Ser Val  Glu Val Leu Lys Lys  Val Val Arg
    4730                 4735                 4740

Tyr Arg  Glu Val Asp Glu Gln  His Gln Leu Val Gln  Trp Phe Trp
    4745                 4750                 4755

His Thr  Leu Glu Glu Phe Ser  Asn Glu Glu Arg Val  Leu Phe Met
    4760                 4765                 4770

Arg Phe  Val Ser Gly Arg Ser  Arg Leu Pro Ala Asn  Thr Ala Asp
    4775                 4780                 4785

Ile Ser  Gln Arg Phe Gln Ile  Met Lys Val Asp Arg  Pro Tyr Asp
    4790                 4795                 4800

Ser Leu  Pro Thr Ser Gln Thr  Cys Phe Phe Gln Leu  Arg Leu Pro
    4805                 4810                 4815

Pro Tyr  Ser Ser Gln Leu Val  Met Ala Glu Arg Leu  Arg Tyr Ala
    4820                 4825                 4830

Ile Asn  Asn Cys Arg Ser Ile  Asp Met Asp Asn Tyr  Met Leu Ser
    4835                 4840                 4845

Arg Asn  Val Asp Asn Ala Glu  Gly Ser Asp Thr Asp  Tyr
    4850                 4855                 4860
```

<210> SEQ ID NO 50
<211> LENGTH: 2971
<212> TYPE: PRT
<213> ORGANISM: Homo sapiens

<400> SEQUENCE: 50

```
Met Ala Lys Asp Val Arg Gln Phe Trp Ser Asn Val Glu Lys Val Val
1               5                   10                  15
```

-continued

```
Gln Phe Lys Gln Gln Ser Arg Leu Glu Glu Lys Arg Lys Lys Ala Leu
            20                  25                  30

Asp Leu His Leu Asp Phe Ile Val Gly Gln Thr Glu Lys Tyr Ser Asp
        35                  40                  45

Leu Leu Ser Gln Ser Leu Asn Gln Pro Leu Thr Ser Ser Lys Ala Gly
    50                  55                  60

Ser Ser Pro Cys Leu Gly Ser Ser Ser Ala Ala Ser Ser Pro Pro Pro
65                  70                  75                  80

Pro Ala Ser Arg Leu Asp Asp Glu Asp Gly Asp Phe Gln Pro Gln Glu
                85                  90                  95

Asp Glu Glu Glu Asp Asp Glu Glu Thr Ile Glu Val Glu Glu Gln Gln
            100                 105                 110

Glu Gly Asn Asp Ala Glu Ala Gln Arg Arg Glu Ile Glu Leu Leu Arg
        115                 120                 125

Arg Glu Gly Glu Leu Pro Leu Glu Glu Leu Leu Arg Ser Leu Pro Pro
    130                 135                 140

Gln Leu Leu Glu Gly Pro Ser Ser Pro Ser Gln Thr Pro Ser Ser His
145                 150                 155                 160

Asp Ser Asp Thr Arg Asp Gly Pro Glu Glu Gly Ala Glu Glu Glu Pro
                165                 170                 175

Pro Gln Val Leu Glu Ile Lys Pro Pro Pro Ser Ala Val Thr Gln Arg
            180                 185                 190

Asn Lys Gln Pro Trp His Pro Asp Glu Asp Asp Glu Glu Phe Thr Ala
        195                 200                 205

Asn Glu Glu Glu Ala Glu Asp Glu Glu Asp Thr Ile Ala Ala Glu Glu
    210                 215                 220

Gln Leu Glu Gly Glu Val Asp His Ala Met Glu Leu Ser Glu Leu Ala
225                 230                 235                 240

Arg Glu Gly Glu Leu Ser Met Glu Glu Leu Leu Gln Gln Tyr Ala Gly
                245                 250                 255

Ala Tyr Ala Pro Gly Ser Gly Ser Ser Glu Asp Glu Asp Glu Asp Glu
            260                 265                 270

Val Asp Ala Asn Ser Ser Asp Cys Glu Pro Glu Gly Pro Val Glu Ala
        275                 280                 285

Glu Glu Pro Pro Gln Glu Asp Ser Ser Ser Gln Ser Asp Ser Val Glu
    290                 295                 300

Asp Arg Ser Glu Asp Glu Glu Asp Glu His Ser Glu Glu Glu Glu Thr
305                 310                 315                 320

Ser Gly Ser Ser Ala Ser Glu Glu Ser Glu Ser Glu Glu Ser Glu Asp
                325                 330                 335

Ala Gln Ser Gln Ser Gln Ala Asp Glu Glu Glu Glu Asp Asp Asp Phe
            340                 345                 350

Gly Val Glu Tyr Leu Leu Ala Arg Asp Glu Glu Gln Ser Glu Ala Asp
        355                 360                 365

Ala Gly Ser Gly Pro Pro Thr Pro Gly Pro Thr Thr Leu Gly Pro Lys
    370                 375                 380

Lys Glu Ile Thr Asp Ile Ala Ala Ala Ala Glu Ser Leu Gln Pro Lys
385                 390                 395                 400

Gly Tyr Thr Leu Ala Thr Thr Gln Val Lys Thr Pro Ile Pro Leu Leu
                405                 410                 415

Leu Arg Gly Gln Leu Arg Glu Tyr Gln His Ile Gly Leu Asp Trp Leu
            420                 425                 430
```

-continued

```
Val Thr Met Tyr Glu Lys Lys Leu Asn Gly Ile Leu Ala Asp Glu Met
        435                 440                 445

Gly Leu Gly Lys Thr Ile Gln Thr Ile Ser Leu Leu Ala His Leu Ala
    450                 455                 460

Cys Glu Lys Gly Asn Trp Gly Pro His Leu Ile Ile Val Pro Thr Ser
465                 470                 475                 480

Val Met Leu Asn Trp Glu Met Glu Leu Lys Arg Trp Cys Pro Ser Phe
                485                 490                 495

Lys Ile Leu Thr Tyr Tyr Gly Ala Gln Lys Glu Arg Lys Leu Lys Arg
            500                 505                 510

Gln Gly Trp Thr Lys Pro Asn Ala Phe His Val Cys Ile Thr Ser Tyr
        515                 520                 525

Lys Leu Val Leu Gln Asp His Gln Ala Phe Arg Arg Lys Asn Trp Arg
    530                 535                 540

Tyr Leu Ile Leu Asp Glu Ala Gln Asn Ile Lys Asn Phe Lys Ser Gln
545                 550                 555                 560

Arg Trp Gln Ser Leu Leu Asn Phe Asn Ser Gln Arg Arg Leu Leu Leu
                565                 570                 575

Thr Gly Thr Pro Leu Gln Asn Ser Leu Met Glu Leu Trp Ser Leu Met
            580                 585                 590

His Phe Leu Met Pro His Val Phe Gln Ser His Arg Glu Phe Lys Glu
        595                 600                 605

Trp Phe Ser Asn Pro Leu Thr Gly Met Ile Glu Gly Ser Gln Glu Tyr
    610                 615                 620

Asn Glu Gly Leu Val Lys Arg Leu His Lys Val Leu Arg Pro Phe Leu
625                 630                 635                 640

Leu Arg Arg Val Lys Val Asp Val Glu Lys Gln Met Pro Lys Lys Tyr
                645                 650                 655

Glu His Val Ile Arg Cys Arg Leu Ser Lys Arg Gln Arg Cys Leu Tyr
            660                 665                 670

Asp Asp Phe Met Ala Gln Thr Thr Thr Lys Glu Thr Leu Ala Thr Gly
        675                 680                 685

His Phe Met Ser Val Ile Asn Ile Leu Met Gln Leu Arg Lys Val Cys
    690                 695                 700

Asn His Pro Asn Leu Phe Asp Pro Arg Pro Val Thr Ser Pro Phe Ile
705                 710                 715                 720

Thr Pro Gly Ile Cys Phe Ser Thr Ala Ser Leu Val Leu Arg Ala Thr
                725                 730                 735

Asp Val His Pro Leu Gln Arg Ile Asp Met Gly Arg Phe Asp Leu Ile
            740                 745                 750

Gly Leu Glu Gly Arg Val Ser Arg Tyr Glu Ala Asp Thr Phe Leu Pro
        755                 760                 765

Arg His Arg Leu Ser Arg Arg Val Leu Leu Glu Val Ala Thr Ala Pro
    770                 775                 780

Asp Pro Pro Pro Arg Pro Lys Pro Val Lys Met Lys Val Asn Arg Met
785                 790                 795                 800

Leu Gln Pro Val Pro Lys Gln Glu Gly Arg Thr Val Val Val Val Asn
                805                 810                 815

Asn Pro Arg Ala Pro Leu Gly Pro Val Pro Val Arg Pro Pro Pro Gly
            820                 825                 830

Pro Glu Leu Ser Ala Gln Pro Thr Pro Gly Pro Val Pro Gln Val Leu
        835                 840                 845

Pro Ala Ser Leu Met Val Ser Ala Ser Pro Ala Gly Pro Pro Leu Ile
```

-continued

```
    850                 855                 860

Pro Ala Ser Arg Pro Pro Gly Pro Val Leu Leu Pro Pro Leu Gln Pro
865                 870                 875                 880

Asn Ser Gly Ser Leu Pro Gln Val Leu Pro Ser Pro Leu Gly Val Leu
                885                 890                 895

Ser Gly Thr Ser Arg Pro Pro Thr Pro Thr Leu Ser Leu Lys Pro Thr
            900                 905                 910

Pro Pro Ala Pro Val Arg Leu Ser Pro Ala Pro Pro Pro Gly Ser Ser
        915                 920                 925

Ser Leu Leu Lys Pro Leu Thr Val Pro Pro Gly Tyr Thr Phe Pro Pro
    930                 935                 940

Ala Ala Ala Thr Thr Thr Ser Thr Thr Thr Ala Thr Ala Thr Thr Thr
945                 950                 955                 960

Ala Val Pro Ala Pro Thr Pro Ala Pro Gln Arg Leu Ile Leu Ser Pro
                965                 970                 975

Asp Met Gln Ala Arg Leu Pro Ser Gly Glu Val Val Ser Ile Gly Gln
            980                 985                 990

Leu Ala Ser Leu Ala Gln Arg Pro  Val Ala Asn Ala Gly  Gly Ser Lys
        995                 1000                1005

Pro Leu  Thr Phe Gln Ile Gln  Gly Asn Lys Leu Thr  Leu Thr Gly
    1010                1015                1020

Ala Gln  Val Arg Gln Leu Ala  Val Gly Gln Pro Arg  Pro Leu Gln
    1025                1030                1035

Met Pro  Pro Thr Met Val Asn  Asn Thr Gly Val Val  Lys Ile Val
    1040                1045                1050

Val Arg  Gln Ala Pro Arg Asp  Gly Leu Thr Pro Val  Pro Pro Leu
    1055                1060                1065

Ala Pro  Ala Pro Arg Pro Pro  Ser Ser Gly Leu Pro  Ala Val Leu
    1070                1075                1080

Asn Pro  Arg Pro Thr Leu Thr  Pro Gly Arg Leu Pro  Thr Pro Thr
    1085                1090                1095

Leu Gly  Thr Ala Arg Ala Pro  Met Pro Thr Pro Thr  Leu Val Arg
    1100                1105                1110

Pro Leu  Leu Lys Leu Val His  Ser Pro Ser Pro Glu  Val Ser Ala
    1115                1120                1125

Ser Ala  Pro Gly Ala Ala Pro  Leu Thr Ile Ser Ser  Pro Leu His
    1130                1135                1140

Val Pro  Ser Ser Leu Pro Gly  Pro Ala Ser Ser Pro  Met Pro Ile
    1145                1150                1155

Pro Asn  Ser Ser Pro Leu Ala  Ser Pro Val Ser Ser  Thr Val Ser
    1160                1165                1170

Val Pro  Leu Ser Ser Ser Leu  Pro Ile Ser Val Pro  Thr Thr Leu
    1175                1180                1185

Pro Ala  Pro Ala Ser Ala Pro  Leu Thr Ile Pro Ile  Ser Ala Pro
    1190                1195                1200

Leu Thr  Val Ser Ala Ser Gly  Pro Ala Leu Leu Thr  Ser Val Thr
    1205                1210                1215

Pro Pro  Leu Ala Pro Val Val  Pro Ala Ala Pro Gly  Pro Pro Ser
    1220                1225                1230

Leu Gln  Pro Ser Gly Ala Ser  Pro Ser Ala Ser Ala  Leu Thr Leu
    1235                1240                1245

Gly Leu  Ala Thr Ala Pro Ser  Leu Ser Ser Ser Gln  Thr Pro Gly
    1250                1255                1260
```

-continued

```
His Pro  Leu Leu Leu Ala Pro  Thr Ser Ser His Val  Pro Gly Leu
    1265                 1270                 1275

Asn Ser  Thr Val Ala Pro Ala  Cys Ser Pro Val Leu  Val Pro Ala
    1280                 1285                 1290

Ser Ala  Leu Ala Ser Pro Phe  Pro Ser Ala Pro Asn  Pro Ala Pro
    1295                 1300                 1305

Ala Gln  Ala Ser Leu Leu Ala  Pro Ala Ser Ser Ala  Ser Gln Ala
    1310                 1315                 1320

Leu Ala  Thr Pro Leu Ala Pro  Met Ala Ala Pro Gln  Thr Ala Ile
    1325                 1330                 1335

Leu Ala  Pro Ser Pro Ala Pro  Pro Leu Ala Pro Leu  Pro Val Leu
    1340                 1345                 1350

Ala Pro  Ser Pro Gly Ala Ala  Pro Val Leu Ala Ser  Ser Gln Thr
    1355                 1360                 1365

Pro Val  Pro Val Met Ala Pro  Ser Ser Thr Pro Gly  Thr Ser Leu
    1370                 1375                 1380

Ala Ser  Ala Ser Pro Val Pro  Ala Pro Thr Pro Val  Leu Ala Pro
    1385                 1390                 1395

Ser Ser  Thr Gln Thr Met Leu  Pro Ala Pro Val Pro  Ser Pro Leu
    1400                 1405                 1410

Pro Ser  Pro Ala Ser Thr Gln  Thr Leu Ala Leu Ala  Pro Ala Leu
    1415                 1420                 1425

Ala Pro  Thr Leu Gly Gly Ser  Ser Pro Ser Gln Thr  Leu Ser Leu
    1430                 1435                 1440

Gly Thr  Gly Asn Pro Gln Gly  Pro Phe Pro Thr Gln  Thr Leu Ser
    1445                 1450                 1455

Leu Thr  Pro Ala Ser Ser Leu  Val Pro Thr Pro Ala  Gln Thr Leu
    1460                 1465                 1470

Ser Leu  Ala Pro Gly Pro Pro  Leu Gly Pro Thr Gln  Thr Leu Ser
    1475                 1480                 1485

Leu Ala  Pro Ala Pro Pro Leu  Ala Pro Ala Ser Pro  Val Gly Pro
    1490                 1495                 1500

Ala Pro  Ala His Thr Leu Thr  Leu Ala Pro Ala Ser  Ser Ser Ala
    1505                 1510                 1515

Ser Leu  Leu Ala Pro Ala Ser  Val Gln Thr Leu Thr  Leu Ser Pro
    1520                 1525                 1530

Ala Pro  Val Pro Thr Leu Gly  Pro Ala Ala Ala Gln  Thr Leu Ala
    1535                 1540                 1545

Leu Ala  Pro Ala Ser Thr Gln  Ser Pro Ala Ser Gln  Ala Ser Ser
    1550                 1555                 1560

Leu Val  Val Ser Ala Ser Gly  Ala Ala Pro Leu Pro  Val Thr Met
    1565                 1570                 1575

Val Ser  Arg Leu Pro Val Ser  Lys Asp Glu Pro Asp  Thr Leu Thr
    1580                 1585                 1590

Leu Arg  Ser Gly Pro Pro Ser  Pro Pro Ser Thr Ala  Thr Ser Phe
    1595                 1600                 1605

Gly Gly  Pro Arg Pro Arg Arg  Gln Pro Pro Pro Pro  Pro Arg Ser
    1610                 1615                 1620

Pro Phe  Tyr Leu Asp Ser Leu  Glu Glu Lys Arg Lys  Arg Gln Arg
    1625                 1630                 1635

Ser Glu  Arg Leu Glu Arg Ile  Phe Gln Leu Ser Glu  Ala His Gly
    1640                 1645                 1650
```

-continued

```
Ala Leu  Ala Pro Val Tyr Gly  Thr Glu Val Leu Asp  Phe Cys Thr
    1655                 1660                 1665

Leu Pro  Gln Pro Val Ala Ser  Pro Ile Gly Pro Arg  Ser Pro Gly
    1670                 1675                 1680

Pro Ser  His Pro Thr Phe Trp  Thr Tyr Thr Glu Ala  Ala His Arg
    1685                 1690                 1695

Ala Val  Leu Phe Pro Gln Gln  Arg Leu Asp Gln Leu  Ser Glu Ile
    1700                 1705                 1710

Ile Glu  Arg Phe Ile Phe Val  Met Pro Pro Val Glu  Ala Pro Pro
    1715                 1720                 1725

Pro Ser  Leu His Ala Cys His  Pro Pro Pro Trp Leu  Ala Pro Arg
    1730                 1735                 1740

Gln Ala  Ala Phe Gln Glu Gln  Leu Ala Ser Glu Leu  Trp Pro Arg
    1745                 1750                 1755

Ala Arg  Pro Leu His Arg Ile  Val Cys Asn Met Arg  Thr Gln Phe
    1760                 1765                 1770

Pro Asp  Leu Arg Leu Ile Gln  Tyr Asp Cys Gly Lys  Leu Gln Thr
    1775                 1780                 1785

Leu Ala  Val Leu Leu Arg Gln  Leu Lys Ala Glu Gly  His Arg Val
    1790                 1795                 1800

Leu Ile  Phe Thr Gln Met Thr  Arg Met Leu Asp Val  Leu Glu Gln
    1805                 1810                 1815

Phe Leu  Thr Tyr His Gly His  Leu Tyr Leu Arg Leu  Asp Gly Ser
    1820                 1825                 1830

Thr Arg  Val Glu Gln Arg Gln  Ala Leu Met Glu Arg  Phe Asn Ala
    1835                 1840                 1845

Asp Lys  Arg Ile Phe Cys Phe  Ile Leu Ser Thr Arg  Ser Gly Gly
    1850                 1855                 1860

Val Gly  Val Asn Leu Thr Gly  Ala Asp Thr Val Val  Phe Tyr Asp
    1865                 1870                 1875

Ser Asp  Trp Asn Pro Thr Met  Asp Ala Gln Ala Gln  Asp Arg Cys
    1880                 1885                 1890

His Arg  Ile Gly Gln Thr Arg  Asp Val His Ile Tyr  Arg Leu Ile
    1895                 1900                 1905

Ser Glu  Arg Thr Val Glu Glu  Asn Ile Leu Lys Lys  Ala Asn Gln
    1910                 1915                 1920

Lys Arg  Met Leu Gly Asp Met  Ala Ile Glu Gly Gly  Asn Phe Thr
    1925                 1930                 1935

Thr Ala  Tyr Phe Lys Gln Gln  Thr Ile Arg Glu Leu  Phe Asp Met
    1940                 1945                 1950

Pro Leu  Glu Glu Pro Ser Ser  Ser Ser Val Pro Ser  Ala Pro Glu
    1955                 1960                 1965

Glu Glu  Glu Glu Thr Val Ala  Ser Lys Gln Thr His  Ile Leu Glu
    1970                 1975                 1980

Gln Ala  Leu Cys Arg Ala Glu  Asp Glu Glu Asp Ile  Arg Ala Ala
    1985                 1990                 1995

Thr Gln  Ala Lys Ala Glu Gln  Val Ala Glu Leu Ala  Glu Phe Asn
    2000                 2005                 2010

Glu Asn  Asp Gly Phe Pro Ala  Gly Glu Gly Glu Glu  Ala Gly Arg
    2015                 2020                 2025

Pro Gly  Ala Glu Asp Glu Glu  Met Ser Arg Ala Glu  Gln Glu Ile
    2030                 2035                 2040

Ala Ala  Leu Val Glu Gln Leu  Thr Pro Ile Glu Arg  Tyr Ala Met
```

```
    2045                2050                2055

Lys Phe  Leu Glu Ala Ser Leu  Glu Glu Val Ser Arg  Glu Glu Leu
    2060                2065                2070

Lys Gln  Ala Glu Glu Gln Val  Glu Ala Ala Arg Lys  Asp Leu Asp
    2075                2080                2085

Gln Ala  Lys Glu Glu Val Phe  Arg Leu Pro Gln Glu  Glu Glu Glu
    2090                2095                2100

Gly Pro  Gly Ala Gly Asp Glu  Ser Ser Cys Gly Thr  Gly Gly Gly
    2105                2110                2115

Thr His  Arg Arg Ser Lys Lys  Ala Lys Ala Pro Glu  Arg Pro Gly
    2120                2125                2130

Thr Arg  Val Ser Glu Arg Leu  Arg Gly Ala Arg Ala  Glu Thr Gln
    2135                2140                2145

Gly Ala  Asn His Thr Pro Val  Ile Ser Ala His Gln  Thr Arg Ser
    2150                2155                2160

Thr Thr  Thr Pro Pro Arg Cys  Ser Pro Ala Arg Glu  Arg Val Pro
    2165                2170                2175

Arg Pro  Ala Pro Arg Pro Arg  Pro Thr Pro Ala Ser  Ala Pro Ala
    2180                2185                2190

Ala Ile  Pro Ala Leu Val Pro  Val Pro Val Ser Ala  Pro Val Pro
    2195                2200                2205

Ile Ser  Ala Pro Asn Pro Ile  Thr Ile Leu Pro Val  His Ile Leu
    2210                2215                2220

Pro Ser  Pro Pro Pro Pro Ser  Gln Ile Pro Pro Cys  Ser Ser Pro
    2225                2230                2235

Ala Cys  Thr Pro Pro Pro Ala  Cys Thr Pro Pro Pro  Ala His Thr
    2240                2245                2250

Pro Pro  Pro Ala Gln Thr Cys  Leu Val Thr Pro Ser  Ser Pro Leu
    2255                2260                2265

Leu Leu  Gly Pro Pro Ser Val  Pro Ile Ser Ala Ser  Val Thr Asn
    2270                2275                2280

Leu Pro  Leu Gly Leu Arg Pro  Glu Ala Glu Leu Cys  Ala Gln Ala
    2285                2290                2295

Leu Ala  Ser Pro Glu Ser Leu  Glu Leu Ala Ser Val  Ala Ser Ser
    2300                2305                2310

Glu Thr  Ser Ser Leu Ser Leu  Val Pro Pro Lys Asp  Leu Leu Pro
    2315                2320                2325

Val Ala  Val Glu Ile Leu Pro  Val Ser Glu Lys Asn  Leu Ser Leu
    2330                2335                2340

Thr Pro  Ser Ala Pro Ser Leu  Thr Leu Glu Ala Gly  Ser Ile Pro
    2345                2350                2355

Asn Gly  Gln Glu Gln Glu Ala  Pro Asp Ser Ala Glu  Gly Thr Thr
    2360                2365                2370

Leu Thr  Val Leu Pro Glu Gly  Glu Glu Leu Pro Leu  Cys Val Ser
    2375                2380                2385

Glu Ser  Asn Gly Leu Glu Leu  Pro Pro Ser Ala Ala  Ser Asp Glu
    2390                2395                2400

Pro Leu  Gln Glu Pro Leu Glu  Ala Asp Arg Thr Ser  Glu Glu Leu
    2405                2410                2415

Thr Glu  Ala Lys Thr Pro Thr  Ser Ser Pro Glu Lys  Pro Gln Glu
    2420                2425                2430

Leu Val  Thr Ala Glu Val Ala  Ala Pro Ser Thr Ser  Ser Ser Ala
    2435                2440                2445
```

```
Thr Ser Ser Pro Glu Gly Pro Ser Pro Ala Arg Pro Pro Arg Arg
    2450                2455                2460

Arg Thr Ser Ala Asp Val Glu Ile Arg Gly Gln Gly Thr Gly Arg
    2465                2470                2475

Pro Gly Gln Pro Pro Gly Pro Lys Val Leu Arg Lys Leu Pro Gly
    2480                2485                2490

Arg Leu Val Thr Val Val Glu Glu Lys Glu Leu Val Gln Arg Arg
    2495                2500                2505

Arg Gln Gln Arg Gly Ala Ala Ser Thr Leu Val Pro Gly Val Ser
    2510                2515                2520

Glu Thr Ser Ala Ser Pro Gly Ser Pro Ser Val Arg Ser Met Ser
    2525                2530                2535

Gly Pro Glu Ser Ser Pro Pro Ile Gly Gly Pro Cys Glu Ala Ala
    2540                2545                2550

Pro Ser Ser Ser Leu Pro Thr Pro Pro Gln Gln Pro Phe Ile Ala
    2555                2560                2565

Arg Arg His Ile Glu Leu Gly Val Thr Gly Gly Gly Ser Pro Glu
    2570                2575                2580

Asn Gly Asp Gly Ala Leu Leu Ala Ile Thr Pro Pro Ala Val Lys
    2585                2590                2595

Arg Arg Arg Gly Arg Pro Pro Lys Lys Asn Arg Ser Pro Ala Asp
    2600                2605                2610

Ala Gly Arg Gly Val Asp Glu Ala Pro Ser Ser Thr Leu Lys Gly
    2615                2620                2625

Lys Thr Asn Gly Ala Asp Pro Val Pro Gly Pro Glu Thr Leu Ile
    2630                2635                2640

Val Ala Asp Pro Val Leu Glu Pro Gln Leu Ile Pro Gly Pro Gln
    2645                2650                2655

Pro Leu Gly Pro Gln Pro Val His Arg Pro Asn Pro Leu Leu Ser
    2660                2665                2670

Pro Val Glu Lys Arg Arg Arg Gly Arg Pro Pro Lys Ala Arg Asp
    2675                2680                2685

Leu Pro Ile Pro Gly Thr Ile Ser Ser Ala Gly Asp Gly Asn Ser
    2690                2695                2700

Glu Ser Arg Thr Gln Pro Pro Pro His Pro Ser Pro Leu Thr Pro
    2705                2710                2715

Leu Pro Pro Leu Leu Val Cys Pro Thr Ala Thr Val Ala Asn Thr
    2720                2725                2730

Val Thr Thr Val Thr Ile Ser Thr Ser Pro Pro Lys Arg Lys Arg
    2735                2740                2745

Gly Arg Pro Pro Lys Asn Pro Pro Ser Pro Arg Pro Ser Gln Leu
    2750                2755                2760

Pro Val Leu Asp Arg Asp Ser Thr Ser Val Leu Glu Ser Cys Gly
    2765                2770                2775

Leu Gly Arg Arg Arg Gln Pro Gln Gly Gln Gly Glu Ser Glu Gly
    2780                2785                2790

Ser Ser Ser Asp Glu Asp Gly Ser Arg Pro Leu Thr Arg Leu Ala
    2795                2800                2805

Arg Leu Arg Leu Glu Ala Glu Gly Met Arg Gly Arg Lys Ser Gly
    2810                2815                2820

Gly Ser Met Val Val Ala Val Ile Gln Asp Asp Leu Asp Leu Ala
    2825                2830                2835
```

-continued

```
Asp Ser  Gly Pro Gly Gly Leu  Glu Leu Thr Pro Pro  Val Val Ser
    2840                 2845                 2850

Leu Thr  Pro Lys Leu Arg Ser  Thr Arg Leu Arg Pro  Gly Ser Leu
    2855                 2860                 2865

Val Pro  Pro Leu Glu Thr Glu  Lys Leu Pro Arg Lys  Arg Ala Gly
    2870                 2875                 2880

Ala Pro  Val Gly Gly Ser Pro  Gly Leu Ala Lys Arg  Gly Arg Leu
    2885                 2890                 2895

Gln Pro  Pro Ser Pro Leu Gly  Pro Glu Gly Ser Val  Glu Glu Ser
    2900                 2905                 2910

Glu Ala  Glu Ala Ser Gly Glu  Glu Glu Glu Gly Asp  Gly Thr Pro
    2915                 2920                 2925

Arg Arg  Arg Pro Gly Pro Arg  Arg Leu Val Gly Thr  Thr Asn Gln
    2930                 2935                 2940

Gly Asp  Gln Arg Ile Leu Arg  Ser Ser Ala Pro Pro  Ser Leu Ala
    2945                 2950                 2955

Gly Pro  Ala Val Ser His Arg  Gly Arg Lys Ala Lys  Thr
    2960                 2965                 2970


<210> SEQ ID NO 51
<211> LENGTH: 240
<212> TYPE: PRT
<213> ORGANISM: Homo sapiens

<400> SEQUENCE: 51

Met Leu Gln Leu Pro Pro Gly Ala Pro Ala Ala Ala Leu Ala Ala Glu
1               5                   10                  15

Pro Arg Gly Ala Asp Ala Gly Glu Leu Thr Arg Ala Ser Arg Arg Ala
            20                  25                  30

Ser Pro Glu Ala Val Ala Gln Gly Gly Ala Arg Arg Ser His Val Ala
        35                  40                  45

Pro Ala Ala Ala Met Ala Asp Ser Gly Thr Ala Gly Gly Ala Ala Leu
    50                  55                  60

Ala Ala Pro Ala Pro Gly Pro Gly Ser Gly Gly Pro Gly Pro Arg Val
65                  70                  75                  80

Tyr Phe Gln Ser Pro Pro Gly Ala Ala Gly Glu Gly Pro Gly Gly Ala
                85                  90                  95

Asp Asp Glu Gly Pro Val Arg Arg Gln Gly Lys Val Thr Val Lys Tyr
            100                 105                 110

Asp Arg Lys Glu Leu Arg Lys Arg Leu Asn Leu Glu Glu Trp Ile Leu
        115                 120                 125

Glu Gln Leu Thr Arg Leu Tyr Asp Cys Gln Glu Glu Glu Ile Pro Glu
    130                 135                 140

Leu Glu Ile Asp Val Asp Glu Leu Leu Asp Met Glu Ser Asp Asp Ala
145                 150                 155                 160

Arg Ala Ala Arg Val Lys Glu Leu Leu Val Asp Cys Tyr Lys Pro Thr
                165                 170                 175

Glu Ala Phe Ile Ser Gly Leu Leu Asp Lys Ile Arg Gly Met Gln Lys
            180                 185                 190

Leu Ser Thr Pro Gln Lys Lys Glu Gly Ser Pro Thr Gln Glu Asn Gly
        195                 200                 205

Gly Ser His Arg Thr Ile Ala Ala Pro Gln Pro Arg Ser Asn Ser Asn
    210                 215                 220

Thr Gly Gly Pro Cys Gly Gln Ala Trp Cys His Glu Gln Gly Ser Ser
225                 230                 235                 240
```

<210> SEQ ID NO 52
<211> LENGTH: 502
<212> TYPE: PRT
<213> ORGANISM: Homo sapiens

<400> SEQUENCE: 52

```
Met Ser Thr Thr Leu Leu Ser Ala Phe Tyr Asp Val Asp Phe Leu Cys
1               5                   10                  15

Lys Thr Glu Lys Ser Leu Ala Asn Leu Asn Leu Asn Asn Met Leu Asp
            20                  25                  30

Lys Lys Ala Val Gly Thr Pro Val Ala Ala Ala Pro Ser Ser Gly Phe
        35                  40                  45

Ala Pro Gly Phe Leu Arg Arg His Ser Ala Ser Asn Leu His Ala Leu
    50                  55                  60

Ala His Pro Ala Pro Ser Pro Gly Ser Cys Ser Pro Lys Phe Pro Gly
65                  70                  75                  80

Ala Ala Asn Gly Ser Ser Cys Gly Ser Ala Ala Ala Gly Gly Pro Thr
                85                  90                  95

Ser Tyr Gly Thr Leu Lys Glu Pro Ser Gly Gly Gly Gly Thr Ala Leu
            100                 105                 110

Leu Asn Lys Glu Asn Lys Phe Arg Asp Arg Ser Phe Ser Glu Asn Gly
        115                 120                 125

Asp Arg Ser Gln His Leu Leu His Leu Gln Gln Gln Gln Lys Gly Gly
    130                 135                 140

Gly Gly Ser Gln Ile Asn Ser Thr Arg Tyr Lys Thr Glu Leu Cys Arg
145                 150                 155                 160

Pro Phe Glu Glu Ser Gly Thr Cys Lys Tyr Gly Glu Lys Cys Gln Phe
                165                 170                 175

Ala His Gly Phe His Glu Leu Arg Ser Leu Thr Arg His Pro Lys Tyr
            180                 185                 190

Lys Thr Glu Leu Cys Arg Thr Phe His Thr Ile Gly Phe Cys Pro Tyr
        195                 200                 205

Gly Pro Arg Cys His Phe Ile His Asn Ala Asp Glu Arg Arg Pro Ala
    210                 215                 220

Pro Ser Gly Gly Ala Ser Gly Asp Leu Arg Ala Phe Gly Thr Arg Asp
225                 230                 235                 240

Ala Leu His Leu Gly Phe Pro Arg Glu Pro Arg Pro Lys Leu His His
                245                 250                 255

Ser Leu Ser Phe Ser Gly Phe Pro Ser Gly His His Gln Pro Pro Gly
            260                 265                 270

Gly Leu Glu Ser Pro Leu Leu Leu Asp Ser Pro Thr Ser Arg Thr Pro
        275                 280                 285

Pro Pro Pro Ser Cys Ser Ser Ala Ser Ser Cys Ser Ser Ser Ala Ser
    290                 295                 300

Ser Cys Ser Ser Ala Ser Ala Ala Ser Thr Pro Ser Gly Thr Pro Thr
305                 310                 315                 320

Cys Cys Ala Ser Ala Ala Ala Ala Leu Arg Leu Leu Tyr Gly Thr Gly
                325                 330                 335

Gly Ala Glu Asp Leu Leu Ala Pro Gly Ala Pro Cys Ala Ala Cys Ser
            340                 345                 350

Ser Ala Ser Cys Ala Asn Asn Ala Phe Ala Phe Gly Pro Glu Leu Ser
        355                 360                 365

Ser Leu Ile Thr Pro Leu Ala Ile Gln Thr His Asn Phe Ala Ala Val
```

-continued

```
    370                 375                 380

Ala Ala Ala Ala Tyr Tyr Arg Ser Gln Gln Gln Gln Gln Gln Gln Gly
385                 390                 395                 400

Leu Ala Pro Pro Ala Gln Pro Pro Ala Pro Pro Ser Ala Thr Leu Pro
                405                 410                 415

Ala Gly Ala Ala Ala Pro Pro Ser Pro Pro Phe Ser Phe Gln Leu Pro
            420                 425                 430

Arg Arg Leu Ser Asp Ser Pro Val Phe Asp Ala Pro Pro Ser Pro Pro
        435                 440                 445

Asp Ser Leu Ser Asp Arg Asp Ser Tyr Leu Ser Gly Ser Leu Ser Ser
    450                 455                 460

Gly Ser Leu Ser Gly Ser Glu Ser Pro Ser Leu Asp Pro Gly Arg Arg
465                 470                 475                 480

Leu Pro Ile Phe Ser Arg Leu Ser Ile Ser Asp Asp Met Ile Ser Cys
                485                 490                 495

Phe Glu Ala Thr Arg Glu
            500


<210> SEQ ID NO 53
<211> LENGTH: 314
<212> TYPE: PRT
<213> ORGANISM: Homo sapiens

<400> SEQUENCE: 53

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240
```

-continued

```
Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310


<210> SEQ ID NO 54
<211> LENGTH: 876
<212> TYPE: PRT
<213> ORGANISM: Homo sapiens

<400> SEQUENCE: 54

Pro His Ser Thr Val Pro Glu His His Pro His Pro Ile Ser Pro Tyr
1               5                   10                  15

Glu His Leu Leu Arg Gly Val Ser Gly Val Asp Leu Tyr Arg Ser His
            20                  25                  30

Ile Pro Leu Ala Phe Asp Pro Thr Ser Ile Pro Arg Gly Ile Pro Leu
        35                  40                  45

Asp Ala Ala Ala Ala Tyr Tyr Leu Pro Arg His Leu Ala Pro Asn Pro
    50                  55                  60

Thr Tyr Pro His Leu Tyr Pro Pro Tyr Leu Ile Arg Gly Tyr Pro Asp
65                  70                  75                  80

Thr Ala Ala Leu Glu Asn Arg Gln Thr Ile Ile Asn Asp Tyr Ile Thr
                85                  90                  95

Ser Gln Gln Met His His Asn Ala Ala Thr Ala Met Ala Gln Arg Ala
            100                 105                 110

Asp Met Leu Arg Gly Leu Ser Pro Arg Glu Ser Ser Leu Ala Leu Asn
        115                 120                 125

Tyr Ala Ala Gly Pro Arg Gly Ile Ile Asp Leu Ser Gln Val Pro His
    130                 135                 140

Leu Pro Val Leu Val Pro Pro Thr Pro Gly Thr Pro Ala Thr Ala Met
145                 150                 155                 160

Asp Arg Leu Ala Tyr Leu Pro Thr Ala Pro Gln Pro Phe Ser Ser Arg
                165                 170                 175

His Ser Ser Ser Pro Leu Ser Pro Gly Gly Pro Thr His Leu Thr Lys
            180                 185                 190

Pro Thr Thr Thr Ser Ser Ser Glu Arg Glu Arg Asp Arg Asp Arg Glu
        195                 200                 205

Arg Asp Arg Asp Arg Glu Arg Glu Lys Ser Ile Leu Thr Ser Thr Thr
    210                 215                 220

Thr Val Glu His Ala Pro Ile Trp Arg Pro Gly Thr Glu Gln Ser Ser
225                 230                 235                 240

Gly Ser Ser Gly Ser Ser Gly Gly Gly Gly Gly Ser Ser Ser Arg Pro
                245                 250                 255

Ala Ser His Ser His Ala His Gln His Ser Pro Ile Ser Pro Arg Thr
            260                 265                 270

Gln Asp Ala Leu Gln Gln Arg Pro Ser Val Leu His Asn Thr Gly Met
        275                 280                 285

Lys Gly Ile Ile Thr Ala Val Glu Pro Ser Thr Pro Thr Val Leu Arg
    290                 295                 300
```

```
Ser Thr Ser Thr Ser Ser Pro Val Arg Pro Ala Ala Thr Phe Pro Pro
305                 310                 315                 320

Ala Thr His Cys Pro Leu Gly Gly Thr Leu Asp Gly Val Tyr Pro Thr
                325                 330                 335

Leu Met Glu Pro Val Leu Leu Pro Lys Glu Ala Pro Arg Val Ala Arg
            340                 345                 350

Pro Glu Arg Pro Arg Ala Asp Thr Gly His Ala Phe Leu Ala Lys Pro
        355                 360                 365

Pro Ala Arg Ser Gly Leu Glu Pro Ala Ser Ser Pro Ser Lys Gly Ser
    370                 375                 380

Glu Pro Arg Pro Leu Val Pro Pro Val Ser Gly His Ala Thr Ile Ala
385                 390                 395                 400

Arg Thr Pro Ala Lys Asn Leu Ala Pro His His Ala Ser Pro Asp Pro
                405                 410                 415

Pro Ala Pro Pro Ala Ser Ala Ser Asp Pro His Arg Glu Lys Thr Gln
            420                 425                 430

Ser Lys Pro Phe Ser Ile Gln Glu Leu Glu Leu Arg Ser Leu Gly Tyr
        435                 440                 445

His Gly Ser Ser Tyr Ser Pro Glu Gly Val Glu Pro Val Ser Pro Val
    450                 455                 460

Ser Ser Pro Ser Leu Thr His Asp Lys Gly Leu Pro Lys His Leu Glu
465                 470                 475                 480

Glu Leu Asp Lys Ser His Leu Glu Gly Glu Leu Arg Pro Lys Gln Pro
                485                 490                 495

Gly Pro Val Lys Leu Gly Gly Glu Ala Ala His Leu Pro His Leu Arg
            500                 505                 510

Pro Leu Pro Glu Ser Gln Pro Ser Ser Ser Pro Leu Leu Gln Thr Ala
        515                 520                 525

Pro Gly Val Lys Gly His Gln Arg Val Val Thr Leu Ala Gln His Ile
    530                 535                 540

Ser Glu Val Ile Thr Gln Asp Tyr Thr Arg His His Pro Gln Gln Leu
545                 550                 555                 560

Ser Ala Pro Leu Pro Ala Pro Leu Tyr Ser Phe Pro Gly Ala Ser Cys
                565                 570                 575

Pro Val Leu Asp Leu Arg Arg Pro Pro Ser Asp Leu Tyr Leu Pro Pro
            580                 585                 590

Pro Asp His Gly Ala Pro Ala Arg Gly Ser Pro His Ser Glu Gly Gly
        595                 600                 605

Lys Arg Ser Pro Glu Pro Asn Lys Thr Ser Val Leu Gly Gly Gly Glu
    610                 615                 620

Asp Gly Ile Glu Pro Val Ser Pro Pro Glu Gly Met Thr Glu Pro Gly
625                 630                 635                 640

His Ser Arg Ser Ala Val Tyr Pro Leu Leu Tyr Arg Asp Gly Glu Gln
                645                 650                 655

Thr Glu Pro Ser Arg Met Gly Ser Lys Ser Pro Gly Asn Thr Ser Gln
            660                 665                 670

Pro Pro Ala Phe Phe Ser Lys Leu Thr Glu Ser Asn Ser Ala Met Val
        675                 680                 685

Lys Ser Lys Lys Gln Glu Ile Asn Lys Lys Leu Asn Thr His Asn Arg
    690                 695                 700

Asn Glu Pro Glu Tyr Asn Ile Ser Gln Pro Gly Thr Glu Ile Phe Asn
705                 710                 715                 720
```

-continued

```
Met Pro Ala Ile Thr Gly Thr Gly Leu Met Thr Tyr Arg Ser Gln Ala
                725                 730                 735

Val Gln Glu His Ala Ser Thr Asn Met Gly Leu Glu Ala Ile Ile Arg
            740                 745                 750

Lys Ala Leu Met Gly Gly Gly Gly Lys Ala Lys Val Ser Gly Arg Pro
        755                 760                 765

Ser Ser Arg Lys Ala Lys Ser Pro Ala Pro Gly Leu Ala Ser Gly Asp
    770                 775                 780

Arg Pro Pro Ser Val Ser Ser Val His Ser Glu Gly Asp Cys Asn Arg
785                 790                 795                 800

Arg Thr Pro Leu Thr Asn Arg Val Trp Glu Asp Arg Pro Ser Ser Ala
                805                 810                 815

Gly Ser Thr Pro Phe Pro Tyr Asn Pro Leu Ile Met Arg Leu Gln Ala
            820                 825                 830

Gly Val Met Ala Ser Pro Pro Pro Pro Gly Leu Pro Ala Gly Ser Gly
        835                 840                 845

Pro Leu Ala Gly Ala His His Ala Trp Asp Glu Glu Pro Lys Pro Leu
    850                 855                 860

Leu Cys Ser Gln Tyr Glu Thr Leu Ser Asp Ser Glu
865                 870                 875


<210> SEQ ID NO 55
<211> LENGTH: 233
<212> TYPE: PRT
<213> ORGANISM: Homo sapiens

<400> SEQUENCE: 55

Ala Ala Ser Arg Trp Ala Arg Lys Ala Val Val Leu Leu Cys Ala Ser
1               5                   10                  15

Asp Leu Leu Leu Leu Leu Leu Leu Leu Pro Pro Pro Gly Ser Cys Ala
            20                  25                  30

Ala Glu Gly Ser Pro Gly Thr Pro Asp Glu Ser Thr Pro Pro Pro Arg
        35                  40                  45

Lys Lys Lys Lys Asp Ile Arg Asp Tyr Asn Asp Ala Asp Met Ala Arg
    50                  55                  60

Leu Leu Glu Gln Trp Glu Lys Asp Asp Asp Ile Glu Glu Gly Asp Leu
65                  70                  75                  80

Pro Glu His Lys Arg Pro Ser Ala Pro Val Asp Phe Ser Lys Ile Asp
                85                  90                  95

Pro Ser Lys Pro Glu Ser Ile Leu Lys Met Thr Lys Lys Gly Lys Thr
            100                 105                 110

Leu Met Met Phe Val Thr Val Ser Gly Ser Pro Thr Glu Lys Glu Thr
        115                 120                 125

Glu Glu Ile Thr Ser Leu Trp Gln Gly Ser Leu Phe Asn Ala Asn Tyr
    130                 135                 140

Asp Val Gln Arg Phe Ile Val Gly Ser Asp Arg Ala Ile Phe Met Leu
145                 150                 155                 160

Arg Asp Gly Ser Tyr Ala Trp Glu Ile Lys Asp Phe Leu Val Gly Gln
                165                 170                 175

Asp Arg Cys Ala Asp Val Thr Leu Glu Gly Gln Val Tyr Pro Gly Lys
            180                 185                 190

Gly Gly Gly Ser Lys Glu Lys Asn Lys Thr Lys Gln Asp Lys Gly Lys
        195                 200                 205

Lys Lys Lys Glu Gly Asp Leu Lys Ser Arg Ser Ser Lys Glu Glu Asn
    210                 215                 220
```

```
Arg Ala Gly Asn Lys Arg Glu Asp Leu
225                 230


<210> SEQ ID NO 56
<211> LENGTH: 206
<212> TYPE: PRT
<213> ORGANISM: Homo sapiens

<400> SEQUENCE: 56

Cys Tyr Arg Tyr Cys Lys Asn Lys Pro Tyr Pro Lys Ser Arg Phe Cys
1               5                   10                  15

Arg Gly Val Pro Asp Ala Lys Ile Arg Ile Phe Asp Leu Gly Arg Lys
            20                  25                  30

Lys Ala Lys Val Asp Glu Phe Pro Leu Cys Gly His Met Val Ser Asp
        35                  40                  45

Glu Tyr Glu Gln Leu Ser Ser Glu Ala Leu Glu Ala Ala Arg Ile Cys
    50                  55                  60

Ala Asn Lys Tyr Met Val Lys Ser Cys Gly Lys Asp Gly Phe His Ile
65                  70                  75                  80

Arg Val Arg Leu His Pro Phe His Val Ile Arg Ile Asn Lys Met Leu
                85                  90                  95

Ser Cys Ala Gly Ala Asp Arg Leu Gln Thr Gly Met Arg Gly Ala Phe
            100                 105                 110

Gly Lys Pro Gln Gly Thr Val Ala Arg Val His Ile Gly Gln Val Ile
        115                 120                 125

Met Ser Ile Arg Thr Lys Leu Gln Asn Lys Glu His Val Ile Glu Ala
    130                 135                 140

Leu Arg Arg Ala Lys Phe Lys Phe Pro Gly Arg Gln Lys Ile His Ile
145                 150                 155                 160

Ser Lys Lys Trp Gly Phe Thr Lys Phe Asn Ala Asp Glu Phe Glu Asp
                165                 170                 175

Met Val Ala Glu Lys Arg Leu Ile Pro Asp Gly Cys Gly Val Lys Tyr
            180                 185                 190

Ile Pro Ser Arg Gly Pro Leu Asp Lys Trp Arg Ala Leu His
        195                 200                 205


<210> SEQ ID NO 57
<211> LENGTH: 482
<212> TYPE: PRT
<213> ORGANISM: Homo sapiens

<400> SEQUENCE: 57

Met Lys Gly Glu Asn Phe Glu Val Gly Ser Lys Val Gln Phe Phe Cys
1               5                   10                  15

Asn Glu Gly Tyr Glu Leu Val Gly Asp Ser Ser Trp Thr Cys Gln Lys
            20                  25                  30

Ser Gly Lys Trp Asn Lys Lys Ser Asn Pro Lys Cys Met Pro Ala Lys
        35                  40                  45

Cys Pro Glu Pro Pro Leu Leu Glu Asn Gln Leu Val Leu Lys Glu Leu
    50                  55                  60

Thr Thr Glu Val Gly Val Val Thr Phe Ser Cys Lys Glu Gly His Val
65                  70                  75                  80

Leu Gln Gly Pro Ser Val Leu Lys Cys Leu Pro Ser Gln Gln Trp Asn
                85                  90                  95

Asp Ser Phe Pro Val Cys Lys Ile Val Leu Cys Thr Pro Pro Pro Leu
            100                 105                 110
```

```
Ile Ser Phe Gly Val Pro Ile Pro Ser Ser Ala Leu His Phe Gly Ser
        115                 120                 125

Thr Val Lys Tyr Ser Cys Val Gly Gly Phe Phe Leu Arg Gly Asn Ser
    130                 135                 140

Thr Thr Leu Cys Gln Pro Asp Gly Thr Trp Ser Ser Pro Leu Pro Glu
145                 150                 155                 160

Cys Val Pro Val Glu Cys Pro Gln Pro Glu Glu Ile Pro Asn Gly Ile
                165                 170                 175

Ile Asp Val Gln Gly Leu Ala Tyr Leu Ser Thr Ala Leu Tyr Thr Cys
            180                 185                 190

Lys Pro Gly Phe Glu Leu Val Gly Asn Thr Thr Thr Leu Cys Gly Glu
        195                 200                 205

Asn Gly His Trp Leu Gly Gly Lys Pro Thr Cys Lys Ala Ile Glu Cys
    210                 215                 220

Leu Lys Pro Lys Glu Ile Leu Asn Gly Lys Phe Ser Tyr Thr Asp Leu
225                 230                 235                 240

His Tyr Gly Gln Thr Val Thr Tyr Ser Cys Asn Arg Gly Phe Arg Leu
                245                 250                 255

Glu Gly Pro Ser Ala Leu Thr Cys Leu Glu Thr Gly Asp Trp Asp Val
            260                 265                 270

Asp Ala Pro Ser Cys Asn Ala Ile His Cys Asp Ser Pro Gln Pro Ile
        275                 280                 285

Glu Asn Gly Phe Val Glu Gly Ala Asp Tyr Ser Tyr Gly Ala Ile Ile
    290                 295                 300

Ile Tyr Ser Cys Phe Pro Gly Phe Gln Val Ala Gly His Ala Met Gln
305                 310                 315                 320

Thr Cys Glu Glu Ser Gly Trp Ser Ser Ser Ile Pro Thr Cys Met Pro
                325                 330                 335

Ile Asp Cys Gly Leu Pro Pro His Ile Asp Phe Gly Ala Cys Thr Lys
            340                 345                 350

Leu Lys Asp Ala Arg Asp Ile Leu Ser Lys Lys Arg His Asp Gly Ser
        355                 360                 365

Ser Ile Cys Asp Ser Ser Pro Ser Leu Ser Phe Gly Ala Val Ala Lys
    370                 375                 380

Thr Trp Glu Asn Thr Lys Glu Ser Pro Ala Thr His Ser Ser Asn Phe
385                 390                 395                 400

Leu Tyr Gly Thr Met Val Ser Tyr Thr Cys Asn Pro Gly Tyr Glu Leu
                405                 410                 415

Leu Gly Asn Pro Val Leu Ile Cys Gln Glu Asp Gly Thr Trp Asn Gly
            420                 425                 430

Ser Ala Pro Ser Cys Ile Ser Ile Glu Cys Asp Leu Pro Thr Ala Pro
        435                 440                 445

Glu Asn Gly Phe Leu Arg Phe Thr Glu Thr Ser Met Gly Ser Ala Val
    450                 455                 460

Gln Tyr Ser Cys Lys Pro Gly His Ile Leu Ala Gly Ser Asp Leu Arg
465                 470                 475                 480

Leu Cys
```

<210> SEQ ID NO 58
<211> LENGTH: 40
<212> TYPE: PRT
<213> ORGANISM: Homo sapiens

<400> SEQUENCE: 58

-continued

```
Thr Pro Gly Pro Gly Ala Gly Phe Tyr Ala Cys Pro Ala Arg Pro Leu
1               5                   10                  15

Val Ser Gly Ile Tyr Ser Phe Arg Trp Val Arg Gly Leu Ala Asp Gln
            20                  25                  30

Glu Arg Asn Trp Gly Leu Ser Gln
        35                  40


<210> SEQ ID NO 59
<211> LENGTH: 352
<212> TYPE: PRT
<213> ORGANISM: Homo sapiens

<400> SEQUENCE: 59

His Glu Ala Arg Leu Lys Arg Ala Ser Ala Pro Thr Phe Asp Asn Asp
1               5                   10                  15

Tyr Ser Leu Ser Glu Leu Leu Ser Gln Leu Asp Ser Gly Val Ser Gln
            20                  25                  30

Ala Val Glu Gly Pro Glu Glu Leu Ser Arg Ser Ser Ser Glu Ser Lys
        35                  40                  45

Leu Pro Ser Ser Gly Ser Gly Lys Arg Leu Ser Gly Val Ser Ser Val
    50                  55                  60

Asp Ser Ala Phe Ser Ser Arg Gly Ser Leu Ser Leu Ser Phe Glu Arg
65                  70                  75                  80

Glu Pro Ser Thr Ser Asp Leu Gly Thr Thr Asp Val Gln Lys Lys Lys
                85                  90                  95

Leu Val Asp Ala Ile Val Ser Gly Asp Thr Ser Lys Leu Met Lys Ile
            100                 105                 110

Leu Gln Pro Gln Asp Val Asp Leu Ala Leu Asp Ser Gly Ala Ser Leu
        115                 120                 125

Leu His Leu Ala Val Glu Ala Gly Gln Glu Glu Cys Ala Lys Trp Leu
    130                 135                 140

Leu Leu Asn Asn Ala Asn Pro Asn Leu Ser Asn Arg Arg Gly Ser Thr
145                 150                 155                 160

Pro Leu His Met Ala Val Glu Arg Arg Val Arg Gly Val Val Glu Leu
                165                 170                 175

Leu Leu Ala Arg Lys Ile Ser Val Asn Ala Lys Asp Glu Asp Gln Trp
            180                 185                 190

Thr Ala Leu His Phe Ala Ala Gln Asn Gly Asp Glu Ser Ser Thr Arg
        195                 200                 205

Leu Leu Leu Glu Lys Asn Ala Ser Val Asn Glu Val Asp Phe Glu Gly
    210                 215                 220

Arg Thr Pro Met His Val Ala Cys Gln His Gly Gln Glu Asn Ile Val
225                 230                 235                 240

Arg Ile Leu Leu Arg Arg Gly Val Asp Val Ser Leu Gln Gly Lys Asp
                245                 250                 255

Ala Trp Leu His Cys Thr Thr Leu Leu Ala Gly Pro Pro Ala His Arg
            260                 265                 270

Gln Ala Ala Gly Gln Ala Ala Gly Gly Glu Cys Glu Arg Pro Asp Ala
        275                 280                 285

Gly Trp Glu Asp Ala Ile Ala Pro Gly Arg Thr Ala Arg Ala Leu Pro
    290                 295                 300

Arg Gly Pro His Pro His Arg Pro Val Leu Arg Arg Gln Arg Leu Gln
305                 310                 315                 320

Pro Ala Gly Thr Asp Thr Pro Ala Arg Gly Pro Arg Arg Arg Gly Thr
```

-continued

```
                325                 330                 335

Arg Ala Leu Pro Gly Cys Ser Cys Ile Gly Ala Leu Ala Arg Arg Pro
            340                 345                 350


<210> SEQ ID NO 60
<211> LENGTH: 18
<212> TYPE: PRT
<213> ORGANISM: Homo sapiens

<400> SEQUENCE: 60

Ile Ile Cys Phe Ile Phe Lys Ala Gln Arg Val Tyr Val Asn His Phe
1               5                   10                  15

Asn Val


<210> SEQ ID NO 61
<211> LENGTH: 170
<212> TYPE: PRT
<213> ORGANISM: Homo sapiens

<400> SEQUENCE: 61

Pro Tyr Asn Gln Pro Gly Ile Cys Tyr Thr Leu Val Arg Leu Pro Asp
1               5                   10                  15

Asp Asp Pro Thr Ala Val Ala Gly Ser Phe Ser Cys Thr Met Lys Phe
            20                  25                  30

Thr Val Arg Asp Cys Asp Pro Asn Thr Gly Val Pro Asp Glu Asp Gly
        35                  40                  45

Tyr Asp Asp Glu Tyr Val Leu Glu Asp Leu Glu Val Thr Val Ser Asp
    50                  55                  60

His Ile Gln Lys Val Leu Lys Pro Asn Phe Ala Ala Ala Trp Glu Glu
65                  70                  75                  80

Val Gly Asp Thr Phe Glu Lys Glu Glu Thr Phe Ala Leu Ser Ser Thr
                85                  90                  95

Lys Thr Leu Glu Glu Ala Val Asn Asn Ile Ile Thr Phe Leu Gly Met
            100                 105                 110

Gln Pro Cys Glu Arg Ser Asp Lys Val Pro Glu Asn Lys Asn Ser His
        115                 120                 125

Ser Leu Tyr Leu Ala Gly Ile Phe Arg Gly Gly Tyr Asp Leu Leu Val
    130                 135                 140

Arg Ser Arg Leu Ala Leu Ala Asp Gly Val Thr Met Gln Val Thr Val
145                 150                 155                 160

Arg Ser Lys Glu Arg Thr Pro Val Asp Val
                165                 170


<210> SEQ ID NO 62
<211> LENGTH: 248
<212> TYPE: PRT
<213> ORGANISM: Homo sapiens

<400> SEQUENCE: 62

Asn Leu Ser Pro Lys Leu Ile Gln Pro Gly Thr Phe Thr Lys Thr Lys
1               5                   10                  15

Glu Asp Ile Leu Glu Ser Lys Ser Glu Gln Thr Lys Ser Lys Gln Arg
            20                  25                  30

Asp Thr Gln Glu Arg Lys Arg Glu Glu Lys Arg Lys Ala Asn Arg Arg
        35                  40                  45

Lys Ser Lys Arg Met Ser Lys Tyr Lys Glu Asn Lys Ser Glu Asn Lys
    50                  55                  60
```

```
Lys Thr Val Pro Gln Lys Lys Met His Lys Ser Val Ser Ser Asn Asp
65                  70                  75                  80

Ala Tyr Asn Phe Asn Leu Glu Glu Gly Val His Leu Thr Pro Phe Arg
                85                  90                  95

Gln Lys Val Ser Asn Asp Ser Asn Arg Glu Glu Asn Asn Glu Ser Glu
            100                 105                 110

Val Ser Leu Cys Glu Ser Ser Gly Ser Gly Asp Asp Ser Asp Asp Leu
        115                 120                 125

Tyr Leu Pro Thr Cys Lys Tyr Ile Gln Asn Pro Thr Ser Asn Ser Asp
    130                 135                 140

Arg Pro Val Thr Arg Pro Leu Ala Lys Arg Ala Leu Lys Tyr Thr Asp
145                 150                 155                 160

Glu Lys Glu Thr Glu Gly Ser Lys Pro Thr Lys Thr Pro Thr Thr Thr
                165                 170                 175

Pro Pro Glu Thr Gln Gln Ser Pro His Leu Ser Leu Lys Asp Ile Thr
            180                 185                 190

Asn Val Ser Leu Tyr Pro Val Val Lys Ile Arg Arg Leu Ser Leu Ser
        195                 200                 205

Pro Lys Lys Asn Lys Ala Ser Pro Ala Val Ala Leu Pro Lys Arg Arg
    210                 215                 220

Cys Thr Ala Ser Val Asn Tyr Lys Glu Pro Thr Leu Ala Ser Lys Leu
225                 230                 235                 240

Arg Arg Gly Asp Pro Phe Thr Asp
                245


<210> SEQ ID NO 63
<211> LENGTH: 228
<212> TYPE: PRT
<213> ORGANISM: Homo sapiens

<400> SEQUENCE: 63

Met Glu Ala Leu Gly Lys Leu Lys Gln Phe Asp Ala Tyr Pro Lys Thr
1               5                   10                  15

Leu Glu Asp Phe Arg Val Lys Thr Cys Gly Gly Ala Thr Val Thr Ile
            20                  25                  30

Val Ser Gly Leu Leu Met Leu Leu Leu Phe Leu Ser Glu Leu Gln Tyr
        35                  40                  45

Tyr Leu Thr Thr Glu Val His Pro Glu Leu Tyr Val Asp Lys Ser Arg
    50                  55                  60

Gly Asp Lys Leu Lys Ile Asn Ile Asp Val Leu Phe Pro His Met Pro
65                  70                  75                  80

Cys Ala Tyr Leu Ser Ile Asp Ala Met Asp Val Ala Gly Glu Gln Gln
                85                  90                  95

Leu Asp Val Glu His Asn Leu Phe Lys Gln Arg Leu Asp Lys Asp Gly
            100                 105                 110

Ile Pro Val Ser Ser Glu Ala Glu Arg His Glu Leu Gly Lys Val Glu
        115                 120                 125

Val Thr Val Phe Asp Pro Asp Ser Leu Asp Pro Asp Arg Cys Glu Ser
    130                 135                 140

Cys Tyr Gly Ala Glu Ala Glu Asp Ile Lys Cys Cys Asn Thr Cys Glu
145                 150                 155                 160

Asp Val Arg Glu Ala Tyr Arg Arg Arg Gly Trp Ala Phe Lys Asn Pro
                165                 170                 175

Asp Thr Ile Glu Gln Cys Arg Arg Glu Gly Phe Ser Gln Lys Met Gln
            180                 185                 190
```

```
Glu Gln Lys Asn Glu Gly Cys Gln Val Tyr Gly Phe Leu Glu Val Asn
        195                 200                 205

Lys Val Ala Gly Asn Phe His Phe Ala Pro Gly Lys Ser Phe Gln Gln
    210                 215                 220

Ser His Val His
225


<210> SEQ ID NO 64
<211> LENGTH: 519
<212> TYPE: PRT
<213> ORGANISM: Homo sapiens
<220> FEATURE:
<221> NAME/KEY: UNSURE
<222> LOCATION: (314)..(314)
<223> OTHER INFORMATION: X = any amino acid
<220> FEATURE:
<221> NAME/KEY: UNSURE
<222> LOCATION: (417)..(417)
<223> OTHER INFORMATION: X = any amino acid

<400> SEQUENCE: 64

Gly Asp Ser Val Lys Thr Ile Ala Lys Leu Trp Asp Ser Lys Met Phe
1               5                   10                  15

Ala Glu Ile Met Met Lys Ile Glu Glu Tyr Ile Lys Lys Gln Ala Lys
            20                  25                  30

Ala Ser Glu Val Met Gly Pro Val Glu Ala Ala Pro Glu Tyr Arg Val
        35                  40                  45

Ile Val Asp Ala Asn Asn Leu Thr Val Glu Ile Glu Asn Glu Leu Asn
    50                  55                  60

Ile Ile His Lys Phe Ile Arg Asp Lys Tyr Ser Lys Arg Phe Pro Glu
65                  70                  75                  80

Leu Glu Ser Leu Val Pro Asn Ala Leu Asp Tyr Ile Arg Thr Val Lys
                85                  90                  95

Glu Leu Gly Asn Ser Leu Asp Lys Cys Lys Asn Asn Glu Asn Leu Gln
            100                 105                 110

Gln Ile Leu Thr Asn Ala Thr Ile Met Val Val Ser Val Thr Ala Ser
        115                 120                 125

Thr Thr Gln Gly Gln Gln Leu Ser Glu Glu Glu Leu Glu Arg Leu Glu
    130                 135                 140

Glu Ala Cys Asp Met Ala Leu Glu Leu Asn Ala Ser Lys His Arg Ile
145                 150                 155                 160

Tyr Glu Tyr Val Glu Ser Arg Met Ser Phe Ile Ala Pro Asn Leu Ser
                165                 170                 175

Ile Ile Ile Gly Ala Ser Thr Ala Ala Lys Ile Met Gly Val Gly Gly
            180                 185                 190

Gly Leu Thr Asn Leu Ser Lys Met Pro Ala Cys Asn Ile Met Leu Leu
        195                 200                 205

Gly Ala Gln Arg Lys Thr Leu Ser Gly Phe Ser Ser Thr Ser Val Leu
    210                 215                 220

Pro His Thr Gly Tyr Ile Tyr His Ser Asp Ile Val Gln Ser Leu Pro
225                 230                 235                 240

Pro Asp Leu Arg Arg Lys Ala Ala Arg Leu Val Ala Ala Lys Cys Thr
                245                 250                 255

Leu Ala Ala Arg Val Asp Ser Phe His Glu Ser Thr Glu Gly Lys Val
            260                 265                 270

Gly Tyr Glu Leu Lys Asp Glu Ile Glu Arg Lys Phe Asp Lys Trp Gln
        275                 280                 285
```

```
Glu Pro Pro Pro Val Lys Gln Val Lys Pro Leu Pro Ala Pro Leu Asp
    290                 295                 300

Gly Gln Arg Lys Lys Arg Gly Gly Arg Xaa Val Arg Gly Pro Gly Gly
305                 310                 315                 320

Pro Val Gly Met Gly Val Met Glu Gly Arg Ser Arg Arg Pro Pro Pro
                325                 330                 335

Ser Arg Leu Pro Gly Ala Ala His Pro Pro Val Pro Arg Tyr Arg Lys
            340                 345                 350

Met Lys Glu Arg Leu Gly Leu Thr Glu Ile Arg Lys Gln Ala Asn Arg
        355                 360                 365

Met Ser Phe Gly Glu Ile Glu Glu Asp Ala Tyr Gln Glu Asp Leu Gly
    370                 375                 380

Phe Ser Leu Gly His Leu Gly Lys Ser Gly Ser Gly Arg Val Arg Gln
385                 390                 395                 400

Thr Gln Val Asn Glu Ala Thr Lys Ala Arg Ile Ser Lys Thr Leu Gln
                405                 410                 415

Xaa Met Gly Gln Thr Gln Val Gly Leu Gly Thr Glu Gly His Lys Val
            420                 425                 430

Gly Gly Ala Gln Ile Ala Ala Ser Leu Ser Ser Pro Gln Arg Thr Leu
        435                 440                 445

Gln Lys Gln Ser Val Val Tyr Gly Gly Lys Ser Thr Ile Arg Asp Arg
    450                 455                 460

Ser Ser Gly Thr Ala Ser Ser Val Ala Phe Thr Pro Leu Gln Gly Leu
465                 470                 475                 480

Glu Ile Val Asn Pro Gln Ala Ala Glu Lys Lys Val Ala Glu Ala Asn
                485                 490                 495

Gln Lys Tyr Phe Ser Ser Met Ala Glu Phe Leu Lys Val Lys Gly Glu
            500                 505                 510

Lys Ser Gly Leu Met Ser Thr
        515
```

<210> SEQ ID NO 65
<211> LENGTH: 662
<212> TYPE: PRT
<213> ORGANISM: Homo sapiens
<220> FEATURE:
<221> NAME/KEY: UNSURE
<222> LOCATION: (59)..(59)
<223> OTHER INFORMATION: X = any amino acid
<220> FEATURE:
<221> NAME/KEY: UNSURE
<222> LOCATION: (640)..(640)
<223> OTHER INFORMATION: X = any amino acid
<220> FEATURE:
<221> NAME/KEY: UNSURE
<222> LOCATION: (642)..(642)
<223> OTHER INFORMATION: X = any amino acid
<220> FEATURE:
<221> NAME/KEY: UNSURE
<222> LOCATION: (650)..(650)
<223> OTHER INFORMATION: X = any amino acid
<220> FEATURE:
<221> NAME/KEY: UNSURE
<222> LOCATION: (653)..(653)
<223> OTHER INFORMATION: X = any amino acid
<220> FEATURE:
<221> NAME/KEY: UNSURE
<222> LOCATION: (658)..(658)
<223> OTHER INFORMATION: X = any amino acid

<400> SEQUENCE: 65

```
Met Ala Ser Lys Arg Lys Ser Thr Thr Pro Cys Met Val Arg Thr Ser
```

-continued

```
1               5                   10                  15

Gln Val Val Glu Gln Asp Val Pro Glu Glu Val Asp Arg Ala Lys Glu
            20                  25                  30

Lys Gly Ile Gly Thr Pro Gln Pro Asp Val Ala Lys Asp Ser Trp Ala
        35                  40                  45

Xaa Glu Leu Glu Asn Ser Ser Lys Glu Asn Glu Val Ile Glu Val Lys
    50                  55                  60

Ser Met Gly Glu Ser Gln Ser Lys Lys Leu Gln Gly Gly Tyr Glu Cys
65                  70                  75                  80

Lys Tyr Cys Pro Tyr Ser Thr Gln Asn Leu Asn Glu Phe Thr Glu His
                85                  90                  95

Val Asp Met Gln His Pro Asn Val Ile Leu Asn Pro Leu Tyr Val Cys
            100                 105                 110

Ala Glu Cys Asn Phe Thr Thr Lys Lys Tyr Asp Ser Leu Ser Asp His
        115                 120                 125

Asn Ser Lys Phe His Pro Gly Glu Ala Asn Phe Lys Leu Lys Leu Ile
    130                 135                 140

Lys Arg Asn Asn Gln Thr Val Leu Glu Gln Ser Ile Glu Thr Thr Asn
145                 150                 155                 160

His Val Val Ser Ile Thr Thr Ser Gly Pro Gly Thr Gly Asp Ser Asp
                165                 170                 175

Ser Gly Ile Ser Val Ser Lys Thr Pro Ile Met Lys Pro Gly Lys Pro
            180                 185                 190

Lys Ala Asp Ala Lys Lys Val Pro Lys Lys Pro Glu Glu Ile Thr Pro
        195                 200                 205

Glu Asn His Val Glu Gly Thr Ala Arg Leu Val Thr Asp Thr Ala Glu
    210                 215                 220

Ile Leu Ser Arg Leu Gly Gly Val Glu Leu Leu Gln Asp Thr Leu Gly
225                 230                 235                 240

His Val Met Pro Ser Val Gln Leu Pro Pro Asn Ile Asn Leu Val Pro
                245                 250                 255

Lys Val Pro Val Pro Leu Asn Thr Thr Lys Tyr Asn Ser Ala Leu Asp
            260                 265                 270

Thr Asn Ala Thr Met Ile Asn Ser Phe Asn Lys Phe Pro Tyr Pro Thr
        275                 280                 285

Gln Ala Glu Leu Ser Trp Leu Thr Ala Ala Ser Lys His Pro Glu Glu
    290                 295                 300

His Ile Arg Ile Trp Phe Ala Thr Gln Arg Leu Lys His Gly Ile Ser
305                 310                 315                 320

Trp Ser Pro Glu Glu Val Glu Glu Ala Arg Lys Lys Met Phe Asn Gly
                325                 330                 335

Thr Ile Gln Ser Val Pro Pro Thr Ile Thr Val Leu Pro Ala Gln Leu
            340                 345                 350

Ala Pro Thr Lys Met Thr Gln Pro Ile Leu Gln Thr Ala Leu Pro Cys
        355                 360                 365

Gln Ile Leu Gly Gln Thr Ser Leu Val Leu Thr Gln Val Thr Ser Gly
    370                 375                 380

Ser Thr Thr Val Ser Cys Ser Pro Ile Thr Leu Ala Val Ala Gly Val
385                 390                 395                 400

Thr Asn His Gly Gln Lys Arg Pro Leu Val Thr Pro Gln Ala Ala Pro
                405                 410                 415

Glu Pro Lys Arg Pro His Ile Ala Gln Val Pro Glu Pro Pro Pro Lys
            420                 425                 430
```

```
Val Ala Asn Pro Pro Leu Thr Pro Ala Ser Asp Arg Lys Lys Thr Lys
        435                 440                 445

Glu Gln Ile Ala His Leu Lys Ala Ser Phe Leu Gln Ser Gln Phe Pro
    450                 455                 460

Asp Asp Ala Glu Val Tyr Arg Leu Ile Glu Val Thr Gly Leu Ala Arg
465                 470                 475                 480

Ser Glu Ile Lys Lys Trp Phe Ser Asp His Arg Tyr Arg Cys Gln Arg
                485                 490                 495

Gly Ile Val His Ile Thr Ser Glu Ser Leu Ala Lys Asp Gln Leu Ala
            500                 505                 510

Ile Ala Ala Ser Arg His Gly Arg Thr Tyr His Ala Tyr Pro Asp Phe
        515                 520                 525

Ala Pro Gln Lys Phe Lys Glu Lys Thr Gln Gly Gln Val Lys Ile Leu
    530                 535                 540

Glu Asp Ser Phe Leu Lys Ser Ser Phe Pro Thr Gln Ala Glu Leu Asp
545                 550                 555                 560

Arg Leu Arg Val Glu Thr Lys Leu Ser Arg Arg Glu Ile Asp Ser Trp
                565                 570                 575

Phe Ser Glu Arg Arg Lys Leu Arg Asp Ser Met Glu Gln Ala Val Leu
            580                 585                 590

Asp Ser Met Gly Ser Gly Gln Lys Arg Pro Arg Cys Gly Lys Pro Pro
        595                 600                 605

Met Val Leu Phe Ser Thr Arg Thr Ala Leu Arg Cys Pro Val Asn Lys
    610                 615                 620

Phe Ser Ala Gln Pro Phe Ala Ser Asn Leu Gln Lys Val Lys Asn Xaa
625                 630                 635                 640

Phe Xaa Leu Leu Lys Glu His Val Cys Xaa Lys Pro Xaa Trp Ala Thr
                645                 650                 655

Pro Xaa Glu Tyr Asp Gln
            660


<210> SEQ ID NO 66
<211> LENGTH: 596
<212> TYPE: PRT
<213> ORGANISM: Homo sapiens

<400> SEQUENCE: 66

Met Arg Arg Ala His Glu Gly Arg Glu Ile Pro Ser Leu Gly Gly Ala
1               5                   10                  15

Arg Arg Arg Glu Val Leu Gln Ala Gly Arg Ser Gln Arg Ala Ala Gly
            20                  25                  30

Arg Arg Arg Arg Arg Gln Glu Leu Glu Leu Gly Val Gly Ser Gly Arg
        35                  40                  45

Pro Gly Gly Pro Pro Pro Gly Pro Gly Arg Arg Gly Thr Cys Ala Ala
    50                  55                  60

Ala Leu Pro Pro Glu Trp Pro Arg Arg Arg Thr Gly Leu Pro Arg Arg
65                  70                  75                  80

Gly Pro Arg Pro Pro Leu Ala Met Ala Lys Trp Leu Asn Lys Tyr Phe
                85                  90                  95

Ser Leu Gly Asn Ser Lys Thr Lys Ser Pro Pro Gln Pro Pro Arg Pro
            100                 105                 110

Asp Tyr Arg Glu Gln Arg Arg Arg Gly Glu Arg Pro Ser Gln Pro Pro
        115                 120                 125

Gln Ala Val Pro Gln Ala Ser Ser Ala Ala Ser Ala Ser Cys Gly Pro
```

-continued

```
    130                 135                 140

Ala Thr Ala Ser Cys Phe Ser Ala Ser Ser Gly Ser Leu Pro Asp Asp
145                 150                 155                 160

Ser Gly Ser Thr Ser Asp Leu Ile Arg Ala Tyr Arg Ala Gln Lys Glu
                165                 170                 175

Arg His Phe Gln Asp Pro Tyr Asn Gly Pro Gly Ser Ser Leu Arg Lys
            180                 185                 190

Leu Arg Ala Met Cys Arg Leu Asp Tyr Cys Gly Gly Ser Gly Glu Pro
        195                 200                 205

Gly Gly Val Gln Arg Ala Phe Ser Ala Ser Ser Ala Ser Gly Ala Ala
    210                 215                 220

Gly Cys Cys Cys Ala Ser Ser Gly Ala Gly Ala Ala Ala Ser Ser Ser
225                 230                 235                 240

Ser Ser Ser Gly Ser Pro His Leu Tyr Arg Ser Ser Ser Glu Arg Arg
                245                 250                 255

Pro Ala Thr Pro Ala Glu Val Arg Tyr Ile Ser Pro Lys His Arg Leu
            260                 265                 270

Ile Lys Val Glu Ser Ala Ala Gly Gly Gly Ala Gly Asp Pro Leu Gly
        275                 280                 285

Gly Ala Cys Ala Gly Gly Arg Thr Trp Ser Pro Thr Ala Cys Gly Gly
    290                 295                 300

Lys Lys Leu Leu Asn Lys Cys Ala Ala Ser Ala Ala Glu Glu Ser Gly
305                 310                 315                 320

Ala Gly Lys Lys Asp Lys Val Thr Ile Ala Asp Asp Tyr Ser Asp Pro
                325                 330                 335

Phe Asp Ala Lys Asn Asp Leu Lys Ser Lys Ala Gly Lys Gly Glu Ser
            340                 345                 350

Ala Gly Tyr Met Glu Pro Tyr Glu Ala Gln Arg Ile Met Thr Glu Phe
        355                 360                 365

Gln Arg Gln Glu Ser Val Arg Ser Gln His Lys Gly Ile Gln Leu Tyr
    370                 375                 380

Asp Thr Pro Tyr Glu Pro Glu Gly Gln Ser Val Asp Ser Asp Ser Glu
385                 390                 395                 400

Ser Thr Val Ser Pro Arg Leu Arg Glu Ser Lys Leu Pro Gln Asp Asp
                405                 410                 415

Asp Arg Pro Ala Asp Glu Tyr Asp Gln Pro Trp Glu Trp Asn Arg Val
            420                 425                 430

Thr Ser Pro Ala Leu Ala Ala Gln Phe Asn Gly Asn Glu Lys Arg Gln
        435                 440                 445

Ser Ser Pro Ser Pro Ser Arg Asp Arg Arg Arg Gln Leu Arg Ala Pro
    450                 455                 460

Gly Gly Gly Phe Lys Pro Ile Lys His Gly Ser Pro Glu Phe Cys Gly
465                 470                 475                 480

Ile Leu Gly Glu Arg Val Asp Pro Ala Val Pro Leu Glu Lys Gln Ile
                485                 490                 495

Trp Tyr His Gly Ala Ile Ser Arg Gly Asp Ala Glu Asn Leu Leu Arg
            500                 505                 510

Leu Cys Lys Glu Cys Ser Tyr Leu Val Arg Asn Ser Gln Thr Ser Lys
        515                 520                 525

His Asp Tyr Pro Leu Ser Leu Arg Ser Asn Gln Gly Phe Met His Met
    530                 535                 540

Lys Leu Ala Lys Thr Lys Glu Lys Tyr Val Leu Gly Gln Asn Ser Pro
545                 550                 555                 560
```

```
Pro Phe Asp Ser Val Pro Glu Val Ile His Tyr Tyr Thr Thr Arg Lys
                565                 570                 575

Leu Pro Ile Lys Gly Ala Glu His Leu Ser Leu Leu Tyr Pro Val Ala
            580                 585                 590

Val Arg Thr Leu
        595


<210> SEQ ID NO 67
<211> LENGTH: 508
<212> TYPE: PRT
<213> ORGANISM: Homo sapiens

<400> SEQUENCE: 67

Met Gly Ser Cys Cys Ser Cys Pro Asp Lys Asp Thr Val Pro Asp Asn
1               5                   10                  15

His Arg Asn Lys Phe Lys Val Ile Asn Val Asp Asp Asp Gly Asn Glu
            20                  25                  30

Leu Gly Ser Gly Ile Met Glu Leu Thr Asp Thr Glu Leu Ile Leu Tyr
        35                  40                  45

Thr Arg Lys Arg Asp Ser Val Lys Trp His Tyr Leu Cys Leu Arg Arg
    50                  55                  60

Tyr Gly Tyr Asp Ser Asn Leu Phe Ser Phe Glu Ser Gly Arg Arg Cys
65                  70                  75                  80

Gln Thr Gly Gln Gly Ile Phe Ala Phe Lys Cys Ala Arg Ala Glu Glu
                85                  90                  95

Leu Phe Asn Met Leu Gln Glu Ile Met Gln Asn Asn Ser Ile Asn Val
            100                 105                 110

Val Glu Glu Pro Val Val Glu Arg Asn Asn His Gln Thr Glu Leu Glu
        115                 120                 125

Val Pro Arg Thr Pro Arg Thr Pro Thr Thr Pro Gly Phe Ala Ala Gln
    130                 135                 140

Asn Leu Pro Asn Gly Tyr Pro Arg Tyr Pro Ser Phe Gly Asp Ala Ser
145                 150                 155                 160

Ser His Pro Ser Ser Arg His Pro Ser Val Gly Ser Ala Arg Leu Pro
                165                 170                 175

Ser Val Gly Glu Glu Ser Thr His Pro Leu Leu Val Ala Glu Glu Gln
            180                 185                 190

Val His Thr Tyr Val Asn Thr Thr Gly Val Gln Glu Glu Arg Lys Asn
        195                 200                 205

Arg Thr Ser Val His Val Pro Leu Glu Ala Arg Val Ser Asn Ala Glu
    210                 215                 220

Ser Ser Thr Pro Lys Glu Glu Pro Ser Ser Ile Glu Asp Arg Asp Pro
225                 230                 235                 240

Gln Ile Leu Leu Glu Pro Glu Gly Val Lys Phe Val Leu Gly Pro Thr
                245                 250                 255

Pro Val Gln Lys Gln Leu Met Glu Lys Glu Lys Leu Glu Gln Leu Gly
            260                 265                 270

Arg Asp Gln Val Ser Gly Ser Gly Ala Asn Asn Thr Glu Trp Asp Thr
        275                 280                 285

Gly Tyr Asp Ser Asp Glu Arg Arg Asp Ala Pro Ser Val Asn Lys Leu
    290                 295                 300

Val Tyr Glu Asn Ile Asn Gly Leu Ser Ile Pro Ser Ala Ser Gly Val
305                 310                 315                 320

Arg Arg Gly Arg Leu Thr Ser Thr Ser Thr Ser Asp Thr Gln Asn Ile
```

-continued

```
                325                 330                 335

Asn Asn Ser Ala Gln Arg Arg Thr Ala Leu Leu Asn Tyr Glu Asn Leu
            340                 345                 350

Pro Ser Leu Pro Pro Val Trp Glu Ala Arg Lys Leu Ser Arg Asp Glu
        355                 360                 365

Asp Asp Asn Leu Gly Pro Lys Thr Pro Ser Leu Asn Gly Tyr His Asn
    370                 375                 380

Asn Leu Asp Pro Met His Asn Tyr Val Asn Thr Glu Asn Val Thr Val
385                 390                 395                 400

Pro Ala Ser Ala His Lys Ile Glu Tyr Ser Arg Arg Arg Asp Cys Thr
                405                 410                 415

Pro Thr Val Phe Asn Phe Asp Ile Arg Arg Pro Ser Leu Glu His Arg
            420                 425                 430

Gln Leu Asn Tyr Ile Gln Val Asp Leu Glu Gly Gly Ser Asp Ser Asp
        435                 440                 445

Asn Pro Gln Thr Pro Lys Thr Pro Thr Thr Pro Leu Pro Gln Thr Pro
    450                 455                 460

Thr Arg Arg Thr Glu Leu Tyr Ala Val Ile Asp Ile Glu Arg Thr Ala
465                 470                 475                 480

Ala Met Ser Asn Leu Gln Lys Ala Leu Pro Arg Asp Asp Gly Thr Ser
                485                 490                 495

Arg Lys Thr Arg His Asn Ser Thr Asp Leu Pro Met
            500                 505


<210> SEQ ID NO 68
<211> LENGTH: 569
<212> TYPE: PRT
<213> ORGANISM: Homo sapiens

<400> SEQUENCE: 68

Met Ser Thr Met Val Tyr Ile Lys Glu Asp Lys Leu Glu Lys Leu Thr
1               5                   10                  15

Gln Asp Glu Ile Ile Ser Lys Thr Lys Gln Val Ile Gln Gly Leu Glu
            20                  25                  30

Ala Leu Lys Asn Glu His Asn Ser Ile Leu Gln Ser Leu Leu Glu Thr
        35                  40                  45

Leu Lys Cys Leu Lys Lys Asp Asp Glu Ser Asn Leu Val Glu Glu Lys
    50                  55                  60

Ser Asn Met Ile Arg Lys Ser Leu Glu Met Leu Glu Leu Gly Leu Ser
65                  70                  75                  80

Glu Ala Gln Val Met Met Ala Leu Ser Asn His Leu Asn Ala Val Glu
                85                  90                  95

Ser Glu Lys Gln Lys Leu Arg Ala Gln Val Arg Arg Leu Cys Gln Glu
            100                 105                 110

Asn Gln Trp Leu Arg Asp Glu Leu Ala Asn Thr Gln Gln Lys Leu Gln
        115                 120                 125

Lys Ser Glu Gln Ser Val Ala Gln Leu Glu Glu Glu Lys Lys His Leu
    130                 135                 140

Glu Phe Met Asn Gln Leu Lys Lys Tyr Asp Asp Asp Ile Ser Pro Ser
145                 150                 155                 160

Glu Asp Lys Asp Thr Asp Ser Thr Lys Glu Pro Leu Asp Asp Leu Phe
                165                 170                 175

Pro Asn Asp Glu Asp Asp Pro Gly Gln Gly Ile Gln Gln Gln His Ser
            180                 185                 190
```

-continued

```
Ser Ala Ala Ala Ala Ala Gln Gln Gly Gly Tyr Glu Ile Pro Ala Arg
        195                 200                 205

Leu Arg Thr Leu His Asn Leu Val Ile Gln Tyr Ala Ser Gln Gly Arg
    210                 215                 220

Tyr Glu Val Ala Val Pro Leu Cys Lys Gln Ala Leu Glu Asp Leu Glu
225                 230                 235                 240

Lys Thr Ser Gly His Asp His Pro Asp Val Ala Thr Met Leu Asn Ile
                245                 250                 255

Leu Ala Leu Val Tyr Arg Asp Gln Asn Lys Tyr Lys Asp Ala Ala Asn
            260                 265                 270

Leu Leu Asn Asp Ala Leu Ala Ile Arg Glu Lys Thr Leu Gly Lys Asp
        275                 280                 285

His Pro Ala Val Ala Ala Thr Leu Asn Asn Leu Ala Val Leu Tyr Gly
    290                 295                 300

Lys Arg Gly Lys Tyr Lys Glu Ala Glu Pro Leu Cys Lys Arg Ala Leu
305                 310                 315                 320

Glu Ile Arg Glu Lys Val Leu Gly Lys Asp His Pro Asp Val Ala Lys
                325                 330                 335

Gln Leu Asn Asn Leu Ala Leu Leu Cys Gln Asn Gln Gly Lys Tyr Glu
            340                 345                 350

Glu Val Glu Tyr Tyr Tyr Gln Arg Ala Leu Glu Ile Tyr Gln Thr Lys
        355                 360                 365

Leu Gly Pro Asp Asp Pro Asn Val Ala Lys Thr Lys Asn Asn Leu Ala
    370                 375                 380

Ser Cys Tyr Leu Lys Gln Gly Lys Phe Lys Gln Ala Glu Thr Leu Tyr
385                 390                 395                 400

Lys Glu Ile Leu Thr Arg Ala His Glu Arg Glu Phe Gly Ser Val Asp
                405                 410                 415

Asp Glu Asn Lys Pro Ile Trp Met His Ala Glu Glu Arg Glu Glu Cys
            420                 425                 430

Lys Gly Lys Gln Lys Asp Gly Thr Ser Phe Gly Glu Tyr Gly Gly Trp
        435                 440                 445

Tyr Lys Ala Cys Lys Val Asp Ser Pro Thr Val Thr Thr Thr Leu Lys
    450                 455                 460

Asn Leu Gly Ala Leu Tyr Arg Arg Gln Gly Lys Phe Glu Ala Ala Glu
465                 470                 475                 480

Thr Leu Glu Glu Ala Ala Met Arg Ser Arg Lys Gln Gly Leu Asp Asn
                485                 490                 495

Val His Lys Gln Arg Val Ala Glu Val Leu Asn Asp Pro Glu Asn Met
            500                 505                 510

Glu Lys Arg Arg Ser Arg Glu Ser Leu Asn Val Asp Val Val Lys Tyr
        515                 520                 525

Glu Ser Gly Pro Asp Gly Gly Glu Glu Val Ser Met Ser Val Glu Trp
    530                 535                 540

Asn Gly Gly Val Ser Gly Arg Ala Ser Phe Cys Gly Lys Arg Gln Gln
545                 550                 555                 560

Gln Gln Trp Pro Gly Arg Arg His Arg
                565
```

<210> SEQ ID NO 69
<211> LENGTH: 180
<212> TYPE: PRT
<213> ORGANISM: Homo sapiens

<400> SEQUENCE: 69

```
Met Gln Ala Glu Gly Gln Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Arg Gly Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Gln Leu His Ile Thr Met Pro Phe
                85                  90                  95

Ser Ser Pro Met Glu Ala Glu Leu Val Arg Arg Ile Leu Ser Arg Asp
            100                 105                 110

Ala Ala Pro Leu Pro Arg Pro Gly Ala Val Leu Lys Asp Phe Thr Val
        115                 120                 125

Ser Gly Asn Leu Leu Phe Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Ala Pro Ser
                165                 170                 175

Gly Gln Arg Arg
            180


<210> SEQ ID NO 70
<211> LENGTH: 386
<212> TYPE: PRT
<213> ORGANISM: Homo sapiens

<400> SEQUENCE: 70

Met Ala Asp Ile Asp Asn Lys Glu Gln Ser Glu Leu Asp Gln Asp Leu
1               5                   10                  15

Asp Asp Val Glu Glu Val Glu Glu Glu Glu Thr Gly Glu Glu Thr Lys
            20                  25                  30

Leu Lys Ala Arg Gln Leu Thr Val Gln Met Met Gln Asn Pro Gln Ile
        35                  40                  45

Leu Ala Ala Leu Gln Glu Arg Leu Asp Gly Leu Val Glu Thr Pro Thr
    50                  55                  60

Gly Tyr Ile Glu Ser Leu Pro Arg Val Val Lys Arg Arg Val Asn Ala
65                  70                  75                  80

Leu Lys Asn Leu Gln Val Lys Cys Ala Gln Ile Glu Ala Lys Phe Tyr
                85                  90                  95

Glu Glu Val His Asp Leu Glu Arg Lys Tyr Ala Val Leu Tyr Gln Pro
            100                 105                 110

Leu Phe Asp Lys Arg Phe Glu Ile Ile Asn Ala Ile Tyr Glu Pro Thr
        115                 120                 125

Glu Glu Glu Cys Glu Trp Lys Pro Asp Glu Glu Asp Glu Ile Ser Glu
    130                 135                 140

Glu Leu Lys Glu Lys Ala Lys Ile Glu Asp Glu Lys Lys Asp Glu Glu
145                 150                 155                 160

Lys Glu Asp Pro Lys Gly Ile Pro Glu Phe Trp Leu Thr Val Phe Lys
                165                 170                 175

Asn Val Asp Leu Leu Ser Asp Met Val Gln Glu His Asp Glu Pro Ile
```

```
            180                 185                 190

Leu Lys His Leu Lys Asp Ile Lys Val Lys Phe Ser Asp Ala Gly Gln
        195                 200                 205

Pro Met Ser Phe Val Leu Glu Phe His Phe Glu Pro Asn Glu Tyr Phe
    210                 215                 220

Thr Asn Glu Val Leu Thr Lys Thr Tyr Arg Met Arg Ser Glu Pro Asp
225                 230                 235                 240

Asp Ser Asp Pro Phe Ser Phe Asp Gly Pro Glu Ile Met Gly Cys Thr
                245                 250                 255

Gly Cys Gln Ile Asp Trp Lys Lys Gly Lys Asn Val Thr Leu Lys Thr
            260                 265                 270

Ile Lys Lys Lys Gln Lys His Lys Gly Arg Gly Thr Val Arg Thr Val
        275                 280                 285

Thr Lys Thr Val Ser Asn Asp Ser Phe Phe Asn Phe Phe Ala Pro Pro
    290                 295                 300

Glu Val Pro Glu Ser Gly Asp Leu Asp Asp Asp Ala Glu Ala Ile Leu
305                 310                 315                 320

Ala Ala Asp Phe Glu Ile Gly His Phe Leu Arg Glu Arg Ile Ile Pro
                325                 330                 335

Arg Ser Val Leu Tyr Phe Thr Gly Glu Ala Ile Glu Asp Asp Asp Asp
            340                 345                 350

Asp Tyr Asp Glu Glu Gly Glu Glu Ala Asp Glu Glu Gly Glu Glu Glu
        355                 360                 365

Gly Asp Glu Glu Asn Asp Pro Asp Tyr Asp Pro Lys Lys Asp Gln Asn
    370                 375                 380

Pro Ala
385


<210> SEQ ID NO 71
<211> LENGTH: 279
<212> TYPE: PRT
<213> ORGANISM: Homo sapiens

<400> SEQUENCE: 71

Leu Leu Arg Cys Val Pro Arg Val Leu Gly Ser Ser Val Ala Gly Leu
1               5                   10                  15

Arg Ala Ala Ala Pro Ala Ser Pro Phe Arg Gln Leu Leu Gln Pro Ala
            20                  25                  30

Pro Arg Leu Cys Thr Arg Pro Phe Gly Leu Leu Ser Val Arg Ala Gly
        35                  40                  45

Ser Glu Arg Arg Pro Gly Leu Leu Arg Pro Arg Gly Pro Cys Ala Cys
    50                  55                  60

Gly Cys Gly Cys Gly Ser Leu His Thr Asp Gly Asp Lys Ala Phe Val
65                  70                  75                  80

Asp Phe Leu Ser Asp Glu Ile Lys Glu Glu Arg Lys Ile Gln Lys His
                85                  90                  95

Lys Thr Leu Pro Lys Met Ser Gly Gly Trp Glu Leu Glu Leu Asn Gly
            100                 105                 110

Thr Glu Ala Lys Leu Val Arg Lys Val Ala Gly Glu Lys Ile Thr Val
        115                 120                 125

Thr Phe Asn Ile Asn Asn Ser Ile Pro Pro Thr Phe Asp Gly Glu Glu
    130                 135                 140

Glu Pro Ser Gln Gly Gln Lys Val Glu Glu Gln Glu Pro Glu Leu Thr
145                 150                 155                 160
```

```
Ser Thr Pro Asn Phe Val Val Glu Val Ile Lys Asn Asp Asp Gly Lys
                165                 170                 175

Lys Ala Leu Val Leu Asp Cys His Tyr Pro Glu Asp Glu Val Gly Gln
            180                 185                 190

Glu Asp Glu Ala Glu Ser Asp Ile Phe Ser Ile Arg Glu Val Ser Phe
        195                 200                 205

Gln Ser Thr Gly Glu Ser Glu Trp Lys Asp Thr Asn Tyr Thr Leu Asn
    210                 215                 220

Thr Asp Ser Leu Asp Trp Ala Leu Tyr Asp His Leu Met Asp Phe Leu
225                 230                 235                 240

Ala Asp Arg Gly Val Asp Asn Thr Phe Ala Asp Glu Leu Val Glu Leu
                245                 250                 255

Ser Thr Ala Leu Glu His Gln Glu Tyr Ile Thr Phe Leu Glu Asp Leu
            260                 265                 270

Lys Ser Phe Val Lys Ser Gln
        275


<210> SEQ ID NO 72
<211> LENGTH: 1253
<212> TYPE: PRT
<213> ORGANISM: Homo sapiens

<400> SEQUENCE: 72

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255
```

```
His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670
```

```
Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                 1015                1020

Leu Val  Pro Gln Gln Gly Phe  Phe Cys Pro Asp Pro  Ala Pro Gly
    1025                 1030                1035

Ala Gly  Gly Met Val His His  Arg His Arg Ser Ser  Ser Thr Arg
    1040                 1045                1050

Ser Gly  Gly Gly Asp Leu Thr  Leu Gly Leu Glu Pro  Ser Glu Glu
    1055                 1060                1065

Glu Ala  Pro Arg Ser Pro Leu  Ala Pro Ser Glu Gly  Ala Gly Ser
    1070                 1075                1080

Asp Val  Phe Asp Gly Asp Leu  Gly Met Gly Ala Ala  Lys Gly Leu
```

```
    1085                1090                1095

Gln Ser  Leu Pro Thr His Asp  Pro Ser Pro Leu Gln  Arg Tyr Ser
    1100                1105                1110

Glu Asp  Pro Thr Val Pro Leu  Pro Ser Glu Thr Asp  Gly Tyr Val
    1115                1120                1125

Ala Pro  Leu Thr Cys Ser Pro  Gln Pro Glu Tyr Val  Asn Gln Pro
    1130                1135                1140

Asp Val  Arg Pro Gln Pro Pro  Ser Pro Arg Glu Gly  Pro Leu Pro
    1145                1150                1155

Ala Ala  Arg Pro Ala Gly Ala  Thr Leu Glu Arg Pro  Lys Thr Leu
    1160                1165                1170

Ser Pro  Gly Lys Asn Gly Val  Val Lys Asp Val Phe  Ala Phe Gly
    1175                1180                1185

Gly Ala  Val Glu Asn Pro Glu  Tyr Leu Thr Pro Gln  Gly Gly Ala
    1190                1195                1200

Ala Pro  Gln Pro His Pro Pro  Pro Ala Phe Ser Pro  Ala Phe Asp
    1205                1210                1215

Asn Leu  Tyr Tyr Trp Asp Gln  Asp Pro Pro Glu Arg  Gly Ala Pro
    1220                1225                1230

Pro Ser  Thr Phe Lys Gly Thr  Pro Thr Ala Glu Asn  Pro Glu Tyr
    1235                1240                1245

Leu Gly  Leu Asp Val
    1250


<210> SEQ ID NO 73
<211> LENGTH: 532
<212> TYPE: PRT
<213> ORGANISM: Homo sapiens
<220> FEATURE:
<221> NAME/KEY: UNSURE
<222> LOCATION: (488)..(488)
<223> OTHER INFORMATION: X = any amino acid

<400> SEQUENCE: 73

Leu Gln Glu Thr Gln Thr Lys Asn Asp Phe Leu Lys Ser Glu Val His
1               5                   10                  15

Asp Leu Arg Val Val Leu His Ser Ala Asp Lys Glu Leu Ser Ser Val
            20                  25                  30

Lys Leu Glu Tyr Ser Ser Phe Lys Thr Asn Gln Glu Lys Glu Phe Asn
        35                  40                  45

Lys Leu Ser Glu Arg His Met His Val Gln Leu Gln Leu Asp Asn Leu
    50                  55                  60

Arg Leu Glu Asn Glu Lys Leu Leu Glu Ser Lys Ala Cys Leu Gln Asp
65                  70                  75                  80

Ser Tyr Asp Asn Leu Gln Glu Ile Met Lys Phe Glu Ile Asp Gln Leu
                85                  90                  95

Ser Arg Asn Leu Gln Asn Phe Lys Lys Glu Asn Glu Thr Leu Lys Ser
            100                 105                 110

Asp Leu Asn Asn Leu Met Glu Leu Leu Glu Ala Glu Lys Glu Arg Asn
        115                 120                 125

Asn Lys Leu Ser Leu Gln Phe Glu Glu Asp Lys Glu Asn Ser Ser Lys
    130                 135                 140

Glu Ile Leu Lys Val Leu Glu Ala Val Arg Gln Glu Lys Gln Lys Glu
145                 150                 155                 160

Thr Ala Lys Cys Glu Gln Gln Met Ala Lys Val Gln Lys Leu Glu Glu
                165                 170                 175
```

```
Ser Leu Leu Ala Thr Glu Lys Val Ile Ser Ser Leu Glu Lys Ser Arg
            180                 185                 190

Asp Ser Asp Lys Lys Val Val Ala Asp Leu Met Asn Gln Ile Gln Glu
        195                 200                 205

Leu Arg Thr Ser Val Cys Glu Lys Thr Glu Thr Ile Asp Thr Leu Lys
    210                 215                 220

Gln Glu Leu Lys Asp Ile Asn Cys Lys Tyr Asn Ser Ala Leu Val Asp
225                 230                 235                 240

Arg Glu Glu Ser Arg Val Leu Ile Lys Lys Gln Glu Val Asp Ile Leu
                245                 250                 255

Asp Leu Lys Glu Thr Leu Arg Leu Arg Ile Leu Ser Glu Asp Ile Lys
            260                 265                 270

Arg Asp Met Leu Cys Glu Asp Leu Leu Met Pro Leu Thr Ala Asp Met
        275                 280                 285

Leu Thr Glu Ala Leu Lys Lys Thr Leu Gly Leu Leu Gln Ser Ala Gln
    290                 295                 300

Glu Arg Thr Ala Lys Lys Glu Ala Leu Ile Gln Glu Leu Gln His Lys
305                 310                 315                 320

Leu Asn Gln Lys Lys Glu Glu Val Glu Gln Lys Lys Asn Glu Tyr Asn
                325                 330                 335

Phe Lys Met Arg Gln Leu Glu His Val Met Asp Ser Ala Ala Glu Asp
            340                 345                 350

Pro Gln Ser Pro Lys Thr Pro Pro His Phe Gln Thr His Leu Ala Lys
        355                 360                 365

Leu Leu Glu Thr Gln Glu Gln Glu Ile Glu Asp Gly Arg Ala Ser Lys
    370                 375                 380

Thr Ser Leu Glu His Leu Val Thr Lys Leu Asn Glu Asp Arg Glu Val
385                 390                 395                 400

Lys Asn Ala Glu Ile Leu Arg Met Lys Glu Gln Leu Arg Glu Met Glu
                405                 410                 415

Asn Leu Arg Met Glu Ser Gln Gln Leu Ile Glu Lys Asn Trp Leu Leu
            420                 425                 430

Gln Gly Gln Leu Asp Asp Ile Lys Arg Gln Lys Glu Asn Ser Asp Gln
        435                 440                 445

Asn His Pro Asp Asn Gln Gln Leu Lys Asn Glu Gln Glu Glu Ser Ile
    450                 455                 460

Lys Glu Arg Leu Ala Lys Ser Lys Ile Val Glu Glu Met Leu Lys Met
465                 470                 475                 480

Lys Ala Asp Leu Glu Glu Val Xaa Lys Cys Pro Phe Asn Lys Glu Met
                485                 490                 495

Glu Cys Leu Arg Met Thr Asp Glu Val Glu Arg Thr Gln Thr Leu Glu
            500                 505                 510

Ser Lys Ala Phe Gln Glu Lys Glu Gln Leu Arg Ser Lys Leu Glu Glu
        515                 520                 525

Met Phe Glu Glu
    530
```

<210> SEQ ID NO 74
<211> LENGTH: 197
<212> TYPE: PRT
<213> ORGANISM: Homo sapiens

<400> SEQUENCE: 74

```
Gly Gly Ala Ala Glu Asp Thr Arg Arg Arg Ala Gly Asp Met Asp Arg
```

```
1               5                   10                  15

Gly Glu Gln Gly Leu Leu Arg Thr Asp Pro Val Pro Glu Glu Gly Glu
            20                  25                  30

Asp Val Ala Ala Thr Ile Ser Ala Thr Glu Thr Leu Ser Glu Glu Glu
        35                  40                  45

Gln Glu Glu Leu Arg Arg Glu Leu Ala Lys Val Glu Glu Glu Ile Gln
    50                  55                  60

Thr Leu Ser Gln Val Leu Ala Ala Lys Glu Lys His Leu Ala Glu Ile
65                  70                  75                  80

Lys Arg Lys Leu Gly Ile Asn Ser Leu Gln Glu Leu Lys Gln Asn Ile
                85                  90                  95

Ala Lys Gly Trp Gln Asp Val Thr Ala Thr Ser Ala Tyr Lys Lys Thr
            100                 105                 110

Ser Glu Thr Leu Ser Gln Ala Gly Gln Lys Ala Ser Ala Ala Phe Ser
        115                 120                 125

Ser Val Gly Ser Val Ile Thr Lys Lys Leu Glu Asp Val Lys Asn Ser
    130                 135                 140

Pro Thr Phe Lys Ser Phe Glu Glu Lys Val Glu Asn Leu Lys Ser Lys
145                 150                 155                 160

Val Gly Gly Thr Lys Pro Ala Gly Gly Asp Phe Gly Glu Val Leu Asn
                165                 170                 175

Ser Ala Ala Asn Ala Ser Ala Thr Thr Thr Glu Pro Leu Pro Glu Lys
            180                 185                 190

Thr Gln Glu Ser Leu
        195


<210> SEQ ID NO 75
<211> LENGTH: 299
<212> TYPE: PRT
<213> ORGANISM: Homo sapiens

<400> SEQUENCE: 75

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Lys Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Asp Ser Leu Gln Leu
145                 150                 155                 160

Val Phe Gly Ile Glu Leu Met Glu Val Asp Pro Ile Gly His Val Tyr
                165                 170                 175
```

-continued

```
Ile Phe Ala Thr Cys Leu Gly Leu Ser Tyr Asp Gly Leu Leu Gly Asp
            180                 185                 190

Asn Gln Ile Met Pro Lys Thr Gly Phe Leu Ile Ile Ile Leu Ala Ile
        195                 200                 205

Ile Ala Lys Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Phe Gly
225                 230                 235                 240

Asp Pro Lys Lys Leu Leu Thr Gln Tyr Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Ile Glu Thr Ser Tyr Val Lys Val Leu His
        275                 280                 285

His Met Val Lys Ile Ser Gly Gly Pro Arg Ile
    290                 295


<210> SEQ ID NO 76
<211> LENGTH: 401
<212> TYPE: PRT
<213> ORGANISM: Homo sapiens
<220> FEATURE:
<221> NAME/KEY: UNSURE
<222> LOCATION: (292)..(292)
<223> OTHER INFORMATION: X = any amino acid
<220> FEATURE:
<221> NAME/KEY: UNSURE
<222> LOCATION: (355)..(355)
<223> OTHER INFORMATION: X = any amino acid

<400> SEQUENCE: 76

Glu Ile Pro Met Asp Leu Thr Val Val Lys Gln Glu Ile Ile Asp Trp
1               5                   10                  15

Pro Gly Thr Glu Gly Arg Leu Ala Gly Gln Trp Val Glu Gln Glu Val
            20                  25                  30

Glu Asp Arg Pro Glu Val Lys Asp Glu Asn Ala Gly Val Leu Glu Val
        35                  40                  45

Lys Gln Glu Thr Asp Ser Ser Leu Val Val Lys Glu Ala Lys Val Gly
    50                  55                  60

Glu Pro Glu Val Lys Glu Glu Lys Val Lys Glu Glu Val Met Asp Trp
65                  70                  75                  80

Ser Glu Val Lys Glu Glu Lys Asp Asn Leu Glu Ile Lys Gln Glu Glu
                85                  90                  95

Lys Phe Val Gly Gln Cys Ile Lys Glu Glu Leu Met His Gly Glu Cys
            100                 105                 110

Val Lys Glu Glu Lys Asp Phe Leu Lys Lys Glu Ile Val Asp Asp Thr
        115                 120                 125

Lys Val Lys Glu Glu Pro Pro Ile Asn His Pro Val Gly Cys Lys Arg
    130                 135                 140

Lys Leu Ala Met Ser Arg Cys Glu Thr Cys Gly Thr Glu Glu Ala Lys
145                 150                 155                 160

Tyr Arg Cys Pro Arg Cys Met Arg Tyr Ser Cys Ser Leu Pro Cys Val
                165                 170                 175

Lys Lys His Lys Ala Glu Leu Thr Cys Asn Gly Val Arg Asp Lys Thr
            180                 185                 190

Ala Tyr Ile Ser Ile Gln Gln Phe Thr Glu Met Asn Leu Leu Ser Asp
        195                 200                 205
```

-continued

```
Tyr Arg Phe Leu Glu Asp Val Ala Arg Thr Ala Asp His Ile Ser Arg
    210                 215                 220

Asp Ala Phe Leu Lys Arg Pro Ile Ser Asn Lys Tyr Met Tyr Phe Met
225                 230                 235                 240

Lys Asn Arg Ala Arg Arg Gln Gly Ile Asn Leu Lys Leu Leu Pro Asn
                245                 250                 255

Gly Phe Thr Lys Arg Lys Glu Asn Ser Thr Phe Phe Asp Lys Lys Lys
            260                 265                 270

Gln Gln Phe Cys Trp His Val Lys Leu Gln Phe Pro Gln Ser Gln Ala
        275                 280                 285

Glu Tyr Ile Xaa Lys Lys Ser Pro Asp Asp Lys Thr Ile Asn Glu Ile
    290                 295                 300

Leu Lys Pro Tyr Ile Asp Pro Glu Lys Ser Asp Pro Val Ile Arg Gln
305                 310                 315                 320

Arg Leu Lys Ala Tyr Ile Arg Ser Gln Thr Gly Val Gln Ile Leu Met
                325                 330                 335

Lys Ile Glu Tyr Met Gln Gln Lys Phe Ser Lys Asp Ile Arg Leu Asp
            340                 345                 350

Pro Tyr Xaa Lys Ser Pro Arg Gln Phe Glu Asp Lys Met Ile Ile Glu
        355                 360                 365

Tyr Pro Thr Leu His Val Val Leu Lys Gly Ser Asn Asn Asp Met Lys
    370                 375                 380

Val Leu His Gln Val Lys Ser Glu Ser Thr Lys Asn Val Gly Asn Glu
385                 390                 395                 400

Asn


<210> SEQ ID NO 77
<211> LENGTH: 1069
<212> TYPE: PRT
<213> ORGANISM: Homo sapiens
<220> FEATURE:
<221> NAME/KEY: UNSURE
<222> LOCATION: (268)..(268)
<223> OTHER INFORMATION: X = any amino acid

<400> SEQUENCE: 77

Gln Leu Ser Ser Phe Ala Lys Gln Ala Leu Ser Gln Ala Gln Lys Ser
1               5                   10                  15

Ile Asp Arg Val Leu Asp Ile Gln Glu Glu Glu Pro Ser Ile Trp Ala
            20                  25                  30

Glu Thr Ile Pro Tyr Gly Glu Pro Gly Ile Ser Ser Pro Val Ser Gly
        35                  40                  45

Gly Trp Asp Thr Ser Thr Trp Gly Leu Lys Ser Asn Thr Glu Pro Gln
    50                  55                  60

Ser Pro Pro Ile Ala Ser Pro Lys Ala Ile Thr Lys Pro Val Arg Arg
65                  70                  75                  80

Thr Val Val Asp Glu Ser Glu Asn Phe Phe Ser Ala Phe Leu Ser Pro
                85                  90                  95

Thr Asp Val Gln Thr Ile Gln Lys Ser Pro Val Val Ser Lys Pro Pro
            100                 105                 110

Ala Lys Ser Gln Arg Pro Glu Glu Glu Val Lys Ser Ser Leu His Glu
        115                 120                 125

Ser Leu His Ile Gly Gln Ser Arg Thr Pro Glu Thr Thr Glu Ser Gln
    130                 135                 140

Val Lys Asp Ser Ser Leu Cys Val Ser Gly Glu Thr Leu Ala Ala Gly
145                 150                 155                 160
```

-continued

```
Thr Ser Ser Pro Lys Thr Glu Gly Lys His Glu Glu Thr Val Asn Lys
                165                 170                 175

Glu Ser Asp Met Lys Val Pro Thr Val Ser Leu Lys Val Ser Glu Ser
            180                 185                 190

Val Ile Asp Val Lys Thr Thr Met Glu Ser Ile Ser Asn Thr Ser Thr
        195                 200                 205

Gln Ser Leu Thr Ala Glu Thr Lys Asp Ile Ala Leu Glu Pro Lys Glu
    210                 215                 220

Gln Lys His Glu Asp Arg Gln Ser Asn Thr Pro Ser Pro Pro Val Ser
225                 230                 235                 240

Thr Phe Ser Ser Gly Thr Ser Thr Thr Ser Asp Ile Glu Val Leu Asp
                245                 250                 255

His Glu Ser Val Ile Ser Glu Ala Gln Arg Ala Arg Xaa Gln Glu Thr
            260                 265                 270

Thr Asp Ser Lys Ser Ser Leu His Leu Met Gln Thr Ser Phe Gln Leu
        275                 280                 285

Leu Ser Ala Ser Ala Cys Pro Glu Tyr Asn Arg Leu Asp Asp Phe Gln
    290                 295                 300

Lys Leu Thr Glu Ser Cys Cys Ser Ser Asp Ala Phe Glu Arg Ile Asp
305                 310                 315                 320

Ser Phe Ser Val Gln Ser Leu Asp Ser Arg Ser Val Ser Glu Ile Asn
                325                 330                 335

Ser Asp Asp Glu Leu Ser Gly Lys Gly Tyr Ala Leu Val Pro Ile Ile
            340                 345                 350

Val Asn Ser Ser Thr Pro Lys Ser Lys Thr Val Glu Ser Ala Glu Gly
        355                 360                 365

Lys Ser Glu Glu Val Asn Glu Thr Leu Val Ile Pro Thr Glu Glu Ala
    370                 375                 380

Glu Met Glu Glu Ser Gly Arg Ser Ala Thr Pro Val Asn Cys Glu Gln
385                 390                 395                 400

Pro Asp Ile Leu Val Ser Ser Thr Pro Ile Asn Glu Gly Gln Thr Val
                405                 410                 415

Leu Asp Lys Val Ala Glu Gln Cys Glu Pro Ala Glu Ser Gln Pro Glu
            420                 425                 430

Ala Leu Ser Glu Lys Glu Asp Val Cys Lys Thr Val Glu Phe Leu Asn
        435                 440                 445

Glu Lys Leu Glu Lys Arg Glu Ala Gln Leu Leu Ser Leu Ser Lys Glu
    450                 455                 460

Lys Ala Leu Leu Glu Glu Ala Phe Asp Asn Leu Lys Asp Glu Met Phe
465                 470                 475                 480

Arg Val Lys Glu Glu Ser Ser Ser Ile Ser Ser Leu Lys Asp Glu Phe
                485                 490                 495

Thr Gln Arg Ile Ala Glu Ala Glu Lys Lys Val Gln Leu Ala Cys Lys
            500                 505                 510

Glu Arg Asp Ala Ala Lys Lys Glu Ile Lys Asn Ile Lys Glu Glu Leu
        515                 520                 525

Ala Thr Arg Leu Asn Ser Ser Glu Thr Ala Asp Leu Leu Lys Glu Lys
    530                 535                 540

Asp Glu Gln Ile Arg Gly Leu Met Glu Glu Gly Glu Lys Leu Ser Lys
545                 550                 555                 560

Gln Gln Leu His Asn Ser Asn Ile Ile Lys Lys Leu Arg Ala Lys Asp
                565                 570                 575
```

-continued

```
Lys Glu Asn Glu Asn Met Val Ala Lys Leu Asn Lys Lys Val Lys Glu
            580                 585                 590

Leu Glu Glu Glu Leu Gln His Leu Lys Gln Val Leu Asp Gly Lys Glu
        595                 600                 605

Glu Val Glu Lys Gln His Arg Glu Asn Ile Lys Lys Leu Asn Ser Met
    610                 615                 620

Val Glu Arg Gln Glu Lys Asp Leu Gly Arg Leu Gln Val Asp Met Asp
625                 630                 635                 640

Glu Leu Glu Glu Lys Asn Arg Ser Ile Gln Ala Ala Leu Asp Ser Ala
                645                 650                 655

Tyr Lys Glu Leu Thr Asp Leu His Lys Ala Asn Ala Ala Lys Asp Ser
            660                 665                 670

Glu Ala Gln Glu Ala Ala Leu Ser Arg Glu Met Lys Ala Lys Glu Glu
        675                 680                 685

Leu Ser Ala Ala Leu Glu Lys Ala Gln Glu Glu Ala Arg Gln Gln Gln
    690                 695                 700

Glu Thr Leu Ala Ile Gln Val Gly Asp Leu Arg Leu Ala Leu Gln Arg
705                 710                 715                 720

Thr Glu Gln Ala Ala Ala Arg Lys Glu Asp Tyr Leu Arg His Glu Ile
                725                 730                 735

Gly Glu Leu Gln Gln Arg Leu Gln Glu Ala Glu Asn Arg Asn Gln Glu
            740                 745                 750

Leu Ser Gln Ser Val Ser Ser Thr Thr Arg Pro Leu Leu Arg Gln Ile
        755                 760                 765

Glu Asn Leu Gln Ala Thr Leu Gly Ser Gln Thr Ser Ser Trp Glu Lys
    770                 775                 780

Leu Glu Lys Asn Leu Ser Asp Arg Leu Gly Glu Ser Gln Thr Leu Leu
785                 790                 795                 800

Ala Ala Ala Val Glu Arg Glu Arg Ala Ala Thr Glu Glu Leu Leu Ala
                805                 810                 815

Asn Lys Ile Gln Met Ser Ser Met Glu Ser Gln Asn Ser Leu Leu Arg
            820                 825                 830

Gln Glu Asn Ser Arg Phe Gln Ala Gln Leu Glu Ser Glu Lys Asn Arg
        835                 840                 845

Leu Cys Lys Leu Glu Asp Glu Asn Asn Arg Tyr Gln Val Glu Leu Glu
    850                 855                 860

Asn Leu Lys Asp Glu Tyr Val Arg Thr Leu Glu Glu Thr Arg Lys Glu
865                 870                 875                 880

Lys Thr Leu Leu Asn Ser Gln Leu Glu Met Glu Arg Met Lys Val Glu
                885                 890                 895

Gln Glu Arg Lys Lys Ala Ile Phe Thr Gln Glu Thr Ile Lys Glu Lys
            900                 905                 910

Glu Arg Lys Pro Phe Ser Val Ser Ser Thr Pro Thr Met Ser Arg Ser
        915                 920                 925

Ser Ser Ile Ser Gly Val Asp Met Ala Gly Leu Gln Thr Ser Phe Leu
    930                 935                 940

Ser Gln Asp Glu Ser His Asp His Ser Phe Gly Pro Met Pro Ile Ser
945                 950                 955                 960

Ala Lys Trp Lys His Leu Tyr Ala Ala Cys Lys Asp Gly Ser Arg Ile
                965                 970                 975

Lys His Ile Glu Asn Leu Gln Ser Gln Leu Lys Leu Arg Glu Gly Glu
            980                 985                 990

Ile Thr His Leu Gln Leu Glu Ile  Gly Asn Leu Glu Lys  Thr Arg Ser
```

-continued

```
        995                 1000                1005

Ile Met  Ala Glu Glu Leu Val  Lys Leu Thr Asn Gln  Asn Asp Glu
    1010                1015                1020

Leu Glu  Glu Lys Val Lys Glu  Ile Pro Lys Leu Arg  Thr Gln Leu
    1025                1030                1035

Arg Asp  Leu Asp Gln Arg Tyr  Asn Thr Ile Leu Gln  Met Tyr Gly
    1040                1045                1050

Glu Lys  Ala Glu Glu Ala Glu  Glu Leu Arg Leu Asp  Leu Glu Asp
    1055                1060                1065

Val


<210> SEQ ID NO 78
<211> LENGTH: 353
<212> TYPE: PRT
<213> ORGANISM: Homo sapiens

<400> SEQUENCE: 78

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Gly Thr Ser Ser Ser
65                  70                  75                  80

Tyr Thr Gly Gly Pro Cys Thr Ser Pro Leu Leu Ala Pro Val Ile Phe
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
```

```
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala


<210> SEQ ID NO 79
<211> LENGTH: 544
<212> TYPE: PRT
<213> ORGANISM: Homo sapiens
<220> FEATURE:
<221> NAME/KEY: UNSURE
<222> LOCATION: (429)..(429)
<223> OTHER INFORMATION: X = any amino acid
<220> FEATURE:
<221> NAME/KEY: UNSURE
<222> LOCATION: (464)..(464)
<223> OTHER INFORMATION: X = any amino acid

<400> SEQUENCE: 79

Val Ser Glu Lys Phe Ile Val Glu Gly Leu Arg Asp Leu Glu Leu Phe
1               5                   10                  15

Gly Glu Gln Pro Pro Gly Asp Thr Arg Arg Lys Thr Asn Asp Ala Ser
            20                  25                  30

Ser Glu Ser Ile Ala Ser Phe Ser Lys Gln Glu Val Met Ser Ser Phe
        35                  40                  45

Leu Pro Glu Gly Gly Cys Tyr Glu Leu Leu Thr Val Ile Gly Lys Gly
    50                  55                  60

Phe Glu Asp Leu Met Thr Val Asn Leu Ala Arg Tyr Lys Pro Thr Gly
65                  70                  75                  80

Glu Tyr Val Thr Val Arg Arg Ile Asn Leu Glu Ala Cys Ser Asn Glu
                85                  90                  95

Met Val Thr Phe Leu Gln Gly Glu Leu His Val Ser Lys Leu Phe Asn
            100                 105                 110

His Pro Asn Ile Val Pro Tyr Arg Ala Thr Phe Ile Ala Asp Asn Glu
        115                 120                 125

Leu Trp Val Val Thr Ser Phe Met Ala Tyr Gly Ser Ala Lys Asp Leu
    130                 135                 140

Ile Cys Thr His Phe Met Asp Gly Met Asn Glu Leu Ala Ile Ala Tyr
145                 150                 155                 160

Ile Leu Gln Gly Val Leu Lys Ala Leu Asp Tyr Ile His His Met Gly
                165                 170                 175

Tyr Val His Arg Ser Val Lys Ala Ser His Ile Leu Ile Ser Val Asp
            180                 185                 190

Gly Lys Val Tyr Leu Ser Gly Leu Arg Ser Asn Leu Ser Met Ile Ser
        195                 200                 205

His Gly Gln Arg Gln Arg Val Val His Asp Phe Pro Lys Tyr Ser Val
    210                 215                 220

Lys Val Leu Pro Trp Leu Ser Pro Glu Val Leu Gln Gln Asn Leu Gln
225                 230                 235                 240

Gly Tyr Asp Ala Lys Ser Asp Ile Tyr Ser Val Gly Ile Thr Ala Cys
                245                 250                 255

Glu Leu Ala Asn Gly His Val Pro Phe Lys Asp Met Pro Ala Thr Gln
            260                 265                 270
```

```
Met Leu Leu Glu Lys Leu Asn Gly Thr Val Pro Cys Leu Leu Asp Thr
        275                 280                 285

Ser Thr Ile Pro Ala Glu Glu Leu Thr Met Ser Pro Ser Arg Ser Val
    290                 295                 300

Ala Asn Ser Gly Leu Ser Asp Ser Leu Thr Thr Ser Thr Pro Arg Pro
305                 310                 315                 320

Ser Asn Gly Asp Trp Pro Ser His Pro Tyr His Arg Thr Phe Ser Pro
                325                 330                 335

His Phe His His Phe Val Glu Gln Cys Leu Gln Arg Asn Pro Asp Ala
            340                 345                 350

Arg Pro Ser Ala Ser Thr Leu Leu Asn His Ser Phe Phe Lys Gln Ile
        355                 360                 365

Lys Arg Arg Ala Ser Lys Ala Leu Pro Glu Leu Leu Arg Pro Val Thr
    370                 375                 380

Pro Ile Thr Asn Phe Glu Gly Ser Gln Ser Gln Asp His Ser Gly Ile
385                 390                 395                 400

Phe Gly Leu Val Thr Asn Leu Glu Glu Leu Glu Val Asp Asp Trp Glu
                405                 410                 415

Phe Glu Pro Leu Gln Thr Val Arg Ile Leu Gln Pro Xaa Asp Ala Glu
            420                 425                 430

Ala Thr Gln Arg Pro Phe Leu Arg Ala Gly His Ile Pro Ala Leu Leu
        435                 440                 445

Gly Arg Leu Gly Arg Lys Asp Ile Leu Pro Gly Lys Leu Thr Ala Xaa
    450                 455                 460

Leu Ile Gly Lys Glu Asn Pro Gly Glu Ile Leu His Cys Ser Lys Ala
465                 470                 475                 480

Phe Glu Thr Gln Gly Asn Leu Asn Asn Gln Gly Ser Gly Gly Ser Lys
                485                 490                 495

Ala Asp Ile Pro Ser Pro Val Ser Ser Gly Asp Leu Leu Arg Arg Arg
            500                 505                 510

Glu Met Leu Leu Trp Pro Trp Glu Leu Asn Ser Lys Pro Arg Val Trp
        515                 520                 525

Leu Leu Lys Pro Glu Asp Arg His Leu Phe Pro Val Leu Ala Thr Ser
    530                 535                 540


<210> SEQ ID NO 80
<211> LENGTH: 604
<212> TYPE: PRT
<213> ORGANISM: Homo sapiens

<400> SEQUENCE: 80

Met Ser Asp Thr Ser Glu Ser Gly Ala Gly Leu Thr Arg Phe Gln Ala
1               5                   10                  15

Glu Ala Ser Glu Lys Asp Ser Ser Ser Met Met Gln Thr Leu Leu Thr
            20                  25                  30

Val Thr Gln Asn Val Glu Val Pro Glu Thr Pro Lys Ala Ser Lys Ala
        35                  40                  45

Leu Glu Val Ser Glu Asp Val Lys Val Ser Lys Ala Ser Gly Val Ser
    50                  55                  60

Lys Ala Thr Glu Val Ser Lys Thr Pro Glu Ala Arg Glu Ala Pro Ala
65                  70                  75                  80

Thr Gln Ala Ser Ser Thr Thr Gln Leu Thr Asp Thr Gln Val Leu Ala
                85                  90                  95

Ala Glu Asn Lys Ser Leu Ala Ala Asp Thr Lys Lys Gln Asn Ala Asp
```

-continued

```
            100                 105                 110

Pro Gln Ala Val Thr Met Pro Ala Thr Glu Thr Lys Lys Val Ser His
        115                 120                 125

Val Ala Asp Thr Lys Val Asn Thr Lys Ala Gln Glu Thr Glu Ala Ala
    130                 135                 140

Pro Ser Gln Ala Pro Ala Asp Glu Pro Glu Pro Glu Ser Ala Ala Ala
145                 150                 155                 160

Gln Ser Gln Glu Asn Gln Asp Thr Arg Pro Lys Val Lys Ala Lys Lys
                165                 170                 175

Ala Arg Lys Val Lys His Leu Asp Gly Glu Glu Asp Gly Ser Ser Asp
            180                 185                 190

Gln Ser Gln Ala Ser Gly Thr Thr Gly Gly Arg Arg Val Leu Lys Gly
        195                 200                 205

Ser Asn Gly Leu Asn Gly Pro Gln Gly Phe Lys Gly Ser His Ser Leu
    210                 215                 220

Leu Gly Pro Gln Gly Ile Lys Asp Ser Val Gly Cys Leu Gly Pro Glu
225                 230                 235                 240

Ser Leu Ala Leu Pro Glu Ile Pro Lys Ala Arg Arg Gly Lys Ala Arg
                245                 250                 255

Arg Arg Ala Ala Lys Leu Gln Ser Ser Gln Glu Pro Glu Ala Pro Pro
            260                 265                 270

Pro Arg Asp Val Ala Leu Leu Gln Gly Arg Ala Asn Asp Leu Val Lys
        275                 280                 285

Tyr Leu Leu Ala Lys Asp Gln Thr Lys Ile Pro Ile Lys Arg Ser Asp
    290                 295                 300

Met Leu Lys Asp Ile Ile Lys Glu Tyr Thr Asp Val Tyr Pro Glu Ile
305                 310                 315                 320

Ile Glu Arg Ala Gly Tyr Ser Leu Glu Lys Val Phe Gly Ile Gln Leu
                325                 330                 335

Lys Glu Ile Asp Lys Asn Asp His Leu Tyr Ile Leu Leu Ser Thr Leu
            340                 345                 350

Glu Pro Thr Asp Ala Gly Ile Leu Gly Thr Thr Lys Asp Ser Pro Lys
        355                 360                 365

Leu Gly Leu Leu Met Val Leu Leu Ser Ile Ile Phe Met Asn Gly Asn
    370                 375                 380

Arg Ser Ser Glu Ala Val Ile Trp Glu Val Leu Arg Lys Leu Gly Leu
385                 390                 395                 400

Arg Pro Gly Ile His His Ser Leu Phe Gly Asp Val Lys Lys Leu Ile
                405                 410                 415

Thr Asp Glu Phe Val Lys Gln Lys Tyr Leu Asp Tyr Ala Arg Val Pro
            420                 425                 430

Asn Ser Asn Pro Pro Glu Tyr Glu Phe Phe Trp Gly Leu Arg Ser Tyr
        435                 440                 445

Tyr Glu Thr Ser Lys Met Lys Val Leu Lys Phe Ala Cys Lys Val Gln
    450                 455                 460

Lys Lys Asp Pro Lys Glu Trp Ala Ala Gln Tyr Arg Glu Ala Met Glu
465                 470                 475                 480

Ala Asp Leu Lys Ala Ala Ala Glu Ala Ala Ala Glu Ala Lys Ala Arg
                485                 490                 495

Ala Glu Ile Arg Ala Arg Met Gly Ile Gly Leu Gly Ser Glu Asn Ala
            500                 505                 510

Ala Gly Pro Cys Asn Trp Asp Glu Ala Asp Ile Gly Pro Trp Ala Lys
        515                 520                 525
```

-continued

```
Ala Arg Ile Gln Ala Gly Ala Glu Ala Lys Ala Lys Ala Gln Glu Ser
    530                 535                 540

Gly Ser Ala Ser Thr Gly Ala Ser Thr Ser Thr Asn Asn Ser Ala Ser
545                 550                 555                 560

Ala Ser Thr Ser Gly Gly Phe Ser Ala Gly Ala Ser Leu Thr Ala Thr
                565                 570                 575

Leu Thr Phe Gly Leu Phe Ala Gly Leu Gly Gly Ala Gly Ala Ser Thr
            580                 585                 590

Ser Gly Ser Ser Gly Ala Cys Gly Phe Ser Tyr Lys
        595                 600
```

<210> SEQ ID NO 81
<211> LENGTH: 4775
<212> TYPE: DNA
<213> ORGANISM: Homo sapiens

<400> SEQUENCE: 81

```
cagtcgcgcg cggtgcagtc gggaggtgga ggcaccggct gcattgtttt cgggatcgag     60

gggtgagggc gctatggcac ccggctgcaa aactgagtta cgcagcgtga caaatggtca    120

gtctaaccaa ccaagtaatg aaggtgatgc catcaaagtt tttgtgcgaa ttcgtcctcc    180

tgcagaaaga tctgggtcag ctgatggaga gcagaactta tgcttatctg tgctgtcctc    240

cacgagtctc cggctgcact ccaaccctga gcccaagacc ttcacgtttg atcatgttgc    300

agatgtggat accactcagg aatctgtatt tgcaactgtg gctaaaagca ttgtggagtc    360

ttgcatgagc ggttataatg gtaccatctt tgcatatgga cagactggct cagggaagac    420

atttactatg atgggaccat ctgaatctga taatttttct cataacctga gaggagtaat    480

cccacgaagt tttgaatatt tgttttcctt aattgatcgt gaaaaagaaa aggctggagc    540

tggaaagagt ttcctttgta agtgttcctt tattgaaatc tacaacgagc agatatatga    600

tctactggac tctgcatcgg ctggactgta cttaagggag catatcaaga agggagtctt    660

tgttgttggt gcggtggagc aggtggtaac ctcagctgct gaagcctatc aggtgctgtc    720

tggaggatgg aggaatagac gtgtggcatc aacatcaatg aacagagaat cgtctaggtc    780

tcatgccgtc tttacaatta caatagagtc aatggagaaa agtaatgaga ttgtgaatat    840

acggacctcc ctactcaacc tggtggattt agcaggatct gaaaggcaaa aagataccca    900

tgcagaaggg atgagattga aggaagcagg taacataaat cgatcattga gctgcctggg    960

ccaagtgatt acagcacttg tcgacgtggg taatggaaaa cagagacatg tttgctacag   1020

agactccaaa cttaccttct tactacggga ttcccttgga ggtaatgcca aaacagccat   1080

aattgcaaat gttcatcctg gatccaggtg ttttggggaa accctatcaa cacttaactt   1140

tgctcaaaga gccaagctga ttaaaaacaa ggcagtagta aatgaagaca cccaaggaaa   1200

tgtgagccag ctccaagctg aagtgaagag gctcaaagaa caactggcgg agcttgcttc   1260

aggacagaca ccaccagaaa gcttcctgac cagagacaaa aagaagacta actatatgga   1320

gtatttccag gaagcaatgt tattctttaa gaaatctgaa caggaaaaga agtctctgat   1380

agaaaaagtt acccaattag aagacctcac cctcaaaaag gaaaaattta ttcaatctaa   1440

taaaatgatt gtgaaattcc gagaggatca aataatacgc ttggaaaagc tccacaagga   1500

atcccgggga ggttttctgc ctgaggagca ggatcgtttg ctctcagaat taaggaatga   1560

gattcaaact ctgcgagaac aaatagagca ccacccccaga gttgcaaagt atgctatgga   1620

aaatcattcc ctcagggagg agaatagaag actgagatta ttagagcctg tgaaaagagc   1680
```

-continued

```
tcaagaaatg gatgcccaga ccattgcaaa actagaaaaa gctttctctg aaataagtgg   1740
catggagaaa agtgacaaaa atcagcaagg attttcacct aaagctcaga aagagccatg   1800
tttgtttgca aacactgaga agttaaaagc acaactcctg caaattcaga cagagctgaa   1860
taattcaaag caagaatatg aagaattcaa agaacttact aggaaaaggc agctagaatt   1920
ggaatcagag cttcagtctt tgcaaaaagc gaaccttaat cttgaaaacc ttttggaagc   1980
aacaaaagcc tgcaagcggc aagaagtttc tcagctgaat aaaattcatg ctgaaacact   2040
taagattata actacaccaa ccaaggccta ccaacttcat tcccgaccag taccaaaatt   2100
aagccctgaa atgggaagct ttggctctct atacactcag aattctagca tattagataa   2160
tgatatatta aatgagccag ttcctcctga gatgaatgaa caagcttttg aggccatttc   2220
tgaagagctt agaacagtgc aggaacaaat gagtgctctt caagccaaac tggatgaaga   2280
agagcataaa aacctaaagc ttcagcagca tgttgacaaa ctggaacatc attctaccca   2340
aatgcaggag cttttctcat cagaaagaat tgattggacc aaacagcagg aagagcttct   2400
ctcacagttg aatgtccttg aaaagcagct tcaagagact caaactaaaa atgacttttt   2460
gaaaagtgag gtacatgacc tgcgagtagt ccttcattct gctgacaagg agctttcttc   2520
agtgaaattg gaatatagtt cattcaaaac gaatcaggag aaagaattca acaaactttc   2580
tgaaagacac atgcatgtac agcttcaatt agataatctc aggttagaaa acgaaaagct   2640
gcttgagagc aaagcctgcc tacaggattc ctatgacaac ttacaagaaa taatgaaatt   2700
tgagattgac caactttcaa gaaacctcca aaacttcaaa aaagaaaatg aaactctgaa   2760
atctgatctg aataatttga tggagcttct tgaggcagaa aaagaacgca ataacaaatt   2820
atcattacag tttgaagaag ataaagaaaa cagttctaaa gaaatcttaa aagttcttga   2880
ggctgtacgt caggagaaac agaaagagac ggccaagtgt gagcagcaga tggcaaaagt   2940
acagaaacta gaagagagct tgcttgctac tgaaaaagtg atcagttccc tggaaaagtc   3000
tagagattct gataagaaag ttgtagctga cctcatgaac cagatccagg agctaagaac   3060
atcggtctgt gagaaaacag aaactataga caccctgaaa caagaactga aggacataaa   3120
ttgcaaatac aactctgctt tggttgacag agaagagagc agagtgttga tcaagaagca   3180
ggaagtggat attctggatc tgaaagaaac ccttaggctg agaatacttt ctgaggacat   3240
agagagggat atgctctgtg aggacctggc tcatgccact gagcagctga acatgctcac   3300
agaggcctca aaaaaacact cggggctgct gcagtctgcc caggaagaac tgaccaagaa   3360
ggaagccctg attcaggaac ttcagcacaa gctaaaccaa aagaaagagg aagtagaaca   3420
gaagaagaat gaatataact tcaaaatgag gcaactagaa catgtgatgg attctgctgc   3480
tgaggatccc cagagtccta agacaccacc tcactttcaa acacatttgg caaaactcct   3540
ggaaacacaa gaacaagaga tagaagatgg aagagcctct aagacttctt tggaacacct   3600
tgtaacaaag ctaaatgaag acagagaagt caaaaatgct gaaatcctca gaatgaagga   3660
gcagttgcgt gaaatggaaa acctacgcct ggaaagtcag cagttaatag agaaaaactg   3720
gctcctgcaa ggtcagctgg atgatattaa aagacaaaag gaaaacagtg atcagaatca   3780
tccagataat caacagctga agaatgaaca agaagaaagt atcaaagaaa gacttgcaaa   3840
aagtaaaata gttgaagaaa tgctgaaaat gaaagcagac ctagaagaag tccaaagtgc   3900
cctttacaac aaagagatgg aatgccttag aatgactgat gaagtcgaac gaacccaaac   3960
tttggagtct aaagcattcc aggaaaaaga acaactgaga tcaaagctgg aagaaatgta   4020
```

-continued

```
tgaagaaaga gagagaacat cccaggagat ggaaatgtta aggaagcagg tggagtgtct   4080

tgctgaggaa aatggaaagt tggtaggtca ccaaaatttg catcagaaga ttcagtacgt   4140

agtgcgacta aagaaggaaa atgtcaggct tgctgaggag acagaaaagt tgcgtgccga   4200

aaatgtattt ttaaaagaaa agaaaagaag tgaatcttga ggattccggt cagctaccta   4260

ggcatcacct tgtttgaaga tgtttcttct cttttacaag taagacctac tcctggccac   4320

ttaggagagc tgaatttatg gaccttaatt attaaatgtt tataaggtgg tggtaaccac   4380

ctcaagtttc tgatgaacat tctgcatcca tatacaccct gtgacagtca gcagtctgct   4440

attaagtggc ctacttcaag gctttgaatc aacttaaggg aaaacctttt gtctttgtaa   4500

aaataaaagc ctgtagctaa ggtttacagt ggacattagc cagatcattt tcttcttaga   4560

ttatgccata atctcctttg attcttatgg aagttctaac aatatatggt ggttccaaca   4620

cctgcagtga gtttaatgac tgacttagta gcaggtacaa gaagcaaact tgttaatata   4680

gattattttt gtattcttac tttaggtatt ttacttgagc attttccatg actgtaaata   4740

aagccatttt ttaagataaa aaaaaaaaaa aaaaa                              4775
```

<210> SEQ ID NO 82
<211> LENGTH: 1388
<212> TYPE: PRT
<213> ORGANISM: Homo sapiens

<400> SEQUENCE: 82

```
Met Ala Pro Gly Cys Lys Thr Glu Leu Arg Ser Val Thr Asn Gly Gln
1               5                   10                  15

Ser Asn Gln Pro Ser Asn Glu Gly Asp Ala Ile Lys Val Phe Val Arg
            20                  25                  30

Ile Arg Pro Pro Ala Glu Arg Ser Gly Ser Ala Asp Gly Glu Gln Asn
        35                  40                  45

Leu Cys Leu Ser Val Leu Ser Ser Thr Ser Leu Arg Leu His Ser Asn
    50                  55                  60

Pro Glu Pro Lys Thr Phe Thr Phe Asp His Val Ala Asp Val Asp Thr
65                  70                  75                  80

Thr Gln Glu Ser Val Phe Ala Thr Val Ala Lys Ser Ile Val Glu Ser
                85                  90                  95

Cys Met Ser Gly Tyr Asn Gly Thr Ile Phe Ala Tyr Gly Gln Thr Gly
            100                 105                 110

Ser Gly Lys Thr Phe Thr Met Met Gly Pro Ser Glu Ser Asp Asn Phe
        115                 120                 125

Ser His Asn Leu Arg Gly Val Ile Pro Arg Ser Phe Glu Tyr Leu Phe
    130                 135                 140

Ser Leu Ile Asp Arg Glu Lys Glu Lys Ala Gly Ala Gly Lys Ser Phe
145                 150                 155                 160

Leu Cys Lys Cys Ser Phe Ile Glu Ile Tyr Asn Glu Gln Ile Tyr Asp
                165                 170                 175

Leu Leu Asp Ser Ala Ser Ala Gly Leu Tyr Leu Arg Glu His Ile Lys
            180                 185                 190

Lys Gly Val Phe Val Val Gly Ala Val Glu Gln Val Val Thr Ser Ala
        195                 200                 205

Ala Glu Ala Tyr Gln Val Leu Ser Gly Gly Trp Arg Asn Arg Arg Val
    210                 215                 220

Ala Ser Thr Ser Met Asn Arg Glu Ser Ser Arg Ser His Ala Val Phe
225                 230                 235                 240
```

-continued

```
Thr Ile Thr Ile Glu Ser Met Glu Lys Ser Asn Glu Ile Val Asn Ile
                245                 250                 255

Arg Thr Ser Leu Leu Asn Leu Val Asp Leu Ala Gly Ser Glu Arg Gln
            260                 265                 270

Lys Asp Thr His Ala Glu Gly Met Arg Leu Lys Glu Ala Gly Asn Ile
        275                 280                 285

Asn Arg Ser Leu Ser Cys Leu Gly Gln Val Ile Thr Ala Leu Val Asp
    290                 295                 300

Val Gly Asn Gly Lys Gln Arg His Val Cys Tyr Arg Asp Ser Lys Leu
305                 310                 315                 320

Thr Phe Leu Leu Arg Asp Ser Leu Gly Gly Asn Ala Lys Thr Ala Ile
                325                 330                 335

Ile Ala Asn Val His Pro Gly Ser Arg Cys Phe Gly Glu Thr Leu Ser
            340                 345                 350

Thr Leu Asn Phe Ala Gln Arg Ala Lys Leu Ile Lys Asn Lys Ala Val
        355                 360                 365

Val Asn Glu Asp Thr Gln Gly Asn Val Ser Gln Leu Gln Ala Glu Val
    370                 375                 380

Lys Arg Leu Lys Glu Gln Leu Ala Glu Leu Ala Ser Gly Gln Thr Pro
385                 390                 395                 400

Pro Glu Ser Phe Leu Thr Arg Asp Lys Lys Lys Thr Asn Tyr Met Glu
                405                 410                 415

Tyr Phe Gln Glu Ala Met Leu Phe Phe Lys Lys Ser Glu Gln Glu Lys
            420                 425                 430

Lys Ser Leu Ile Glu Lys Val Thr Gln Leu Glu Asp Leu Thr Leu Lys
        435                 440                 445

Lys Glu Lys Phe Ile Gln Ser Asn Lys Met Ile Val Lys Phe Arg Glu
    450                 455                 460

Asp Gln Ile Ile Arg Leu Glu Lys Leu His Lys Glu Ser Arg Gly Gly
465                 470                 475                 480

Phe Leu Pro Glu Glu Gln Asp Arg Leu Leu Ser Glu Leu Arg Asn Glu
                485                 490                 495

Ile Gln Thr Leu Arg Glu Gln Ile Glu His His Pro Arg Val Ala Lys
            500                 505                 510

Tyr Ala Met Glu Asn His Ser Leu Arg Glu Glu Asn Arg Arg Leu Arg
        515                 520                 525

Leu Leu Glu Pro Val Lys Arg Ala Gln Glu Met Asp Ala Gln Thr Ile
    530                 535                 540

Ala Lys Leu Glu Lys Ala Phe Ser Glu Ile Ser Gly Met Glu Lys Ser
545                 550                 555                 560

Asp Lys Asn Gln Gln Gly Phe Ser Pro Lys Ala Gln Lys Glu Pro Cys
                565                 570                 575

Leu Phe Ala Asn Thr Glu Lys Leu Lys Ala Gln Leu Leu Gln Ile Gln
            580                 585                 590

Thr Glu Leu Asn Asn Ser Lys Gln Glu Tyr Glu Glu Phe Lys Glu Leu
        595                 600                 605

Thr Arg Lys Arg Gln Leu Glu Leu Glu Ser Glu Leu Gln Ser Leu Gln
    610                 615                 620

Lys Ala Asn Leu Asn Leu Glu Asn Leu Leu Glu Ala Thr Lys Ala Cys
625                 630                 635                 640

Lys Arg Gln Glu Val Ser Gln Leu Asn Lys Ile His Ala Glu Thr Leu
                645                 650                 655

Lys Ile Ile Thr Thr Pro Thr Lys Ala Tyr Gln Leu His Ser Arg Pro
```

-continued

```
            660                 665                 670

Val Pro Lys Leu Ser Pro Glu Met Gly Ser Phe Gly Ser Leu Tyr Thr
        675                 680                 685

Gln Asn Ser Ser Ile Leu Asp Asn Asp Ile Leu Asn Glu Pro Val Pro
    690                 695                 700

Pro Glu Met Asn Glu Gln Ala Phe Glu Ala Ile Ser Glu Glu Leu Arg
705                 710                 715                 720

Thr Val Gln Glu Gln Met Ser Ala Leu Gln Ala Lys Leu Asp Glu Glu
                725                 730                 735

Glu His Lys Asn Leu Lys Leu Gln Gln His Val Asp Lys Leu Glu His
            740                 745                 750

His Ser Thr Gln Met Gln Glu Leu Phe Ser Ser Glu Arg Ile Asp Trp
        755                 760                 765

Thr Lys Gln Gln Glu Glu Leu Leu Ser Gln Leu Asn Val Leu Glu Lys
    770                 775                 780

Gln Leu Gln Glu Thr Gln Thr Lys Asn Asp Phe Leu Lys Ser Glu Val
785                 790                 795                 800

His Asp Leu Arg Val Val Leu His Ser Ala Asp Lys Glu Leu Ser Ser
                805                 810                 815

Val Lys Leu Glu Tyr Ser Ser Phe Lys Thr Asn Gln Glu Lys Glu Phe
            820                 825                 830

Asn Lys Leu Ser Glu Arg His Met His Val Gln Leu Gln Leu Asp Asn
        835                 840                 845

Leu Arg Leu Glu Asn Glu Lys Leu Leu Glu Ser Lys Ala Cys Leu Gln
    850                 855                 860

Asp Ser Tyr Asp Asn Leu Gln Glu Ile Met Lys Phe Glu Ile Asp Gln
865                 870                 875                 880

Leu Ser Arg Asn Leu Gln Asn Phe Lys Lys Glu Asn Glu Thr Leu Lys
                885                 890                 895

Ser Asp Leu Asn Asn Leu Met Glu Leu Leu Glu Ala Glu Lys Glu Arg
            900                 905                 910

Asn Asn Lys Leu Ser Leu Gln Phe Glu Glu Asp Lys Glu Asn Ser Ser
        915                 920                 925

Lys Glu Ile Leu Lys Val Leu Glu Ala Val Arg Gln Glu Lys Gln Lys
    930                 935                 940

Glu Thr Ala Lys Cys Glu Gln Gln Met Ala Lys Val Gln Lys Leu Glu
945                 950                 955                 960

Glu Ser Leu Leu Ala Thr Glu Lys Val Ile Ser Ser Leu Glu Lys Ser
                965                 970                 975

Arg Asp Ser Asp Lys Lys Val Val Ala Asp Leu Met Asn Gln Ile Gln
            980                 985                 990

Glu Leu Arg Thr Ser Val Cys Glu  Lys Thr Glu Thr Ile  Asp Thr Leu
        995                 1000                1005

Lys Gln  Glu Leu Lys Asp Ile  Asn Cys Lys Tyr Asn  Ser Ala Leu
    1010                1015                1020

Val Asp  Arg Glu Glu Ser Arg  Val Leu Ile Lys Lys  Gln Glu Val
    1025                1030                1035

Asp Ile  Leu Asp Leu Lys Glu  Thr Leu Arg Leu Arg  Ile Leu Ser
    1040                1045                1050

Glu Asp  Ile Glu Arg Asp Met  Leu Cys Glu Asp Leu  Ala His Ala
    1055                1060                1065

Thr Glu  Gln Leu Asn Met Leu  Thr Glu Ala Ser Lys  Lys His Ser
    1070                1075                1080
```

```
Gly Leu  Leu Gln Ser Ala Gln  Glu Glu Leu Thr Lys  Lys Glu Ala
    1085                 1090                 1095

Leu Ile  Gln Glu Leu Gln His  Lys Leu Asn Gln Lys  Lys Glu Glu
    1100                 1105                 1110

Val Glu  Gln Lys Lys Asn Glu  Tyr Asn Phe Lys Met  Arg Gln Leu
    1115                 1120                 1125

Glu His  Val Met Asp Ser Ala  Ala Glu Asp Pro Gln  Ser Pro Lys
    1130                 1135                 1140

Thr Pro  Pro His Phe Gln Thr  His Leu Ala Lys Leu  Leu Glu Thr
    1145                 1150                 1155

Gln Glu  Gln Glu Ile Glu Asp  Gly Arg Ala Ser Lys  Thr Ser Leu
    1160                 1165                 1170

Glu His  Leu Val Thr Lys Leu  Asn Glu Asp Arg Glu  Val Lys Asn
    1175                 1180                 1185

Ala Glu  Ile Leu Arg Met Lys  Glu Gln Leu Arg Glu  Met Glu Asn
    1190                 1195                 1200

Leu Arg  Leu Glu Ser Gln Gln  Leu Ile Glu Lys Asn  Trp Leu Leu
    1205                 1210                 1215

Gln Gly  Gln Leu Asp Asp Ile  Lys Arg Gln Lys Glu  Asn Ser Asp
    1220                 1225                 1230

Gln Asn  His Pro Asp Asn Gln  Gln Leu Lys Asn Glu  Gln Glu Glu
    1235                 1240                 1245

Ser Ile  Lys Glu Arg Leu Ala  Lys Ser Lys Ile Val  Glu Glu Met
    1250                 1255                 1260

Leu Lys  Met Lys Ala Asp Leu  Glu Glu Val Gln Ser  Ala Leu Tyr
    1265                 1270                 1275

Asn Lys  Glu Met Glu Cys Leu  Arg Met Thr Asp Glu  Val Glu Arg
    1280                 1285                 1290

Thr Gln  Thr Leu Glu Ser Lys  Ala Phe Gln Glu Lys  Glu Gln Leu
    1295                 1300                 1305

Arg Ser  Lys Leu Glu Glu Met  Tyr Glu Glu Arg Glu  Arg Thr Ser
    1310                 1315                 1320

Gln Glu  Met Glu Met Leu Arg  Lys Gln Val Glu Cys  Leu Ala Glu
    1325                 1330                 1335

Glu Asn  Gly Lys Leu Val Gly  His Gln Asn Leu His  Gln Lys Ile
    1340                 1345                 1350

Gln Tyr  Val Val Arg Leu Lys  Lys Glu Asn Val Arg  Leu Ala Glu
    1355                 1360                 1365

Glu Thr  Glu Lys Leu Arg Ala  Glu Asn Val Phe Leu  Lys Glu Lys
    1370                 1375                 1380

Lys Arg  Ser Glu Ser
    1385
```

BREAST CANCER ANTIGENS

RELATED APPLICATIONS

This application claims priority under 35 U.S.C. § 119 from U.S. provisional application Ser. No. 60/291,150, filed May 15, 2001.

FIELD OF THE INVENTION

The invention relates to use of novel breast cancer-associated nucleic acid molecules and the polypeptides they encode as markers for cancer, including breast cancer. The invention also relates to the use of a panel of breast cancer-associated nucleic acid molecules and the polypeptides they encode and their use as markers for breast cancer. In addition, the invention relates to the use of such nucleic acid molecules and the polypeptides they encode for diagnosing breast cancer, and monitoring the breast cancer's response to treatment.

BACKGROUND OF THE INVENTION

Breast cancer is a malignant proliferation of epithelial cells lining the ducts or lobules of the breast (Harrison's Principles of Internal Medicine, 14/e, McGraw-Hill Companies, New York, 1998). Although much progress has been made toward understanding the biological basis of breast cancer and in its diagnosis and treatment, it is still one of the leading causes of death among women in the United States. Inherent difficulties in the diagnosis and treatment of cancer include among other things, the existence of many different subgroups of cancer and the concomitant variation in appropriate treatment strategies to maximize the likelihood of positive patient outcome.

The traditional method of breast cancer diagnosis and staging is through the use of biopsy examination, for example, histological examination of a tissue sample. Once a diagnosis is made, the treatment options traditionally include surgical intervention, chemotherapy, radiotherapy, and adjuvant systemic therapies. Surgical therapy may be lumpectomy or more extensive mastectomy. Adjuvants may include but are not limited to chemotherapy, radiotherapy, and endocrine therapies such as castration; administration of LHRH agonists, antiestrogens, such as tamoxifen, high-dose progestogens; adrenalectomy; and/or aromatase inhibitors (Harrison's Principles of Internal Medicine, 14/e, McGraw Hill Companies, New York, 1998).

An accurate diagnostic test for breast cancer is critical to allow patients to receive appropriate cancer treatment when such treatment may be less invasive (e.g. the cancer is smaller) and has a high likelihood of successfully eliminating the cancer. Currently available tests are useful, but may require expensive procedures, such as mammography, followed by surgical biopsy. A less invasive and less expensive diagnostic test for breast cancer would allow better access to diagnostic services for more women, and may increase the likelihood of successful outcome for breast cancer patients.

Another element of key importance in the successful treatment of breast cancer is the selection and implementation of an appropriate combination of therapeutic approaches. For example, depending on a breast cancer patient's prognosis, therapy may include surgical intervention in combination with adjuvant therapy or it may only include surgical intervention. In addition, for some patients pretreatment with chemotherapy or radiotherapy is utilized prior to surgical intervention, but in other patients adjuvant therapies are used following surgical intervention.

Determination of appropriate treatment for an individual cancer patient is complex with a wide variety of treatments and possible treatment combinations. For example, chemotherapy is a common method of cancer treatment, with more than 50 different chemotherapeutic agents available. These therapeutic agents can be used in a wide range of dosages both singly and in combinational therapies with other chemotherapeutic agents, surgery, and/or radiotherapy. The available methods for designing strategies for treating breast cancer patients are complex and inexact. Therefore it is important to monitor the impact of the treatment on the cancer. By monitoring the effectiveness of a treatment strategy, the treatment can be modified as necessary to improve the chances for long-term patient survival.

Because of the importance of selecting appropriate treatment regimens for breast cancer patients, and for following their progress, the development of methods to monitor treatment as well as to sensitively diagnose breast cancer is of key interest to those in the medical community and their patients. Although available diagnostic procedures for breast cancer may be partially successful, the methods for detecting breast cancer and monitoring its treatment remain unsatisfactory. There is a critical need for diagnostic tests that can detect breast cancer at its early stages, when appropriate treatment may substantially increase the likelihood of positive outcome for the patient. It is also important that breast cancer treatment be monitored to allow the treatment to be adapted as necessary to best serve the patient's clinical needs. Such diagnostic and monitoring methods will enable medical care professionals to identify breast cancer, select optimal treatment regimens for individual patients, and to assess the cancer before, during, and after treatment.

SUMMARY OF THE INVENTION

The invention provides methods for diagnosing breast cancer based on the identification of certain breast cancer-associated polypeptides and the encoding nucleic acid molecules that encode the polypeptides. The polypeptides or fragments thereof, are, antigens that elicit immune responses in breast cancer. The identified antigens and/or the nucleic acid molecules that encode them can be utilized as markers for diagnosing breast cancer, for following the course of treatment of breast cancer, and for assessing breast cancer treatments.

According to one aspect of the invention, method for diagnosing breast cancer in a subject are provided. The methods include obtaining a biological sample from a subject, contacting the sample with at least two different breast cancer-associated polypeptides encoded by nucleic acid molecules comprising a nucleotide sequence selected from the group consisting of SEQ ID NOs:1-40, and 81, and determining specific binding between the breast cancer-associated polypeptides and agents in the sample, wherein the presence of specific binding is diagnostic for breast cancer in the subject. In some embodiments, the biological sample is contacted with at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs:1-40, and 81. In certain embodiments, the methods further include contacting the biological sample with a breast cancer-associated polypeptide other than those encoded by nucleic acid molecules comprising a nucleotide sequence selected from the group consisting of SEQ ID NOs:1-40, and 81.

According to yet another aspect of the invention, methods for determining onset, progression, or regression, of breast cancer in a subject are provided. The methods include obtaining from a subject a first biological sample, contacting the first sample with at least two different breast cancer-associated polypeptides encoded by nucleic acid molecules comprising a nucleotide sequence selected from the group consisting of SEQ ID NOs: 1-40, and 81, and determining specific binding between agents in the first sample and the at least two different breast cancer-associated polypeptides. The methods also include obtaining from the subject a second biological sample, contacting the second biological sample with at least two different breast cancer-associated polypeptides encoded by nucleic acid molecules comprising a nucleotide sequence selected from the group consisting of SEQ ID NOs:1-40, and 81, determining specific binding between agents in the second sample and the at least two different breast cancer-associated polypeptides, and comparing the determination of binding in the first sample to the determination of specific binding in the second sample as a determination of the onset, progression, or regression of the breast cancer. In some embodiments, binding is determined between the agents and at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs:1-40, and 81. In certain embodiments, the methods also include determining binding between the agents and a breast cancer-associated polypeptide other than those encoded by a nucleic acid molecule comprising a nucleotide sequence selected from the group consisting of SEQ ID NOs:1-40, and 81.

According to another aspect of the invention, methods for selecting a course of treatment of a subject having or suspected of having breast cancer are provided. The methods include obtaining from the subject a biological sample, contacting the sample with at least two different breast cancer-associated polypeptides encoded by nucleic acid molecules comprising a nucleotide sequence selected from the group consisting of SEQ ID NOs: 1-40, and 81, determining specific binding between agents in the sample that are differentially expressed in different types of cancer, and the breast cancer-associated polypeptides, and selecting a course of treatment appropriate to the cancer of the subject. In some embodiments, the treatment is administering antibodies that specifically bind to the breast cancer-associated polypeptides. In certain embodiments, the antibodies are labeled with one or more cytotoxic agents. In come embodiments, the sample is contacted with at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs:1-40, and 81. In certain embodiments the methods also include contacting the sample with a breast cancer-associated polypeptide other than those encoded by a nucleic acid molecule comprising a nucleotide sequence selected from the group consisting of SEQ ID NOs: 1-40, and 81.

According to another aspect of the invention, methods for diagnosing cancer in a subject are provided. The methods include obtaining a biological sample from a subject, contacting the sample with a breast cancer-associated polypeptide encoded by a nucleic acid molecule comprising a nucleotide sequence selected from the group consisting of SEQ ID NOs:19, 20, 21, 22, 23, 24, 33, 36, 39, and 81 and determining specific binding between the breast cancer-associated polypeptide and agents in the sample, wherein the presence of specific binding is diagnostic for cancer in the subject. In some embodiments, the cancer is breast cancer.

According to another aspect of the invention, methods for determining onset, progression, or regression, of cancer in a subject are provided. The methods include obtaining from a subject a first biological sample, contacting the first sample with a breast cancer associated polypeptide encoded by a nucleic acid molecule comprising a nucleotide sequence selected from the group consisting of SEQ ID NOs: 19, 20, 21, 22, 23, 24, 33, 36, 39, and 81 determining specific binding between agents in the first sample and the breast cancer-associated, obtaining from a subject a second biological sample, contacting the second sample with a breast cancer associated polypeptide encoded by a nucleic acid molecule comprising a nucleotide sequence selected from the group consisting of SEQ ID NOs: 19, 20, 21, 22, 23, 24, 33, 36, 39, and 81, determining specific binding between agents in the second sample and the breast cancer-associated polypeptide, and comparing the determination of binding in the first sample to the determination of specific binding in the second sample as a determination of the onset, progression, or regression of cancer. In some embodiments, the cancer is breast cancer.

According to another aspect of the invention, methods for selecting a course of treatment of a subject having or suspected of having cancer are provided. The methods include obtaining from the subject a biological sample, contacting the sample with a breast cancer-associated polypeptide encoded by a nucleic acid molecule comprising a nucleotide sequence selected from the group consisting of SEQ ID NOs: 19, 20, 21, 22, 23, 24, 33, 36, 39, and 81, determining specific binding between agents in the sample that are differentially expressed in different types of cancer, and the breast cancer-associated polypeptide, and selecting a course of treatment appropriate to the cancer of the subject. In some embodiments, the treatment is administering antibodies that specifically bind to the breast cancer-associated polypeptide. In certain embodiments, the antibodies are labeled with one or more cytotoxic agents. In some embodiments, the cancer is breast cancer.

In some embodiments of the foregoing methods, the sample is blood. In other embodiments of the foregoing methods, the sample is lymph node fluid or breast discharge fluid. In some embodiments of the forgoing methods, the agents are antibodies or antigen-binding fragments thereof.

According to another aspect of the invention, methods for diagnosing breast cancer in a subject are provided. The methods include obtaining a biological sample from a subject, contacting the sample with antibodies or antigen-binding fragments thereof, that bind specifically to at least two different breast cancer-associated polypeptides encoded by nucleic acid molecules comprising a nucleotide sequence selected from the group consisting of SEQ ID NOs:1-40, and 81, and determining specific binding between the antibodies or antigen-binding fragments thereof and breast cancer-associated polypeptides in the sample, wherein the presence of specific binding is diagnostic for breast cancer in the subject. In some w embodiments, the biological sample is contacted with antibodies or antigen-binding fragments thereof, that bind specifically to at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs:1-40, and 81. In certain embodiments, the methods also include contacting the biological sample with an antibody or antigen-binding fragment thereof, that binds specifically to a breast cancer-associated polypeptide other than those encoded by nucleic acid molecules comprising a nucleotide sequence selected from the group consisting of SEQ ID NOs:1-40, and 81.

According to another aspect of the invention, methods for determining onset, progression, or regression, of breast cancer in a subject are provided. The methods include obtaining from a subject a first biological sample, contacting the first sample with antibodies or antigen-binding fragments thereof, that bind specifically to at least two different breast cancer-associated polypeptides encoded by nucleic acid molecules comprising a nucleotide sequence selected from the group consisting of SEQ ID NOs:1-40, and 81, determining specific binding between breast cancer-associated polypeptides in the first sample and the antibodies or antigen-binding fragments thereof. The methods also include obtaining from the subject a second biological sample, contacting the second sample with antibodies or antigen-binding fragments thereof, that bind specifically to at least two different breast cancer-associated polypeptides encoded by nucleic acid molecules comprising a nucleotide sequence selected from the group consisting of SEQ ID NOs:1-40, and 81, determining specific binding between breast cancer-associated polypeptides in the second sample and the antibodies or antigen-binding fragments thereof, and comparing the determination of specific binding in the first sample to the determination of specific binding in the second sample as a determination of the onset, progression, or regression of breast cancer. In some embodiments, binding is determined between the breast cancer-associated polypeptides and antibodies or antigen-binding fragments thereof, that bind specifically to least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs:1-40, and 81. In certain embodiments, the methods also include determining binding between the breast cancer-associated polypeptide and an antibody or antigen-binding fragment thereof, that binds specifically to a breast cancer-associated polypeptide other than those encoded by nucleic acid molecules comprising a nucleotide sequence selected from the group consisting of SEQ ID NOs:1-40, and 81.

According to yet another aspect of the invention methods for selecting a course of treatment of a subject having or suspected of having breast cancer are provided. The methods include obtaining from the subject a biological sample, contacting the sample with antibodies or antigen-binding fragments thereof that bind specifically to at least two different breast cancer-associated polypeptides encoded by nucleic acid molecules comprising a nucleotide sequence selected from the group consisting of SEQ ID NOs:1-40, and 81, determining specific binding between breast cancer-associated polypeptides in the sample that are differentially expressed in different types of cancer, and the antibodies or antigen-binding fragments thereof, and selecting a course of treatment appropriate to the cancer of the subject. In some embodiments, the treatment is administering antibodies that specifically bind to the breast cancer-associated polypeptides. In certain embodiments, the antibodies are labeled with one or more cytotoxic agents. In some embodiments, the sample is contacted with antibodies or antigen-binding fragments thereof, that bind specifically to least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs:1-40, and 81. In certain embodiments, the methods also include contacting the sample with an antibody or antigen-binding fragment thereof, that binds specifically to a breast cancer-associated polypeptide other than those encoded by a nucleic acid molecule comprising a nucleotide sequence selected from the group consisting of SEQ ID NOs: 1-40, and 81.

According to yet another aspect of the invention, methods for diagnosing cancer in a subject are provided. The methods include obtaining a biological sample from a subject, contacting the sample with an antibody or antigen-binding fragment thereof, that binds specifically to a breast cancer-associated polypeptide encoded by a nucleic acid molecule comprising a nucleotide sequence selected from the group consisting of SEQ ID NOs:19, 20, 21, 22, 23, 24, 33, 36, 39, and 81, and determining specific binding between the antibody or antigen-binding fragment thereof and the breast cancer-associated polypeptide in the sample, wherein the presence of specific binding is diagnostic for cancer in the subject. In some embodiments, the cancer is breast cancer.

According to another aspect of the invention, methods for determining onset, progression, or regression, of cancer in a subject, are provided. The methods include obtaining from a subject a first biological sample, contacting the first sample with antibodies or antigen-binding fragments thereof, that bind specifically to a breast cancer-associated polypeptides encoded by a nucleic acid molecule comprising a nucleotide sequence selected from the group consisting of SEQ ID NOs: 19, 20, 21, 22, 23, 24, 33, 36, 39, and 81 determining specific binding between breast cancer-associated polypeptides in the first sample and the antibodies or antigen-fragments thereof, obtaining from a subject a second biological sample, contacting the second sample with antibodies or antigen-binding fragments thereof, that bind specifically to a breast cancer-associated polypeptides encoded by a nucleic acid molecule comprising a nucleotide sequence selected from the group consisting of SEQ ID NOs: 19, 20, 21, 22, 23, 24, 33, 36, 39, and 81, determining specific binding between breast cancer-associated polypeptides in the second sample and the antibodies or antigen-binding fragments thereof, and comparing the determination of specific binding in the first sample to the determination of specific binding in the second sample as a determination of the onset, progression, or regression of cancer. In some embodiments, the cancer is breast cancer.

According to yet another aspect of the invention, methods for selecting a course of treatment of a subject having or suspected of having cancer are provided. The methods include obtaining from the subject a biological sample, contacting the sample with antibodies or antigen-binding fragments thereof that bind specifically to at least two different breast cancer-associated polypeptides encoded by nucleic acid molecules comprising a nucleotide sequence selected from the group consisting of SEQ ID NOs: 19, 20, 21, 22, 23, 24, 33, 36, 39, and 81, determining specific binding between breast cancer-associated polypeptides in the sample that are differentially expressed in different types of cancer, and the antibodies or antigen-binding fragments thereof, and selecting a course of treatment appropriate to the cancer of the subject. In some embodiments, the treatment is administering antibodies that specifically bind to the breast cancer-associated polypeptide. In certain embodiments, the antibodies are labeled with one or more cytotoxic agents. In some embodiments, the cancer is breast cancer.

In some embodiments of the foregoing methods, the sample is selected from the group consisting of: tissue, cells, lymph node fluid, blood, and breast discharge fluid. In certain embodiments of the foregoing methods, the tissue is breast tissue. In other embodiments the tissue is lymph node tissue. In other embodiments of the foregoing methods, the cells are from lymph node fluid or breast discharge fluid. In some embodiments of the foregoing methods, the antibodies are monoclonal or polyclonal antibodies. In some embodiments of the foregoing methods, the antibodies are chimeric, human, or humanized antibodies. In certain embodiments, the antibodies are single chain antibodies. In some embodiments of the foregoing methods, the antigen-binding fragments are $F(ab')_2$, Fab, Fd, or Fv fragments.

According to another aspect of the invention, kits for the diagnosis of breast cancer in a subject are provided. The kits include at least two different breast cancer-associated polypeptides encoded by nucleic acid molecules comprising a nucleotide sequence selected from the group consisting of: SEQ ID NOs: 1-40, and 81, one or more control antigens, and instructions for the use of the polypeptides in the diagnosis of breast cancer. In some embodiments, the breast cancer-associated polypeptides are bound to a substrate. In certain embodiments, the one or more agents are antibodies or antigen-binding fragments thereof. In some embodiments, the kit comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs:1-40, and 81. In certain embodiments, the kits also include a breast cancer-associated polypeptide other than those encoded by a nucleic acid molecule comprising a nucleotide sequence selected from the group consisting of SEQ ID NOs:1-40, and 81.

According to yet another aspect of the invention, kits for the diagnosis of breast cancer in a subject are provided. The kits include antibodies or antigen-binding fragments thereof that bind specifically to at least two different breast cancer-associated polypeptides encoded by nucleic acid molecules comprising a nucleotide sequence selected from the group consisting of SEQ ID NOs: 1-40, and 81, one or more control agents, and instructions for the use of the agents in the diagnosis of breast cancer. In some embodiments, the one or more agents are antibodies or antigen-binding fragments thereof. In some embodiments, the one or more agents are bound to a substrate. In some embodiments, the kit comprises antibodies or antigen-binding fragments thereof, that bind specifically to least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs:1-40, and 81. In certain embodiments the kits also include an antibody or antigen-binding fragment thereof, that binds specifically to a breast cancer-associated polypeptide other than those encoded by a nucleic acid molecule comprising a nucleotide sequence selected from the group consisting of SEQ ID NOs:1-40, and 81.

According to another aspect of the invention, protein microarrays are provided. The protein microarrays include at least two different breast cancer-associated polypeptides, wherein the breast cancer-associated polypeptides are encoded by nucleic acid molecules comprising a nucleotide sequence selected from the group consisting of: SEQ ID NOs: 1-40, and 81, fixed to a solid substrate. In some embodiments, the microarray comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs:1-40, and 81. In certain embodiments the protein microarray also includes a breast cancer-associated polypeptide other than those encoded by a nucleic acid molecule comprising a nucleotide sequence selected from the group consisting of SEQ ID NOs: 1-40, and 81. In some embodiments, the protein microarray includes at least one control polypeptide molecule.

According to yet another aspect of the invention, protein microarrays are provided. The protein microarrays include antibodies or antigen-binding fragments thereof, that specifically bind at least two different breast cancer-associated polypeptides encoded by nucleic acid molecules comprising a nucleotide sequence selected from the group consisting of: SEQ ID NOs:1-40, and 81, fixed to a solid substrate. In some embodiments, the microarray comprises antibodies or antigen-binding fragments thereof, that bind specifically to least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different breast cancer-associated polypeptides encoded by nucleic acid molecules comprising a nucleotide sequence selected from the group consisting of SEQ ID NOs: 1-40, and 81. In certain embodiments, the microarray also includes an antibody or antigen-binding fragment thereof, that binds specifically to a breast cancer-associated polypeptide other than those encoded by a nucleic acid molecule comprising a nucleotide sequence selected from the group consisting of SEQ ID NOs:1-40, and 81. In some embodiments, the protein microarray also includes at least one control polypeptide molecule. In some embodiments, the antibodies are monoclonal or polyclonal antibodies. In other embodiments, the antibodies are chimeric, human, or humanized antibodies. In some embodiments, the antibodies are single chain antibodies. In some embodiments, the antigen-binding fragments are $F(ab')_2$, Fab, Fd, or Fv fragments.

According to yet another aspect of the invention, nucleic acid microarrays are provided. The nucleic acid microarrays include at least two nucleic acids selected from the group consisting of SEQ ID NOs:1-40, and 81, fixed to a solid substrate. In some embodiments, the microarray comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different nucleic acid molecules comprising a nucleotide sequence selected from the group consisting of SEQ ID NOs: 1-40, and 81. In certain embodiments, the nucleic acid microarray also includes a nucleic acid molecule other than those selected from the group consisting of SEQ ID NOs:1-40, and 81. In certain embodiments, the nucleic acid microarray also includes at least one control nucleic acid molecule.

According to another aspect of the invention, methods for diagnosing breast cancer in a subject are provided. The methods include obtaining from the subject a biological sample, and determining the expression of at least two breast cancer-associated nucleic acid molecules or expression products thereof in the sample, wherein the nucleic acid molecules comprise a nucleotide sequence selected from the group consisting of: SEQ ID NO: 1-40, and 81, wherein the expression is diagnosis of the breast cancer in the subject. In some embodiments, expression is determined for at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35,36,37, 38,39, or 40 nucleic acid molecules comprising a nucleotide sequence selected from the group consisting of SEQ ID NOs:1-40, and 81. In certain embodiments the method also includes determining expression of a breast cancer-associated nucleic acid molecule other than those comprising a nucleotide sequence selected from the group consisting of SEQ ID NOs:1-40, and 81. In some embodiments, the sample is selected from the group consisting of: tissue, cells, lymph node fluid, blood, and breast discharge fluid. In some embodiments, the tissue is breast tissue. In other embodiment, the tissue is lymph node tissue. In some embodiments, the cells are from lymph node fluid or breast discharge fluid. In some embodiments, the expression of breast cancer-associated nucleic acid molecules is determined by a method selected from the group consisting of nucleic acid hybridization and nucleic acid amplification. In certain embodiments, the hybridization is performed using a nucleic acid microarray.

According to another aspect of the invention, methods for determining onset, progression, or regression, of breast cancer in a subject are provided. The methods include obtaining from a subject a first biological sample, determining a level of expression of at least two breast cancer-associated nucleic acid molecules or expression products thereof in the first sample, wherein the nucleic acid molecules are selected from the group consisting of: SEQ ID NOs: 1-40, and 81, obtaining from the subject a second biological sample, determining a level of expression of at least two breast cancer-associated nucleic acid molecules or expression products thereof in the second sample, wherein the nucleic acid molecules are selected from the group consisting of: SEQ ID NOs: 1-40, and 81, and comparing the level of expression in the first sample to the level of expression in the second sample as a determination of the onset, progression, or regression of the breast cancer. In some embodiments, expression is determined for at least 3, 4, 5, 6, 7, 8, 9, 10, 11, 12, 13, 14, 15, 16, 17, 18, 19, 20,21, 22, 23, 24, 25, 26, 27, 28, 29, 30, 31, 32, 33, 34, 35, 36, 37, 38, 39, or 40 nucleic acid molecules selected from the group consisting of SEQ ID NOs:1-40, and 81. In certain embodiments, the method also includes determining expression for a breast cancer-associated nucleic acid molecule other than those comprising a nucleotide sequence selected from the group consisting of SEQ ID NOs:1-40, and 81. In some embodiments, the sample is selected from the group consisting of: tissue, cells, lymph node fluid, blood and breast discharge fluid. In some embodiments, the tissue is breast tissue. In other embodiments, the tissue is lymph node tissue. In some embodiments, the cells are from lymph node fluid or breast discharge fluid. In some embodiments, the expression of breast cancer-associated nucleic acid molecules is determined by a method selected from the group consisting of nucleic acid hybridization and nucleic acid amplification. In certain embodiments, the hybridization is performed using a nucleic acid microarray.

According to another aspect of the invention, kits for the diagnosis of cancer in a subject are provided. The kits include a breast cancer-associated polypeptide encoded by a nucleic acid molecule comprising a nucleotide sequence selected from the group consisting of: SEQ ID NOs: 19, 20, 21, 22, 23, 24, 33, 36, 39; and 81, one or more control antigens; and instructions for the use of the polypeptide and control antigens in the diagnosis of cancer. In some embodiments, the breast cancer-associated polypeptide is bound to a substrate. In certain embodiments, the one or more agents are antibodies or antigen-binding fragments thereof. In some embodiments the cancer is breast cancer.

According to another aspect of the invention, kits for the diagnosis of cancer in a subject are provided. The kits include antibodies or antigen-binding fragments thereof that bind specifically to a breast cancer-associated polypeptide encoded by a nucleic acid molecule comprising a nucleotide sequence selected from the group consisting of SEQ ID NOs: 19, 20, 21, 22, 23, 24, 33, 36, 39, and 81 one or more control agents; and instructions for the use of the antibodies, antigen-binding fragments, and agents in the diagnosis of cancer. In some embodiments, the one or more agents are antibodies or antigen-binding fragments thereof. In certain embodiments the one or more agents are bound to a substrate. In some embodiments, the cancer is breast cancer.

According to yet another aspect of the invention, protein microarrays are provided. The protein microarrays include a breast cancer-associated polypeptide, wherein the breast cancer-associated polypeptide is encoded by a nucleic acid molecule comprising a nucleotide sequence selected from the group consisting of: SEQ ID NOs: 19, 20, 21, 22, 23, 24, 33, 36, 39, and 81, fixed to a solid substrate. In some embodiments, the protein microarray also includes at least one control polypeptide molecule.

According to another aspect of the invention, protein microarrays are provided. The protein microarrays include antibodies or antigen-binding fragments thereof, that specifically bind a breast cancer-associated polypeptide encoded by a nucleic acid molecule comprising a nucleotide sequence selected from the group consisting of: SEQ ID NOs: 19, 20, 21, 22, 23, 24, 33, 36, 39, and 81, fixed to a solid substrate. In some embodiments, the protein microarray also includes at least one control polypeptide molecule. In certain embodiments, the antibodies are monoclonal or polyclonal antibodies. In some embodiments, the antibodies are chimeric, human, or humanized antibodies. In certain embodiments, the antibodies are single chain antibodies. In some embodiments, the antigen-binding fragments are $F(ab')_2$, Fab, Fd, or Fv fragments.

According to another aspect of the invention, nucleic acid microarrays are provided. The nucleic acid microarrays include a nucleic acid selected from the group consisting of SEQ ID NOs: 19, 20, 21, 22, 23, 24, 33, 36, 39, and 81, fixed to a solid substrate. In some embodiments, the nucleic acid microarray also includes at least one control nucleic acid molecule.

According to another aspect of the invention, methods for diagnosing cancer in a subject are provided. The methods include obtaining from the subject a biological sample, and determining the expression of a breast cancer-associated nucleic acid molecule or expression product thereof in the sample, wherein the nucleic acid molecule comprises a nucleotide sequence selected from the group consisting of: SEQ ID NO: 19, 20, 21, 22, 23, 24, 33, 36, 39, and 81, wherein the expression is diagnostic of cancer in the subject. In some embodiments, the sample is selected from the group consisting of: tissue, cells, lymph node fluid, blood, and breast discharge fluid. In certain embodiments, the tissue is breast tissue. In other embodiments, the tissue is lymph node tissue. In some embodiments, the tissue is cells from lymph node fluid or breast discharge fluid. In some embodiments, the expression of breast cancer-associated nucleic acid molecules is determined by a method selected from the group consisting of nucleic acid hybridization and nucleic acid amplification. In certain embodiments, the hybridization is performed using a nucleic acid microarray. In some embodiments, the cancer is breast cancer.

According to yet another aspect of the invention, methods for determining onset, progression, or regression, of cancer in a subject are provided. The methods include obtaining from a subject a first biological sample, determining a level of expression of a breast cancer-associated nucleic acid molecule or expression products thereof in the first sample, wherein the nucleic acid molecule is selected from the group consisting of: SEQ ID NOs: 19, 20, 21, 22, 23, 24, 33, 36, 39, and 81, obtaining from the subject a second biological sample, determining a level of expression of a breast cancer-associated nucleic acid molecule or expression product thereof in the second sample, wherein the nucleic acid molecule is selected from the group consisting of: SEQ ID NOs: 19, 20, 21, 22, 23, 24, 33, 36, 39, and 81, and comparing the level of expression in the first sample to the level of expression in the second sample as a determination of the onset, progression, or regression of the cancer. In some embodiments, the sample is selected from the group consisting of: tissue, cells, lymph node fluid, blood, and breast discharge fluid. In certain embodiments, the tissue is breast tissue. In some embodiments, the tissue is lymph node tissue. In other embodiments, the tissue is cells from lymph node fluid or breast discharge fluid. In some embodiments, the expression of breast cancer-associated nucleic acid molecules is determined by a method selected from the group consisting of nucleic acid hybridization and nucleic acid amplification. In certain embodiments, the hybridization is performed using a nucleic acid microarray. In some embodiments, the cancer is breast cancer.

In preferred embodiments of the foregoing methods and compositions, the breast cancer-associated antigens encoded by SEQ ID NOs:1-40, and 81 are polypeptides comprising, respectively, the amino acid sequences set forth in SEQ ID NOs:41-80, and 82, or fragments thereof containing an epitope amino acid sequence.

In certain embodiments of the foregoing methods and compositions, nucleic acid molecules that are fragments of SEQ ID NOs:1-40, and 81, are included. Preferred fragments are those that encode fragments of SEQ ID NOs:41-80, and 82 that include epitopes. Certain preferred fragments include 20 or more contiguous nucleotides of SEQ ID NOs:1-40, and 81 more preferably 25, 30, 35, 40, 50, 60, 70, 80, 90, 100, 150, 200, 250, 300, 400, 500, or more contiguous nucleotides.

According to another aspect of the invention, methods for diagnosing cancer in a subject are provided. The methods include obtaining a non-testis biological sample from a subject, determining the level of expression of one or more cancer-associated nucleic acid molecule comprising a nucleotide sequences selected from the group consisting of SEQ ID NOs: 22, 31, 32, 33, 34, 40, and 81, comparing the level of expression of the nucleic acid molecule in the subject sample to a level of expression of the nucleic acid molecule in a control tissue, wherein a determination that the level of expression of the nucleic acid in the sample from the subject is greater than about three times the level of expression of the nucleic acid in the control tissue, indicates cancer in the subject. In some embodiments, the level of expression of the nucleic acid in the sample from the subject is at least about 3, 4, 5, 6, 7, 8, 9, 10, 15, 20, 30, 40, or 50 times the level of expression in the control tissue. In certain embodiments, expression is determined for at least 2, 3, 4, 5, 6, or 7 nucleic acid molecules comprising a nucleotide sequence selected from the group consisting of SEQ ID NOs: 22, 31, 32, 33, 34, 40, and 81. In some embodiments, the sample is selected from the group consisting of: tissue and cells. In some embodiments, the cancer is breast cancer. In certain embodiments, the tissue is breast tissue. In some embodiments, the expression of cancer-associated nucleic acid molecules is determined by a method selected from the group consisting of nucleic acid hybridization and nucleic acid amplification. In some embodiments, the hybridization is performed using a nucleic acid microarray. In other embodiments, the nucleic acid amplification is real-time RT-PCR or RT-PCR.

According to yet another aspect of the invention, methods for determining onset, progression, or regression, of cancer in a subject are provided. The methods include obtaining from a subject a first and a second biological sample, wherein the samples comprise the same tissue type and are obtained at different times, determining a level of expression of one or more cancer-associated nucleic acid molecules or expression products thereof in the first and second biological samples, wherein the nucleic acid molecules comprise nucleotide sequences selected from the group consisting of: SEQ ID NOs: 22, 31, 32, 33, 34, 40, and 81, comparing the level of expression of one or more cancer-associated nucleic acid molecules in the first and the second biological samples to the level of expression of the one or more cancer-associated nucleic acid molecules in a control sample, wherein a higher level of expression of the one or more cancer-associated nucleic acid molecules in the first sample than in the second sample indicates regression of cancer, wherein a lower level of expression of the one or more cancer-associated nucleic acid molecules in the first sample than the second sample indicates progression of cancer, and wherein a level of expression of the cancer-associated nucleic acid molecule in the first sample that is less than three times higher than the level of expression of the cancer-associated nucleic acid molecule in the control sample and a level of expression of the cancer-associated nucleic acid molecules in the second sample that is three or more times higher than the level in the control sample, indicates onset of cancer. In some embodiments the level of expression of the one or more nucleic acid molecules in the sample from the subject is at least about 3, 4, 5, 6, 7, 8, 9, 10, 15, 20, 30, 40, or 50 times the level of expression in the control tissue. In certain embodiments, expression is determined for at least 2, 3, 4, 5, 6, or 7 nucleic acid molecules comprising a nucleotide sequence selected from the group consisting of SEQ ID NOs: 22, 31, 32, 33, 34, 40, and 81. In some embodiments, the sample is selected from the group consisting of: tissue and cells. In certain embodiments, the cancer is breast cancer. In some embodiments, the tissue is breast tissue.

According to another aspect of the invention, methods for diagnosing cancer in a subject are provided. The methods include obtaining a biological sample from a subject, determining the level of expression of a cancer-associated nucleic acid molecule comprising a nucleotide sequence selected from the group consisting of SEQ ID NOs: 33 and 81, and comparing the level of expression of the nucleic acid molecule in the subject sample to a level of expression of the nucleic acid in a control tissue, wherein a determination that the level of expression of the nucleic acid in the sample from the subject is greater than about three times of the level of expression of the nucleic acid in the control tissue, indicates cancer in the subject. In some embodiments, the level of expression of the nucleic acid in the sample from the subject is at least about 3, 4, 5, 6, 7, 8, 9, 10, 15, 20, 30, 40, or 50 times the level of expression in the control tissue. In certain embodiments, the sample is selected from the group consisting of: tissue and cells. In some embodiments, the cancer is colon cancer. In some embodiments, the tissue is colorectal tissue. In some embodiments, the expression of cancer-associated nucleic acid molecules is determined by a method selected from the group consisting of nucleic acid hybridization and nucleic acid amplification. In certain embodiments, the hybridization is performed using a nucleic acid microarray. In other embodiments, the nucleic acid amplification is real-time RT-PCR or RT-PCR.

According to yet another aspect of the invention, methods for determining onset, progression, or regression, of cancer in a subject are provided. The methods include obtaining from a subject a first and a second biological sample, wherein the samples comprise the same tissue type and are obtained at different times, determining a level of expression of a cancer-associated nucleic acid molecule or expression product thereof in the first and second biological samples, wherein the nucleic acid molecule comprises a nucleotide sequence selected from the group consisting of: SEQ ID NOs: 33 and 81, and comparing the level of expression of the cancer-associated nucleic acid molecule of the first and the second biological samples to the level of expression of the cancer-associated nucleic acid molecule in a control sample, wherein a higher level of expression of the cancer-associated nucleic acid molecule in the first sample than in the second sample indicates regression of cancer, wherein a lower level of expression of the cancer-associated nucleic acid molecule in the first sample than the second sample indicates progression of cancer, and wherein a level of expression of the cancer-associated nucleic acid molecule in the first sample that is less than three times higher than the level of expression of the cancer-associated nucleic acid molecule in the control sample, and a level of expression of the cancer-associated nucleic acid molecules in the second sample that is three or more times higher than the level in the control sample, indicates onset of cancer. In some embodiments, the level of expression of the one or more nucleic acid molecules in the sample from the subject is at least about 3, 4, 5, 6, 7, 8, 9, 10, 15, 20, 30, 40, or 50 times the level of expression in the control tissue. In certain embodiments, the sample is selected from the group consisting of: tissue and cells. In some embodiments, the cancer is colon cancer. In some embodiments, the tissue is colorectal tissue.

The use of the foregoing nucleic acid molecules and polypeptides in the preparation of medicaments also is embraced by the invention. In preferred embodiments, the medicaments are useful in the treatment of cancer, and particularly breast cancer.

BRIEF DESCRIPTION OF THE DRAWINGS

FIG. 1A shows real-time analysis of the level of NY-BR-41 mRNA expression (femtograms (fg) of homologous cDNA±S.E.M.). FIG. 1B shows real-time analysis of the level of mRNA encoding NY-BR-62 showing low-level ubiquitous expression (±S.E.M.). FIG. 1C shows real-time analysis of the level of mRNA encoding NY-BR-85 showing low-level ubiquitous expression (±S.E.M).

DETAILED DESCRIPTION OF THE INVENTION

Figure 1:
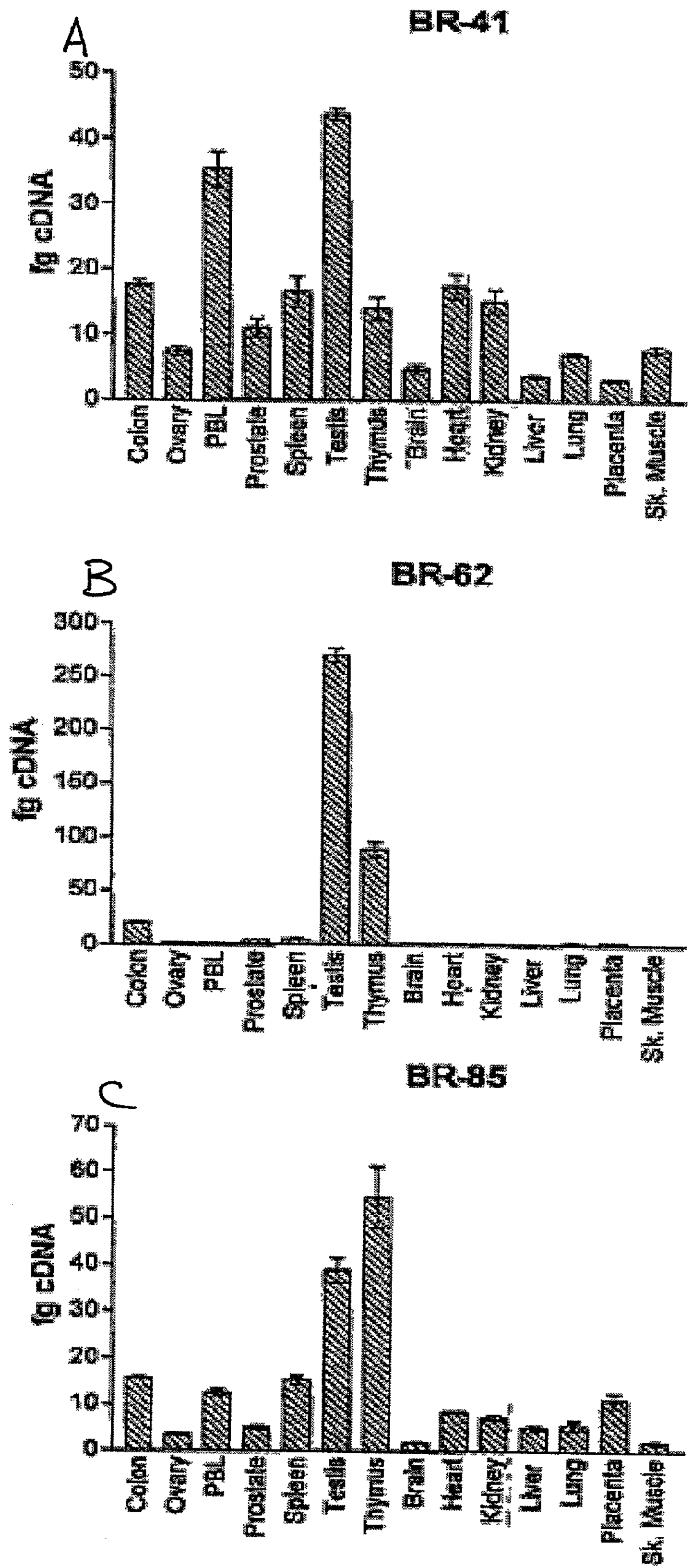
FIG. 1 shows mRNA expression pattern of three antigens associated with a breast cancer-related serological response.

The invention described herein relates to the identification of polypeptides that elicit specific immune responses in subjects with cancer, particularly breast cancer. Breast cancer-associated polypeptides have been identified through SEREX screening of patients with cancer. The SEREX method (serological analysis of antigens by recombinant expression cloning), has been described by Sahin et al. (*Proc. Natl. Acad. Sci. USA* 92:11810-11813, 1995). The newly identified breast cancer-associated polypeptides and the encoding nucleic acid molecules thereof may be used as markers for cancer, including breast cancer, and may be used in the diagnosis and treatment assessment of breast cancer in humans. In addition, sets of at least two breast cancer-associated polypeptides and the encoding nucleic acid molecules thereof, may be used as markers in the diagnosis and treatment assessment of breast cancer in humans.

Polypeptides that elicit specific immune responses in breast cancer have now been identified and this identification allows use of these newly identified breast cancer-associated polypeptides or the encoding nucleic acids molecules thereof in cancer diagnostic assays and kits. In addition, sets of at least two of these new or previously identified polypeptides or the encoding nucleic acid molecules thereof, may be used in breast cancer diagnostic assays and kits. Such assays and kits are useful to detect breast cancer in human subjects, and for staging the progression, regression, or onset of breast cancer in subjects. The methods and kits described herein may also be used to evaluate treatments for breast cancer.

As used herein, “breast cancer-associated polypeptides” means polypeptides that elicit specific immune responses in animals having breast cancer and thus, include breast cancer-associated antigens and fragments of breast cancer-associated antigens, that are recognized by the immune system (e.g., by antibodies and/or T lymphocytes). The invention also relates to the use of the nucleic acid molecules that encode the breast cancer-associated polypeptides. In all embodiments, human breast cancer-associated polypeptides and the encoding nucleic acid molecules thereof, are preferred. As used herein, the “encoding nucleic acid molecules thereof” means the nucleic acid molecules that code for the polypeptides.

As used herein, a subject is preferably a human, non-human primate, cow, horse, pig, sheep, goat, dog, cat, or rodent. In all embodiments, human subjects are preferred. In some embodiments, the subject is suspected of having cancer and in preferred embodiments the subject is suspected of having breast cancer. In some embodiments the subject has been diagnosed with cancer, and in preferred embodiments the subject has been diagnosed with breast cancer.

As used herein, “different types” of cancer may include different histological types, different tumor types (e.g., invasive ductal carcinoma, invasive pleomorphic lobular carcinoma), different cell types, and different stages of cancer (e.g., primary tumor or metastatic growth).

Methods for identifying subjects suspected of having breast cancer may include but are not limited to: manual examination, biopsy, subject’s family medical history, subject’s medical history, or a number of imaging technologies such as mammography, magnetic resonance imaging, magnetic resonance spectroscopy, or positron emission tomography. Diagnostic methods for breast cancer and the clinical delineation of breast cancer diagnoses are well-known to those of skill in the medical arts.

As used herein, a biological sample includes, but is not limited to: tissue, cells, or body fluid (e.g. blood, lymph node fluid, or nipple discharge fluid). The fluid sample may include cells and/or fluid. The tissue and cells may be obtained from a subject or may be grown in culture (e.g. from a cell line).

As used herein, a biological sample is tissue or cells obtained (e.g., from a breast tissue biopsy or aspiration) using methods well-known to those of ordinary skill in the related medical arts. In some embodiments, the tissue is breast tissue, in other embodiments, the tissue is colorectal tissue. The phrase "suspected of being cancerous" as used herein means a breast cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Because of the variability of the cell types in diseased-tissue biopsy material, and the variability in sensitivity of the diagnostic methods used, the sample size required for analysis may range from 1, 10, 50, 100, 200, 300, 500, 1000, 5000, 10,000, to 50,000 or more cells. The appropriate sample size may be determined based on the cellular composition and condition of the biopsy and the standard preparative steps for this determination and subsequent isolation of the nucleic acid for use in the invention are well known to one of ordinary skill in the art. An example of this, although not intended to be limiting, is that in some instances a sample from the biopsy may be sufficient for assessment of RNA expression without amplification, but in other instances the lack of suitable cells in a small biopsy region may require use of RNA conversion and/or amplification methods or other methods to enhance resolution of the nucleic acid molecules. Such methods, which allow use of limited biopsy materials, are well known to those of ordinary skill in the art and include, but are not limited to: direct RNA amplification, reverse transcription of RNA to cDNA, amplification of cDNA, or the generation of radio-labeled nucleic acids.

In some embodiments, the breast cancer-associated nucleic acid molecules from the group of nucleic acid sequences numbered 1 through 40, and 81 in Table 8 (SEQ ID NOs: 1-40, and 81) and the breast cancer-associated polypeptides encoded by SEQ ID NOs: 1-40, and 81, are the group of polypeptide sequences SEQ ID NOs: 41 through 80 and 82 in Table 8. In some embodiments, breast cancer-associated polypeptides may include polypeptides other than those encoded by nucleic acid molecules comprising a nucleotide sequence selected from the group consisting of SEQ ID NOs:1-40, and 81.

The level of expression of some cancer-associated nucleic acid molecules or cancer-associated polypeptide molecules of the invention can be used to diagnose cancer (e.g. breast cancer or colon cancer) in a subject. In these tissues a determination of the level of expression of the cancer-associated nucleic acids and/or polypeptides is diagnostic of cancer if the level of expression is above a baseline level determined for that tissue type. The baseline level of expression can be determined using standard methods known to those of skill in the art. Such methods include, for example, assaying a number of histologically normal tissue samples from subjects that are clinically normal (i.e. do not have clinical signs of cancer in that tissue type) and determining the mean level of expression for the samples. For example, the baseline level of a cancer-associated molecule used in the diagnosis of breast cancer, would be the level of expression of that cancer-associated molecule in normal breast control tissue and the baseline level of a cancer-associated molecule used in the diagnosis of colon cancer, would be the level of expression of that cancer-associated molecule in normal colorectal control tissue. The level of expression of a cancer-associated molecule in a tissue sample from a subject can be compared to the baseline level of expression of the cancer associated molecules in control tissue samples as a determination and diagnosis of cancer in the subject.

In some cases, levels of expression of one or more cancer-associated molecules that are preferably about three or more times higher than the level of expression of those cancer-associated molecules in a normal control tissue indicates cancer in the tissue. In other cases, e.g. BR-41 (SEQ ID NO: 27) a lower level of expression (preferably less than about 20% of the control level), of a cancer-associated molecule in a subject tissue sample as compared to the level in a normal control tissue indicates breast cancer in that patient sample. Thus, in some tissues there is a baseline level of expression of a cancer-associated molecule of the invention, and it is that baseline level that determines the level above (or below) which expression indicates cancer in the tissue. Therefore, as described herein, in some tissues, the level of expression of the nucleic acid molecules of the invention or the polypeptides they encode indicate cancer in the tissue when the level of expression of the nucleic acid molecule is greater than about three times the level in a control tissue sample of that type of tissue. A level of nucleic acid expression of greater than 3, 4, 5, 6, 7, 8, 9, 10, 15, 20, 24, 30, 40, 50 or more times the level of nucleic acid expression in the control tissue indicates cancer in the tissue.

The invention involves in some aspects diagnosing or monitoring cancer by determining the level of expression of one or more cancer-associated nucleic acid molecules and/or determining the level of expression of one or more cancer-associated polypeptides they encode. In some important embodiments, this determination is performed by assaying a tissue sample from a subject for the level of expression of one or more cancer-associated nucleic acid molecules or for the level of expression of one or more cancer-associated polypeptides encoded by the nucleic acid molecules of the invention.

The expression of the molecules of the invention may be determined using routine methods known to those of ordinary skill in the art. These methods include, but are not limited to: direct RNA amplification, reverse transcription of RNA to cDNA, real-time RT-PCR, amplification of cDNA, hybridization, and immunologically based assay methods, which include, but are not limited to immunohistochemistry, antibody sandwich capture assay, ELISA, and enzyme-linked immunospot assay (EliSpot assay). For example, the determination of the presence of level of nucleic acid molecules of the invention in a subject or tissue can be carried out via any standard nucleic acid determination assay, including the polymerase chain reaction, or assaying with labeled hybridization probes. Such hybridization methods include, but are not limited to microarray techniques.

These methods of determining the presence and/or level of the molecules of the invention in cells and tissues may include use of labels to monitor the presence of the molecules of the invention. Such labels may include, but are not limited to radiolabels or chemiluminescent labels, which may be utilized to determine whether a molecule of the invention is expressed in a cell or tissue, and to determine the level of expression in the cell or tissue. For example, a fluorescently labeled or radiolabeled antibody that selectively binds to a polypeptide of the invention may be contacted with a tissue or cell to visualize the polypeptide in vitro or in vivo. These and other in vitro and in vivo imaging methods for determining the presence of the nucleic acid and polypeptide molecules of the invention are well known to those of ordinary skill in the art.

The invention involves in some embodiments, diagnosing or monitoring breast cancer in subjects by determining the presence of an immune response to at least two breast cancer-associated polypeptides. In some embodiments, cancer, such as breast cancer, in subjects may be diagnosed or monitored by determining the presence of an immune response to one of the novel breast cancer-associated polypeptides described herein. In preferred embodiments, this determination is performed by assaying a bodily fluid obtained from the subject, preferably blood, lymph node fluid, or breast discharge fluid, for the presence of antibodies against at least two breast cancer-associated polypeptides or the nucleic acid molecules that encode the cancer-associated polypeptides, or for the presence of antibodies against one of the novel breast cancer-associated polypeptides or the encoding nucleic acid molecules thereof as described herein. This determination may also be performed by assaying a tissue or cells from the subject for the presence of at least two breast cancer-associated polypeptides and/or the encoding nucleic acid molecules thereof, or assaying a tissue or cells from the subject for the presence of one of the novel breast cancer-associated polypeptides or the encoding nucleic acid molecules thereof as described herein.

Measurement of the immune response against one of the novel breast cancer-associated polypeptides described herein, or at least two breast cancer-associated polypeptides in a subject over time by sequential determinations permits monitoring of the disease and/or the effects of a course of treatment. For example, a sample, such as blood, lymph node fluid, or breast discharge fluid, may be obtained from a subject, tested for an immune response to one of the novel breast cancer-associated polypeptides or may be tested for an immune response to at least two breast cancer-associated polypeptides and at a second, subsequent time, another sample, such as blood, may be obtained from the subject and similarly tested. The results of the first and second (subsequent) tests can be compared as a measure of the onset, regression or progression of breast cancer, or, if breast-cancer treatment was undertaken during the interval between obtaining the samples, the effectiveness of the treatment may be evaluated by comparing the results of the two tests.

The invention also involves in some embodiments diagnosing or monitoring breast cancer by determining the presence of at least two breast cancer-associated polypeptides and the encoding nucleic acid molecules thereof, or by determining the presence of one of the novel breast cancer-associated polypeptides and the encoding nucleic acid molecules thereof as described herein. In some important embodiments, this determination is performed by assaying a tissue sample from subject, preferably one believed to be cancerous, for the presence of at least two breast cancer-associated polypeptides or the encoding nucleic acid molecules thereof, or for the presence of one of the novel breast cancer-associated polypeptides and the encoding nucleic acid molecules thereof as described herein.

In all embodiments, treatment for breast cancer may include, but is not limited to: surgical intervention, chemotherapy, radiotherapy, and adjuvant systemic therapies. In a preferred embodiment, treatment may include administering antibodies that specifically bind to the breast cancer-associated antigen. Optionally, an antibody can be linked to one or more detectable markers, antitumor agents or immunomodulators. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope may be an alpha-emitting isotope such as $^{225}$Ac, $^{211}$At, $^{212}$Bi, or $^{213}$Bi. Alternatively, the cytotoxic radionuclide may be a beta-emitting isotope such as $^{186}$Rh, $^{188}$Rh, $^{90}$Y, $^{131}$I or $^{67}$Cu. Further, the cytotoxic radionuclide may emit Auger and low energy electrons such as the isotopes $^{125}$I, $^{123}$I or $^{77}$Br.

Suitable chemical toxins or chemotherapeutic agents include members of the enediyne family of molecules, such as chalicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouaracil. Other chemotherapeutic agents are known to those skilled in the art.

Agents that act on the tumor neovasculature can include tubulin-binding agents such as combrestatin A4 (Griggs et al., Lancet Oncol. 2:82, 2001) and angiostatin and endostatin (reviewed in Rosen, Oncologist 5:20, 2000, incorporated by reference herein). Immunomodulators may also be conjugated to breast cancer-associated antibodies.

The invention thus involves in one aspect, breast cancer-associated polypeptides, genes encoding those polypeptides, functional modifications and variants of the foregoing, useful fragments of the foregoing, as well as diagnostics relating thereto, and diagnostic uses thereof. In some embodiments, the breast cancer-associated polypeptide genes correspond to SEQ ID NOs: 1-40, and 81. Encoded polypeptides (e.g., proteins), peptides and antisera thereto are also preferred for diagnosis and correspond to SEQ ID NOs: 41-80, and 82. In some embodiments, the method or kit may include breast cancer-associated polypeptide genes in addition to those corresponding to SEQ ID NOs. 1-40, and 81 and the encoded polypeptides (e.g. proteins), peptides, and antisera thereto in addition to those corresponding to SEQ ID NOs:41-80, and 82.

Some of the amino acid sequences identified by SEREX as breast cancer-associated polypeptides, and the nucleotide sequences encoding them, are newly identified and some are sequences deposited in databases such as GenBank. The use of the newly identified sequences in diagnostic assays for cancer is novel, as is the use of sets of at least two of the sequences in breast cancer diagnostic assays and kits. Homologs and alleles of the breast cancer-associated polypeptide nucleic acids of the invention can be identified by conventional techniques. Thus, an aspect of the invention is those nucleic acid sequences that code for breast cancer-associated antigens and antigenic fragments thereof. As used herein, a homolog to a breast cancer-associated polypeptide is a polypeptide from a human or other animal that has a high degree of structural similarity to the identified breast cancer-associated polypeptides.

Identification of human and other organism homologs of breast cancer-associated polypeptides will be familiar to those of skill in the art. In general, nucleic acid hybridization is a suitable method for identification of homologous sequences of another species (e.g., human, cow, sheep), which correspond to a known sequence. Standard nucleic acid hybridization procedures can be used to identify related nucleic acid sequences of selected percent identity. For example, one can construct a library of cDNAs reverse transcribed from the mRNA of a selected tissue (e.g., breast) and use the nucleic acids that encode breast cancer-associated polypeptide identified herein to screen the library for related nucleotide sequences. The screening preferably is performed using high-stringency conditions to identify those sequences that are closely related by sequence identity.

Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high-stringency conditions, as used herein, refers, for example, to hybridization at 65° C. in hybridization buffer (3.5× SSC, 0.02% Ficoll, 0.02% polyvinyl pyrrolidone, 0.02% Bovine Serum Albumin, 2.5 mM $NaH_2PO_4$(pH 7), 0.5% SDS, 2 mM EDTA). SSC is 0.15M sodium chloride/0.015M sodium citrate, pH 7; SDS is sodium dodecyl sulphate; and EDTA is ethylenediaminetetracetic acid. After hybridization, the membrane upon which the DNA is transferred is washed, for example, in 2× SSC at room temperature and then at 0.1-0.5× SSC/0.1× SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of breast cancer-associated polypeptide nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general, homologs and alleles typically will share at least 90% nucleotide identity and/or at least 95% amino acid identity to the sequences of breast cancer-associated antigen, antigenic fragment thereof, and antigen precursor thereof nucleic acid and polypeptides, respectively, in some instances will share at least 95% nucleotide identity and/or at least 97% amino acid identity, and in other instances will share at least 97% nucleotide identity and/or at least 99% amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for breast cancer-associated polypeptide genes, a Southern blot may be performed using the foregoing conditions, together with a detectably labeled probe (e.g. radioactive or chemiluminescent probes). After washing the membrane to which the DNA is finally transferred, the membrane can be placed against X-ray film or a phosphorimager to detect the radioactive or chemiluminescent signal. In screening for the expression of breast cancer-associated polypeptide nucleic acids, Northern blot hybridizations using the foregoing conditions can be performed on samples taken from breast cancer patients or subjects suspected of having a condition characterized by abnormal cell proliferation or neoplasm of the breast of lymph node tissues. Amplification protocols such as polymerase chain reaction using primers that hybridize to the sequences presented also can be used for detection of the breast cancer-associated polypeptide genes or expression thereof.

Identification of related sequences can also be achieved using polymerase chain reaction (PCR) and other amplification techniques suitable for cloning related nucleic acid sequences. Preferably, PCR primers are selected to amplify portions of a nucleic acid sequence believed to be conserved (e.g., a catalytic domain, a DNA-binding domain, etc.). Again, nucleic acids are preferably amplified from a tissue-specific library (e.g., breast). One also can use expression cloning utilizing the antisera described herein to identify nucleic acids that encode related antigenic proteins in humans or other species using the SEREX procedure to screen the appropriate expression libraries. (See: Sahin et al. *Proc. Natl. Acad. Sci. USA* 92:11810-11813, 1995).

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating breast cancer-associated polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1-20 nucleotides). In preferred embodiments, these modified nucleic acid molecules and/or the polypeptides they encode retain at least one activity or function of the unmodified nucleic acid molecule and/or the polypeptides, such as antigenicity, receptor binding, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides nucleic acid molecules that encode antigenic fragments of breast cancer-associated proteins.

Fragments, can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Fragments also can be used to produce fusion proteins for generating antibodies or determining binding of the polypeptide fragments, or for generating immunoassay components. Likewise, fragments can be employed to produce nonfused fragments of the breast cancer-associated polypeptides, useful, for example, in the preparation of antibodies, and in immunoassays. Preferred fragments are antigenic fragments, which are recognized by agents that specifically bind to breast cancer-associated polypeptides. As used herein, breast cancer-associated antibodies, are antibodies that specifically bind to breast cancer-associated polypeptides.

The invention also permits the construction of breast cancer-associated polypeptide gene "knock-outs" or "knock-ins" in cells and in animals, providing materials for studying certain aspects of breast cancer and immune system responses to breast cancer by regulating the expression of breast cancer-associated polypeptides. For example, a knock-in mouse may be constructed and examined for clinical parallels between the model and a breast cancer-infected mouse with upregulated expression of a breast cancer-associated polypeptide, which may be useful to trigger an immune reaction to the polypeptide. Such a cellular or animal model may also be useful for assessing treatment strategies for breast cancer.

Alternative types of animal models for breast cancer may be developed based on the invention. Stimulating an immune response to a breast cancer-associated polypeptide in an animal may provide a model in which to test treatments, and assess the etiology of breast cancers.

The invention also provides isolated polypeptides (including whole proteins and partial proteins) encoded by the foregoing breast cancer-associated nucleic acids. Such polypeptides are useful, for example, alone or as fusion proteins to generate antibodies, and as components of an immunoassay or diagnostic assay. Breast cancer-associated polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, such as breast cancer-associated antigen fragments including antigenic peptides also can be synthesized chemically using well-established methods of peptide synthesis.

Fragments of a polypeptide preferably are those fragments that retain a distinct functional capability of the polypeptide. Functional capabilities that can be retained in a fragment of a polypeptide include interaction with antibodies (e.g. antigenic fragments), interaction with other polypeptides or fragments thereof, selective binding of nucleic acids or proteins, and enzymatic activity. One important activity is the ability to provoke in a subject an immune response. As will be recognized by those skilled in the art, the size of the fragment will depend upon factors such as whether the epitope recognized by an antibody is a linear epitope or a conformational epitope. Thus, some antigenic fragments of breast cancer-associated polypeptides will consist of longer segments while others will consist of shorter segments, (e.g. 5, 6, 7, 8, 9, 10, 11 or 12 or more amino acids long, including each integer up to the full length of the breast cancer-associated polypeptide). Those skilled in the art are well versed in methods for selecting antigenic fragments of proteins. The skilled artisan will also realize that conservative amino acid substitutions may be made in breast cancer-associated polypeptides to provide functionally equivalent variants, or homologs of the foregoing polypeptides, i.e, the variants retain the functional capabilities of the breast cancer-associated antigen polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants or homologs of the breast cancer-associated polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, upon determining that a peptide is a breast cancer-associated polypeptide, one can make conservative amino acid substitutions to the amino acid sequence of the peptide, and still have the polypeptide retain its specific antibody-binding characteristics.

Conservative amino-acid substitutions in the amino acid sequence of breast cancer-associated polypeptides to produce functionally equivalent variants of breast cancer-associated polypeptides typically are made by alteration of a nucleic acid encoding a breast cancer-associated polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a breast cancer-associated polypeptide. Where amino acid substitutions are made to a small unique fragment of a breast cancer-associated polypeptide, such as an antigenic epitope recognized by autologous or allogeneic sera or cytolytic T lymphocytes, the substitutions can be made by directly synthesizing the peptide. The activity of functionally equivalent fragments of breast cancer-associated polypeptides can be tested by cloning the gene encoding the altered breast cancer-associated polypeptide into a bacterial or mammalian expression vector, introducing the vector into an appropriate host cell, expressing the altered polypeptide, and testing for a functional capability of the breast cancer-associated polypeptides as disclosed herein. Peptides that are chemically synthesized can be tested directly for function, e.g., for binding to antisera recognizing associated antigens.

The invention as described herein has a number of uses, some of which are described elsewhere herein. First, the invention permits isolation of the breast cancer-associated protein molecules. A variety of methodologies well-known to the skilled practitioner can be utilized to obtain isolated breast cancer-associated polypeptide molecules. The polypeptide may be purified from cells that naturally produce the polypeptide, by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating breast cancer-associated polypeptides. These include, but are not limited to, immunochromatography, HPLC, size-exclusion chromatography, ion-exchange chromatography, and immune-affinity chromatography.

The isolation and identification of breast cancer-associated polypeptides also permits the artisan to diagnose a disorder characterized by expression of breast cancer-associated polypeptides, and characterized preferably by an immune response against the breast cancer-associated polypeptides.

The methods related to breast cancer-associated polypeptide immune responses involve determining the immune response (antibody or cellular) against one or more breast cancer-associated polypeptides. The immune response can be assayed by any of the various immunoassay methodologies known to one of ordinary skill in the art. For example, the antigenic breast cancer-associated polypeptides can be used as a target to capture antibodies from a sample, such as a blood sample drawn from a patient in an ELISA assay.

The methods related to breast cancer-associated polypeptide expression involve determining expression of one or more breast cancer-associated nucleic acids, and/or encoded breast cancer-associated polypeptides and/or peptides derived therefrom and comparing the expression with that in a breast cancer-free subject. Such determinations can be carried out via any standard nucleic acid determination assay, including the polymerase chain reaction, or assaying with labeled hybridization probes. Such hybridization methods include, but are not limited to microarray techniques.

The invention also makes it possible to isolate proteins that specifically bind to breast cancer-associated antigens as disclosed herein, including antibodies and cellular binding partners of the breast cancer-associated polypeptides. Additional uses are described further herein.

The invention also involves agents such as polypeptides that bind to breast cancer-associated polypeptides. Such binding agents can be used, for example, in screening assays to detect the presence or absence of breast cancer-associated polypeptides and complexes of breast cancer-associated polypeptides and their binding partners and in purification protocols to isolate breast cancer-associated polypeptides and complexes of breast cancer-associated polypeptides and their binding partners. Such agents also may be used to inhibit the native activity of the breast cancer-associated polypeptides, for example, by binding to such polypeptides.

The invention, therefore, embraces peptide binding agents which, for example, can be antibodies or fragments of antibodies having the ability to selectively bind to breast cancer-associated polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complimentarily determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complimentarily determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to breast cancer-associated polypeptides, and complexes of both breast cancer-associated polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the breast cancer-associated polypeptide. This process can be repeated through several cycles of reselection of phage that bind to the breast cancer-associated polypeptide. Repeated rounds lead to enrichment of phage bearing particular sequences. DNA sequence analysis can be conducted to identify the sequences of the expressed polypeptides. The minimal linear portion of the sequence that binds to the breast cancer-associated polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the breast cancer-associated polypeptides.

Thus, the breast cancer-associated polypeptides of the invention, including fragments thereof, can be used to screen peptide libraries, including phage display libraries, to identify and select peptide binding partners of the breast cancer-associated polypeptides of the invention. Such molecules can be used, as described, for screening assays, for purification protocols, for interfering directly with the functioning of breast cancer-associated polypeptides and for other purposes that will be apparent to those of ordinary skill in the art. For example, isolated breast cancer-associated polypeptides can be attached to a substrate (e.g., chromatographic media, such as polystyrene beads, or a filter), and then a solution suspected of containing the binding partner may be applied to the substrate. If a binding partner that can interact with breast cancer-associated polypeptides is present in the solution, then it will bind to the substrate-bound breast cancer-associated polypeptide. The binding partner then may be isolated.

As detailed herein, the foregoing antibodies and other binding molecules may be used for example, to identify tissues expressing protein or to purify protein. Antibodies also may be coupled to specific diagnostic labeling agents for imaging of cells and tissues that express breast cancer-associated polypeptides or to therapeutically useful agents according to standard coupling procedures. Diagnostic agents include, but are not limited to, barium sulfate, iocetamic acid, iopanoic acid, ipodate calcium, diatrizoate sodium, diatrizoate melamine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium.

The invention also includes methods to monitor the onset, progression, or regression of breast cancer in a subject by, for example, obtaining samples at sequential times from a subject and assaying such samples for the presence and/or absence of an antigenic response that is a marker of the condition. A subject may be suspected of having breast cancer or may be believed not to have breast cancer and in the latter case, the sample may serve as a normal baseline level for comparison with subsequent samples.

Onset of a condition is the initiation of the changes associated with the condition in a subject. Such changes may be evidenced by physiological symptoms, or may be clinically asymptomatic. For example, the onset of breast cancer may be followed by a period during which there may be breast cancer-associated physiological changes in the subject, even though clinical symptoms may not be evident at that time. The progression of a condition follows onset and is the advancement of the physiological elements of the condition, which may or may not be marked by an increase in clinical symptoms. In contrast, the regression of a condition is a decrease in physiological characteristics of the condition, perhaps with a parallel reduction in symptoms, and may result from a treatment or may be a natural reversal in the condition.

A marker for breast cancer may be the specific binding of a breast cancer-associated polypeptide with an antibody. Onset of a breast cancer condition may be indicated by the appearance of such a marker(s) in a subject's samples where there was no such marker(s) determined previously. For example, if marker(s) for breast cancer are determined not to be present in a first sample from a subject, and breast cancer marker(s) are determined to be present in a second or subsequent sample from the subject, it may indicate the onset of cancer.

Progression and regression of a breast cancer condition may be generally indicated by the increase or decrease, respectively, of marker(s) in a subject's samples over time. For example, if marker(s) for breast cancer are determined to be present in a first sample from a subject and additional marker(s) or more of the initial marker(s) for breast cancer are determined to be present in a second or subsequent sample from the subject, it may indicate the progression of cancer. Regression of cancer may be indicated by finding that marker(s) determined to be present in a sample from a subject are not determined to be found, or found at lower amounts in a second or subsequent sample from the subject.

The progression and regression of a breast cancer condition may also be indicated based on characteristics of the breast cancer-associated polypeptides determined in the subject. For example, some breast cancer-associated polypeptides may be abnormally expressed at specific stages of breast cancer (e.g. early-stage breast cancer-associated polypeptides; mid-stage breast cancer-associated polypeptides; and late-stage breast cancer-associated polypeptides). Another example, although not intended to be limiting, is that breast cancer-associated polypeptides may be differentially expressed in primary tumors versus metastases, thereby allowing the stage and/or diagnostic level of the disease to be established, based on the identification of selected breast cancer-associated polypeptides in a subject sample.

Another method of staging breast cancer may be based on variation in a subject's immune response to breast cancer-associated polypeptides, which may or may not be abnormally expressed in the subject. Variability in the immune response to the polypeptides may be used to indicate the stage of breast cancer in a subject, for example, some breast cancer-associated polypeptides may trigger an immune response at different stages of the breast cancer than that triggered by other breast cancer-associated polypeptides.

Different types of breast cancer, including, but not limited to: ductal carcinoma in situ (DCIS), invasive ductal carcinoma (IDC), invasive lobular carcinoma (ILC), invasive pleomorphic lobular carcinoma, inflammatory breast cancer, medullary carcinoma, mucinous carcinoma (also known as colloid carcinoma), Paget's disease of the nipple, Phyllodes tumor, tubular carcinoma, and adenocarcinoma, may express different breast cancer-associated polypeptides and the encoding nucleic acid molecules thereof, or may have different spatial or temporal expression patterns. Such variations may allow cancer-specific diagnosis and subsequent treatment tailored to the patient's specific condition. These breast cancer-specific diagnoses may also be based on the variations in immune responses to the different breast cancer-associated polypeptides.

The invention includes kits for assaying the presence of breast cancer-associated polypeptides and/or antibodies that specifically bind to breast cancer-associated polypeptides. An example of such a kit may include the above-mentioned polypeptides bound to a substrate, for example a dipstick, which is dipped into a blood or body fluid sample of a subject. The surface of the substrate may then be processed using procedures well known to those of skill in the art, to assess whether specific binding occurred between the polypeptides and agents (e.g. antibodies) in the subject's sample. For example, procedures may include, but are not limited to, contact with a secondary antibody, or other method that indicates the presence of specific binding.

Another example of a kit may include an antibody or antigen-binding fragment thereof, that binds specifically to a breast cancer-associated polypeptide. The antibody or antigen-binding fragment thereof, may be applied to a tissue or cell sample from a patient with breast cancer and the sample then processed to assess whether specific binding occurs between the antibody and a polypeptide or other component of the sample. In addition, the antibody or antigen-binding fragment thereof, may be applied to a body fluid sample, such as breast discharge fluid or lymph node fluid, from a subject, either suspected of having breast cancer, diagnosed with breast cancer, or believed to be free of breast cancer. As will be understood by one of skill in the art, such binding assays may also be performed with a sample or object contacted with an antibody and/or breast cancer-associated polypeptide that is in solution, for example in a 96-well plate or applied directly to an object surface.

The foregoing kits can include instructions or other printed material on how to use the various components of the kits for diagnostic purposes.

The invention further includes nucleic acid or protein microarrays with breast cancer-associated peptides or nucleic acids encoding such polypeptides. In this aspect of the invention, standard techniques of microarray technology are utilized to assess expression of the breast cancer-associated polypeptides and/or identify biological constituents that bind such polypeptides. The constituents of biological samples include antibodies, lymphocytes (particularly T lymphocytes), and the like. Protein microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485):1760-1763, 2000. Nucleic acid arrays, particularly arrays that bind breast cancer-associated peptides, also can be used for diagnostic applications, such as for identifying subjects that have a condition characterized by breast cancer-associated polypeptide expression.

Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate.

Targets are peptides or proteins and may be natural or synthetic. The tissue may be obtained from a subject or may be grown in culture (e.g. from a cell line). In some embodiments of the invention, one or more control peptide or protein molecules are attached to the substrate. Preferably, control peptide or protein molecules allow determination of factors such as peptide or protein quality and binding characteristics, reagent quality and effectiveness, hybridization success, and analysis thresholds and success.

Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast, Nature Genetics*, Vol.21, January 1999, the entire contents of which is incorporated by reference herein.

According to the present invention, nucleic acid microarray substrates may include but are not limited to glass, silica, aluminosilicates, borosilicates, metal oxides such as alumina and nickel oxide, various clays, nitrocellulose, or nylon. In all embodiments, a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of more than two of the breast cancer-associated polypeptide nucleic acid molecules set forth herein, or one of the novel breast cancer-associated polypeptide nucleic acid molecules as described herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or oligonucleotide to the substrate. These agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium. In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezo-electric delivery. Probes may be covalently linked to the substrate with methods that include, but are not limited to, UV-irradiation. In another embodiment probes are linked to the substrate with heat.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

In some embodiments, one or more control nucleic acid molecules are attached to the substrate. Preferably, control nucleic acid molecules allow determination of factors such as binding characteristics, reagent quality and effectiveness, hybridization success, and analysis thresholds and success.

EXAMPLES

Example 1

Methods

Construction of cDNA Libraries

Tumor samples from breast cancer patients 184 (invasive ductal carcinoma), 297 (invasive ductal carcinoma), 257 (invasive ductal carcinoma), and 263 (invasive pleomorphic lobular carcinoma) were obtained as surgical specimens and used in the construction of cDNA libraries. A cDNA library was also prepared from the SK-BR-3 breast cancer cell line (ATCC #HTB-30). Total RNA was prepared by the guanidinium thiocyanate method and purified to poly $A^+$ RNA using the Dynabeads mRNA Purification Kit (Dynal, Lake Success, N.Y. Two bacteriophage expression vectors were utilized; the lambda ZAP vector (Stratagene, La Jolla, Calif.) was used for cDNA derived from the tumor of patient 184 and the SK-BR-3 cell line, and the lambda TRIPLX vector (Clontech Laboratories Inc., Palo Ala, Calif.) was used for cDNA derived from the tumors of patients 297, 257 and 263). Manufacturers' protocols were used for cDNA synthesis and ligation into appropriate vectors. Following in vitro packaging, libraries containing 1-2×$10^6$ primary recombinants were obtained. cDNA libraries were not amplified prior to immunoscreening.

Immunoscreening

Sera were obtained from individuals undergoing diagnostic or therapeutic procedures.

To remove antibodies reactive with vector-related antigens, sera (1:10 dilution) were absorbed by passage through columns containing Sepharose 4B coupled to lysates of *E. coli* Y1090 and bacteriophage infected *E. coli* BNN97 (5 Prime→3 Prime, Inc., Boulder, Colo.), followed by a 15 hour incubation with nitrocellulose filters precoated with proteins derived it from *E. coli* and *E.coli*/phage lysates (mock experimental membranes). Library screenings W were performed as described in Scanlan, et al., *Int. J. Cancer* 76:652-658 (1998) and Scanlan, et al., *Int. J. Cancer* 83:456-64, (1999), using preabsorbed patient sera at a dilution of 1:200. A total of 5-6×$10^5$ recombinants were screened per cDNA library. Serum reactive phage clones were converted to plasmid forms by in vivo excision. Plasmid DNA was sequenced at the Cornell University DNA Service (Ithaca, N.Y.) using an ABI Prism automated DNA sequencer (Applied Biosystems, Foster City, Calif.).

Two assays were employed to determine allogeneic serum reactivity. In the case of allogeneic sera derived from breast cancer patients and normal individuals, a previously described plaque assay was used (See Scanlan, et al., *Int. J. Cancer* 76:652-658 1998; Scanlan, et al., *Int. J. Cancer* 83:456-64, 1999). Briefly, 1500 pfu of monoclonal phage encoding individual serologically defined breast cancer antigens were mixed with an equal number of negative control phage (phage without cDNA inserts) and used to infect exponentially growing *E. coli* XL-1 Blue MRF' (Stratagene). Following a 15 hour amplification phase, plaque-derived proteins were transferred to 47 mm nitrocellulose membrane discs and tested for reactivity with individual serum samples (1:200 dilution).

Subsequent screening of serum samples from patients with other forms of cancer (lung, colon, ovarian, esophageal) was carried out using a modification of the plaque assay, termed a spot assay. In this method, 80×120 mm nitrocellulose membranes were precoated with a film of NZY/0.7% Agarose/2.5 mM IPTG and placed on a reservoir layer of NZY/0.7% Agarose in a 86×128 mm Omni Tray (Nalge Nunc International Corp., Naperville, Ill.). Approximately $1.0\times10^5$ pfu of monoclonal phage encoding individual serologically defined breast cancer antigens, in a volume of 20 μl, were mixed with 20 μl of exponentially growing *E. coli* XL-1 Blue MRF and spotted (0.7 μl aliquots) on the precoated nitrocellulose membranes. Membranes were incubated for 15 hours at 37° C. A total of 46 different serologically defined breast cancer antigens were spotted in duplicate per nitrocellulose membrane. The agarose film was then removed from the membrane and the filters were processed for reactivity with individual serum samples (1:200 dilution), as described in Scanlan, et al., *Int. J. Cancer* 76:652-658 (1998) and Scanlan, et al., *Int. J. Cancer* 83:456-64, (1999). Serum reactivity detected by the spot assay was verified in the plaque assay, and both assays appear to have comparable specificity and sensitivity.

Northern Blot Analysis and Standard Reverse Transcription (RT)-PCR

Northern blots containing normal tissue poly $A^+$ RNA (2 μg/lane) were obtained commercially (Clontech Laboratories, Inc., Palo Alto, Calif.). Random-primed $^{32}P$ labeled probes consisting of 300-600 bp PCR products from coding sequences of selected seroreactive cDNA clones were hybridized for 1.5 hours in ExpressHyb (Clontech Laboratories) at 68° C., and washed at high stringency (2 times, 30 min. each, 0.1×SSC/0.1% SDS at 65° C.). The resultant Northern blots were developed with Biomax MS autoradiography films (Eastman Kodak Co., Rochester, N.Y.).

The mRNA expression pattern of a selected set of serologically defined breast cancer antigens was also determined by standard RT-PCR, using a panel of normal tissue RNA from lung, testis, small intestine, breast, liver, and placenta (Clontech Laboratories). The cDNA preparations used as templates in the RT-PCR reactions were synthesized using MuLV reverse transcriptase as described in Scanlan, et al., *Int. J. Cancer* 83:456-64, (1999). As a control for genomic DNA contamination, all cDNA synthesis reactions were set up in duplicate with additional samples lacking reverse transcriptase. The cDNA was then amplified by PCR (30 cycles), using gene specific primers (Gibco, BRL, Grand Island, N.Y.) and AmpliTaq Gold DNA polymerase (Applied Biosystems, Foster City, Calif.), as described in Scanlan, et al., *Int. J. Cancer* 83:456-64, (1999).

Real-Time Quantitative Reverse Transcription-PCR

Total RNA from ten different breast cancer specimens was prepared by the guanidinium thiocyanate method using standard procedures. Total RNA from normal breast consisted of a pool of RNA from two healthy individuals (Clontech Laboratories). RNA (1 μg) was reverse transcribed into cDNA using the TaqMan EZ RT-PCR kit (PE Biosystems). As a control for genomic DNA contamination, all cDNA synthesis reactions were set up in duplicate with additional samples lacking reverse transcriptase. Reagents were purchased from Applied Biosystems, except where noted. Multiplex PCR reactions were prepared using 2.5 μl of cDNA diluted in TaqMan Universal PCR Master Mix supplemented with VIC—(Applied Biosystems proprietary dye) labeled human beta glucuronidase endogenous control probe/primer mix, 200 nM FAM (6-carboxy-fluorescein) labeled gene-specific TaqMan probe, and a predetermined, optimum concentration of corresponding gene-specific forward and reverse primers (300-900 nM). Triplicate PCR reactions were prepared for each cDNA sample. PCR consisted of 40 cycles of 95° C. denaturation (15 seconds) and 60° C. annealing/extension (60 seconds). Thermal cycling and fluorescent monitoring were performed using an ABI 7700 sequence analyzer (Applied Biosystems). The point at which the PCR product was first detected above a fixed threshold, termed cycle threshold (Ct), was determined, and normalized against the Ct value of the endogenous control product (ΔCt=Ct FAM−Ct VIC). The quantity of gene-specific transcripts present in the breast cancer cDNA samples relative to normal breast tissue was calculated by comparing the normalized cycle thresholds in tumor with non-malignant breast tissue (ΔΔCt=ΔCt of tumor−ΔCt of normal breast), and determining the relative concentration (Relative Concentration=$2^{-\Delta\Delta Ct}$).

In addition, a selected set of FAM-labeled gene-specific TaqMan probe/primer combinations were used to amplify a panel of 14 normal tissue cDNA preparations, which had been normalized against 6 housekeeping genes and purported to be virtually free of genomic DNA (Clontech Laboratories). The relative abundance of gene-specific transcripts in normal tissues was determined by comparison with a standard curve generated from the Ct values of known concentrations of plasmid DNA containing the relevant gene. Because cDNA derived from normal breast tissue was not included in the commercially obtained panel, a cDNA preparation derived from normal breast tissue (see above) was normalized according to the Ct values for beta glucuronidase, and the concentration of gene-specific transcripts in normal breast tissue was also calculated relative to its expression in testis, using the formula described above.

Results

Identification of Human Breast Cancer Antigens by SEREX Analysis

Serum samples from six individuals with breast cancer were used to immunoscreen tumor-derived cDNA expression libraries via the SEREX method. In four of the six cases, autologous patient sera were used to screen cDNA libraries prepared from the corresponding primary breast cancer. In the other two cases, allogeneic patient sera were used to screen a cDNA library prepared from the SK-BR-3 cell line. As shown in Table 1, ninety-four serologically defined breast cancer antigens were identified. They were designated NY-BR-8 through NY-BR-101.

TABLE 1

Immunoscreening of cDNA Expression Libraries from Breast Cancer with Autologous and Allogeneic Patient Sera (SEREX)

| Tumor Type | Serum Source | Breast Cancer cDNA Library Designation | Number of Distinct Antigens Identified by SEREX (Known[1]/Novel[2]) | Antigens with Non-Cancer Related Serological Profiles | Antigens with Cancer-related Serological Profiles |
|---|---|---|---|---|---|
| Invasive ductal carcinoma | Autologous | 184 | 17 (12/5) | 13 | 4 |
| Invasive ductal carcinoma | Autologous | 297 | 6 (6/0) | 5 | 1 |
| Invasive ductal carcinoma | Autologous | 257 | 9 (8/1) | 4 | 5 |
| Invasive pleomorphic lobular carcinoma | Autologous | 263 | 13 (9/4) | 5 | 8 |
| SK-BR-3 (established breast cancer cell line) | Allogeneic-1 | 9993 | 34 (27/7) | 14 | 20 |
| SK-BR-3 | Allogeneic-2 | 9993 | 15 (12/3) | 9 | 6 |
| Totals | | | 94 (74/20) | 50 | 44 |

[1]Identical to GenBank Entries.
[2]Identities limited to expressed sequence tags (ESTs)

These 94 antigens (Tables 2 through 4) represent 74 known gene products and 17 novel proteins, and could be categorized on the basis of cellular localization, subcellular targeting motifs, known function, or sequence similarities.

TABLE 2

SEREX-Defined Breast Cancer Antigens: Reactivity with Sera From Normal Individuals

| NY-BR-Antigen | Identity/Similarities (Unigene cluster) | SEREX Database ID Number[1] of Equivalent Isolate (Tumor Source[2]) | Reactivity with Normal Sera | Reactivity with Breast Cancer Sera |
|---|---|---|---|---|
| | | Known Gene Products | | |
| 8 | H2K binding factor 2 (Hs.278573) | 439 (RC), 1201 (MEL), 8 (GC) | 1/16 | 2/10 |
| 13 | Zuotin related factor 1 (Hs.82254) | 6 (GC) | 3/12 | 3/10 |
| 17 | NP220 (Hs.169984) | 1531 (OC) | 1/12 | 2/10 |
| 22 | Protein phosphatase 1B (Hs.5687) | | 1/12 | 1/10 |
| 23 | DKFZp434L0117 (Hs.63795) | | 1/12 | 1/10 |
| 27 | MHC Class 1 HLA Cw-0304 (Hs.277477) | | 4/25 | 2/25 |
| 29 | Proteosome subunit p112 (Hs.3887) | | 6/12 | 4/10 |
| 30 | GPDH (Hs.169476) | | 4/12 | 3/10 |
| 32 | Ribosomal protein L34 (Hs.250895) | | 2/25 | 2/25 |
| 35 | VEGFB (Hs.78781) | | 1/12 | 2/10 |
| 36 | COL6A2 (Hs.4217) | | 4/19 | 6/20 |
| 42 | Vacuolar sorting protein 45B (Hs.6650) | | 1/17 | 1/25 |
| 43 | Defender against cell death-1 (Hs.82890) | | 8/25 | 5/25 |
| 50 | Sphingosine-1-phosphate lyase 1 (Hs.186613) | | 7/12 | 5/10 |
| 60 | HIP-55 (Hs.180766) | | 2/25 | 1/25 |
| 61 | TGFB1 anti-apoptotic factor-1 (Hs.75822) | 1057 (BC) | 1/25 | 2/25 |
| 66 | FBI-1 (Hs.104640) | | 1/20 | 2/20 |
| 68 | Heme oxygenase 2 (Hs.63908) | | 2/20 | 2/20 |
| 70 | KIAA0713 protein (Hs.88756) | 159 (LC) | 1/20 | 4/20 |
| 71 | KIAA1002 protein (Hs.102483) | | 2/20 | 4/20 |
| 74 | U2 snRNP auxiliary factor-2 (Hs.103962) | 786 (HD), 430 (RC) | 5/16 | 1/20 |
| 78 | RNA helicase-related protein (Hs.8765) | | 3/25 | 1/25 |
| 80 | TCP1 ring complex pp 5 (Hs.1708) | | 1/20 | 1/20 |
| 82 | KIAA0801 protein (Hs.17585) | | 1/20 | 3/20 |
| 88 | Talin (Hs.278559) | 608 (PC) | 1/20 | 1/20 |
| 89 | Candidate of metastasis 1 (Hs.8603) | | 1/20 | 1/20 |
| 90 | NAP-22 (Hs.79516) | | 1/20 | 2/20 |
| 95 | KIAA0376 protein (Hs.4791) | 1777 (CC), 357 (RC), 551 (GC), 955 (BC) | 11/20 | 11/20 |
| 100 | BRACA-1 AP 2 (Hs.122764) | 1785 (CC), 1158 (RC), 190 (PC), 1616 (OC), 807 (BC) | 2/19 | 2/20 |
| | | Novel Gene Products | | |
| 15 | Putative nuclear protein (Hs.178175) | | 1/12 | 1/10 |
| 16 | Similar to Ankyrin (Hs.190251) | 1792 (CC) | 4/12 | 6/10 |
| 18 | RNA splicing factor similarity (Hs.11065) | | 2/12 | 1/10 |
| 20 | Similar to calmodulin (Hs.239812) | | 1/12 | 1/10 |
| 24 | Similar to CDC 10 proteins (Hs.99741) | | 1/12 | 1/10 |
| 40 | None (Hs.149190) | | 1/12 | 2/10 |
| 81 | Phospholipase C beta similarity (Hs.75280) | | 1/20 | 1/20 |

TABLE 2-continued

SEREX-Defined Breast Cancer Antigens: Reactivity with Sera From Normal Individuals

| NY-BR-Antigen | Identity/Similarities (Unigene cluster) | SEREX Database ID Number[1] of Equivalent Isolate (Tumor Source[2]) | Reactivity with Normal Sera | Reactivity with Breast Cancer Sera |
|---|---|---|---|---|
| 86 | Oxysterol binding protein similarity (Hs.233495) | 319 (GC) | 2/17 | 2/20 |
| 87 | 2 possible reading frames (Hs.18946) | | 1/25 | 1/25 |

[1]SEREX database ID number from http://www.licr.org/SEREX.html.
[2]Abbreviations: BC, breast cancer; CC, colon cancer; HD, Hodgkin's disease; GC, gastric cancer; LC, lung cancer; MEL, melanoma; OC, ovarian cancer; PC, prostate cancer; RC, renal cancer

TABLE 3

SEREX-Defined Breast Cancer Antigens: Antigens Associated with Autoimmune Disease

| NY-BR-Antigen | Identity (Unigene Cluster) | SEREX Database ID Number[1] of Equivalent Isolate (Tumor Source[2]) | Autoimmunue Disease Associations[3] | Reactivity with Normal Sera | Reactivity with Breast Cancer Sera |
|---|---|---|---|---|---|
| 9 | Ifn inducible autoantigen 16 (Hs.155530) | | SLE | 1/12 | 1/10 |
| 12 | RNA pol. II 23kDa subunit (Hs.24301) | | SLE, PSS | 1/12 | 1/10 |
| 14 | Proteasome activator subunit 3/Ki nuclear autoantigen (Hs.152978) | | SLE | 1/12 | 1/10 |
| 28 | Glutathione S-transferase theta-1 (Hs.77490) | | AH | 1/12 | 2/10 |
| 31 | Ribosomal phosphoprotein P1 (Hs.177592) | | SLE | 5/25 | 2/25 |
| 39 | DBI-related protein (Hs.15250) | 244 (RC), 1328 (GC), 1031 (BC) | AD | 1/16 | 1/12 |
| 47 | Dynamin 1-like protein (Hs.180628) | | Sclero | 0/20 | 1/20 |
| 58 | Aldolase A (Hs.273415) | 79 (LC) | RA | 0/20 | 1/20 |
| 59 | PARP (Hs.177766) | 432 (CC), 698 (RC) 939 (BC) | SLE, SS, RA, PSS | 1/18 | 1/20 |
| 64 | Alanyl-tRNA synthetase (Hs.75102) | 471 (RC) | PM | 0/20 | 1/20 |
| 65 | Nuclear matrix protein 238 (Hs.272822) | | PM, AH | 0/20 | 1/20 |
| 69 | Centromere protein F (Hs.77204) | 626 (PC), 1557 (EC), 809 (BC) | SLE, Sclero | 8/20 | 1/20 |
| 91 | U1 snRNP (Hs.180789) | 24 (GC), 349 (CC), 1267 (RC), 751 (BC) | SLE, SS, RA, PM, Sclero | 3/20 | 6/20 |
| 93 | Human autoantigen (Hs.75682) | | SS, SLE, Sclero, RA | 0/20 | 1/20 |
| 97 | Sjogren syndrome antigen A1 (Hs.1042) | | SS, SLE | 0/20 | 1/20 |
| 101 | Vinculin (Hs.75350) | 1288 (BC) | thrombocytopenia | 0/20 | 1/20 |

[1]SEREX database ID number from http://www.licr.org/SEREX.html.
[2]Tumor tissue abbreviations: BC, breast cancer; CC, colon cancer; EC, esophageal cancer; GC, gastric cancer; LC, lung cancer; _____, no additional isolates; PC, prostate cancer; RC, renal cancer.
[3]Autoimmune disease abbreviations; AH, autoimmune hepatitis; AD, autoimmune diabetes; PM, polymyositis; PSS, Progressive Systemic Sclerosis; RA, Rheumatoid Arthritis; Sclero, scleroderma; SLE, systemic lupus erythematosus; SS, Sjogren's Syndrome

TABLE 4

SEREX-Defined Breast Cancer Antigens: Antigens Detected with Sera from a Single Breast Cancer Patient[1]

| NY-BR-Antigen | Identity/Similarities/Motifs (Unigene cluster) |
|---|---|
| | Known Gene Products |
| 10 | Desmoplakin I (Hs.74316) |
| 11 | RING 3 gene product (Hs.75243) |
| 19 | CGI-149 protein (Hs.241266) |
| 21 | KIAA0708 (Hs.117177) |
| 26 | Modulator recognition factor (Hs.920) |
| 33 | GSPTI (Hs.2707) |
| 37 | HRIHFB2157 gene product (Hs.4552) |
| 44 | BMAL1e protein (Hs.74515) |
| 48 | Sorting nexin 6 (Hs.76127) |
| 52 | Transcriptional activator SRCAP (Hs.87908) |
| 54 | SOM172 gene product (Hs.100623) |
| 67 | TIS11D gene product (Hs.78909) |
| 76 | MAGE A3 (Hs.36978) |
| 77 | SMRT corepressor (Hs.120980) |
| 83 | KIAA0081 protein. (Hs.78871) |
| 92 | Ribosomal protein L10 (Hs.29797) |

TABLE 4-continued

SEREX-Defined Breast Cancer Antigens: Antigens Detected with Sera from a Single Breast Cancer Patient[1]

| NY-BR-Antigen | Identity/Similarities/Motifs (Unigene cluster) |
|---|---|
| | Novel Gene Products |
| 38 | SCR repeat domain (not clustered) |
| 46 | None (not clustered) |
| 49 | Ankyrin repeat domain (Hs.55565) |
| 51 | None (Hs.128685) |
| 73 | Similar to coatomer proteins (Hs.217001) |
| 85 | Nuclear localization signals (Hs.105153) |
| 84 | Transmembrane domain (Hs.206196) |
| 99 | RNA splicing factors similarity (Hs.183438) |

[1]Antigens reacted with sera from single breast cancer patients (1/25), but not with sera from normal individuals (0/25), colon cancer patients (0/19), lung cancer patients (0/15), ovarian cancer patients (0/15) or esophageal cancer patients (0/15), and no equivalent isolates of these antigens were found in the SEREX database.

Thirty-nine antigens were known or predicted nuclear proteins, and include DNA binding proteins (e.g., BR-8, -21, -55, and -66), transcription factors (e.g., BR-11, -52, -77, and -79), RNA binding proteins (e.g., BR-17, -18, -74 and -91), and RNA/DNA helicases (BR-65, -78 and -82).

Twenty-four antigens were known or predicted cytoplasmic proteins, and include metabolic enzymes (e.g., BR-28, -30, -39 and -58), ribosomal proteins (e.g., BR-31, -32, -64 and -92), cytoskeletal proteins (BR-10, -88 and -101), sorting proteins (e.g., BR-42, -44, -48 and -80), adaptor proteins (BR-34 and BR-41) and proteins involved in the ubiquitin pathway (BR-29 and BR-37). Six antigens localized to the plasma membrane (BR-27, -43, -56, -57, -82 and -90) and two were extracellular gene products (BR-35 and BR-36). The nucleotide sequences of all novel clones have been deposited in the GenBank database (sequential accession numbers AF308284-AF308300). The cDNA sequences coding for the 94 antigens identified in this study were also compared to sequences deposited in the SEREX database, which can be accessed at the Ludwig Institute for Cancer Research web site at: http:/www.licr.org/SEREX.html. Examination of this database revealed that 25 of the 94 breast cancer antigens defined in this study (26%) were also identified through SEREX analysis of breast cancer and other tumor types (Tables 2, 3 and 5).

single breast cancer patient; b) antigens that reacted exclusively with sera from two or more breast cancer patients; and c) antigens that reacted with sera from patients having other forms of cancer in addition to breast cancer patients. Of the 40 antigens having a cancer-related serological profile, 24 antigens reacted with sera from only one breast cancer patient, either the autologous patient or a single allogeneic patient, and are listed in Table 4. Sixteen of the 40 antigens having a cancer-related serological profile reacted with sera from more than one cancer patient (breast cancer patients and/or patients with other tumor types), and are listed in Table 5. Four of these antigens [gC1Q/BR-56, Her2neu/BR-57, BR-62, and tumor protein D52 (TPD52)/BR-63] reacted with sera from more than one breast cancer patient, but not with sera from patients with other forms of cancer. The remaining antigens listed in Table 5 react with sera from both breast cancer patients and individuals with other forms of cancer. In terms of known tumor antigens, LAGE-1/BR-53, a cancer-testis antigen highly homologous to NY-ESO-1, was isolated in the current study. In accordance with results

TABLE 5

SEREX-Defined Breast Cancer Antigens: Antigens Reactive with Sera from Breast Cancer Patients and Patients with Other Forms of Cancer[1]

| NY-BR-Antigen | Identity/Similarities/Motifs (Unigene Cluster) | SEREX Database ID Number[2] of Equivalent Isolate (Tumor Source[3]) | Seroreactivity Breast Cancer | Colon Cancer | Lung Cancer | Ovarian Cancer | Esophageal Cancer |
|---|---|---|---|---|---|---|---|
| 25 | KIAA0854 protein, (Hs.30209) | 128 (RC) | 1/25 | 1/19 | 0/15 | 1/15 | 0/15 |
| 34 | SHB adaptor protein (Hs.173752) | | 1/25 | 0/19 | 0/15 | 1/15 | 0/15 |
| 41 | SNT-1 adaptor (Hs.251394) | | 1/25 | 0/19 | 1/15 | 0/15 | 0/15 |
| 45 | Kinesin 2 (Hs.117977) | 332 (GC), 96 (SM), 797 (RC) | 2/25 | 0/19 | 0/15 | 0/15 | 0/15 |
| 53 | LAGE-1[4] (Hs.167379) | | 4/25 | 1/19 | 2/15 | 1/15 | 2/15 |
| 55 | Nucleosome assembly protein-1 (Hs.179662) | 126 (RC), 1137 (MEL) | 1/25 | 1/19 | 1/15 | 0/15 | 0/15 |
| 56 | gC1Q binding protein (Hs.78614) | | 2/25 | 0/19 | 0/15 | 0/15 | 0/15 |
| 57 | HER2 nue/erbB2 (Hs.173664) | | 2/25 | 0/19 | 0/15 | 0/15 | 0/15 |
| 62 | Novel, kinesin similarity (Hs.278323) | | 2/25 | 0/19 | 0/15 | 0/15 | 0/15 |
| 63 | Tumor protein D52 (Hs.2384) | | 2/25 | 0/19 | 0/15 | 0/15 | 0/15 |
| 72 | MAGE A6 (Hs.198263) | | 1/25 | 0/19 | 0/15 | 1/15 | 0/15 |
| 75 | Novel (Hs.5111) | 1184 (MEL) | 2/25 | 0/19 | 0/15 | 0/15 | 1/15 |
| 79 | Tata element modulatory factor 1 (Hs.74985) | 246 (GC) | 1/25 | 0/19 | 0/15 | 0/15 | 0/15 |
| 94 | Tumor protein p53 (Hs.1846) | 33 (CC) | 1/25 | 3/19 | 0/15 | 1/15 | 2/15 |
| 96 | Novel, S/T kinase domain (Hs.4789) | 296 (MEL) | 2/25 | 0/19 | 0/15 | 0/15 | 0/15 |
| 98 | MAGE D (Hs.4943) | | 3/25 | 0/19 | 1/15 | 0/15 | 0/15 |

[1]Antigens did not react with sera from normal individuals (0/25).
[2]SEREX database ID number from http://www.licr.org/SEREX.html.
[3]Abbreviations: BC, breast cancer; CC, colon cancer; GC, gastric cancer; MEL, melanoma; ____, no additional isolates; RC, renal cancer; SM, seminoma.
[4]Assays for LAGE-1 seroreactivity were performed using a recombinant phage expressing the highly homologous NY-ESO-1 protein.

Reactivity Patterns of Sera from Normal Individuals and Cancer Patients with SEREX-Defined Breast Cancer Antigens To determine whether immune recognition of the isolated antigens was cancer related, allogeneic sera samples obtained from 25 normal blood donors and 24 additional patients with breast cancer were tested for reactivity against the panel of antigens using the plaque assay. Fifty four of the 94 antigens (57%) had a serological profile that was not restricted to cancer patients, as evidenced by their reactivity with normal sera (Tables 1 and 2), or their known association with autoimmune disease (Tables 1 and 3). The remaining 40 antigens had a cancer-related serological profile, reacting only with sera from cancer patients (Tables 1,4 and5).

The 40 antigens having a cancer-related serological profile were further tested for reactivity with serum panels from colon, lung, ovarian, and esophageal cancer patients using the spot assay, and the following seroreactivity patterns were defined: a) antigens that reacted with serum from only a of previous serologic surveys (see: Stockert, et al., *J. Exp Med.* 187:1349-54, 1998), LAGE-1/NY-ESO-1 had the highest frequency of cancer-related seroreactivity; antibody responses were detected in patients with breast (4/20), colon (1/19), lung (2/15), ovarian (1/15) and esophageal cancer (2/15). Similarly, a cancer-related serological response was also detected against p53/BR-94 (1/25 breast cancer, 3/19 colon cancer, 1/15 ovarian cancer and 2/15 esophageal cancer patients), and Her2neu/BR-57 (2/25 breast cancers patents), confirming previous surveys of seroreactivity against these antigens (see: Scanlan, et al., *Int. J. Cancer* 76:652-8,1998; Disis, et al., *Cancer Res.* 54:16-20, 1994; Labrecque, et al., *Cancer Res.* 53:3468-71, 1993). In addition, a new set of immunogenic breast cancer antigens was defined in this study, including known proteins such as kinesin 2/BR-45, gC1Q binding protein/BR-56, TPD52/BR-63, and MAGE-D/BR-98, as well as novel gene products such as NY-BR-62, NY-BR-75, and NY-BR-96.

Expression Patterns of mRNA Encoding Serologically Defined Breast Cancer Antigens in Normal Tissues A preliminary in silico mRNA expression profile of all gene products identified in this study was based on the tissue distribution of expressed sequence tags (ESTs) in the human EST database. Products with no EST matches, or those having EST matches limited to tumor tissue, fetal tissue, or a single normal tissue were further examined by Northern blotting and RT-PCR. Gene products with restricted EST profiles include the three well-characterized cancer-testis antigens MAGE-A3/BR-76, MAGE-A6/BR-72 and LAGE-1/BR-53, which are expressed exclusively in normal testis and a range of different tumor types (Chen, et al., *Proc. Natl. Acad. Sci. USA* 94:1914-18, 1997), and four putative tissue-restricted antigens, including a known gene product, SNT-1/BR-41, and 3 novel proteins identified in this study, BR-49, -62, and -85. All seven of these antigens showed a cancer-related serological profile.

The mRNA expression profiles of BR-41, -49, -62, and -85 were examined in Northern blots of non-normalized mRNA preparations derived from 16 different human tissues. Expression of SNT-1/BR-41, BR-62 and BR-85 was restricted to testis, appearing as a 3.2 kB mRNA transcript, a 4.0 kB mRNA transcript, and 2.4 KB and 3.2 KB mRNA transcripts, respectively. Expression of BR-49 was widespread, appearing as a 4.2 kB hybridization signal in 10 of 16 normal tissues (absent in spleen, ovary, PBL, heart, brain, and skeletal muscle). The mRNA expression patterns of BR-41, -49, -62, and -85 were also analyzed by conventional RT-PCR, and transcripts for these 4 gene products were found in all normal tissues tested (lung, testis, small intestine, breast, liver, and placenta).

The detection of BR-41, -62, and -85 mRNA in normal tissues by RT-PCR but not by Northern blotting indicates low-level ubiquitous expression. To examine this further, real-time RT-PCR was used to quantify mRNA expression in a panel of normalized cDNA preparations from 15 different human tissues. PCR amplification of cDNA coding for BR-41, -62, and -85 yielded distinct values for cycle threshold (Ct), which were compared to the Ct values obtained from a set of homologous cDNA standards of known concentration. As shown in FIG. 1, the highest levels of BR-41 mRNA expression (FIG. 1 A) in the normalized cDNA panel were detected in testis (equivalent to 43.8 fg of cDNA) and peripheral blood leukocytes (equivalent to 35.4 fg of cDNA), and lower levels (less 18.0 fg of cDNA) in each of the remaining 12 normal tissues. Because cDNA from normal breast tissue was not included in this commercially obtained cDNA panel, the concentration of BR-41 mRNA in normal mammary gland was calculated relative to normal testis, and determined to be approximately 170 times higher in normal breast tissue compared to testis, and was equivalent 7300 fg of cDNA. The highest levels of BR-62 mRNA expression (FIG. 1B) were detected in normal testis (271 fg of cDNA), thymus (89 fg of cDNA), and colon (20 fg of cDNA), with lower levels (less 6 fg of cDNA) detected in each of the remaining 11 normal tissues. The concentration of BR-62 mRNA in normal breast was equivalent to 0.8 fg of cDNA. The highest levels of BR-85 mRNA expression (FIG. 1C) were detected in normal thymus (54 fg of cDNA) and testis (39 fg of cDNA), while lower levels (less than 16 fg of cDNA) were detected in each of the remaining 12 normal tissues. The concentration of BR-85 mRNA in normal breast was equivalent to 8.0 fg of cDNA.

Expression Levels of mRNA Encoding Serologically Defined Breast Cancer Antigens in Normal and Malignant Breast Tissue The mRNA expression levels of eleven antigens associated with a cancer-related serological response (Table 5) and/or showing differential mRNA expression were measured in 10 breast cancer specimens and normal breast tissue by real-time RT-PCR. The relative level of mRNA expression in breast cancer compared to normal breast tissue was calculated on the basis of differences in normalized Ct values between the two tissues. Overexpression was defined as an mRNA expression level that is three times higher in tumor compared to normal breast tissue. As shown in Table 6, mRNA transcripts encoding 6/10 antigens, BR-56, -57, -62, -63, -85, and -98, were overexpressed in at least one breast cancer specimen. Four of these ten antigens were frequently overexpressed in breast cancer, including Her2neu/BR-57 (3/10 cases), BR-62 (6/10 cases), TPD52/BR-63 (5/10 cases), and BR-85 (9/10 cases). Exceptionally high levels of mRNA expression in breast cancer were associated with Her2neu/BR-57 (107 times that of normal breast in patient # 7), BR-62 (53 times that of normal breast in patient # 8), and TPD52/BR-63 (132 times that of normal breast in patent # 8). In contrast expression of SNT-1/BR-41 mRNA was consistently lower in breast cancer relative to normal breast tissue, with apparent down-regulated expression (defined as an expression level of less than 20% of normal breast) occurring in 7/10 cases. The remaining products, kinesin 2/BR-45, BR-75 and BR-96, had similar mRNA expression levels in tumor and normal breast tissue.

TABLE 6

Quantitative Analysis of mRNA Encoding SEREX Defined Breast Cancer Antigens in Normal and Malignant Breast Tissue: Relation Between mRNA Level and Immunogenicity

| Antigen | Ratio of mRNA in breast cancer to mRNA in normal breast ('+' indicates serum antibody reactivity[1]) | | | | | | | | | |
|---|---|---|---|---|---|---|---|---|---|---|
| | 1 | 2 | 3 | 4 | 5 | 6 | 7 | 8 | 9 | 10[2] |
| BR-41 | 0.01 | 0.19 | 0.04 | 0.26 | 0.38 | 0.11 | 0.10 | 0.86 | 0.03 | 0.07 |
| BR-45/Kinesin 2 | 0.50 | 0.35 | 0.41 | 0.25 | 0.34 | 0.27 | 0.43 | 0.85 | 0.23 | 0.57 |
| BR-56/gC1Q | 0.66 | 0.49 | 0.22 | 0.83 | 0.40 | 0.44 | 0.69 | 0.77 | 0.44 | 3.71(+) |
| BR-57/Her2neu | 0.30 | 1.17 | 2.48 | 2.18 | 1.43 | 65.49 | 107.39 | 5.91 | 0.44 | 1.81(+) |
| BR-62 | 1.21 | 1.65 | 0.26 | 2.20 | 5.19 | 3.80 | 4.22 | 53.44 | 15.49 | 12.21(+) |
| BR-63/TP D52 | 1.44 | 4.08 | 0.91 | 7.36 | 6.26 | 2.08 | 2.88 | 132.51 | 1.67 | 5.33(+) |
| BR-75 | 2.27 | 0.34 | 0.48 | 0.59 | 0.43 | 0.34 | 0.37 | 0.78 | 0.36 | 1.06(+) |
| BR-85 | 5.55 | 6.28 | 1.15 | 6.65 | 3.17 | 4.98 | 5.91 | 11.42 | 10.34 | 11.34(+) |

TABLE 6-continued

Quantitative Analysis of mRNA Encoding SEREX Defined Breast Cancer Antigens in Normal and Malignant Breast Tissue: Relation Between mRNA Level and Immunogenicity

| | Ratio of mRNA in breast cancer to mRNA in normal breast ('+' indicates serum antibody reactivity[1]) | | | | | | | | | |
|---|---|---|---|---|---|---|---|---|---|---|
| Antigen | 1 | 2 | 3 | 4 | 5 | 6 | 7 | 8 | 9 | 10[2] |
| BR-96 | 0.53 | 1.09 | 0.45 | 0.65 | 0.39 | 0.33 | 0.56 | 0.81 | 0.31 | 1.26 |
| BR-98/MAGE D | 0.16 | 2.10 | 0.58 | 2.55 | 0.73(+) | 0.58 | 0.67(+) | 12.67 | 1.44 | 0.60 |

[1]Serum reactivity of patients # 1, 3, 5, 6, 7, 8, 9 and 10 assessed in the plaque assay.
[2]Patient # 10 referred to as allogeneic-1 in Table 1.

The relationship between upregulation of gene expression and serological reactivity was examined in 8 breast cancer patients whose tumors and sera were available for typing (informative cases, patients #1, 3, 5, 6, 7, 8, 9, 10). Serum antibodies against BR-56, -57, -62, -63, -75, and -85 were detected in breast cancer patient #10. In this case, mRNA transcripts encoding 4/6 of these antigens were overexpressed in the autologous tumor (BR-56, -62, -63, and -85). None of the other cases showed seroreactivity against the amplified/overexpressed SEREX-defined antigens.

Example 2

Method

Real-time PCR examination of NY-BR-62 mRNA in colon cancer tissue and normal colon tissue was also performed using the methods described above. Samples of colon cancer tissue from 9 patients were tested and the ratio of NY-BR-62 mRNA in the cancer tissues to mRNA in normal tissues were compared.

Results

Results from the real-time PCR examination of NY-BR-62 mRNA in colon cancer tissue and normal tissue are shown in Table 7. Nine samples of colon cancer tissue were tested and the ratio of NY-BR-62 mRNA in the cancer tissues to mRNA in normal tissues were compared. The results indicated that NY-BR-62 gene expression was upregulated in colon cancer when compared to its expression level in normal tissue counterpart.

TABLE 7

Real-time PCR of NY-BR-62 in colon cancer tissues.

| | Ratio of NY-BR-62 mRNA in cancer to mRNA in its normal tissue counterpart | | | | | | | | |
|---|---|---|---|---|---|---|---|---|---|
| Tumor Type | Patient #1 | #2 | #3 | #4 | #5 | #6 | #7 | #8 | #9 |
| Colon Cancer | 22.39 | 20.04 | 3.54 | 5.82 | 4.93 | 15.98 | 9.81 | 28.27 | 3.57 |

TABLE 8

Sequence Identification numbers

| Sequence Name | Nucleotide SEQ ID NO | Protein SEQ ID NO. |
|---|---|---|
| NY-BR-10 | 1 | 41 |
| NY-BR-11 | 2 | 42 |
| NY-BR-19 | 3 | 43 |
| NY-BR-21 | 4 | 44 |
| NY-BR-26 | 5 | 45 |
| NY-BR-33 | 6 | 46 |
| NY-BR-37 | 7 | 47 |
| NY-BR-44 | 8 | 48 |
| NY-BR-48 | 9 | 49 |
| NY-BR-52 | 10 | 50 |
| NY-BR-54 | 11 | 51 |
| NY-BR-67 | 12 | 52 |
| NY-BR-76 | 13 | 53 |
| NY-BR-77 | 14 | 54 |
| NY-BR-83 | 15 | 55 |
| NY-BR-92 | 16 | 56 |
| NY-BR-38 | 17 | 57 |
| NY-BR-46 | 18 | 58 |
| NY-BR-49 | 19 | 59 |
| NY-BR-51 | 20 | 60 |
| NY-BR-73 | 21 | 61 |
| NY-BR-85 | 22 | 62 |
| NY-BR-84 | 23 | 63 |
| NY-BR-99 | 24 | 64 |
| NY-BR-25 | 25 | 65 |
| NY-BR-34 | 26 | 66 |
| NY-BR-41 | 27 | 67 |
| NY-BR-45 | 28 | 68 |
| NY-BR-53 | 29 | 69 |
| NY-BR-55 | 30 | 70 |
| NY-BR-56 | 31 | 71 |
| NY-BR-57 | 32 | 72 |
| NY-BR-62 | 33 | 73 |
| NY-BR-63 | 34 | 74 |
| NY-BR-72 | 35 | 75 |
| NY-BR-75 | 36 | 76 |
| NY-BR-79 | 37 | 77 |
| NY-BR-94 | 38 | 78 |
| NY-BR-96 | 39 | 79 |
| NY-BR-98 | 40 | 80 |
| KNSL7 (Genbank No: AB035898) | 81 | 82 |

Other aspects of the invention will be clear to the skilled artisan and need not be repeated here. Each reference cited herein is incorporated by reference in its entirety.

The terms and expressions that have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for diagnosing cancer in a subject comprising:

obtaining a biological sample from a subject, contacting the sample with a breast cancer-associated polypeptide encoded by a nucleic acid molecule comprising the nucleotide sequence set forth as SEQ ID NO: 33, and determining specific binding between the breast cancer-associated polypeptide and agents in the sample, wherein the presence of specific binding is diagnostic for cancer in the subject.

2. The method of claim 1, wherein the agents are antibodies or antigen-binding fragments thereof.

3. The method of claim 1, wherein the cancer is breast cancer.

4. A method for diagnosing cancer in a subject comprising:

obtaining a biological sample from a subject, contacting the sample with an antibody or antigen-binding fragment thereof, that binds specifically to a breast cancer-associated polypeptide encoded by a nucleic acid molecule comprising the nucleotide sequence set forth as SEQ ID NO: 33, and determining specific binding between the antibody or antigen-binding fragment thereof and the breast cancer-associated polypeptide in the sample, wherein the presence of specific binding is diagnostic for cancer in the subject.

5. The method of claim 4, wherein the sample is selected from the group consisting of: tissue, cells, lymph node fluid, blood, and breast discharge fluid.

6. The method of claim 4, wherein the antibodies are monoclonal or polyclonal antibodies.

7. The method of claim 4, wherein the cancer is breast cancer.

8. A method for determining onset, progression, or regression, of cancer in a subject, comprising:

obtaining from a subject a first biological sample, contacting the first sample with a breast cancer associated polypeptide encoded by a nucleic acid molecule comprising the-a nucleotide sequence set forth as SEQ ID NO: 33, determining specific binding between agents in the first sample and the breast cancer-associated polypeptide, obtaining from a subject a second biological sample, contacting the second sample with a breast cancer associated polypeptide encoded by a nucleic acid molecule comprising the a-nucleotide sequence set forth as SEQ ID NO: 33, determining specific binding between agents in the second sample and the breast cancer-associated polypeptide, and comparing the determination of binding in the first sample to the determination of specific binding in the second sample as a determination of the onset, progression, or regression of cancer.

9. The method of claim 8, wherein the agents are antibodies or antigen-binding fragments thereof.

10. The method of claim 8, wherein the cancer is breast cancer.

11. A method for determining onset, progression, or regression, of cancer in a subject, comprising:

obtaining from a subject a first biological sample, contacting the first sample with antibodies or antigen-binding fragments thereof, that bind specifically to a breast cancer-associated polypeptide encoded by a nucleic acid molecule comprising the nucleotide sequence set forth as SEQ ID NO: 33, determining specific binding between the breast cancer-associated polypeptide in the first sample and the antibodies or antigen-fragments thereof, obtaining from a subject a second biological sample, contacting the second sample with antibodies or antigen-binding fragments thereof, that bind specifically to a breast cancer-associated polypeptide encoded by a nucleic acid molecule comprising the nucleotide sequence set forth as SEQ ID NO: 33, determining specific binding between breast cancer-associated polypeptide in the second sample and the antibodies or antigen-binding fragments thereof, and comparing the determination of specific binding in the first sample to the determination of specific binding in the second sample as a determination of the onset, progression, or regression of cancer.

12. The method of claim 11, wherein the sample is selected from the group consisting of: tissue, cells, lymph node fluid, blood, and breast discharge fluid.

13. The method of claim 11, wherein the antibodies are monoclonal or polyclonal antibodies.

14. The method of claim 11, wherein the cancer is breast cancer.

15. A kit for the diagnosis of cancer in a subject, comprising:

a breast cancer-associated polypeptide encoded by a nucleic acid molecule comprising the a nucleotide sequence set forth as SEQ ID NO: 33, one or more control antigens; and instructions for the use of the polypeptide and control antigens in the diagnosis of cancer.

16. The kit of claim 15, wherein the breast cancer-associated polypeptide is bound to a substrate.

17. A method for diagnosing cancer in a subject comprising:

obtaining from the subject a biological sample, and determining the expression of a breast cancer-associated nucleic acid molecule or expression product thereof in the sample, wherein the nucleic acid molecule comprises the a nucleotide sequence set forth as SEQ ID NO: 33, wherein the expression is diagnostic of cancer in the subject.

18. The method of claim 17, wherein the sample is selected from the group consisting of: tissue, cells, lymph node fluid, blood, and breast discharge fluid.

19. The method of claim 17, wherein the expression of breast cancer-associated nucleic acid molecules is determined by a method selected from the group consisting of nucleic acid hybridization and nucleic acid amplification.

20. A method for determining onset, progression, or regression, of cancer in a subject comprising:

obtaining from a subject a first biological sample, determining a level of expression of a breast cancer-associated nucleic acid molecule or expression products thereof in the first sample, wherein the nucleic acid molecule comprises SEQ ID NO:33, obtaining from the subject a second biological sample, determining a level of expression of a breast cancer-associated nucleic acid molecule or expression product thereof in the second sample, wherein the nucleic acid molecule comprises SEQ ID NO: 33, and comparing the level of expression in the first sample to the level of expression in the second sample as a determination of the onset, progression, or regression of the cancer.

21. The method of claim 20, wherein the sample is selected from the group consisting of: tissue, cells, lymph node fluid, blood, and breast discharge fluid.

22. The method of claim 20, wherein the expression of breast cancer-associated nucleic acid molecules is determined by a method selected from the group consisting of nucleic acid hybridization and nucleic acid amplification.

23. A method for diagnosing cancer in a subject comprising:

obtaining a non-testis biological sample from a subject, determining the level of expression of a cancer-associated nucleic acid molecule comprising the a-nucleotide sequence set forth as SEQ ID NO: 33, and comparing the level of expression of the nucleic acid molecule in the subject sample to a level of expression of the nucleic acid molecule in a control tissue, wherein a determination that the level of expression of the nucleic acid in the sample from the subject is greater than about three times the level of expression of the nucleic acid in the control tissue, indicates cancer in the subject.

24. A method for determining onset, progression, or regression, of cancer in a subject comprising:

obtaining from a subject a first and a second biological sample, wherein the samples comprise the same tissue type and are obtained at different times, determining a level of expression of a cancer-associated nucleic acid molecule or expression product thereof in the first and second biological samples, wherein the nucleic acid molecule comprises the nucleotide sequence set forth as: SEQ ID NO: 33, comparing the level of expression of the cancer-associated nucleic acid molecule in the first and the second biological samples to the level of expression of the cancer-associated nucleic acid molecule in a control sample, wherein a higher level of expression of the cancer-associated nucleic acid molecule in the first sample than in the second sample indicates regression of cancer, wherein a lower level of expression of the cancer-associated nucleic acid molecule in the first sample than the second sample indicates progression of cancer, and wherein a level of expression of the cancer-associated nucleic acid molecule in the first sample that is less than three times higher than the level of expression of the cancer-associated nucleic acid molecule in the control sample and a level of expression of the cancer-associated nucleic acid molecules in the second sample that is three or more times higher than the level in the control sample, indicates onset cancer.

25. A method for diagnosing cancer in a subject comprising:

obtaining a biological sample from a subject, determining the level of expression of a cancer-associated nucleic acid molecule comprising the a nucleotide sequence set forth as SEQ ID NO: 33, and comparing the level of expression of the nucleic acid molecule in the subject sample to a level of expression of the nucleic acid in a control tissue, wherein a determination that the level of expression of the nucleic acid in the sample from the subject is greater than about three times of the level of expression of the nucleic acid in the control tissue, indicates cancer in the subject.

26. The method of claim 25, wherein the cancer is colon cancer.

27. A method for determining onset, progression, or regression, of cancer in a subject comprising:

obtaining from a subject a first and a second biological sample, wherein the samples comprise the same tissue type and are obtained at different times, determining a level of expression of a cancer-associated nucleic acid molecule or expression product thereof in the first and second biological samples, wherein the nucleic acid molecule comprises the a-nucleotide sequence set forth as-SEQ ID NO:33, and comparing the level of expression of the cancer-associated nucleic acid molecule of the first and the second biological samples to the level of expression of the cancer-associated nucleic acid molecule in a control sample, wherein a higher level of expression of the cancer-associated nucleic acid molecule in the first sample than in the second sample indicates regression of cancer, wherein a lower level of expression of the cancer-associated nucleic acid molecule in the first sample than the second sample indicates progression of cancer, and wherein a level of expression of the cancer-associated nucleic acid molecule in the first sample that is less than three times higher than the level of expression of the cancer-associated nucleic acid molecule in the control sample, and a level of expression of the cancer-associated nucleic acid molecules in the second sample that is three or more times higher than the level in the control sample, indicates onset of cancer.

28. The method of claim 27, wherein the cancer is colon cancer.

* * * * *

UNITED STATES PATENT AND TRADEMARK OFFICE

CERTIFICATE OF CORRECTION

PATENT NO. : 7,335,467 B2
APPLICATION NO. : 10/146473
DATED : February 26, 2008
INVENTOR(S) : Scanlan et al.

It is certified that error appears in the above-identified patent and that said Letters Patent is hereby corrected as shown below:

In the Claims:

Claim 8, column 313, line 26 should read as shown below.
--prising the nucleotide sequence set forth as SEQ ID--

Claim 8, column 313, line 33 should read as shown below.
--comprising the nucleotide sequence set forth as SEQ--

Claim 17, column 314, line 26 should read as shown below.
--prises the nucleotide sequence set forth as SEQ ID--

Claim 23, column 314, line 63 should read as shown below.
--nucleic acid molecule comprising the nucleotide--

Claim 27, column 316, line 16 should read as shown below.
--nucleic acid molecule comprises the nucleotide--

Claim 27, column 316, line 17 should read as shown below.
--sequence set forth as SEQ ID NO:33, and--

Signed and Sealed this

Twenty-fourth Day of June, 2008

JON W. DUDAS
*Director of the United States Patent and Trademark Office*